(12) United States Patent
Campbell et al.

(10) Patent No.: US 11,426,399 B2
(45) Date of Patent: Aug. 30, 2022

(54) TREATMENT OF AGING-ASSOCIATED DISEASE WITH MODULATORS OF LEUKOTRIENE A4 HYDROLASE

(71) Applicant: Alkahest, Inc., San Carlos, CA (US)

(72) Inventors: Meghan Kerrisk Campbell, San Francisco, CA (US); Eva Czirr, Foster City, CA (US); Balazs Szoke, San Carlos, CA (US)

(73) Assignee: Alkahest, Inc., San Carlos, CA (US)

( * ) Notice: Subject to any disclaimer, the term of this patent is extended or adjusted under 35 U.S.C. 154(b) by 0 days.

(21) Appl. No.: 16/412,275

(22) Filed: May 14, 2019

(65) Prior Publication Data

US 2019/0350917 A1 Nov. 21, 2019

Related U.S. Application Data

(60) Provisional application No. 62/694,921, filed on Jul. 6, 2018, provisional application No. 62/671,882, filed on May 15, 2018.

(51) Int. Cl.

| | | |
|---|---|---|
| *A61K 31/47* | (2006.01) | |
| *A61K 31/197* | (2006.01) | |
| *A61K 31/085* | (2006.01) | |
| *C07K 16/40* | (2006.01) | |
| *A61P 25/28* | (2006.01) | |
| *A61K 31/353* | (2006.01) | |

(52) U.S. Cl.
CPC ............ *A61K 31/47* (2013.01); *A61K 31/085* (2013.01); *A61K 31/197* (2013.01); *A61K 31/353* (2013.01); *A61P 25/28* (2018.01); *C07K 16/40* (2013.01); *C07K 2317/76* (2013.01)

(58) Field of Classification Search
CPC .......... C07K 16/40; C07K 14/81; C12N 9/14; A61P 25/28
See application file for complete search history.

(56) References Cited

U.S. PATENT DOCUMENTS

| | | | |
|---|---|---|---|
| 5,700,816 A | * | 12/1997 | Isakson ...................... A61P 1/00 514/326 |
| 8,278,302 B2 | | 10/2012 | Grundl et al. |
| 8,680,280 B2 | | 3/2014 | Duran et al. |
| 8,742,115 B2 | | 6/2014 | Frank et al. |
| 9,233,950 B2 | | 1/2016 | Frank et al. |
| 10,213,421 B2 | | 2/2019 | Fetscher et al. |
| 10,245,285 B2 | | 4/2019 | Braithwaite et al. |
| 10,357,513 B2 | | 7/2019 | Braithwaite et al. |
| 2005/0272051 A1 | | 12/2005 | Helgadottir et al. |
| 2016/0272649 A1 | | 9/2016 | Arnaiz et al. |
| 2017/0319567 A1 | | 11/2017 | Nivens et al. |
| 2018/0110839 A1 | | 4/2018 | Bell et al. |
| 2018/0117014 A1 | | 5/2018 | Springman et al. |
| 2018/0117041 A1 | | 5/2018 | Dong et al. |
| 2018/0127424 A1 | | 5/2018 | Guilford |
| 2019/0105314 A1 | | 4/2019 | Braithwaite et al. |
| 2019/0111042 A1 | | 4/2019 | Braithwaite et al. |
| 2019/0151300 A1 | | 5/2019 | Fetscher et al. |
| 2019/0167719 A1 | | 6/2019 | Braithwaite et al. |

FOREIGN PATENT DOCUMENTS

| | | |
|---|---|---|
| CL | 201601255 | 11/2016 |
| CL | 201702017 | 4/2018 |
| WO | WO2004029237 A1 | 4/2004 |
| WO | WO2005011736 A1 | 2/2005 |
| WO | WO2009032870 A2 | 3/2009 |
| WO | WO2010115836 A1 | 10/2010 |
| WO | WO2012045803 A1 | 4/2012 |
| WO | WO2013149926 A1 | 10/2013 |
| WO | WO2013149986 A1 | 10/2013 |
| WO | WO2013149987 A1 | 10/2013 |
| WO | WO2017189919 A2 | 11/2017 |
| WO | WO2018034712 A1 | 2/2018 |
| WO | WO2018187503 A1 | 10/2018 |
| WO | WO2018200560 A1 | 11/2018 |
| WO | WO2019075351 A1 | 4/2019 |

OTHER PUBLICATIONS

Medical Dictionary "Active Ingredient" excerpt accessed from medical-dictionary.thefreedictionary.com on Mar. 2, 2022 (Year: 2022).*

Iversen et al., Significance of Leukotriene-A4 Hydrolase in the Pathogenesis of Psoriasis, Skin Pharmacology, 1997, vol. 10, pp. 169-177.

Extended European Search Report for corresponding European Application No. 19803142.9 dated Mar. 17, 2022, 18 pages.

Chao et al., Protective effects of pinostilbene, a resveratrol methylated derivative, against 6-hydroxdopamine-induced neurotoxicity in SH-SY5Y cells, J Nutr Biochem, Jun. 2010;21(6):482-9.

* cited by examiner

*Primary Examiner* — Adam Weidner

(74) *Attorney, Agent, or Firm* — Mandar A. Joshi; Bret E. Field; Bozicevic, Field & Francis LLP

(57) ABSTRACT

Methods and compositions for treating and/or preventing aging-related conditions are described. The compositions used in the methods include inhibitors or antagonists of leukotriene A4 hydrolase ("LTA4H") with efficacy in treating and/or preventing aging-related conditions such as neurocognitive disorders.

17 Claims, 52 Drawing Sheets

TREATMENT OF AGING-ASSOCIATED DISEASE WITH MODULATORS OF LEUKOTRIENE A4 HYDROLASE

I. CROSS-REFERENCE TO RELATED APPLICATIONS

Pursuant to 35 U.S.C. § 119 (e), this application claims priority to the filing dates of: United States Provisional Patent Application No. 62/671,882, filed May 15, 2018 and U.S. Provisional Patent Application No. 62/694,921, filed Jul. 6, 2018; the disclosures of which applications are herein incorporated by reference.

II. INTRODUCTION

Field

This invention pertains to the prevention and treatment of aging-associated disease. The invention relates to the use of modulators of leukotriene A4 hydrolase ("LTA4H"), to treat and/or prevent conditions associated with aging, such as cognitive disorders, motor disorders, and neuroinflammation.

Background

The following is offered as background information only and is not admitted as prior art to the present invention.

Aging is an important risk factor for multiple human diseases including cognitive impairment, cancer, arthritis, vision loss, osteoporosis, diabetes, cardiovascular disease, and stroke. In addition to normal synapse loss during natural aging, synapse loss is an early pathological event common to many neurodegenerative conditions and is the best correlate to the neuronal and cognitive impairment associated with these conditions. As such, aging remains the single most dominant risk factor for dementia-related neurodegenerative diseases such as Alzheimer's disease (AD) (Bishop N. A. et al., *Neural mechanisms of ageing and cognitive decline*. Nature 464(7288), 529-535 (2010); Heeden T. et al., *Insights into the ageing mind: a view from cognitive neuroscience*. Nat. Rev. Neurosci. 5(2), 87-96 (2004); Mattson, M. P., et al., *Ageing and neuronal vulnerability*. Nat. Rev. Neurosci. 7(4), 278-294 (2006)). Similarly, a decline in motor skills correlates with aging. (Hoogendam Y Y, et al., *Older Age Relates to Worsening of Fine Motor Skills: A Population-Based Study of Middle-Aged and Elderly Persons*. Front. Aging Neurosci. 6 (2014)). Additionally, neuroinflammation has been associated with aging in both healthy brains and in diseased brains such as in AD. (Lynch M A, *Age-related neuroinflammatory changes negatively impact on neuronal function*. Front. Aging Neurosci. 1(6), 1-8 (2010)). Aging affects all tissues and functions of the body including the central nervous system, and neurodegeneration and a decline in functions such as cognition or motor skills, can severely impact quality of life. Treatment for cognitive decline, motor impairment, neuroinflammation, and neurodegenerative disorders has had limited success in preventing and reversing impairment. It is therefore important to identify new treatments for maintaining cognitive and motor integrity by protecting against, countering, or reversing the effects of aging.

Leukotriene A4 hydrolase ("LTA$_4$H" or "LTA4H") is a soluble, monomeric enzyme that converts lipid metabolite leukotriene A4 ("LTA$_4$" or "LTA4") to leukotriene B4 ("LTB$_4$" or "LTB4"). The LTA$_4$H enzyme through its ability to produce the LTB4 lipid metabolite has been characterized as proinflammatory. Additionally, LTB4 lipid metabolite is associated with neutrophil recruitment. Thus, the LTA4H enzyme has been implicated in such diseases as atherosclerosis, atherosclerotic coronary artery disease, rheumatoid arthritis, cystic fibrosis, chronic obstructive pulmonary disease, sepsis, adult respiratory distress syndrome, inflammatory bowel disease, and asthma. (Snelgrove R J, *Leukotriene A4 Hydrolase: An Anti-Inflammatory Role for A Proinflammatory Enzyme*, Thorax 66:550-51 (2011); Shim Y M, et al., *Leukotriene A4 Hydrolase An Evolving Therapeutic Target*, Inflammatory Diseases—Immunopathology, Clinical and Pharmacological Bases (Dr. Mahin Khatami (Ed.)), 253-278, (2012)).

The LTA4H enzyme has recently been characterized as having an additional catalytic activity. LTA4H not only exhibits the epoxide hydrolase activity converting LTA4 to LTB4, but an additional aminopeptidase activity (or "peptidase" activity), cleaving Pro-Gly-Pro peptides (P-G-P) to Pro+Gly-Pro. This aminopeptidase activity is thought to contribute an anti-inflammatory role for LTA4H by reducing accumulation of P-G-P. (Snelgrove, et al. *A critical role for LTA4H in limiting chronic pulmonary neutrophilic inflammation*, Science 330(6000):90-4 (2010)). This discovery may provide insights into the clinical failures of LTA4H inhibitors within inflammatory diseases. Modulators of the LTA4H enzyme have been described, including small molecule inhibitors. These include small molecules that: bind both the epoxide hydrolase pocket and the aminopeptidase active site, such as SC-57461A; and selectively bind the epoxide hydrolase binding pocket of LTA4H, such as pinostilbene hydrate (Low C M et al., *The development of novel LTA4H modulators to selectively target LTB4 generation*. Sci. Rep. 7, 44449 (2017)).

The second class of Leukotrienes ("LTs") are the cysteinyl leukotrienes (Cys-LT), LTC4, LTD4, and LTE4, which are ligands for the cysteinyl leukotriene receptors type 1 and 2 (CysLT1R, CysLT2R), GPR17, and others. (Ghosh, A., et al., *Cysteinyl Leukotrienes and Their Receptors: Emerging Therapeutic Targets in Central Nervous System Disorders*. CNS Neurosci Ther, 22(12): p. 943-51 (2016)). LTs in general have been associated with inflammation and studied for their role in diseases such as asthma. (Y. Michael Shim, M. P., *Leukotriene A4 Hydrolase—An Evolving Therapeutic Target in Inflammatory Diseases—Immunopathology, Clinical and Pharmacological Bases*, M. Khatami, Editor. InTech. p. 253-78 (2012)). More recently, Cys-LTs have been shown to influence central nervous system diseases including traumatic brain injury, Alzheimer's disease (AD), Parkinson's disease, multiple sclerosis, epilepsy, Huntington's disease, and depression. (Ghosh A, supra). For example, LTD4 and CysLT1R are increased in transgenic mouse models of AD and administration of CysLT1R antagonists, Pranlukast and Montelukast, alleviate some of the pathological symptoms in these mice. (Tang, S. S., et al., *Protective effect of pranlukast on Abeta(1)(-)(4)(2)-induced cognitive deficits associated with downregulation of cysteinyl leukotriene receptor 1*. Int J Neuropsychopharmacol, 17(4): p. 581-92 (2014); Tang, S. S., et al., *Leukotriene D4 induces cognitive impairment through enhancement of CysLT(1) R-mediated amyloid-beta generation in mice*. Neuropharmacology, 65: p. 182-92 (2013); Wang, X. Y., et al., *Leukotriene D4 induces amyloid-beta generation via CysLT(1)R-mediated NF-kappaB pathways in primary neurons*. Neurochem Int, 62(3): p. 340-47 (2013); and Herbst-Robinson, K. J., et al., *Inflammatory Eicosanoids Increase Amyloid Precursor Protein Expression via Activation of

*Multiple Neuronal Receptors*. Sci Rep, 5: p. 18286 (2015)), Additionally, administration of Montelukast in aged mice reduces brain inflammation, increases neurogenesis, and improves cognition. (Marschallinger, J., et al., *Structural and functional rejuvenation of the aged brain by an approved anti-asthmatic drug*. Nat Commun, 6: p. 8466 (2015)). While the Cys-LTs have been shown to influence the CNS, the production of LTB4 by LTA4H has not be implicated in cognition or diseases of the CNS.

III. SUMMARY

The present invention recognizes that as people age, the amounts of certain plasma proteins also increase. The present invention recognizes that such proteins can be referred to as "pro-aging factors," and modulation of their activity or concentration in the blood circulation can protect or even reverse certain aging-related symptoms and/or disease. The present invention is also based on work demonstrating that the LTA4H enzyme and its product LTB4 occur at higher concentrations in older subjects than in younger subjects. The present invention shows that the introduction of exogenous LTA4H enzyme in vivo results in a reduction of cognitive ability, neuronal cell survival, and proliferation of neural stem/progenitor cells in young animals. The present also demonstrates, among other things, that modulation of the LTA4H enzyme through pharmacological intervention in vivo leads to an improvement in cognition and reduction in inflammatory markers in aged animals. The present invention also recognizes that modulation of the LTA4H enzyme through pharmacological intervention may cause a reduction in the progression or reverse certain aging-associated symptoms or disease.

The present invention is based on targeting the LTA4H enzyme for treating and/or preventing age-related disorders, such as cognitive impairment conditions, age-related dementia, impairment of motor function, neuroinflammation, and neurodegenerative disease. The present invention recognizes, among other things, the need for new therapies and new mechanisms of action for the treatment and/or prevention of cognitive impairment, age-related dementia, motor impairment, neuroinflammation, and neurodegenerative disease. The present compositions of the invention relate to a solution for the failures and shortcomings of current therapies through utilization of inhibitors of the LTA4H enzyme in the treatment and/or prevention of cognitive impairment, age-related dementia, motor impairment, neuroinflammation, and neurodegenerative disease.

An embodiment of the invention includes treating a subject diagnosed with a cognitive impairment by administering to the subject an effective amount of one or more LTA4H modulatory agents. Another embodiment of the invention includes administering the effective amount of one or more LTA4H modulatory agents and subsequently monitoring the subject for improved cognitive function. Another embodiment of the invention includes treating a subject diagnosed with a cognitive impairment by administering to the subject an effective amount of one or more LTA4H modulatory agents wherein the one or more LTA4H modulatory agents are administered in a manner resulting in improved cognitive function, improved neurogenesis, or reduced neuroinflammation.

An embodiment of the invention includes treating a subject diagnosed with a neurodegenerative motor disorder such as, by way of example and not limitation, Parkinson's Disease, by administering to the subject an effective amount of one or more LTA4H modulatory agents. Another embodiment of the invention includes administering the effective amount of one or more LTA4H modulatory agents and subsequently monitoring the subject for improved motor function. Another embodiment of the invention includes treating a subject diagnosed with a neurodegenerative motor disorder by administering to the subject an effective amount of one or more LTA4H modulatory agents wherein the one or more LTA4H modulatory agents are administered in a manner resulting in improved motor function, neurogenesis, or reduced neuroinflammation.

An embodiment of the invention includes treating a subject diagnosed with neuroinflammation or a neuroinflammation-associated disorder by administering to the subject an effective amount of one or more LTA4H modulatory agents. Another embodiment of the invention includes administering the effective amount of one or more LTA4H modulatory agents and subsequently monitoring the subject for reduced neuroinflammation. Another embodiment of the invention includes treating a subject diagnosed with neuroinflammation or a neuroinflammation-associated disorder by administering to the subject an effective amount of one or more LTA4H modulatory agents wherein the one or more LTA4H modulatory agents are administered in a manner resulting in reduced neuroinflammation.

Another embodiment of the invention includes utilizing an inhibitor of the LTA4H enzyme as the one or more LTA4H modulatory agent(s). Further embodiments contemplate using one or more LTA4H modulatory agent(s) that selectively inhibits the epoxide hydrolase activity of LTA4H, and not the aminopeptidase activity of LTA4H. A further embodiment contemplates using one or more LTA4H modulatory agent(s) that inhibits both the epoxide hydrolase activity of LTA4H and the aminopeptidase activity of LTA4H. A further embodiment of the invention contemplates the LTA4H modulatory agent(s) having the ability to selectively bind to one or more sites on the LTA4H enzyme, such as by way of example and not limitation, the epoxide hydrolase active site and/or the aminopeptidase active site.

An embodiment of the invention includes treating a subject diagnosed with a cognitive impairment, impaired motor function, or neuroinflammation or a decline in neurogenesis by administering to the subject an effective amount of one or more LTA4H modulatory agent(s), with the subject following an exercise regimen after the administration. Another embodiment of the invention includes following an exercise regimen that is prescribed to the subject. Another embodiment of the invention includes the subject exercising at a higher intensity and/or greater frequency than the subject exercised preceding the administration. Another embodiment of the invention includes the subject exercising at a similar intensity and/or frequency as the subject exercised preceding the administration.

IV. INCORPORATION BY REFERENCE

All publications and patent applications mentioned in this specification are herein incorporated by reference to the same extent as if each individual publication or patent application was specifically and individually indicated to be incorporated by reference.

V. BRIEF DESCRIPTION OF THE DRAWINGS

Figure 4A:
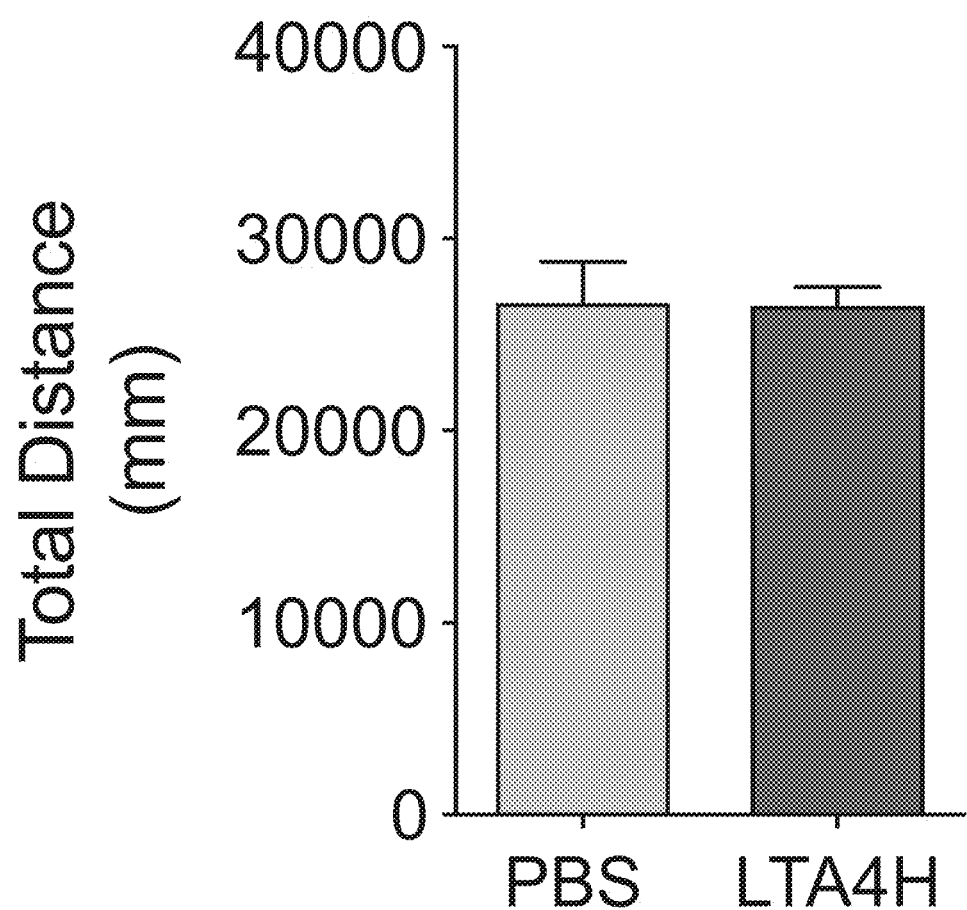

FIG. 4A reports the total distance travelled in an open field test in young mice treated with recombinant human LTA4H protein or phosphate buffered saline (PBS) control.

Figure 4B:
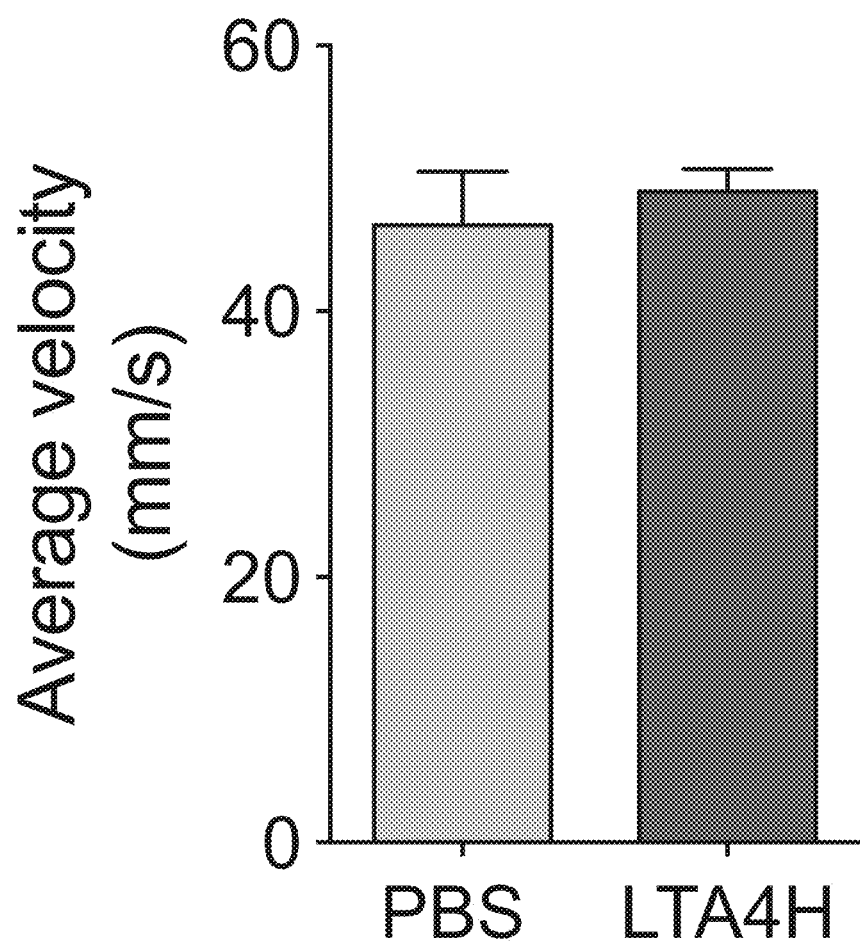

FIG. 4B reports the average velocity in an open field test in young mice treated with recombinant human LTA4H protein or phosphate buffered saline (PBS) control.

Figure 4C:
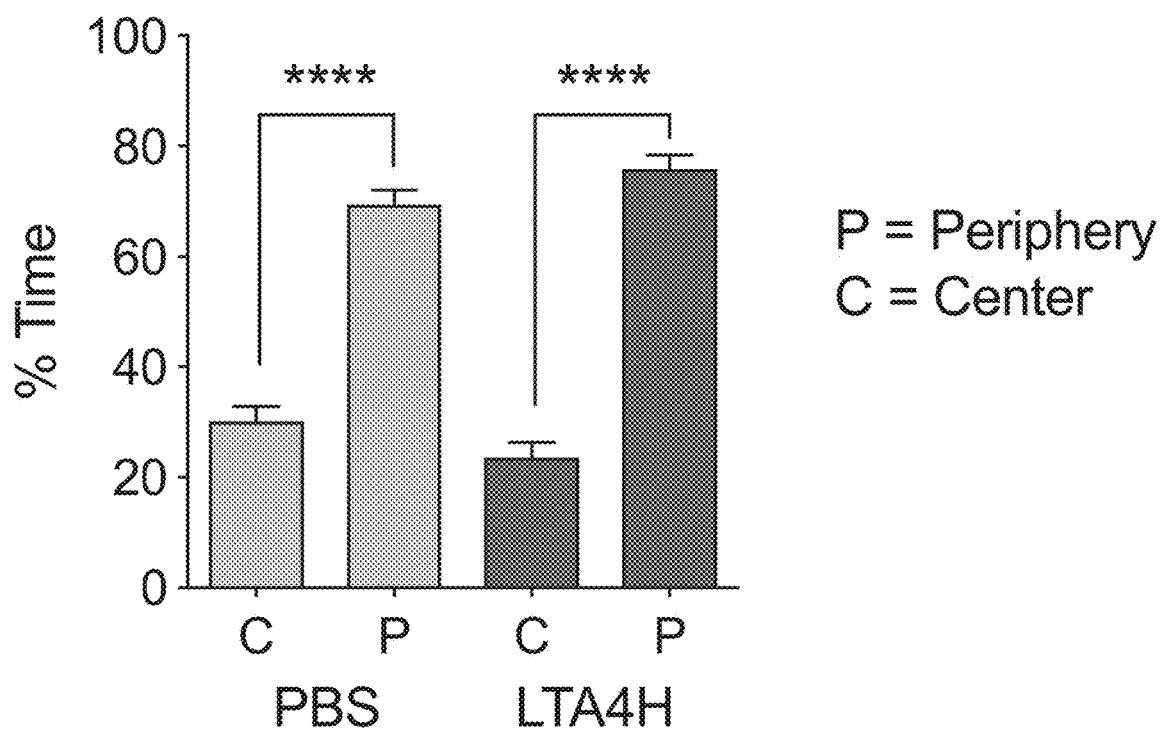

FIG. 4C reports the percent time spent in the periphery or center in an open field test in young mice treated with recombinant human LTA4H protein or phosphate buffered saline (PBS) control.

Figure 5A:
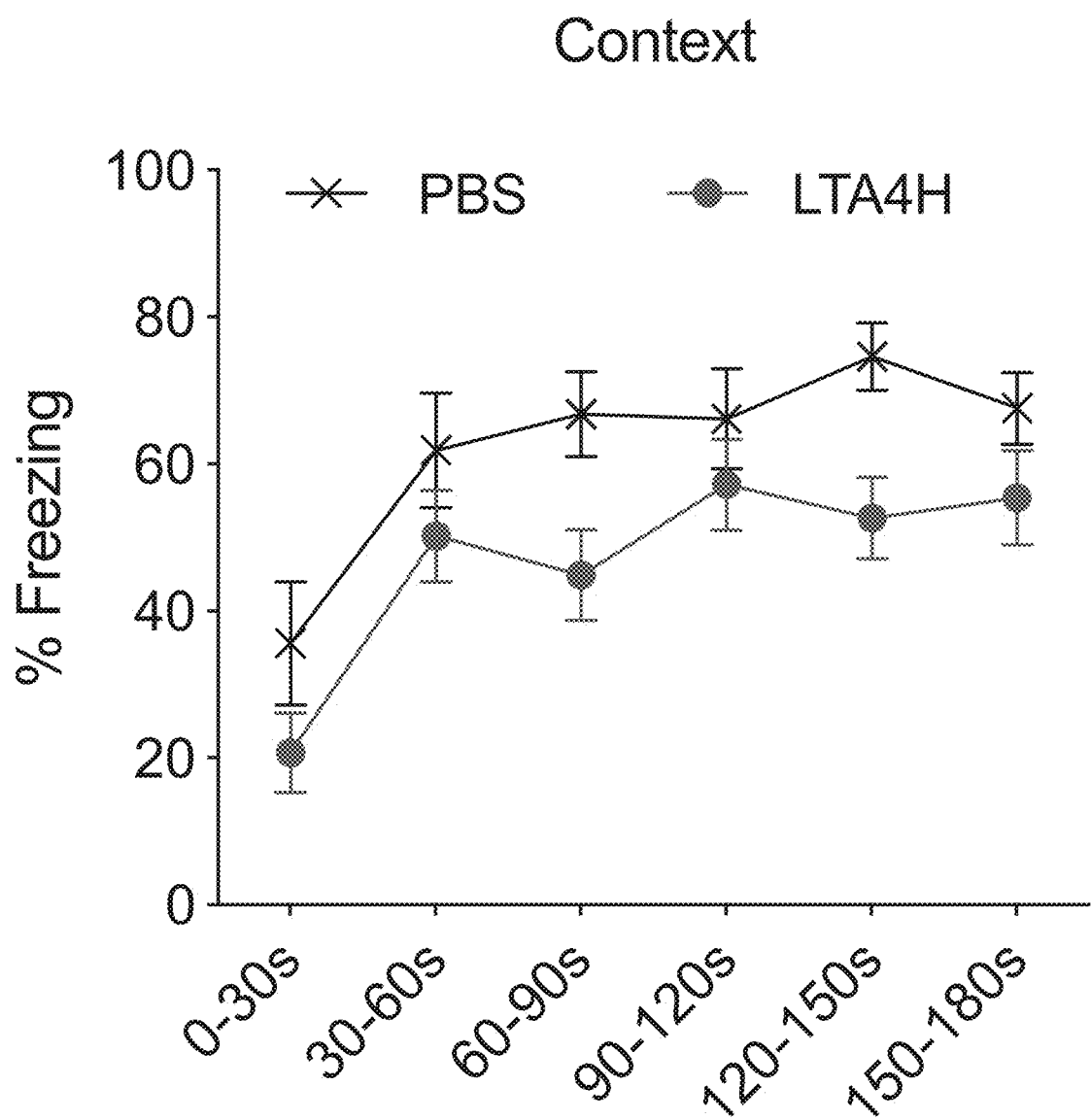

FIG. 5A depicts the percent time spent freezing in 30 sec bins in a contextual fear conditioning task in young mice treated with recombinant human LTA4H protein or phosphate buffered saline (PBS) control.

Figure 5B:
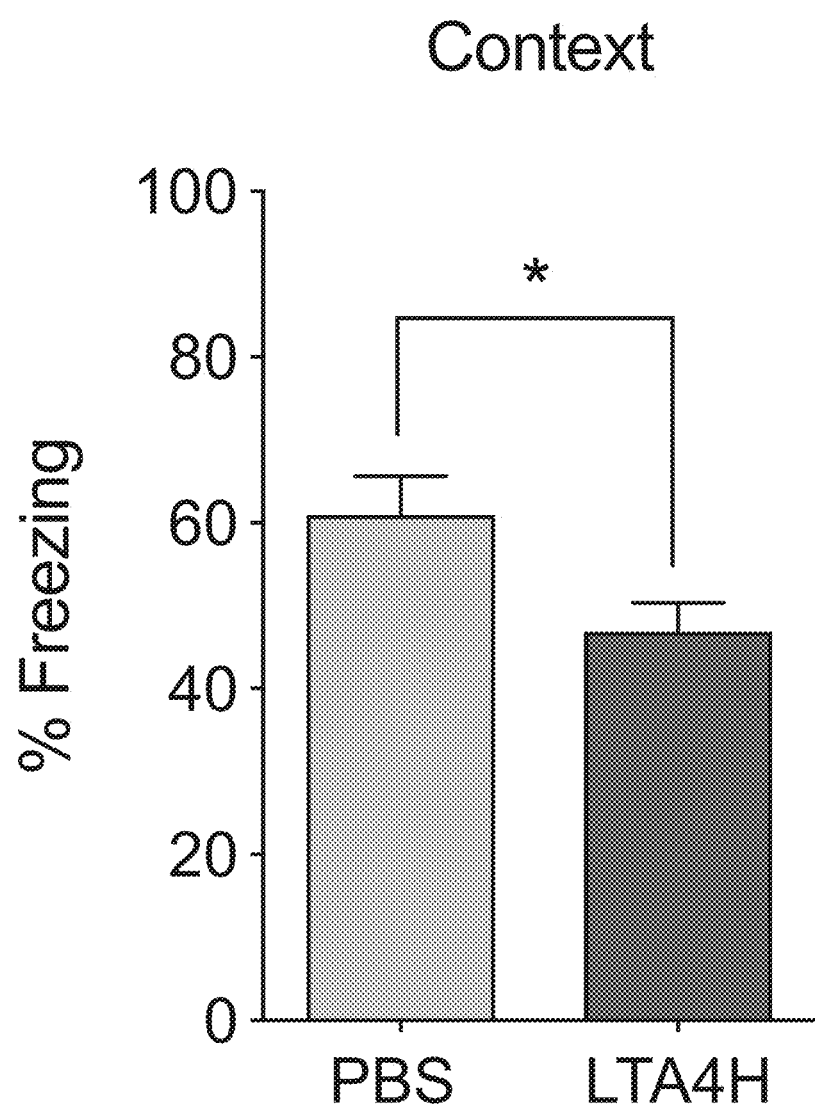

FIG. 5B depicts the percent time spent freezing during the whole duration of the contextual fear conditioning task in young mice treated with recombinant human LTA4H protein or phosphate buffered saline (PBS) control.

Figure 5C:
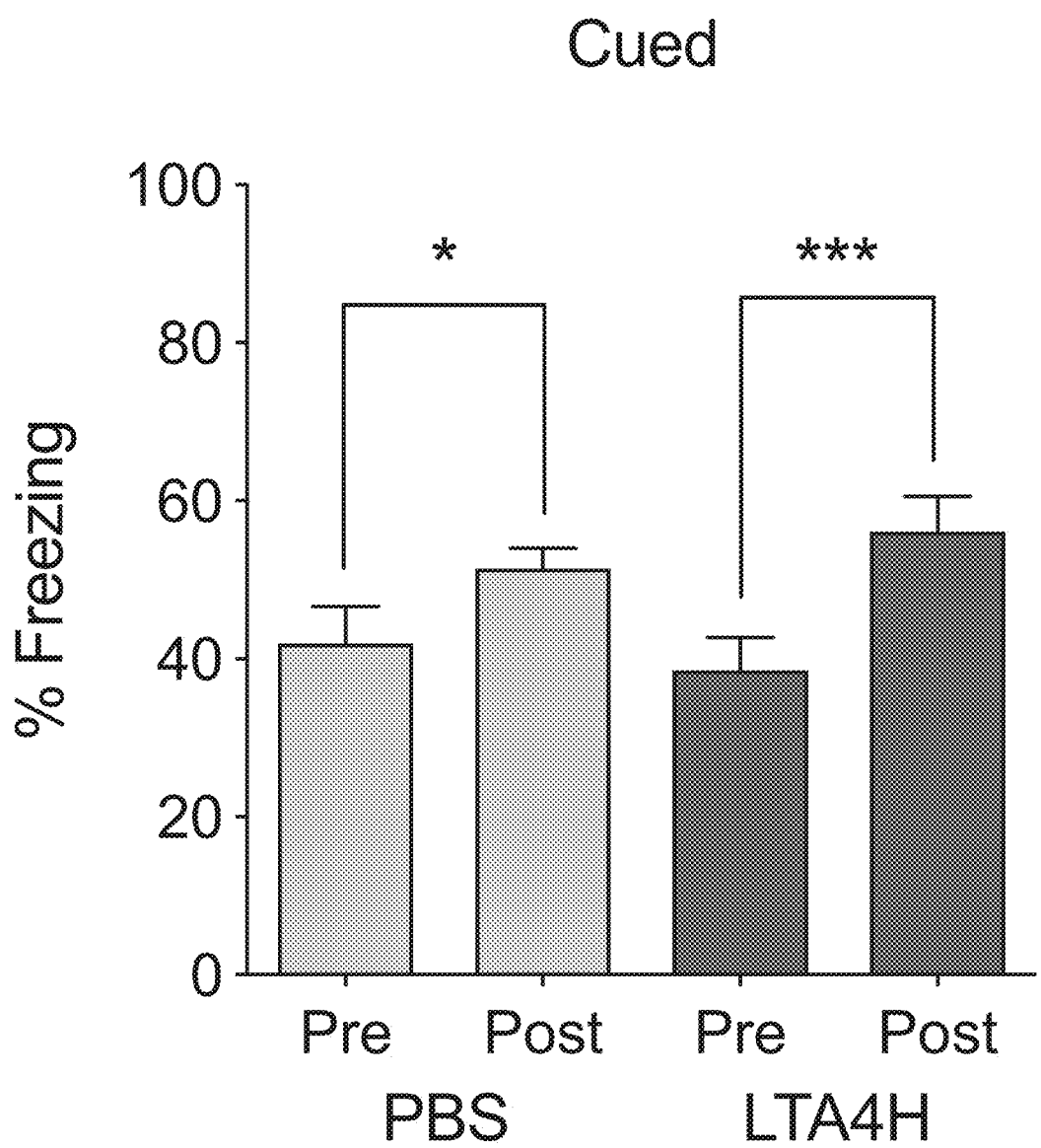

FIG. 5C depicts the time spent freezing pre and post-cue tone in a cued fear conditioning task in young mice treated with recombinant human LTA4H protein or phosphate buffered saline (PBS) control.

Figure 6:
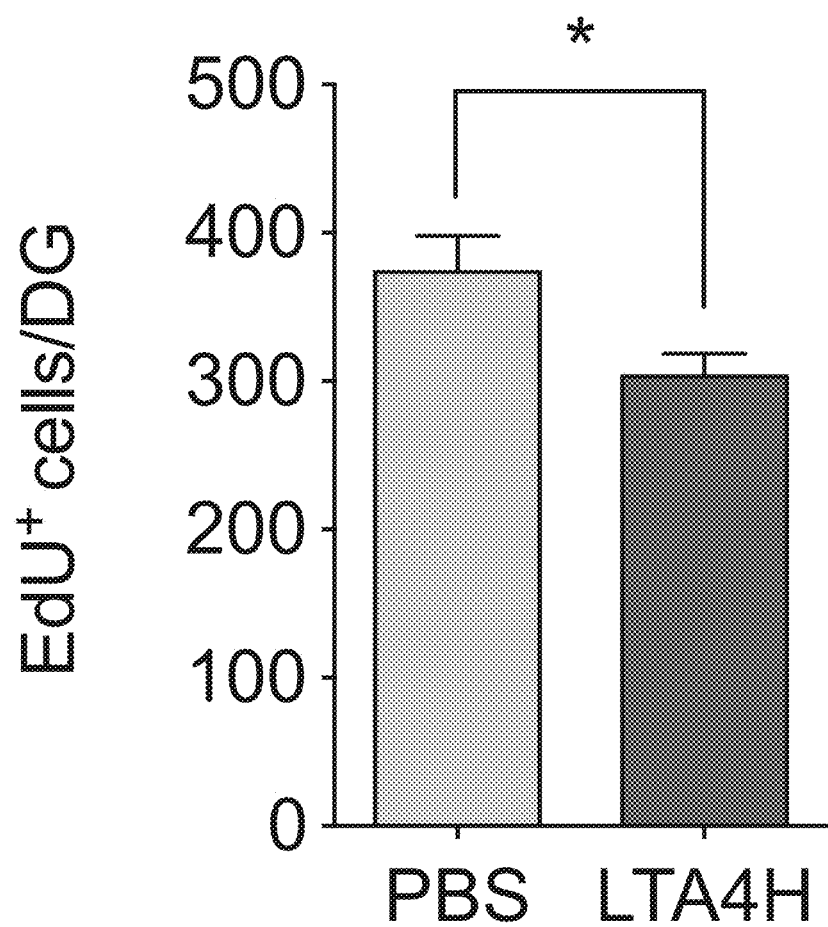

FIG. 6 reports the number of EdU-labeled cells within granule cell layer of the hippocampus in young mice treated with recombinant human LTA4H protein or phosphate buffered saline (PBS) control.

Figure 7:
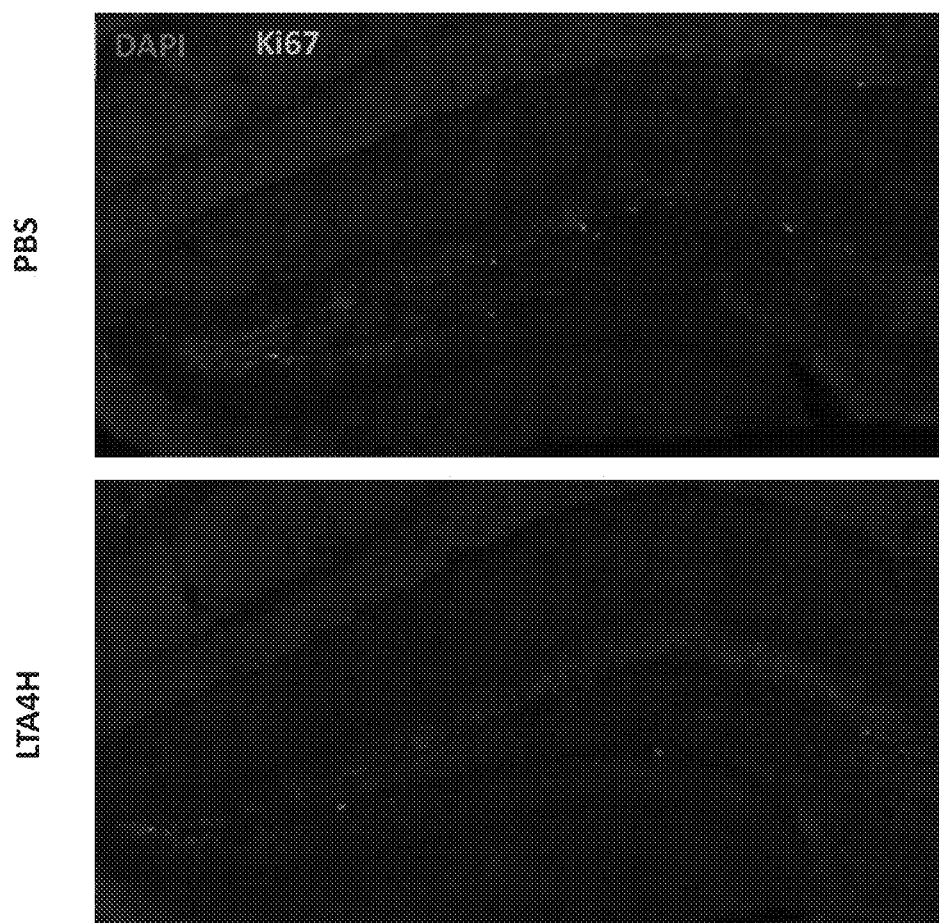

FIG. 7 depicts cell nuclei labeled with DAPI (blue) and dividing Ki67 (green) labeled cells in the dentate gyrus in young mice treated with recombinant human LTA4H protein or phosphate buffered saline (PBS) control.

Figure 8:
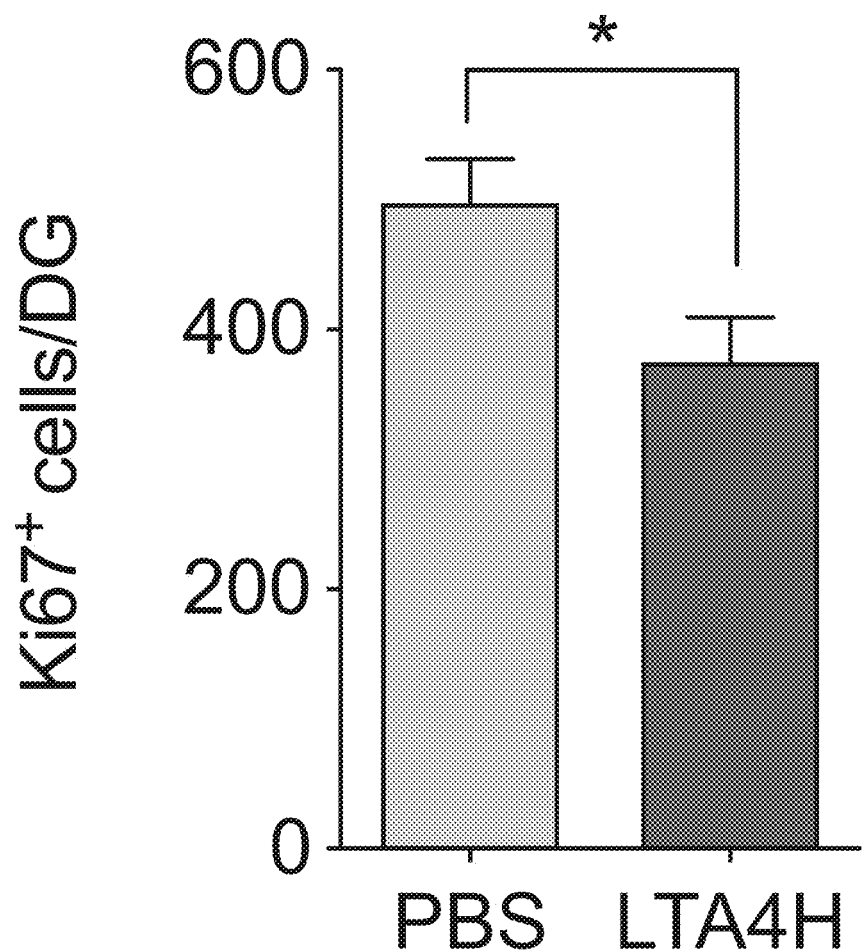

FIG. 8 reports the number of Ki67-labeled dividing cells in the blade of the dentate gyrus in the hippocampus in young mice treated with recombinant human LTA4H protein or phosphate buffered saline (PBS) control.

Figure 9:
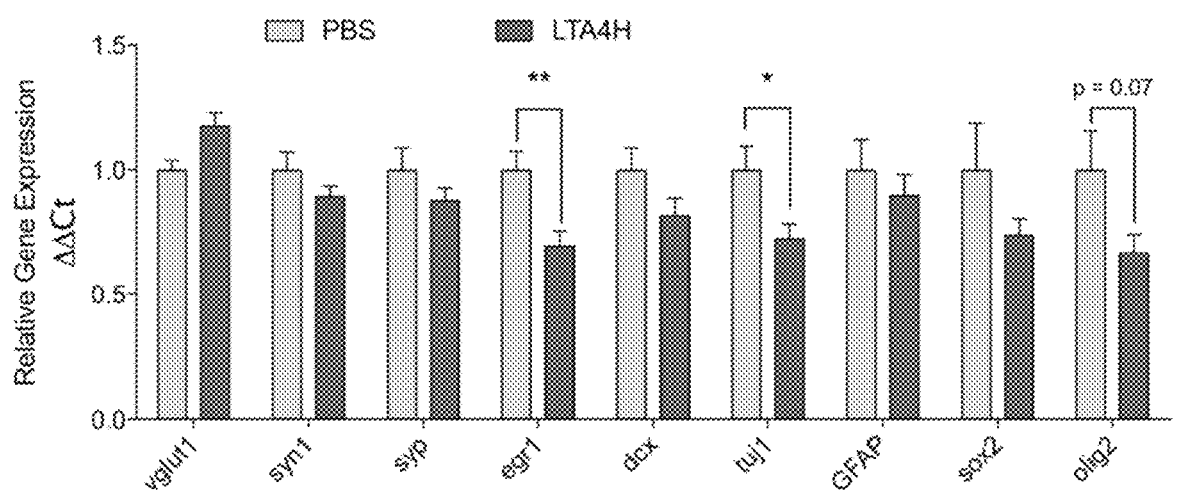

FIG. 9 reports the results of quantitative polymerase chain reaction (qPCR) quantifying mRNA levels of vesicular glutamate receptor (vglut1), synapsin 1 (syn1), synaptophysin (syp), early growth response 1 (egr1), doublecortin (dcx), beta III tubulin (tuj1), glial acidic fibrillary protein (gfap), SRY-Box 2 (sox2), and oligodendrocyte transcription factor 2 in young mice treated with recombinant human LTA4H protein or phosphate buffered saline (PBS) control.

Figure 10:
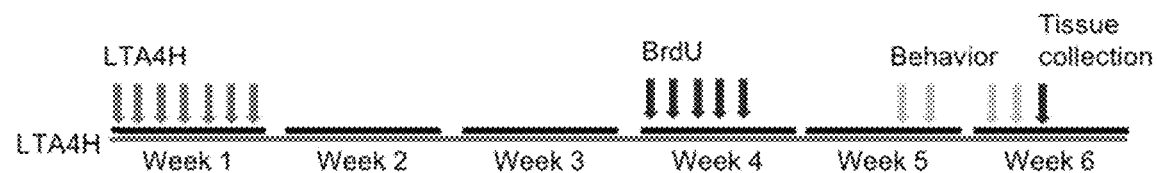

FIG. 10 depicts treatment paradigm 2 of LTA4H recombinant protein administered for 1 week at the start of the study (pulse) or continuously for 6 weeks, or phosphate buffered saline (PBS) in 8-week old (young) wild-type (C57BL/6) mice.

Figure 11A:
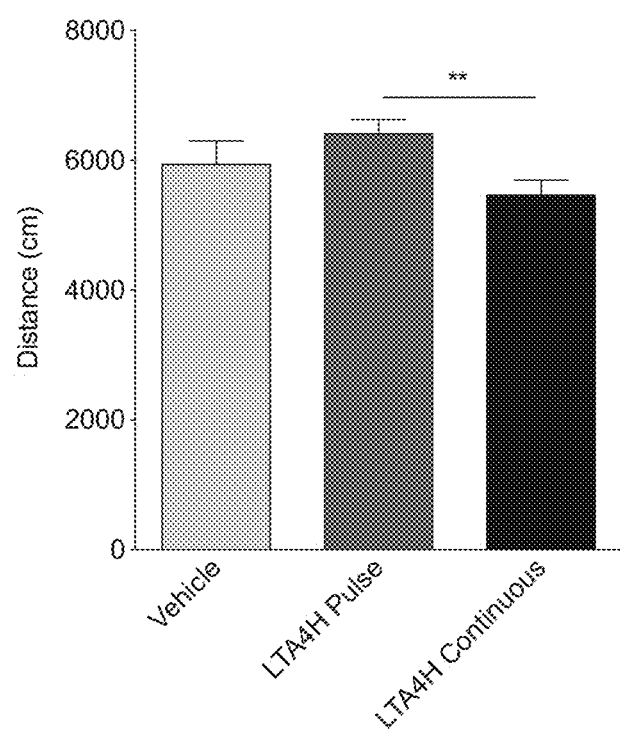

FIG. 11A reports the total distance travelled in an open field test in young mice treated with recombinant human LTA4H protein or phosphate buffered saline (PBS) control.

Figure 11B:
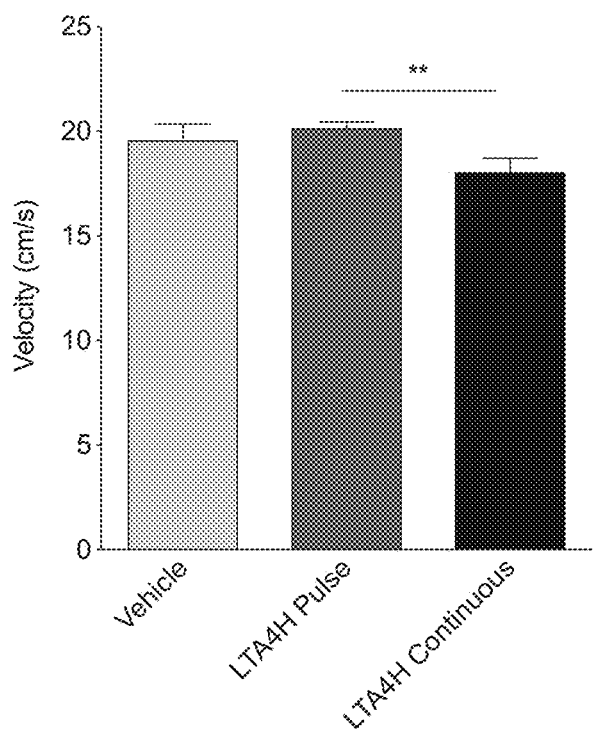

FIG. 11B reports the average velocity in an open field test in young mice treated with recombinant human LTA4H protein or phosphate buffered saline (PBS) control.

Figure 11C:
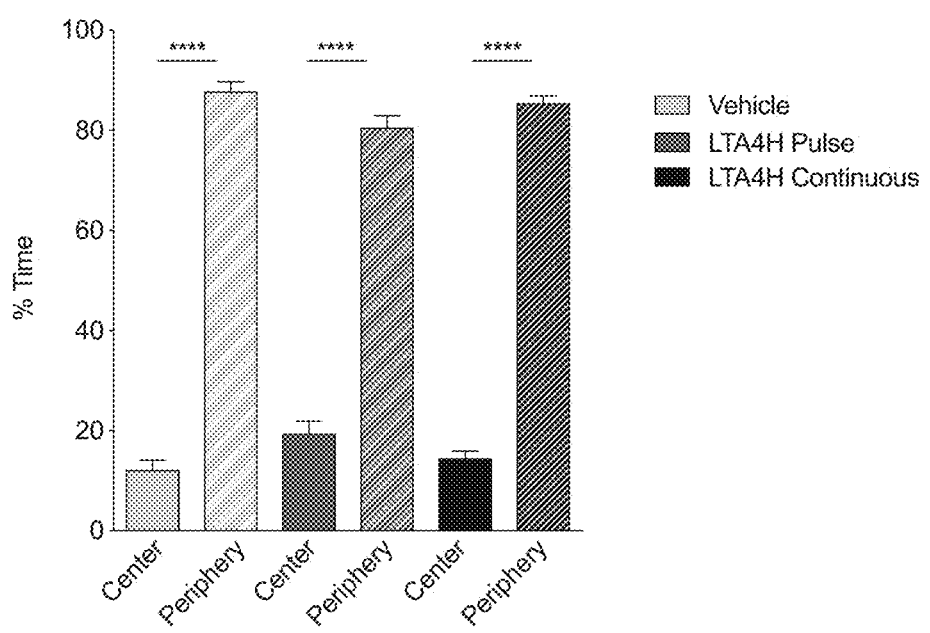

FIG. 11C reports the percent time spent in the periphery or center in an open field test in young mice treated with recombinant human LTA4H protein or phosphate buffered saline (PBS) control.

Figure 12A:
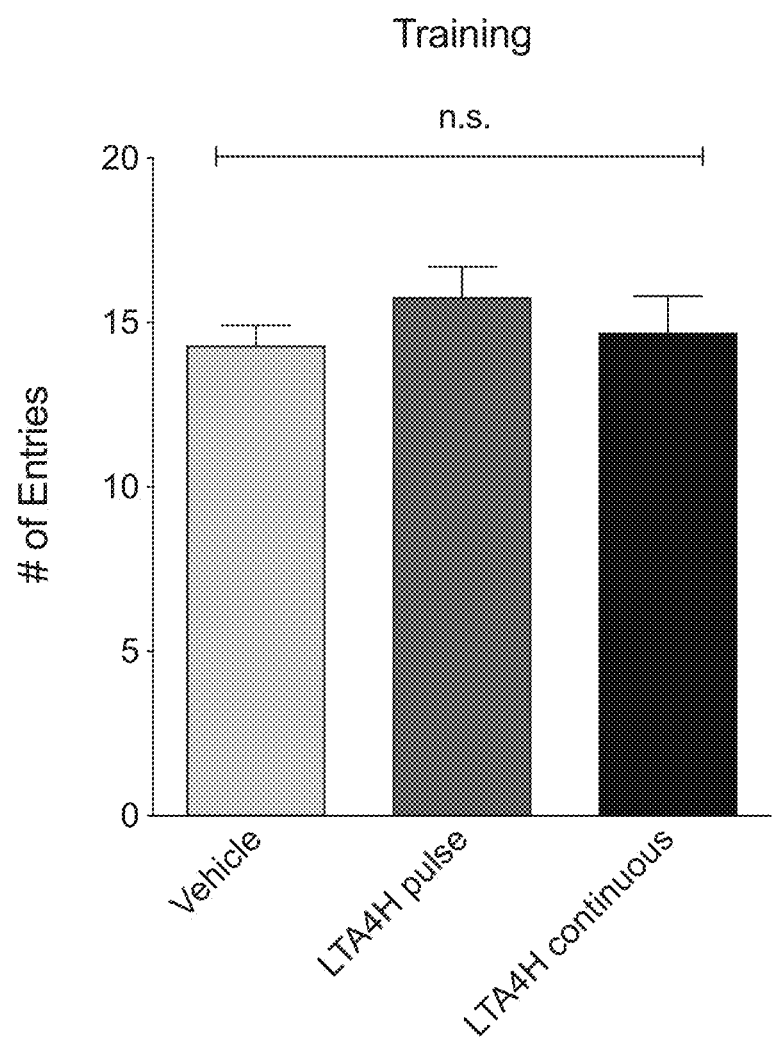

FIG. 12A reports the number entries made into the familiar arm during training of the Y-maze task of young mice treated with recombinant human LTA4H protein or phosphate buffered saline (PBS).

Figure 12B:
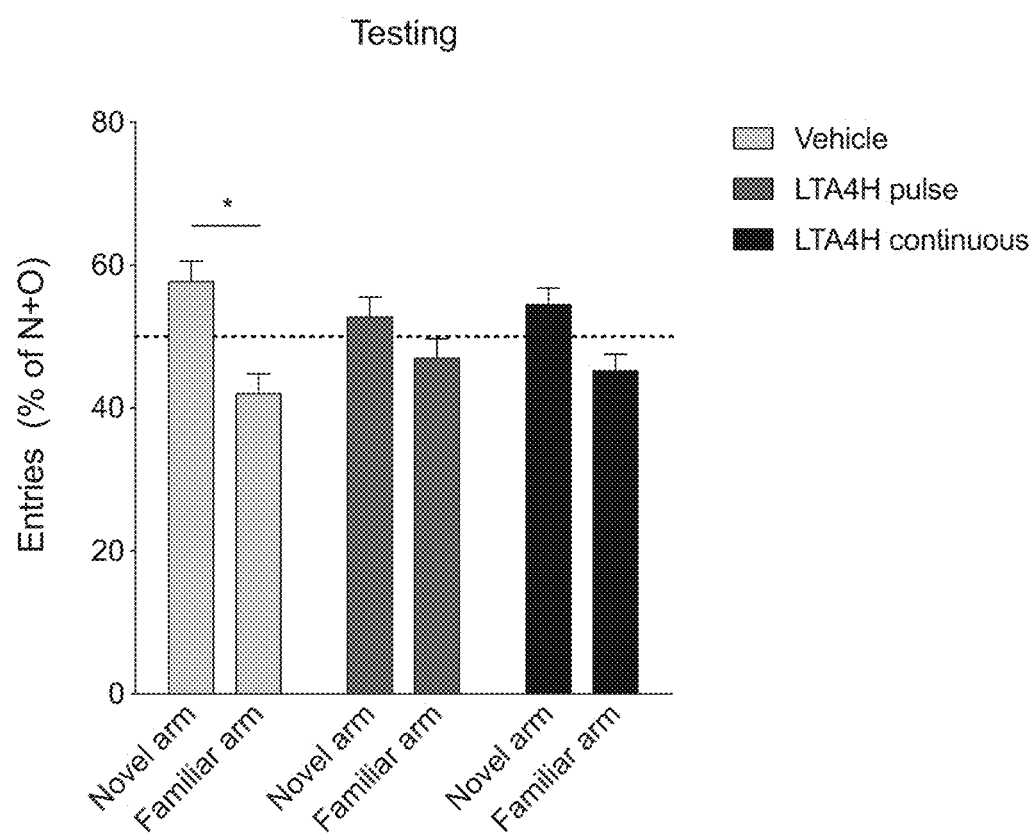

FIG. 12B reports the percentage of the number of entries into the novel and familiar arms of the Y-maze during testing in young mice treated with recombinant human LTA4H protein or phosphate buffered saline (PBS).

Figure 13:
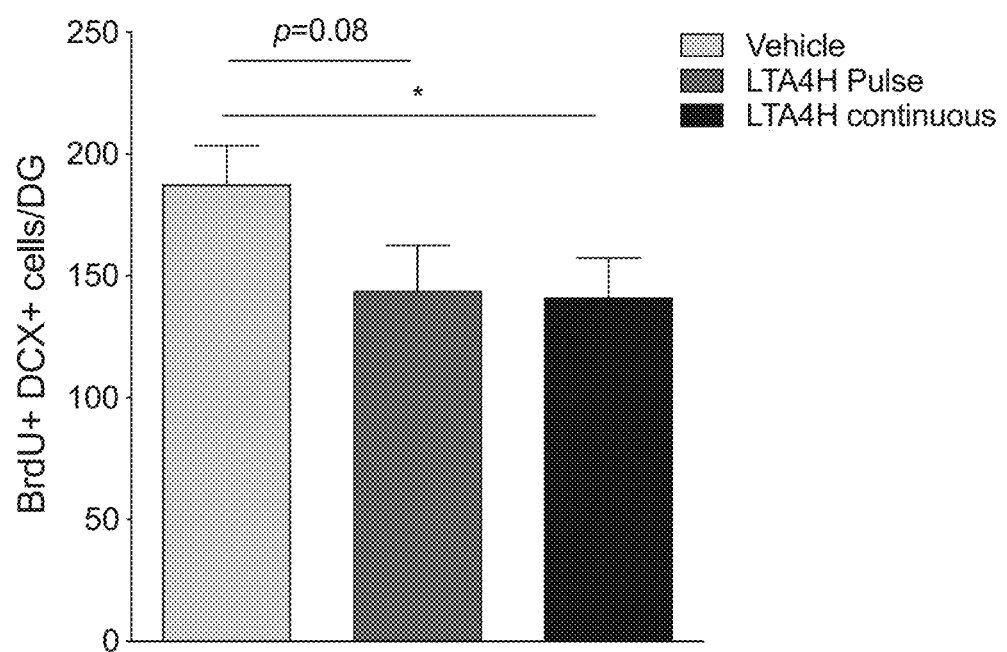

FIG. 13 reports the number of BrdU and DCX co-labeled cells within granule cell layer of the hippocampus in young mice treated with recombinant human LTA4H protein or phosphate buffered saline (PBS) control.

Figure 14:
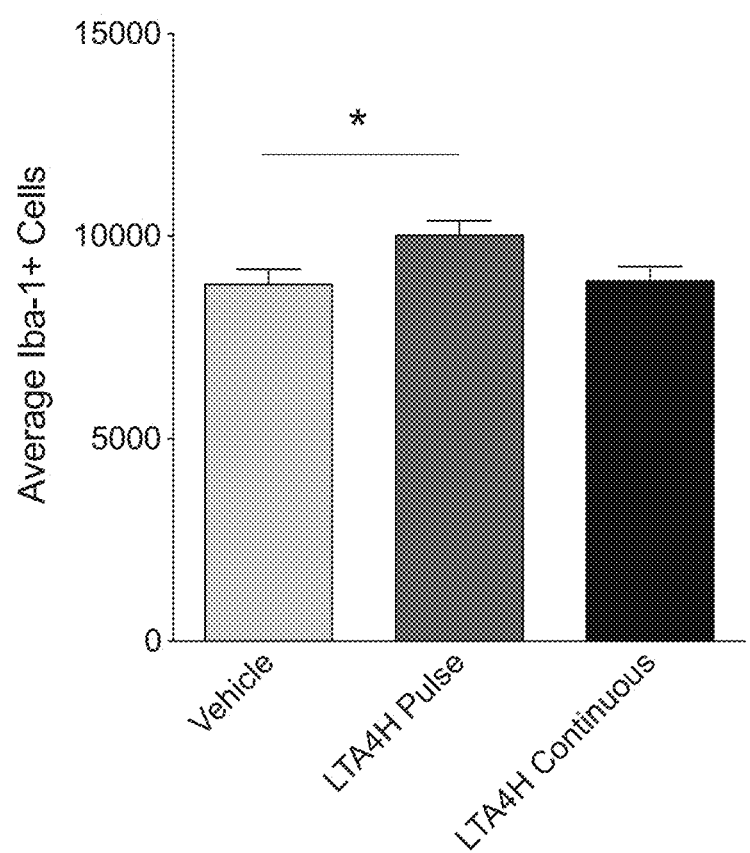

FIG. 14 reports the average number of Iba1-labeled microglia in the hippocampus in young mice treated with recombinant human LTA4H protein or phosphate buffered saline (PBS) control.

Figure 15:
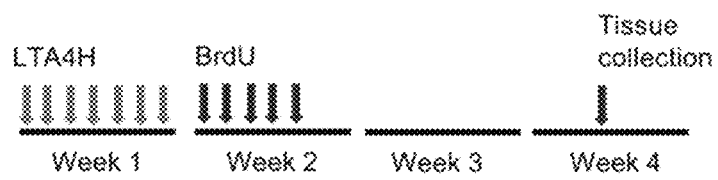

FIG. 15 depicts treatment paradigm 3 of LTA4H recombinant protein or phosphate buffered saline (PBS) administration in 8-week old (young) wild-type (C57BL/6) mice.

Figure 16:
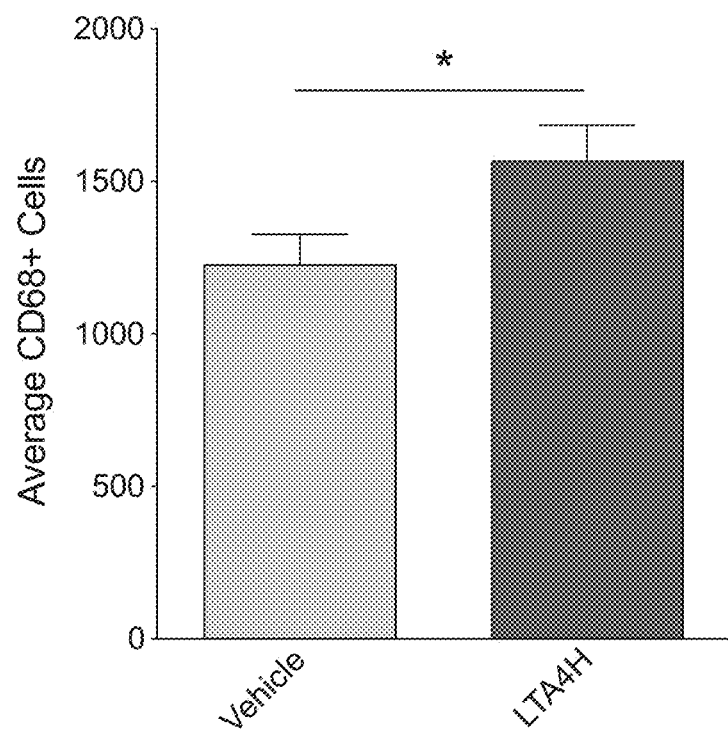

FIG. 16 reports the average number of CD68 puncta in the hippocampus in young mice treated with recombinant human LTA4H protein or phosphate buffered saline (PBS) control.

Figure 17A:
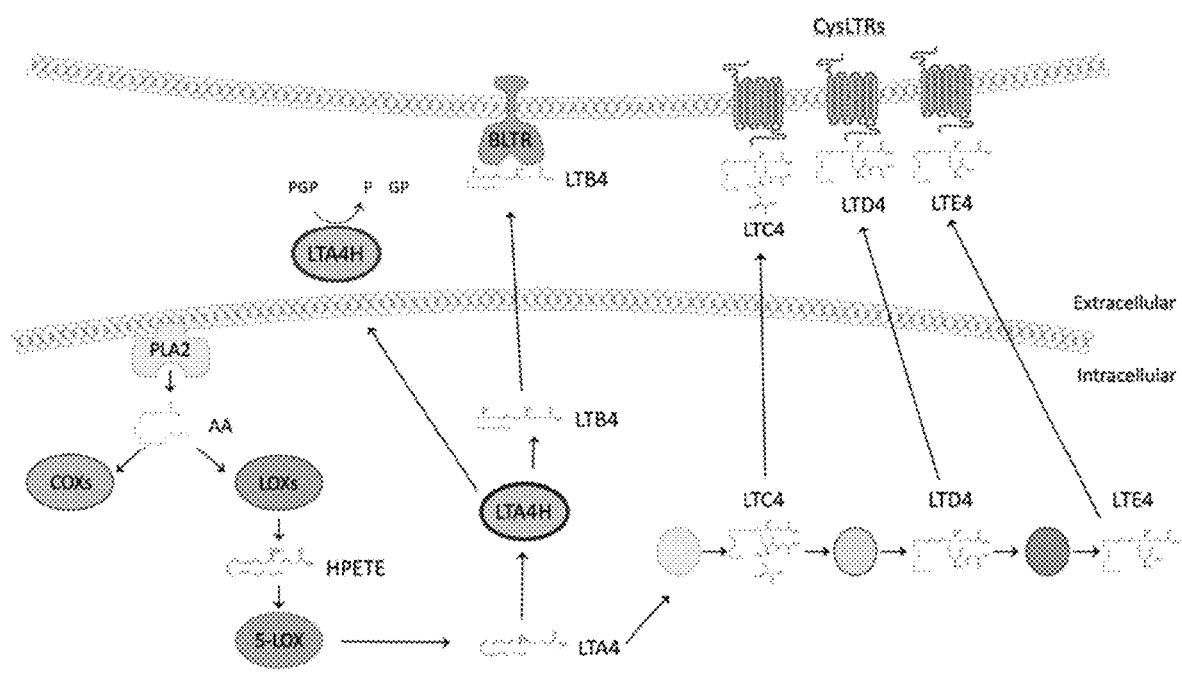

FIG. 17A displays a schematic of the LTA4H biochemical signaling pathway.

Figure 17B:
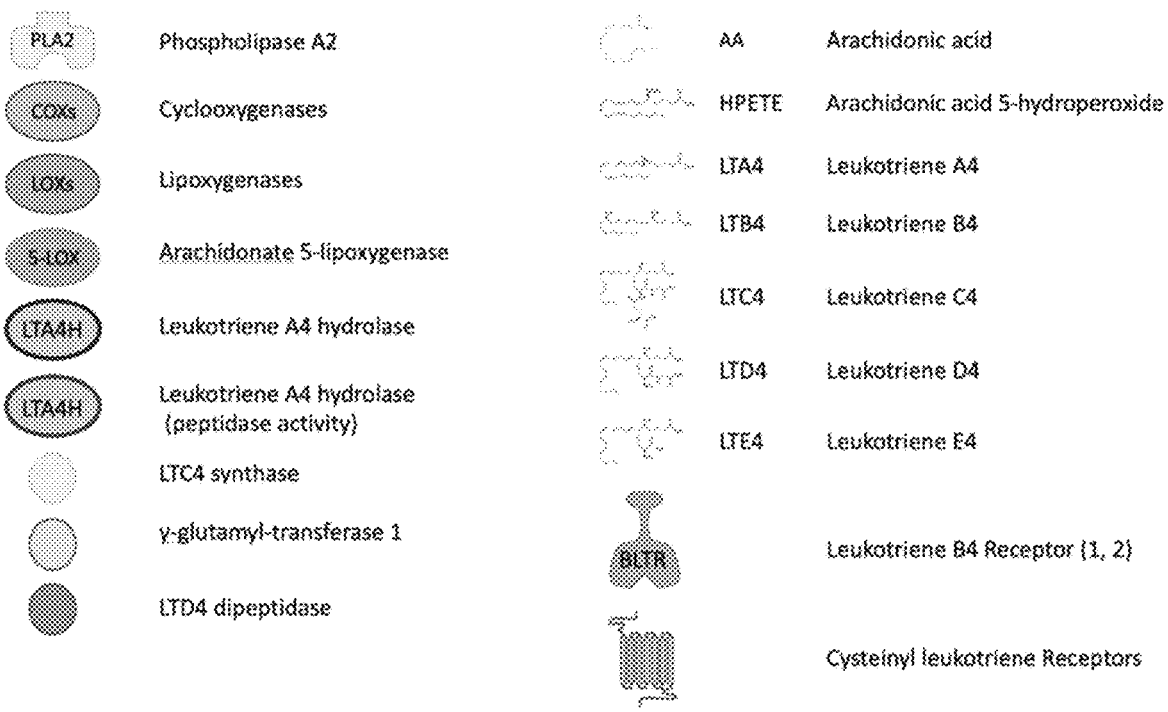

FIG. 17B displays a key to accompany the schematic in FIG. 17A.

Figure 18A:
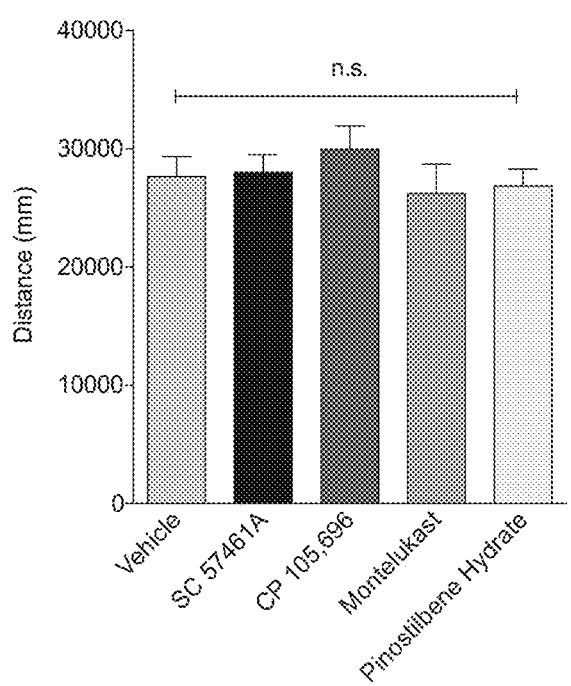

FIG. 18A reports the total distance travelled in an open field test in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 18B:
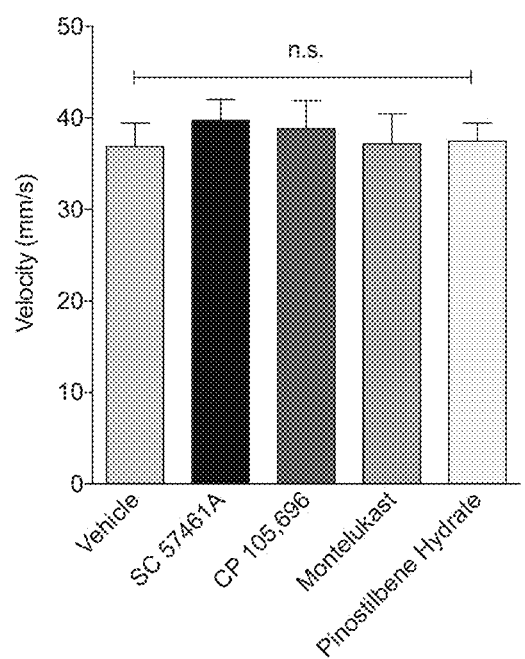

FIG. 18B reports the average velocity in an open field test in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 18C:
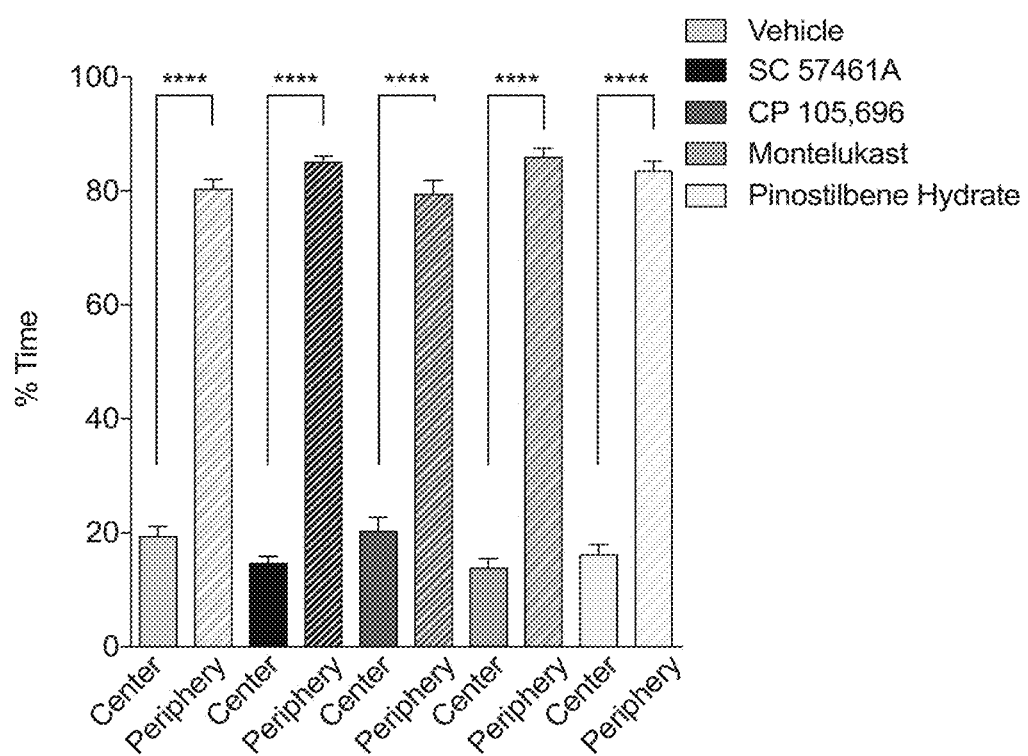

FIG. 18C reports the percent time spent in the periphery or center in an open field test in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19A:
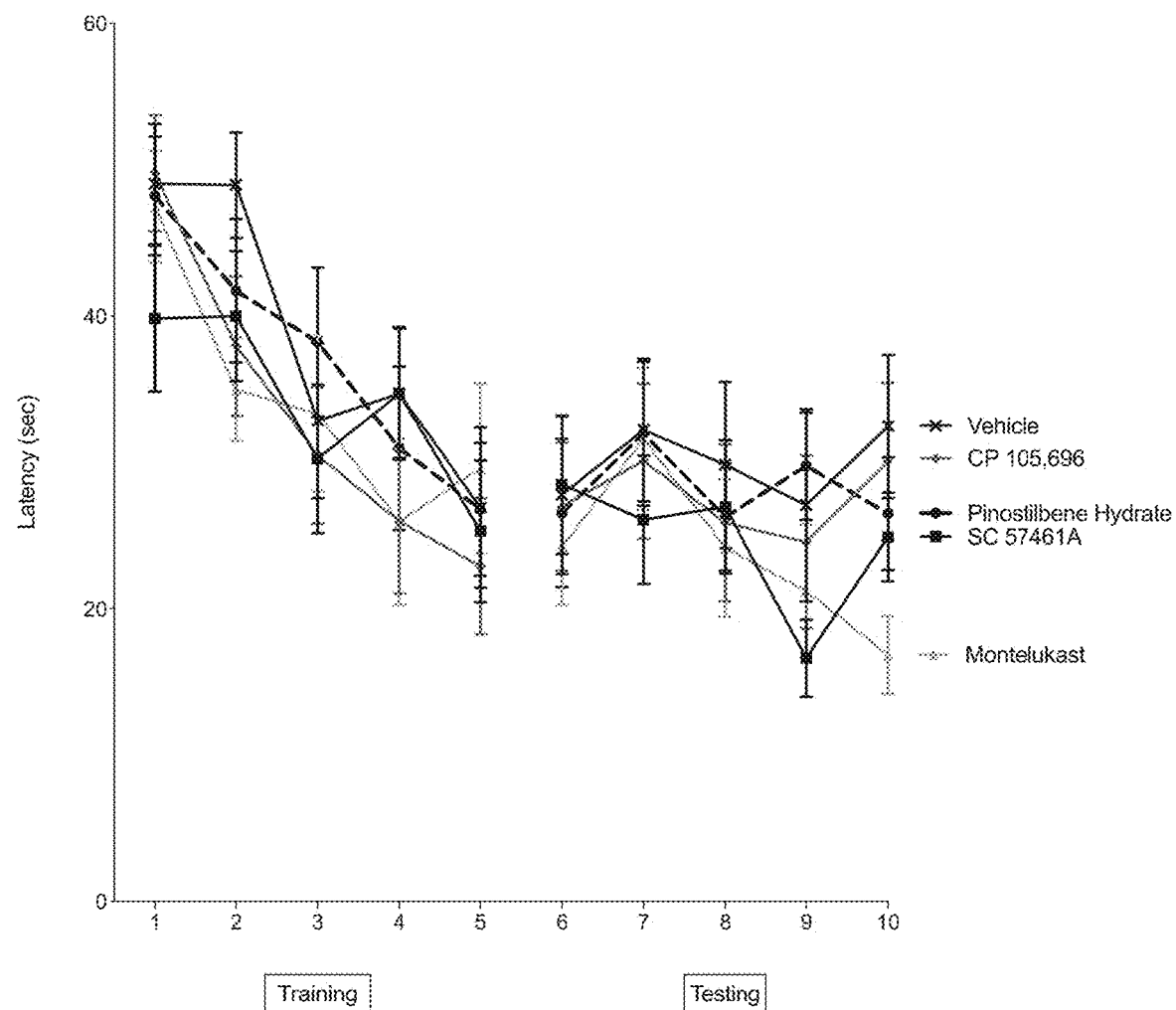

FIG. 19A reports the latency to find the platform in the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19B:
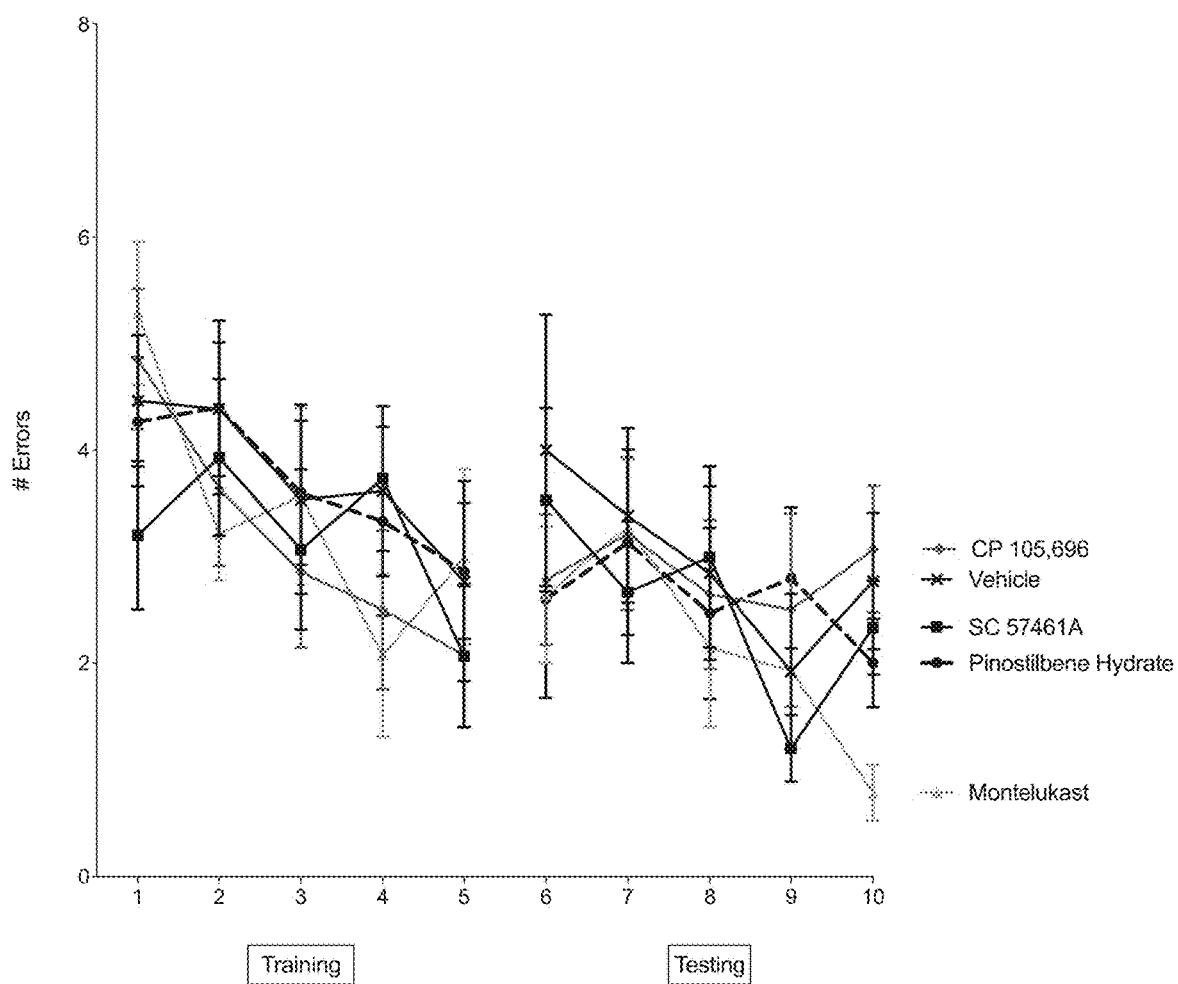

FIG. 19B reports the number of errors made in finding the platform in the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19C:
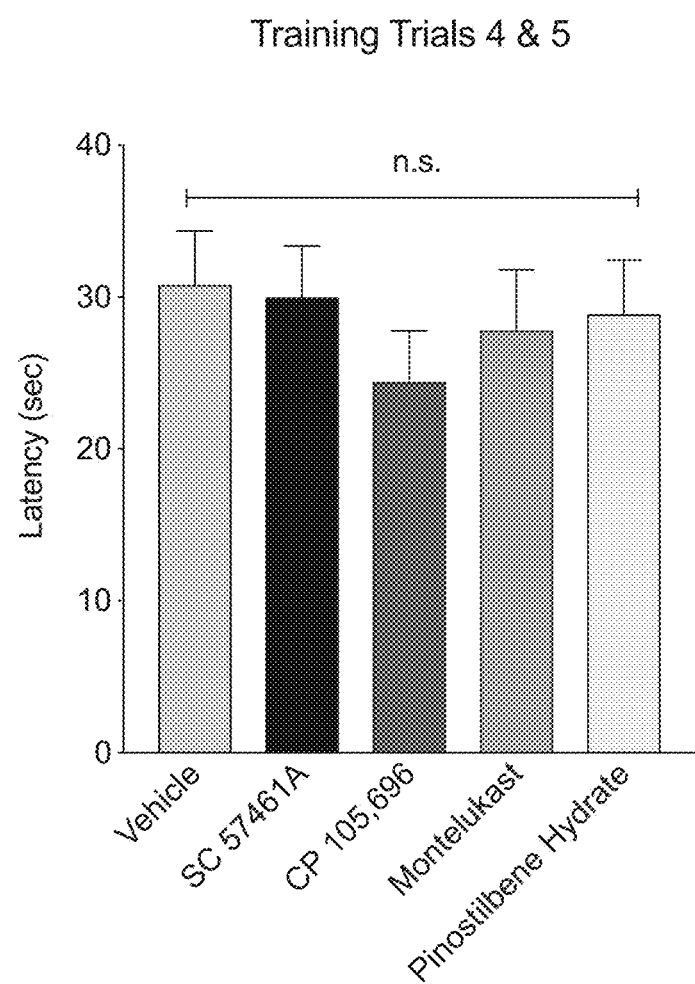

FIG. 19C reports the latency to find the platform in the last two trials of training of the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19D:
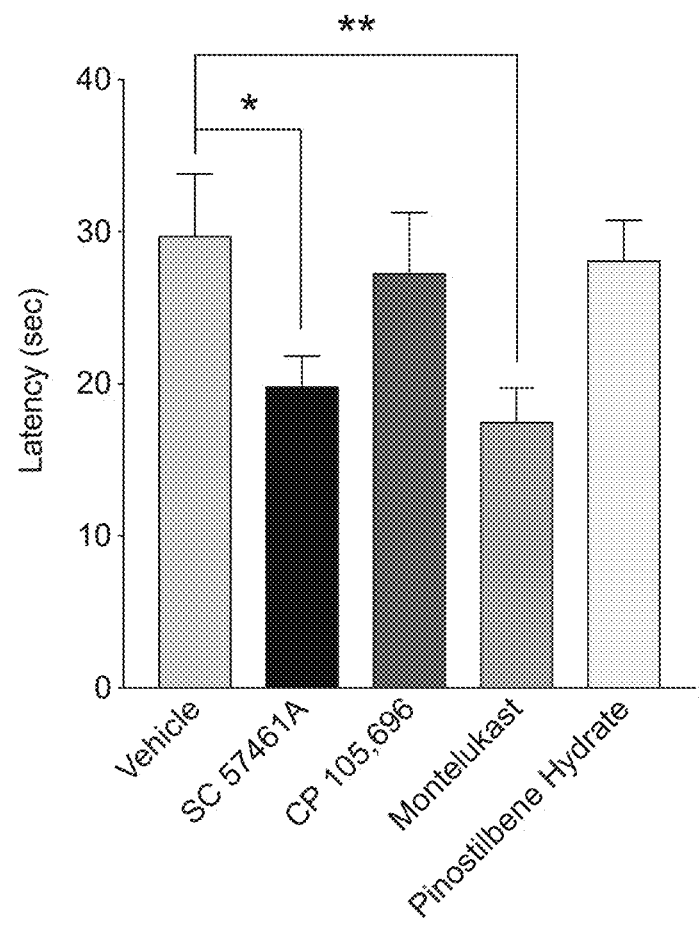

FIG. 19D reports the latency to find the platform in the last two trials of testing of the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19E:
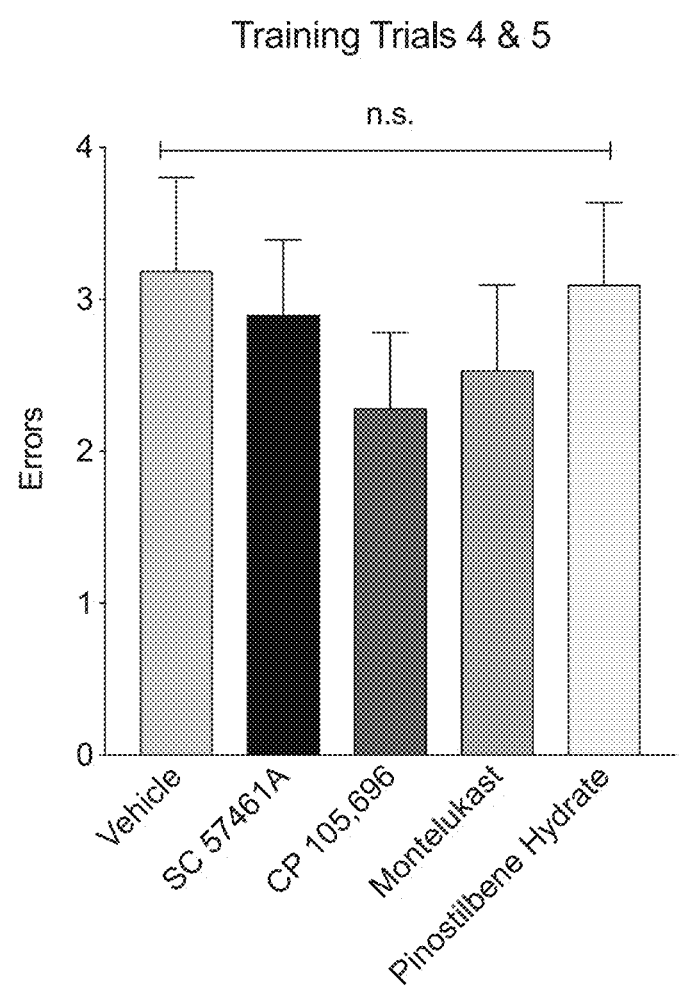

FIG. 19E reports the number of errors made in finding the platform in the last two trials of training of the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 19F:
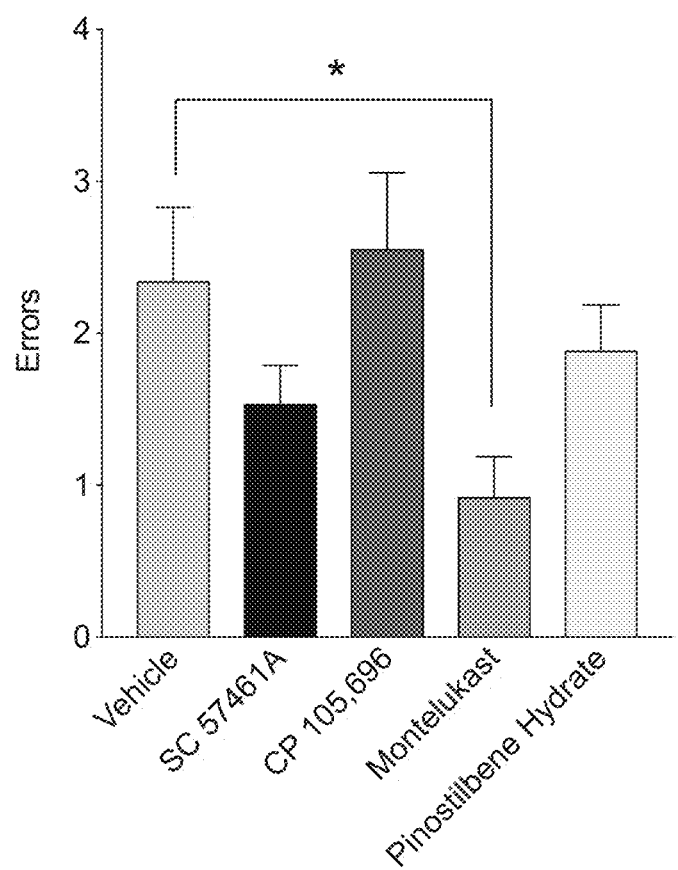

FIG. 19F reports the number of errors made in finding the platform in the last two trials of testing of the radial arm water maze in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 20A:
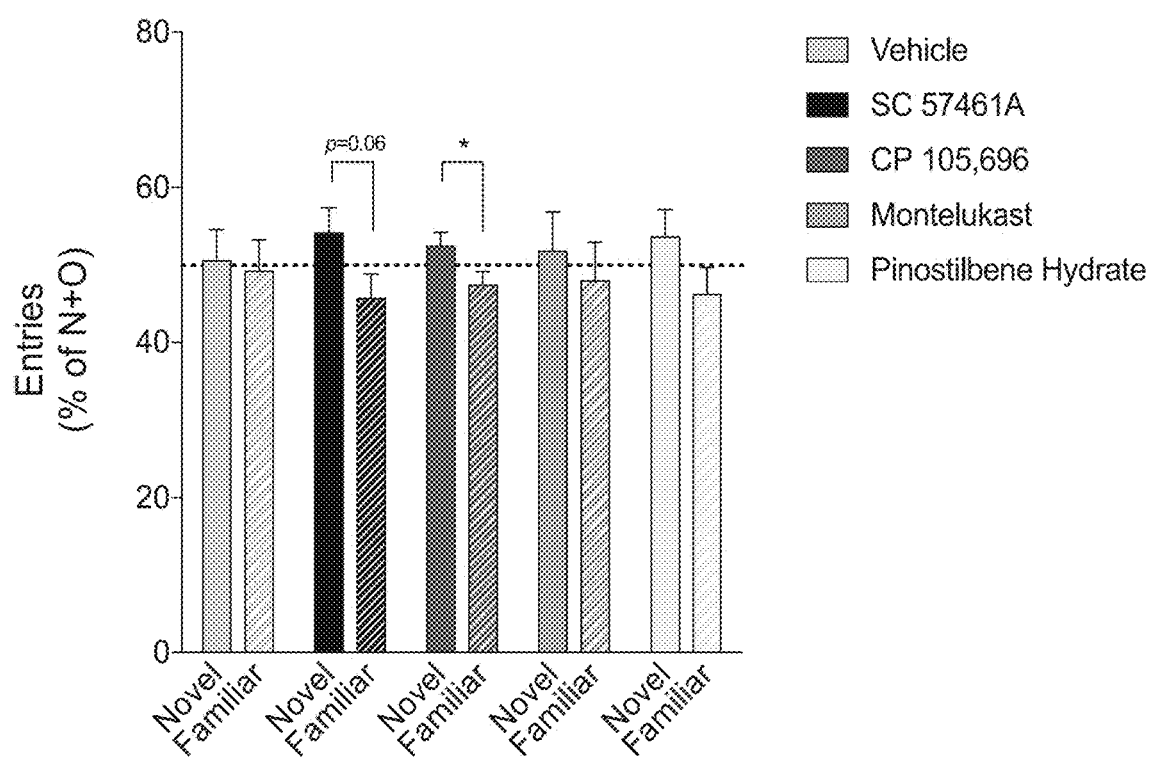

FIG. 20A reports the percentage of the number of entries into the novel and familiar arms of the Y-maze during testing in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 20B:
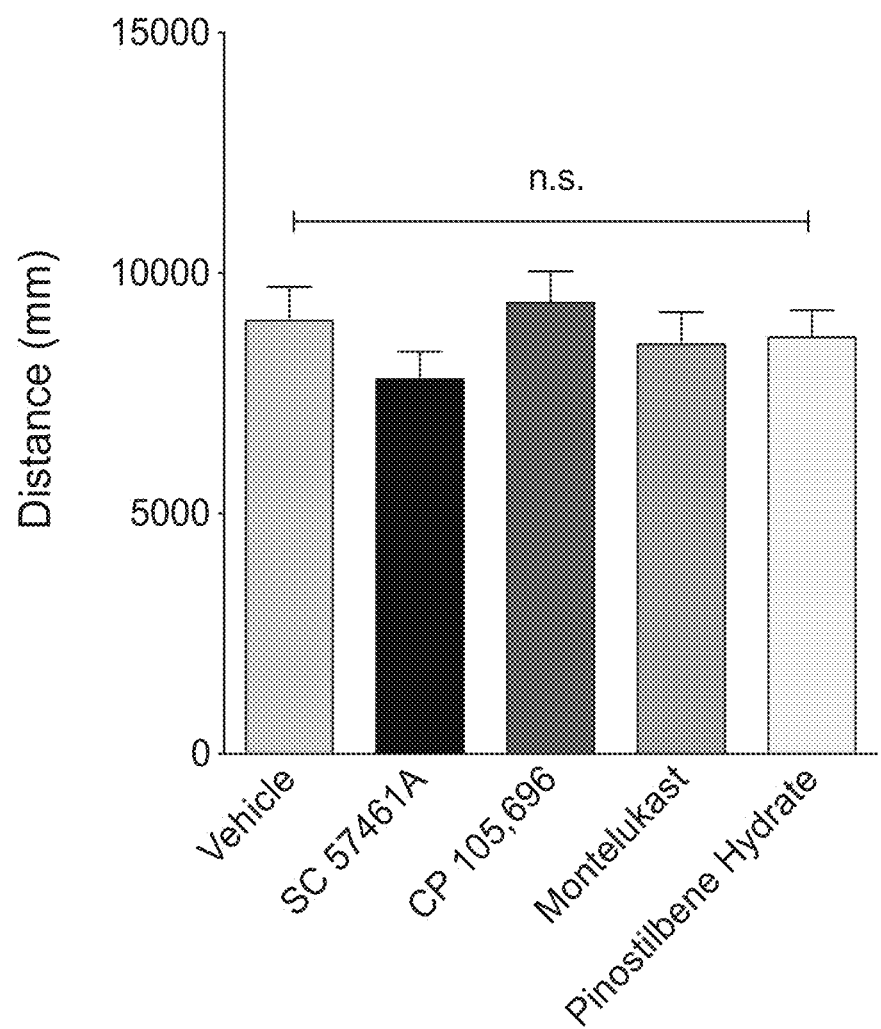

FIG. 20B reports the total distance traveled in the Y-maze during testing in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 21A:
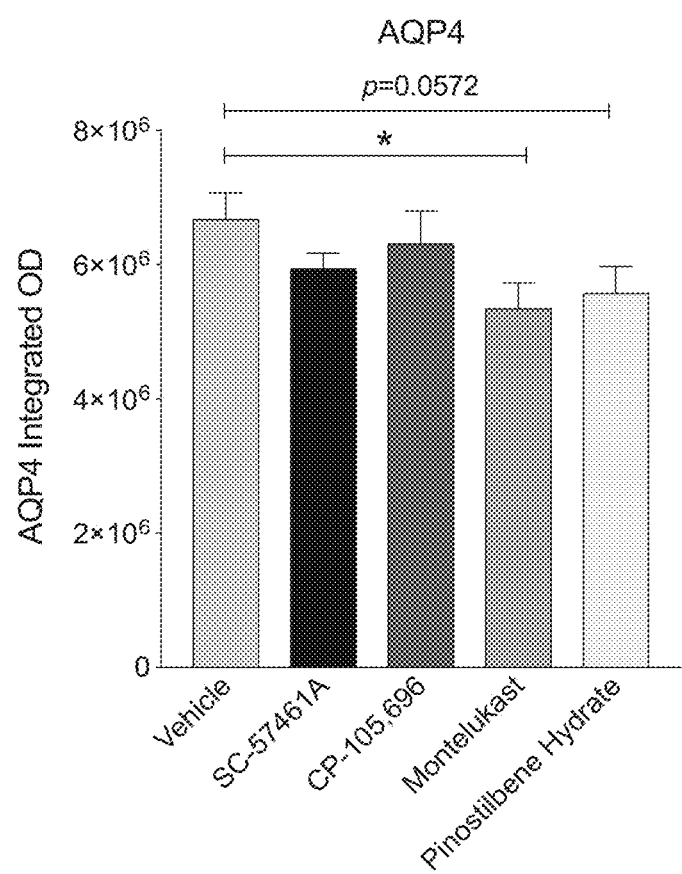

FIG. 21A reports the average integrated optical density of aquaporin-4 (AQP4) in the hippocampus of aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 21B:
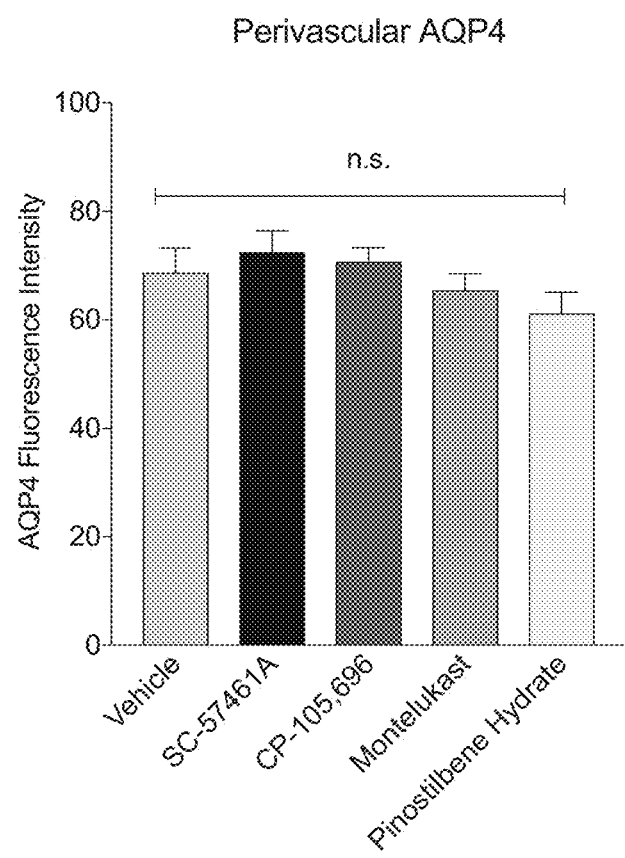

FIG. 21B reports the average fluorescence intensity of aquaporin-4 (AQP4) in the perivascular space in the hippocampus of aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 21C:
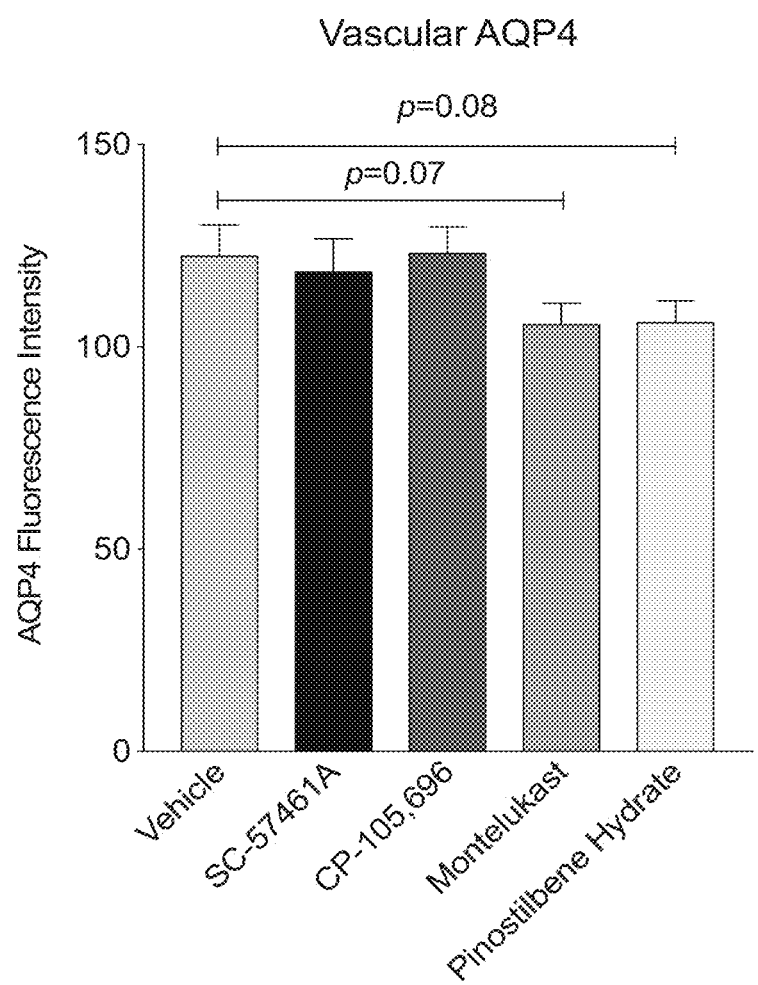

FIG. 21C reports the average fluorescence intensity of aquaporin-4 (AQP4) immediately surround blood vessels (vascular) of hippocampus of aged mice treated for one month with vehicle, the LTA4H hydrolase and peptidase inhibitor SC 57461A, the LTB4 receptor inhibitor CP 105, 696, the cysteinyl leukotriene receptor inhibitor Montelukast, and the LTA4H hydrolase inhibitor pinostilbene hydrate.

Figure 22:
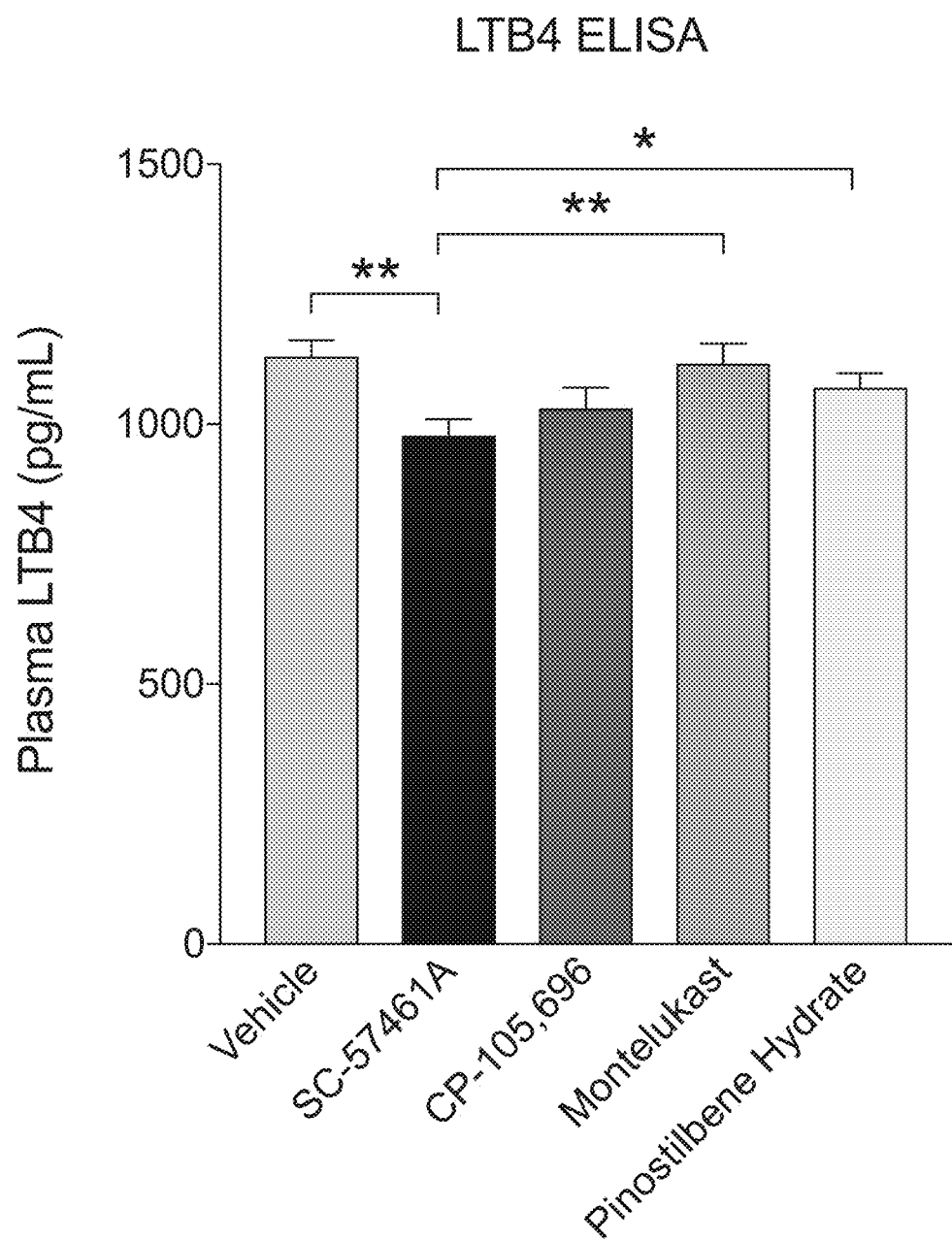

FIG. 22 reports the total plasma concentrations of LTB4 measured by ELISA in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

FIG. 23A-F reports the results of quantitative polymerase chain reaction (qPCR) quantifying mRNA levels of ionized calcium-binding adapter molecule 1 (Iba-1), interleukin 6 (IL-6), interleukin 1-beta (IL-1β), Eotaxin, nuclear factor kappa-light-chain-enhancer of activated B cells (NF-κB), and tumor necrosis factor alpha (TNFα) in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 24A:
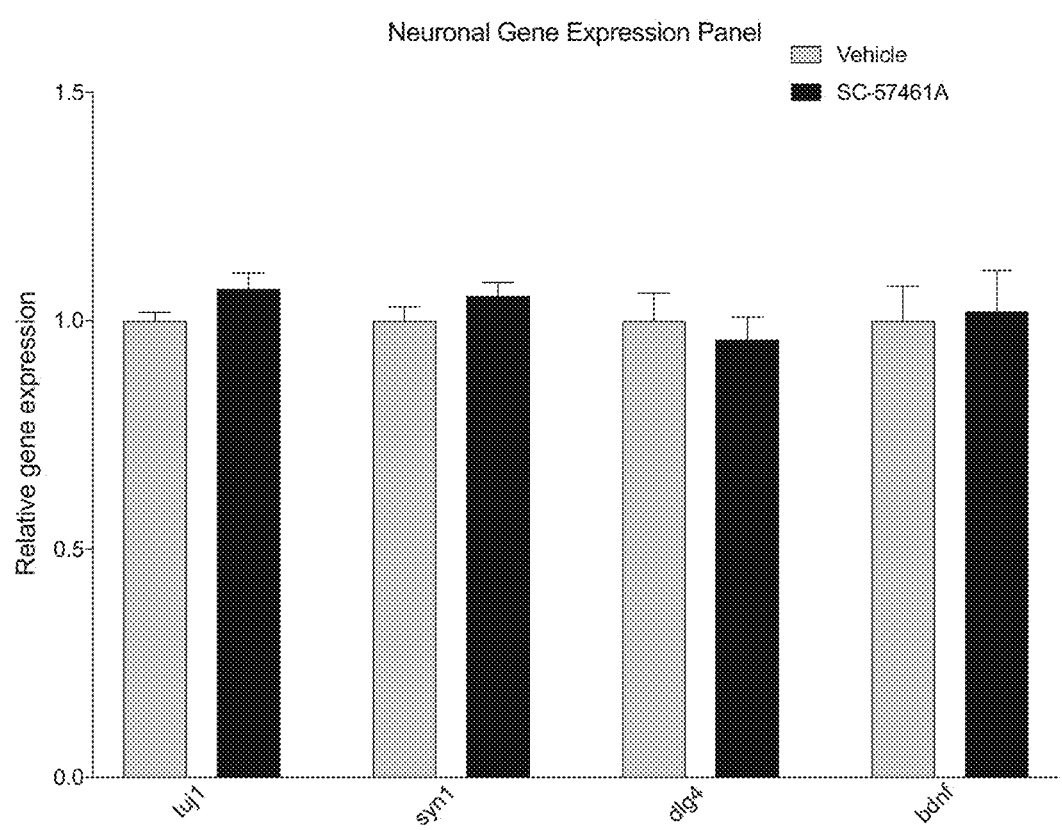

FIG. 24A reports the results of quantitative polymerase chain reaction (qPCR) quantifying mRNA levels of the neuronal genes tuj1, syn1, dlg4, and bdnf in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 24B:
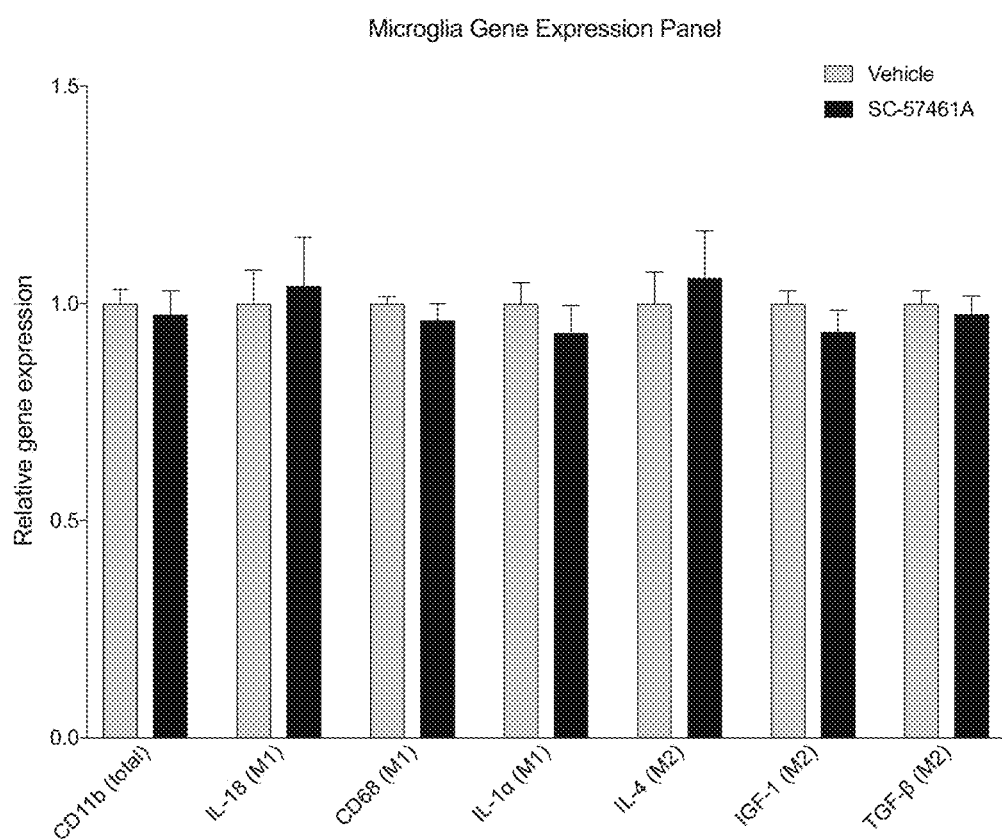

FIG. 24B reports the results of quantitative polymerase chain reaction (qPCR) quantifying mRNA levels of microglia genes, cluster of differentiation molecule 11 b (CD11b), interleukin 18 (IL-18), cluster of differentiation (CD68), interleukin 1α (IL-1α), interleukin 4 (IL-4), insulin-like growth factor 1 (IGF-1), and transforming growth factor β (TGFβ) in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 24C:
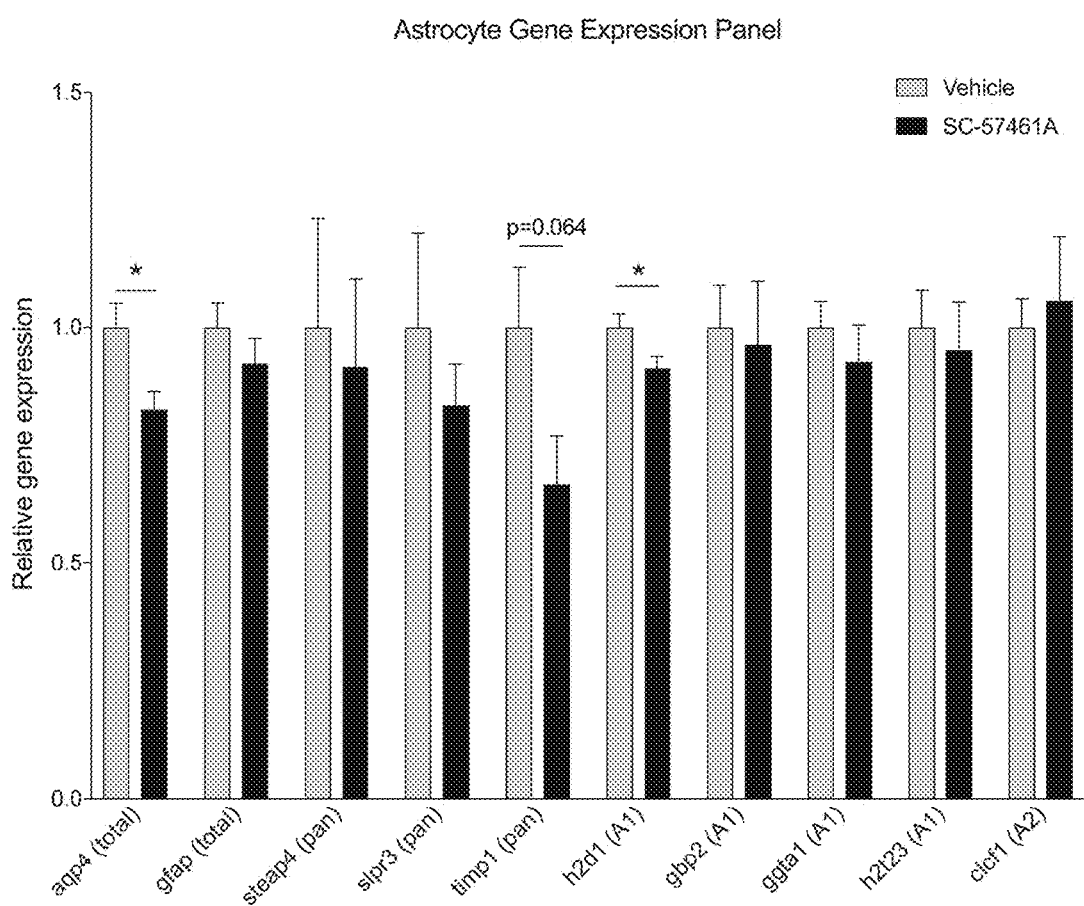

FIG. 24C reports the results of quantitative polymerase chain reaction (qPCR) quantifying mRNA levels astrocytic genes, aquaporin 4 (aqp4), glial acidic fibrillary protein (gfap), six transmembrane epithelial antigen of prostate 4 (steap4), sphingosine-1-phosphate receptor 1 (slpr3), tissue inhibitor of metalloproteinases (timp1), H2 class I histocompatibility antigen (h2d1), guanylate-binding protein 2 (gbp2), N-acetyllactosaminide alpha-1 3-galactosyltransferase (ggta1), H2T23 protein (h2t23), and cardiotrophin-like cytokine factor 1 (cicf1) in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

Figure 24D:
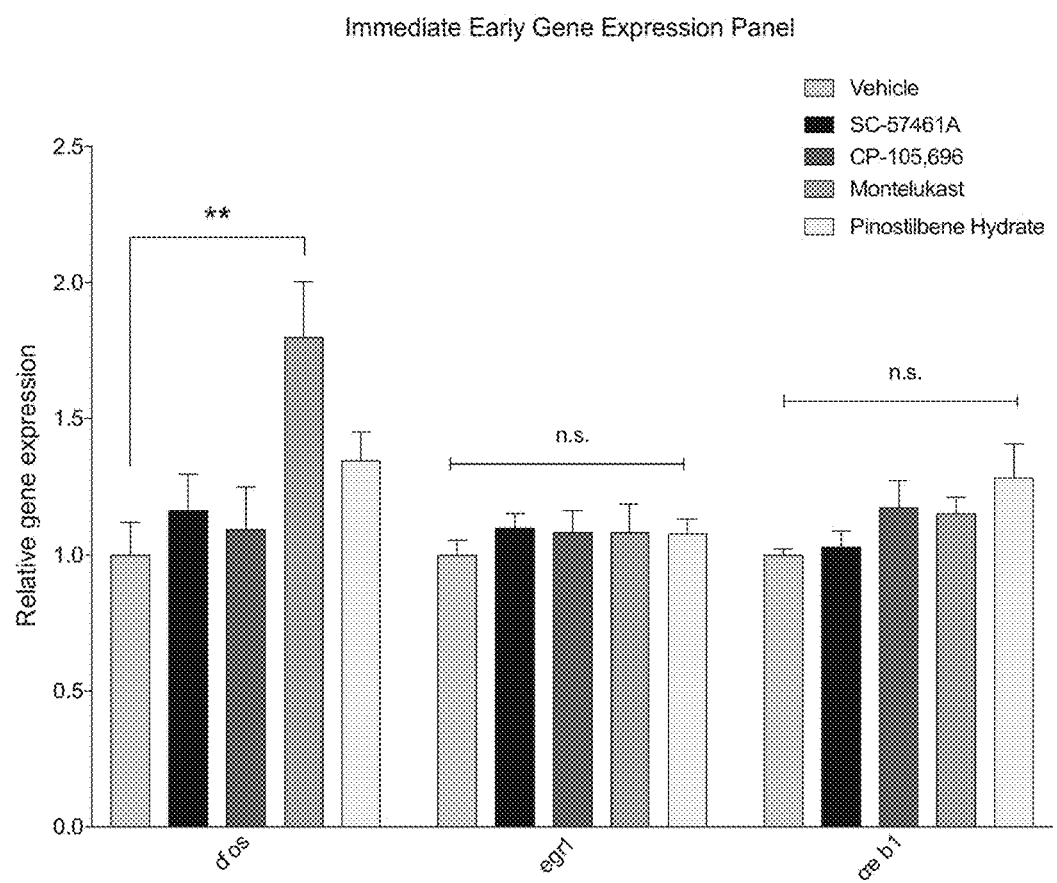

FIG. 24D reports the results of quantitative polymerase chain reaction (qPCR) quantifying mRNA levels of immediate early genes, cfos, egr1, and creb1 in aged mice treated for one month with vehicle, the LTA4H hydrolase and peptidase inhibitor SC 57461A, the LTB4 receptor inhibitor CP 105,696, the cysteinyl leukotriene receptor inhibitor Montelukast, and the LTA4H hydrolase inhibitor pinostilbene hydrate.

VI. DETAILED DESCRIPTION

A. Introduction

The present invention relates to the identification and discovery of methods and compositions for the treatment and/or prevention of cognitive and motor impairment, including age-associated dementia, decline in motor skills, neuroinflammation, and neurodegenerative disease. Described herein are methods and compositions for the treatment of subjects suffering from such disorders, which are aspects of the present invention. The methods and compositions described herein are useful in: preventing or treating cognitive or motor impairment, age-associated dementia or motor impairment, neuroinflammation, and neurodegenerative disease; ameliorating the symptoms of cognitive or motor impairment, age-associated dementia or motor impairment, neuroinflammation, and neurodegenerative disease; slowing progression of aging-associated cognitive or motor impairment, age-associated dementia or motor impairment, neuroinflammation, and neurodegenerative disease; and/or reversing the progression of aging-associated cognitive or motor impairment, age-associated dementia or motor impairment, neuroinflammation, and neurodegenerative disease. An implementation of the invention includes using the LTA4H modulatory agent(s) as treatment. An embodiment of the invention includes the LTA4H modulatory agent(s). Another embodiment of the invention includes using an LTA4H modulating agent which selectively inhibits the epoxide hydrolase activity of the LTA4H enzyme. Another embodiment of the invention includes using an LTA4H modulating agent which inhibits both the epoxide hydrolase activity and the aminopeptidase activity of the LTA4H enzyme. Another embodiment of the invention includes one or more LTA4H modulating agent(s) that bind to the epoxide hydrolase and/or aminopeptidase active site(s).

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

B. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

By "an individual suffering from or at risk of suffering from an aging-associated impairment" is meant an individual that is about more than 50% through its expected lifespan, such as more than 60%, e.g., more than 70%, such as more than 75%, 80%, 85%, 90%, 95% or even 99% through its expected lifespan. The age of the individual will depend on the species in question. Thus, this percentage is based on the predicted life-expectancy of the species in question. For example, in humans, such an individual is 50 year old or older, e.g., 60 years old or older, 70 years old or older, 80 years old or older, 90 years old or older, and usually no older than 100 years old, such as 90 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old or older, or any age between 50-1000, that suffers from an aging-associated condition as further described below, e.g., cognitive or motor impairment associated with the natural aging process; an individual that is about 50 years old or older, e.g., 60 years old or older, 70 years old or older, 80 years old or older, 90 years old or older, and usually no older than 100 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old, that has not yet begun to show symptoms of an aging-associated condition e.g., cognitive or motor impairment; an individual of any age that is suffering from a cognitive or motor impairment due to an aging-associated disease, as described further below, and an individual of any age that has been diagnosed with an aging-associated disease that is typically accompanied by cognitive or motor impairment, where the individual has not yet begun to show symptoms of cognitive or motor impairment. The corresponding ages for non-human subjects are known and are intended to apply herein.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc. The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease. In another embodiment of the invention, "treatment" refers to reducing local tissue or blood levels of neutrophils to a more homeostatic state, i.e. to levels observed in a healthy individual of the same or similar age.

In some embodiments, the aging-associated condition that is treated is an aging-associated impairment in cognitive ability in an individual. By cognitive ability, or "cognition," it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

In some embodiments, the aging-associated condition that is treated is an aging-associated impairment in motor ability in an individual. By motor ability, it is meant the motor processes that include the ability to perform complex muscle-and-nerve actions that produce movement such as fine motor skills producing small or precise movements (e.g. writing, tying shoes) and gross motor skills for large movements (e g walking, running, kicking). By "motor decline", it is meant a progressive decrease in one or more of these abilities, e.g., a decline in find movement or gross motor skills, etc. By "motor impaired" and "motor impairment", it is meant a reduction in motor ability/skills relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated motor impairment," it is meant an impairment or decline in motor ability that is typically associated with aging, including, for example, motor impairment associated with the natural aging process and motor impairment or decline associated with an aging-associated disorder, that is, a disorder that is seen with increasing frequency with increasing senescence, e.g., a neurodegenerative condition such as Parkinson's disease, amyotrophic lateral sclerosis, and the like.

In some embodiments, the aging-associated condition that is treated is an aging-associated increase in neuroinflammation in an individual. By "neuroinflammation" it is meant biochemical and cellular responses of the nervous system to injury, infection, or neurodegenerative diseases. Such responses are directed at decreasing the triggering factors by involving central nervous system immunity to defend against potential harm. Neurodegeneration occurs in the central nervous system and exhibits hallmarks of loss of neuronal structure and function. Neuroinflammatory diseases or neuroinflammatory-associated conditions or diseases, includes by way of example and not limitation, neurodegenerative diseases such as Alzheimer's disease; Parkinson's disease, multiple sclerosis and the like.

C. Treatment

Aspects of the methods of the inventions described herein include treatment of a subject with an LTA4H modulatory agent, e.g., as described above. An embodiment includes treatment of a human subject with an LTA4H modulatory agent. One of skill in the art would recognize that methods of treatment of subjects with LTA4H modulatory agents are recognized in the art. By way of example, and not limitation, one embodiment of the methods of the inventions described herein is comprised of administering an LTA4H modulatory agent to a subject for treatment and/or prevention of cognitive impairment and/or age-related dementia. The LTA4H modulatory agent may be administered through one or more routes such as IP, IV, PO, and the like. Additionally, the LTA4H modulatory agent may be administered one or more time per day, such as once per day, twice per day, thrice per day, four time per day, etc., and such doses may be administered chronically (e.g. greater that one month, greater than two months, greater than 3 to five months, greater than six months, greater than one year, etc.), or acutely for a shorter time span (e.g. shorter than one month).

Aspects of the methods described herein include use of LTA4H modulatory agents. Any convenient LTA4H modulatory agent may find use in the disclosed methods. In some instances, the LTA4H modulatory agent is a small molecule. Naturally occurring or synthetic small molecule compounds of interest include numerous chemical classes, such as organic molecules, e.g., small organic compounds having a molecular weight of more than 50 and less than about 2,500 daltons. The compounds can include functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. In some embodiments, the LTA4H modulatory agent may be a small organic molecule that selectively binds to the LTA4H enzyme and reduces (i.e. antagonizes) one or more of its activities including, for example, its epoxide hydrolase activity and/or its aminopeptidase activity. In some cases, the LTA4H modulatory agent may be a small organic molecule that selectively binds to the LTA4H enzyme and augments (i.e. acts an agonist) one or more of its activities including, for example, its epoxide hydrolase activity and/or its aminopeptidase activity. In some embodiments, the LTA4H modulatory agent is a selective or competitive inhibitor of LTA4H. The LTA4H modulatory agent can also be a pharmaceutically acceptable salt thereof of a LTA4H inhibitor.

In certain embodiments, the small molecule LTA4H modulatory agent is a peptide or a peptidomimetic compound. In certain embodiments, the peptide or peptidomimetic compound comprises one or more of leucine, proline, valine, norvaline, isoleucine, norleucine, methionine and arginine. In certain embodiments, the LTA4H modulatory agent is a peptidomimetic derivative comprising a hydroxamic acid group. In certain embodiments, the LTA4H modulatory agent is a heterocyclic compound. Non-limiting examples of heterocyclic compounds include a piperadine derivative, a piperazine derivative, an oxazole derivative, a thiozole derivative, an imidazole derivative, a pyridine derivative, a pyrimidine derivative, a benzoxazole derivative, a benzothiazole derivative, a benzoimidazole derivative, a thiazolopyridine derivative, a thiazolopyrazine derivative, a diazabicyclo[2.2.1]heptane derivative, a benzodioxane derivative, and an arylpyrazole derivative. In certain embodiments, the LTA4H modulatory agent is an aryl compound. In some cases, the aryl compound is a stilbenoid derivative (e.g., a resveratrol derivative). In some cases, the LTA4H modulatory agent is an aryl or biaryl substituted heterocycle derivative. In will be understood that any convenient small molecule LTA4H modulatory agent may find use in the subject methods.

In certain embodiments, the LTA4H modulatory compound is a peptide derivative. In certain embodiments the LTA4H modulatory agent is described by the formula (I):

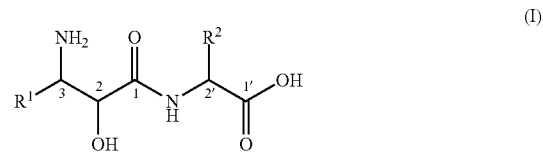

(I)

where:

R¹ is selected from alkyl, substituted alkyl, cycloalkanoalkyl, phenyl, substituted phenyl, benzyl, substituted benzyl; and R² is selected from hydrogen, alkyl, substituted alkyl, hydroxylalkyl, mercaptoalkyl, carboxyamidoalkyl, alkoxyalkyl, alkylmercaptoalkyl, carboxylalkyl, aryl, substituted aryl, aralkyl, substituted aralkyl, amidinealkyl, substituted amidinealkyl, or a pharmaceutically acceptable salt, or solvate thereof.

In some embodiments, R¹ is a benzyl group or a substituted benzyl group and R² is an isobutyl group. In certain embodiments, R¹ a benzyl group, or a substituted benzyl group and R² is —CH₂CH₂CH₂NHC(═NH)NH₂. In certain cases, the compound of formula (I) is a racemate. In certain cases, the compound of formula (I) is an enantiomer thereof. In certain cases, the configuration of the compound is (2S,3R,2'R), (2S,3S,2'S) or (2S,3S,2'R).

In certain embodiments, the compound of formula (I) is selected from (2S,3R)-3-amino-2-hydroxy-4-phenylbutanoyl-(R)-leucine, (2S,3S)-3-amino-2-hydroxy-4-phenylbutanoyl-(R)-leucine, (2S,3R)-3-amino-2-hydroxy-4-p-nitrophenylbutanoyl-(S)-leucine, (2S,3R)-3-amino-2-hydroxy-4-phenylbutanoyl-(R)-valine, (2S,3R)-3-amino-2-hydroxy-4-phenylbutanoyl-(S)-norvaline, (2S,3R)-3-amino-2-hydroxy-4-phenylbutanoyl-(S)-methionine, (2S,3R)-3-amino-2-hydroxy-4-phenylbutanoyl-(S)-isoleucine, (2S, 3R)-3-amino-2-hydroxy-4-phenylbutanoyl-(R)-norleucine, (2RS,3RS)-3-amino-2-hydroxy-4-p-chlorophenylbutanoyl-(S)-leucine, (2RS,3RS)-3-amino-2-hydroxy-4-o-chlorophenylbutanoyl-(S)-leucine, (2RS,3RS)-3-amino-2-hydroxy-4-p-methylphenylbutanoyl-(S)-leucine, (2S,3R)-3-amino-2-hydroxy-4-p-aminophenylbutanoyl-(S)-leucine, (2RS,3RS)-3-amino-2-hydroxy-4-hydroxyphenylbutanoyl-(S)-leucine, (2S,3R)-3-amino-2-hydroxy-4-p-hydroxyphenylbutanoyl-(S)-leucine.

In certain embodiments, the compound of formula (I) is selected from (2S,3R)-3-amino-2-hydroxyl-4-phenylbutanoyl-(S)-arginine, (2S,3R)-3-amino-2-hydroxy-4-p-hydroxyphenyl-butanoyl-(S)-arginine, (2RS,3RS)-3-amino-2-hydroxy-4-p-methylphenyl-butanoyl-(S)-arginine.

In certain embodiments, the compound of formula (I) is the compound know as ubenimex (bestatin), which has the following structure:

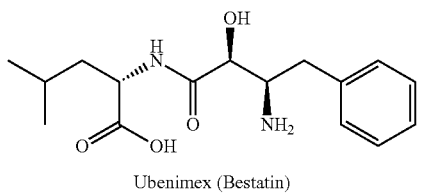 [SMILES: CC(C)C[C@H](NC(=O)[C@@H](O)[C@H](N)Cc1ccccc1)C(=O)O]

Ubenimex (Bestatin)

Ubenimex analogs and derivatives useful in the methods of the invention include LTA4H inhibitor compounds described in U.S. Pat. Nos. 4,185,156; 4,189,604; 4,370,318; and 4,474,764, and G.B. Pat. Nos. 1,510,477, 1,510,323, each of which is incorporated herein by reference.

In certain embodiments, the LTA4H modulatory compound is a peptiodomietic derivative. In certain cases, the peptiodomietic derivative comprises a hydroxamic acid group. In certain embodiments the LTA4H modulatory agent is described by the formula (II):

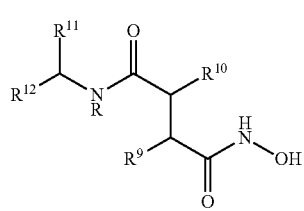

(II)

where:

$R^9$ is selected from hydrogen, hydroxy, amino, methyl, and thrifluoromethyl;

$R^{10}$ is $R_{10a}$—$(X)_n$-(ALK)-, wherein $R^{10a}$ is selected from hydrogen, a $C_1$-$C_6$ alkyl, $C_2$-$C_6$ alkenyl, $C_2$-$C_6$ alkynyl, cycloalkyl, aryl, or heterocycle group, any of which may be unsubstituted or substituted by ($C_1$-$C_6$)alkyl, ($C_1$-$C_6$)alkoxy, hydroxy, mercapto, ($C_1$-$C_6$)alkylthio, amino, trifluoromethyl, cyano, nitro, —COOH, —CONH$_2$, —COOR$^A$, —NHCOR$^A$, —CONHR$^A$, —NHR$^A$, —NR$^A$R$^B$, or CON-R$^A$R$^B$ wherein R$^A$ and R$^B$ are independently a ($C_1$-$C_6$)alkyl group;

ALK represents a straight or branched divalent $C_1$-$C_6$ alkylene, $C_2$-$C_6$ alkenylene, $C_2$-$C_6$ alkynylene radical, and may be interrupted by one or more non-adjacent —NH—, —O— or —S— linkages;

X represents —NH—, —O— or —S—, and n is 0 or 1;

R is selected from hydrogen or $C_1$-$C_6$ alkyl;

$R^{11}$ is a characterizing group of a natural or non-natural amino acid in which any functional groups may be protected; and $R_4$ represents an ester or thioester group, or a pharmaceutically acceptable salt, hydrate or solvate thereof.

In certain embodiments, the compound of formula (II) is selected from, 2S-(3S-Hydroxycarbamoyl-2R-isobutyl-hex-5-enoylamino)-3-phenylpropionic acid cyclopentyl ester, 2S-(3S-Hydroxycarbamoyl-2R-isobutyl-hex-5-enoylamino)-3-phenylpropionic acid benzyl ester, 2S-{2R-[1S-Hydroxycarbamoyl-2-(thiophen-2-ylsulphanyl)-ethyl]-4-methyl-pentanoylamino}-3-phenyl-propionic acid isopropyl ester, 2S-(3S-Hydroxycarbamoyl-2R-isobutyl-hex-5-enoylamino)-4-methyl-pentanoic acid cyclopentyl ester, 2S-{2R-[1S-Hydroxycarbamoyl-2-(thiophen-2-ylsulphanyl)-ethyl]-4-methyl-pentanoylamino}-3-phenyl-propionic acid isopropyl ester, 2S-(3S-Hydroxycarbamoyl-2R-isobutyl-hex-5-enoylamino)-3-phenylpropionic acid methyl ester, 2S-(3S-Hydroxycarbamoyl-2R-isobutyl-hex-5-enoylamino)-3-phenylpropionic acid ethyl ester, 2S-(3S-Hydroxycarbamoyl-2R-isobutyl-hex-5-enoylamino)-3-phenyl-propionic acid isopropyl ester, 3R-(2-Phenyl-1S-methylcarboxy-ethylcarbamoyl)-2S, 5-dimethylhexanohydroxamic acid, 2S-(3S-Hydroxycarbamoyl-2R-isobutyl-hex-5-enoylamino)-3-phenyl-propionic acid tert-butyl ester, 2S-(2R-Hydroxycarbamoylmethyl-4-methyl-pentanoylamino)-3-phenyl-propionic acid isopropyl ester, 2S-[2R—(S-Hydroxy-hydroxycarbamoyl-methyl)-4-methyl-pentanoytamine]-3-phenyl-propionic acid isopropyl ester, 2S-[2R-(1S-Hydroxycarbamoyl-ethyl)-4-methyl-pentanoylamino]-3-phenyl-propionic acid isopropyl ester, 2S-(2R-Hydroxycarbamoylmethyl-octanoylamino)-3-phenyl-propionic acid isopropyl ester, 2S-[2R—(S-Hydroxy-hydroxycarbamoyl-methyl)-4-methyl-pentanoylamino]-3-phenyl-propionic acid cyclopentyl ester, 2S-(3S-Hydroxycarbamoyl-2R-isobutyl-hex-5-enoylamino)-3S-methyl-pentanoic acid cyclopentyl ester, 2S-(3S-Hydroxycarbamoyl-2R-isobutyl-hex-5-enoylamino)-3-phenylpropionic acid 2-methoxy-ethyl ester, 2S-[2R-(1S-Hydroxycarbamoyl-ethyl)-4-methyl-pentanoylamino]-3-phenyl-propionic acid 2-methoxy-ethyl ester, 2S-(3S-Hydroxycarbamoyl-2R-isobutyl-hexanoylamino)-3,3-dimethyl-butyric acid 2-methoxy-ethyl ester, 2S-[2R—(S-Hydroxycarbamoyl-methoxy-methyl)-4-methyl-pentanoylamino]-3-phenyl-propionic acid isopropyl ester, 2S-[2-R-(1S-Hydroxycarbamoyl-ethyl)-4-methyl-pentanoylamino]-3,3-dimethyl-butyric acid 2-methoxy-ethyl ester, 2S-(3S-Hydroxycarbamoyl-2R-isobutyl-hex-5-enoylamino)-3,3-dimethyl-butyric acid 2-methoxy-ethyl ester, 2S-(3S-Hydroxycarbamoyl-2R-isobutyl-hexanoylamino)-3-phenylpropionic acid isopropyl ester, 2S-(3S-Hydroxycarbamoyl-2R-isobutyl-hex-5-enoylamino)-3,3-dimethyl-butyric acid isopropyl ester, 2R-(3S-Hydroxycarbamoyl-2R-isobutyl-hex-5-enoylamino)-3-phenylpropionic acid isopropyl ester, 2S-[2R—(S-Hydroxycarbamoyl-methoxy-methyl)-4-methyl-pentanoylamino]-3,3-dimethyl-butyric acid isopropyl ester, 2S-{(3S-Hydroxycarbamoyl-2R-isobutyl-hex-5-enoyl)-methyl-amino)-3-phenylpropionic acid isopropyl ester, 3-Cyclohexyl-2S-(3S-hydroxycarbamoyl-2R-isobutyl-hex-5-enoylamino)-propionic acid cyclopentyl ester, 2S-(3S-Hydroxycarbamoyl-2R-isobutyl-hex-5-enoylamino)-3-phenylpropionic acid 1-methyl-piperidin-4-yl ester, 2S-(3S-Hydroxycarbamoyl-2R-isobutyl-hex-5-enoylamino)-3-phenylpropionic acid 1-ethyl-propyl ester, 2S-(3S-Hydroxycarbamoyl-2R-isobutyl-hex-5-enoylamino)-3-phenylpropionic acid 1S-methyl-butyl ester, 2S-

(3S-Hydroxycarbamoyl-2R-isobutyl-hex-5-enoylamino)-3-phenylpropionic acid cyclohexyl ester, 2S-{2R-[1S-Hydroxycarbamoyl-2-(thiophen-2-ylsulphanyl)-ethyl]-4-methyl-pentanoylamino}-3,3-dimethyl-butyric acid isopropyl ester, 2S-(3S-Hydroxycarbamoyl-2R-isobutyl-hex-5-enoylamino)-3-phenylpropionic acid 1 R-methyl-butyl ester, 2S-(3S-Hydroxycarbamoyl-2R-isobutyl-hex-5-enoylamino)-3-phenylpropionic acid tetrahydro-furan-3(R,S)-yl ester, 2S-(3S-Hydroxycarbamoyl-2R-isobutyl-hex-5-enoylamino)-3,3-dimethyl-butyric acid cyclopentyl ester, 2S-[2R-(1S-Cyclopentyl-hydroxycarbamoyl-methyl)-4-methyl-pentanoylamino]-3-phenyl-propionic acid cyclopentyl ester, 2S-[2R-(1S-Hydroxy-hydroxycarbamoyl-methyl)-pent-4-ynoylamino]-3-phenylpropionic acid cyclopentyl ester, 2S-(3S-Hydroxycarbamoyl-2R-isobutyl-hex-5-enoylamino)-3-pyridin-3-yl-propionic acid cyclopentyl ester, 3-tert-Butoxy-2S-(3S-hydroxycarbamoyl-2R-isobutyl-hex-5-enoylamino)-propionic acid cyclopentyl ester, 2S-3S-Hydroxycarbamoyl-2R-isobutyl-hex-5-enoylamino)-2-phenylethanoic acid cyclopentyl ester, 2S-[5-(2-Chlorophenyl)-2R-(1S-hydroxy-hydroxycarbamoyl-methyl)-pent-4-ynoylamino]-3-phenylpropionic acid cyclopentyl ester, and 2S-(3S-Hydroxycarbamoyl-2R-isobutyl-6-phenyl-hex-5-enoylamino)-3-phenyl-propionic acid cyclopentyl ester, and pharmaceutically acceptable salts, hydrates and esters thereof.

In certain embodiments, the compound of formula (II) is the compound known as tosedostat (CHR-2797), which has the following structure:

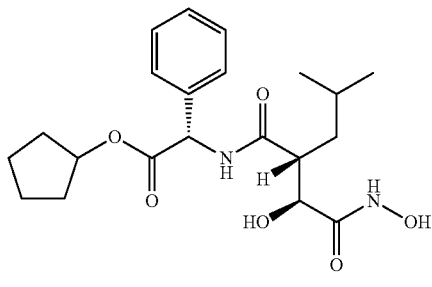

Tosedostat

In certain cases, tosedostat is converted intracellularly into an active form, known as CHR79888, which has the following structure:

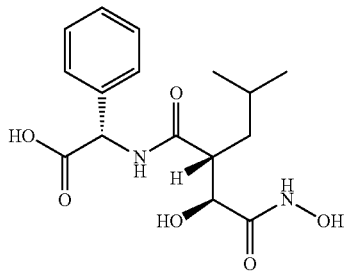

(Tosedostat active form)

Tosedostat analogs and derivatives useful in the methods of the invention include compounds described in U.S. Pat. Nos. 6,462,023, 5,861,436; and 6,545,051; and International Patent Application Nos. WO1999046241A1; and WO2000044373A1.

In certain embodiments, the LTA4H modulatory agent is a heterocyclic compound. In some cases, the heterocyclic compound is a benzoxazole derivative, a benzothiazole derivative, or a benzoimidazole derivative. In certain embodiments the LTA4H modulatory agent is described by the formula (III):

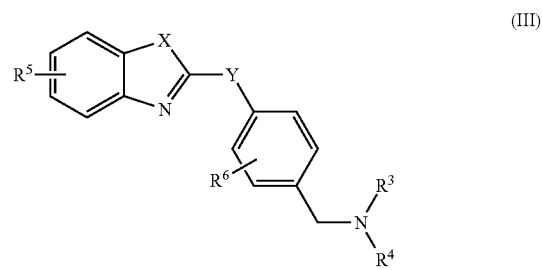

where:
X is selected from the group consisting of $NR^5a$, O, and S, with $R^{5a}$ being one of H and $CH_3$;
Y is selected from the group consisting of $CH_2$, and O;
$R^5$ is selected from the group consisting of H, $OCH_3$, Cl, F, Br, I, OH, $NH_2$, CN, $CF_3$ and $CH_3$;
$R^6$ is H or F; and
$R^3$ and $R^4$ are each independently selected from the group consisting of:
A) H, C1-7alkyl, C3-7alkenyl, wherein the carbon in said alkenyl that is attached to the nitrogen member has only single bonds, C3-7alkynyl, wherein the carbon in said alkynyl that is attached to the nitrogen member has only single bonds, C3-7cycloalkyl optionally benzofused, C5-7cycloalkenyl, —C3-7cycloalkylC1-7alkyl, —C1-7alkylC3-7cycloalkyl and phenyl, wherein each of the substituents A) is independently substituted with 0, 1, or 2 $R^Q$, and each of said $R^Q$ is a substituent at a carbon member that is at least one carbon member removed from the nitrogen member;
B) a substituent $HetR^a$;
C) —C1-7alkylC(O)$R^x$, optionally substituted with $CH_2R^{Ar}$ or $CH_2R^{Ar'}$;
D) —C2-5alkylC(O)$R^x$, wherein two valence allowed carbon members in the C2-5alkyl of said C2-5alkylC(O)$R^x$ are part of a saturated C3-6carbocycle;
E) —C2-5alkylOH wherein two valence allowed carbon members in the C2-5alkyl of said —C2-5alkylOH are part of a saturated C3-6carbocycle;
F) —C0-4alkylphenyl, wherein the phenyl in said —C0-4alkylphenyl is fused at two adjacent carbon members in said phenyl to $R^f$, or is benzofused;
G) —C0-4alkyl$Ar^6$, where $Ar^6$ is a 6-membered heteroaryl having a carbon member point of attachment and having one or two —N=heteroatom members, and benzofused;
H) —C0-4alkyl$Ar^5$, where $Ar^5$ is a 5-membered heteroaryl, having one heteroatom member selected from the group consisting of O, S, and >$NR^Y$, and having 0 or 1 —N=additional heteroatom member, optionally containing two carbonyl groups, and optionally benzofused;
I) —C1-4alkyl$Ar^{5'}$, where $Ar^{5'}$ is a 5-membered heteroaryl containing 3 or 4 nitrogen members, optionally substituted with RY, and having a valence allowed site as a point of attachment;

J) —C0-4alkylAr$^{66}$, where Ar$^{66}$ is a C0-4alkyl-attached phenyl fused at valence allowed sites to a 6-membered heteroaryl, wherein said 6-membered heteroaryl has one or two —N═heteroatom members;

K) —C0-4alkylAr$^{65}$, where Ar$^{65}$ is a C0-4alkyl-attached phenyl fused at valence allowed sites to a 5-membered heteroaryl, said 5-membered heteroaryl having one heteroatom member selected from the group consisting of O, S, and >NR$^Y$, and said 5-membered heteroaryl having 0 or 1 additional heteroatom member which is —N═;

L) one of 2-(4-ethyl-phenoxy)-benzothiazole, 2-(4-ethyl-phenoxy)-benzooxazole, and 2-(4-ethyl-phenoxy)-1H-benzoimidazole; and M) SO$_2$C$_{l4}$alkyl;

alternatively R$^2$ and R$^3$ are taken together with the nitrogen to which they are attached to form a heterocyclic ring that contains at least one heteroatom member that is said attachment nitrogen, said heterocyclic ring being selected from the group consisting of:

i) a 4-7 membered heterocyclic ring HetR$^b$, said 4-7 membered heterocyclic ring HetR$^b$ having one heteroatom member that is said attachment nitrogen, and being substituted with 0, 1, or 2 substituents at the same or at different substitution members, said substituents being selected from the group consisting of —RY, —CN, —C(O)R$^Y$, —C$_{0-4}$alkylCO$_2$R$^Y$, —C$_{0-4}$alkylC(O)CO$_2$R$^Y$, —C$_{0-4}$alkylOR$^Y$, —C$_{0-4}$alkylC(O)NR$^Y$R$^Z$, —C$_{0-4}$alkylNR$^Y$C(O)R$^Z$, —C(O)NR$^Z$OR$^Y$, —C$_{0-4}$alkylNR$^Y$C(O)CH$_2$OR$^Y$, —C$_{0-4}$alkylNR$^Y$C(O)CH$_2$C(O)R$^Y$, —C$_{0-4}$alkylNR$^Y$CO$_2$R$^Y$, —C$_{0-4}$alkylNR$^Y$C(O)NR$^Y$R$^Z$, —C$_{0-4}$alkylNR$^Y$C(S)NR$^Y$R$^Z$, —NR$^Y$C(O)CO$_2$R$^Y$, —NR$^Y$R$^Z$, —C$_{0-4}$alkylNR$^Y$SO$_2$R$^Y$, 1,3-dihydro-indol-2-one-1-yl, 1,3-dihydro-benzoimidazol-2-one-1-yl, tetrazol-5-yl, 1-R$^Y$-1H-tetrazol-5-yl, R$^Y$-triazolyl, 2-R$^Y$-2H-tetrazol-5-yl, pyrrolidine-2-thion-1-yl, piperidine-2-thion-1-yl, —C$_{0-4}$alkylC(O)N(R$^Y$)(SO$_2$R$^Y$), —C$_{0-4}$alkylN(R$^Y$)(SO$_2$)NR$^Y$R$^Y$, —C$_{0-4}$alkylN(R$^Y$)(SO$_2$)NR$^Y$CO$_2$R$^Y$, halo,

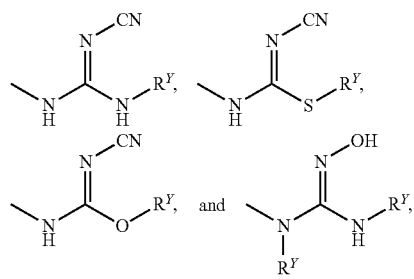

ii) a 5-7 membered heterocyclic ring HetR$^c$, said 5-7 heterocyclic ring HetR$^c$ having one additional heteroatom member separated from said attachment nitrogen by at least one carbon members, said additional heteroatom member being selected from the group consisting of O, S(═O)$_{0-2}$, and >NR$^M$, said 5-7 membered heterocyclic ring HetR$^c$ having 0 or 1 carbonyl members, and being substituted with 0, 1, or 2 substituents at the same or at different carbon substitution members, said substituents being selected from the group consisting of —C(O)R$^Y$, —CO$_2$R$^Y$—C$_{3-4}$alkylCO$_2$R$^Y$ and R$^Z$;

iii) one of imidazolidin-1-yl, 2-imidazolin-1-yl, pyrazol-1-yl, imidazol-1-yl, 2H-tetrazol-2-yl, 1H-tetrazol-1-yl, pyrrol-1-yl, 2-pyrrolin-1-yl, and 3-pyrrolin-1-yl, wherein each of said 2H-tetrazol-2-yl and 1H-tetrazol-1-yl is substituted at the carbon member with 0 or 1 of —C$_{0-4}$alkylR$^Z$, —C$_{0-4}$alkylSR$^Y$, —C$_{0-4}$alkylCO$_2$R$^Y$, and substituent HetR$^a$; and iv) one of 1,2,3,4-tetrahydro-quinolin-1-yl, 1,2,3,4-tetrahydro-isoquinolin-2-yl, indol-1-yl, isoindol-2-yl, indolin-1-yl, benzimidazol-1-yl, 2,8-diaza-spiro[4.5]decan-1-one-8-yl, 4-{[(2-tert-butoxycarbonylamino-cyclobutanecarbonyl)-amino]-methyl}-piperidin-1-yl, 4-{[(2-amino-cyclobutanecarbonyl)-amino]-methyl}-piperidin-1-yl, 3,9-diaza-spiro[5.5]undecane-3-carboxylic acid-9-yl tert-butyl ester, 4-oxo-1-phenyl-1,3,8-triaza-spiro[4.5]dec-8-yl, and 4-oxo-1,3,8-triaza-spiro[4.5]dec-8-yl;

wherein substituent HetR$^a$ is a 4-7 membered heterocyclic ring having a carbon member point of attachment and containing a member >NR$^M$ as a heteroatom member, and said heteroatom member being separated from said carbon member point of attachment by at least 1 additional carbon member;

R$^K$ is selected from the group consisting of H, —C$_{1-4}$alkyl, —C$_{0-4}$alkylR$^{Ar}$ each optionally substituted with 1, 2, or 3 substituents R$^N$;

R$^L$ is selected from the group consisting of —CO$_2$R$^S$ and —C(O)NR$^S$R$^{S'}$;

R$^M$ is selected from the group consisting of R$^Z$, indol-7-yl, —SO$_2$R$^Y$, —C$_{3-4}$alkylCO$_2$R$^Y$, CO$_2$R$^Y$, —C(O)NR$^Z$OR$^Y$, —C(O)R$^Y$, —C(O)C$_1$ 4alkylOR$^Y$, —C$_{0-4}$alkylC(O)NR$^S$R$^{S'}$, —C$_{0-4}$alkylC(O)CO$_2$R$^Y$, 1,3-dihydro-indol-2-one-1-yl, 1,3-dihydro-benzoimidazol-2-one-1-yl, tetrazol-5-yl, 1-R$^Y$-1H-tetrazol-5-yl, R$^Y$-triazolyl, 2-R$^Y$-2H-tetrazol-5-yl and —C$_{0-4}$alkylC(O)N(R$^Y$)(SO$_2$R$^Y$), each optionally substituted with 1, 2 or 3 substituents R$^N$;

R$^N$ is selected from the group consisting of OCH$_3$, Cl, F, Br, I, OH, NH$_2$, CN, CF$_3$, CH$_3$, OC(O)CH$_3$, and NO$_2$; R$^P$ is selected from the group consisting of R$^Y$, —C$_{2-4}$alkylOR$^Y$, R$^{Ar}$, —C$_{1-2}$alkylCO$_2$R$^Y$, —C$_{1-2}$alkylCONR$^S$R$^{S'}$, indol-7-yl, and —SO$_2$C$_{1-4}$alkyl;

R$^Q$ is selected from the group consisting of fluoro, chloro, bromo, iodo, trifluoromethyl, trichloromethyl, —CN, —C$_{1-4}$alkyl, —C$_{0-4}$alkylR$^{Ar}$, —C$_{0-4}$alkylR$^{Ar'}$, —C$_{0-4}$alkylOR$^Y$, —C$_{0-4}$alkylCO$_2$R$^Y$, —C$_{0-4}$alkylNR$^Y$R$^Z$, —C$_{0-4}$alkylNR$^Y$COR$^Y$, —C$_{0-4}$alkylNR$^Y$CONR$^Y$R$^Z$, —C$_{0-4}$alkylNR$^Y$SO$_2$R$^Y$, and —C$_{0-4}$alkylSR$^Y$;

R$^S$ and R$^{S'}$ are independently selected from the group consisting of H, —C$_{1-4}$alkyl, and —C$_{0-4}$alkylphenyl; alternatively, R$^S$ and R$^{S'}$ are taken together with the nitrogen member to which said R$^S$ and R$^{S'}$ are attached to form a 4-7 membered heterocyclic ring having 0 or 1 additional heteroatom member selected from the group consisting of O, S, and >NR$^Y$, provided that said additional heteroatom member is separated by at least two carbon members from said nitrogen member to which said R$^S$ and R$^{S'}$ are attached, and provided that where R$^Y$ is C$_{0-4}$alkylR$^{Ar}$, then R$^{Ar}$ is not substituted with R$^L$; R$^W$ is selected from the group consisting of R$^Y$, and —C$_{3-7}$cycloalkyl;

R$^X$ is selected from the group consisting of —OR$^Y$, —NR$^Y$R$^Z$, —C$_{1-4}$alkyl, and —C$_{0-4}$alkylR$^{Ar}$;

R$^Y$ is selected from the group consisting of H, —C$_{1-4}$alkyl, —C$_{0-4}$alkylR$^{Ar}$ and —C$_{0-4}$alkylR$^{Ar'}$, each optionally substituted with 1, 2, or 3 substituents R$^N$;

R$^Z$ is selected from the group consisting of R$^Y$, —C$_{2-4}$alkylOR$^Y$, —C$_{1-2}$alkylCO$_2$R$^Y$, —C$_{1-2}$alkylC(O)NR$^S$R$^{S'}$, and —C$_{2-4}$alkylNR$^S$R$^{S'}$;

when R$^Y$ and R$^Z$ are attached to a nitrogen member, R$^Y$ and R$^Z$ are selected as defined above, or R$^Y$ and R$^Z$ are taken together with the R$^Y$— and R$^Z$— attached nitrogen member to form a 4-7 membered heterocyclic ring HetR$^d$ having 0 or 1 additional heteroatom members selected from the group consisting of O, S, and >NR$^M$, said 4-7 membered heterocyclic ring HetR$^d$ having 0 or 1 carbonyl members, and said 4-7 membered heterocyclic ring HetR$^d$ having 0 or 1 valence allowed carbon members substituted with at least one of R$^M$, —CO$_2$H, and —C$_{0-1}$ alkylOR$^Y$;

R$^{Ar}$ is a moiety with a carbon member attachment point and said moiety is selected from the group consisting of phenyl, pyridyl, pyrimidyl, and pyrazinyl, wherein each valence allowed carbon member in each of said moieties is independently substituted with at least one of 0, 1, 2 or 3 R$^N$, and 0 or 1 R$^L$;

R$^{Ar'}$ is a 3-8 membered ring, having 0, 1 or 2 heteroatom members selected from the group consisting of O, S, N, and >NR$^Y$, having 0, 1, or 2 unsaturated bonds, having 0 or 1 carbonyl members, wherein each valence allowed member in each of said rings is independently substituted with 0, 1, or 2 R$^K$; and R$^f$ is a linear 3-to 5-membered hydrocarbon moiety having 0 or 1 unsaturated carbon-carbon bonds and having 0 or 1 carbonyl members.

In some embodiments, the compound of formula (III) is selected from, 2-[4-(2-Piperidin-1-yl-ethoxy)-phenoxy]-benzooxazole, (1-{2-[4-(Benzooxazol-2-yloxy)-phenoxy]ethyl}piperidin-4-yl)-methanol, 1-{2-[4-(Benzooxazol-2-yloxy)-phenoxy]-ethyl}-piperidin-4-ol, 2-[4 (Benzooxazol-2-yloxy)-phenoxy]-ethyl}-dibutyl-amine, (1-{2-[4-(Benzooxazol-2-yloxy)-phenoxy]-ethyl}-piperidin-2-yl)-methanol, 1-{3-[4-(Benzooxazol-2-yloxy)-phenoxy]-propyl}-4 phenyl-piperidin-4-ol, 1-{3-[4-(Benzooxazol-2-yloxy)-phenoxy]-propyl}-4-benzyl-piperidin-4-ol, 2-[4-(2-Piperidin-1-yl-ethyl)-phenoxy]-benzooxazole, 3-[4-(Benzooxazol-2-yloxy)-phenyl]-propyl}-cyclohexyl-ethyl-amine, 1-{3-[4-(Benzooxazol-2-yloxy)-phenyl]-propyl}-piperidin-4-ol, 1-{3-[4-(Benzooxazol-2-yloxy)-phenoxy]-2-hydroxy-propyl}-4-phenyl-piperidin-4-ol, 1-[2-(4-Benzooxazol-2-ylmethyl-phenoxy)-ethyl]-piperidine-4-carboxylic acid ethyl ester, 2-[4-(2-Pyrrolidin-1-yl-ethoxy)-phenoxy]-benzooxazole,{3-[4-(Benzooxazol-2-yloxy)-phenoxy]-propyl}-dimethyl-amine, 2-[4-(Benzooxazol-2-yloxy)-phenoxy]-ethyl}-dimethyl-amine, 2-[4-(2-Azepan-1-yl-ethoxy)-phenoxy-benzooxazole, 1-{2-[4-(Benzooxazol-2-yloxy)-phenoxy]-ethyl}-4-phenyl-piperidin-4-ol, {2-[4-(Benzooxazol-2-yloxy)-phenoxy]-ethyl}-cyclohexyl-ethyl-amine, 2-{4-[2-(2-Ethyl-piperidin-1-yl)-ethoxy]-phenoxy}-benzooxazole, 1-{2-[4-(Benzooxazol-2-yloxy)-phenoxy]-ethyl}-4-phenyl-piperidine-4-carbonitrile, 1-(1-{2-[4-(Benzooxazol-2-yloxy)-phenoxy]-ethyl}-4-phenyl-piperidin-4-yl)-ethanone, 2-{4-[2-(4-Methyl-piperidin-1-yl)-ethoxy]-phenoxy}-benzooxazole, 1-{2-[4-(Benzooxazol-2-yloxy)-phenoxy]-ethyl}-4-(4-chloro-phenyl)-piperidin-4-ol, 1-{2-[4-(Benzooxazol-2-yloxy)-phenoxy]-ethyl-4-(4-bromo-phenyl)-piperidin-4-ol, 1-{2-[4-(Benzooxazol-2-yloxy)-phenoxy]-ethyl}-4-(4-chloro-3-trifluoromethyl-phenyl)piperidin-4-ol, 1-{2-[4-(Benzooxazol-2-yloxy)-phenoxy]-ethyl}-4-benzyl-piperidin-4-ol, 2-[4-(Benzooxazol-2-yloxy)-phenoxy]-ethyl}-cyclohexyl-methyl-amine, {2-[4-(Benzooxazol-2-yloxy)-phenoxy]-ethyl}-cyclopropylmethyl-propyl-amine, {2-[4-(Benzooxazol-2-yloxy)-phenoxy]-ethyl}-butyl-ethyl-amine, 2-({2-[4-(Benzooxazol-2-yloxy)-phenoxy]-ethyl}-benzyl-amino)-ethanol, 2-{4-[2-(4-Benzyl-piperidin-1-yl)-ethoxy]-phenoxy}-benzooxazole, (1-{2-[4-(Benzooxazol-2-yloxy)-phenoxy]-ethyl}-piperidin-3-yl)-methanol, 2-({2-[4-(Benzooxazol-2-yloxy)-phenoxy]-ethyl}-propyl-amino)-ethanol, 2-[4-(2-Azetidin-1-yl-ethoxy)-phenoxy]benzooxazole, N-(1-{2-[4-(Benzooxazol-2-yloxy)-phenoxy]-ethyl}-piperidin-4-yl)-2-phenyl-acetamide, 1-{2-[4-(Benzooxazol-2-yloxy)-phenoxy]-ethyl}-piperidine-3-carboxylic acid ethyl ester, 2-{4-[3-(4-Phenyl-piperidin-1-yl)-propoxy]-phenoxy}-benzooxazole, 1-{2-[4-(Benzooxazol-2-yloxy)-phenyl]-ethyl}-4-phenyl-piperidin-4-ol, {2-[4-(Benzooxazol-2-yloxy)-phenyl]-ethyl}-cyclohexyl-ethyl-amine, 2-[4-(2-Pyrrolidin-1-yl-ethyl)-phenoxy]-benzooxazole, 2-[4-(2-Azepan-1-yl-ethyl)-phenoxy]-benzooxazole, 2-[4-(Benzooxazol-2-yloxy)-phenyl]-ethyl}-cyclopropylmethyl-propyl-amine, {2-[4-(Benzooxazol-2-yloxy)-phenyl]-ethyl}-dibutyl-amine, 1-{2-[4-(Benzooxazol-2-yloxy)-phenyl]-ethyl}-piperidin-4-ol, 1-{2-[4-(Benzooxazol-2-yloxy)-phenyl]-ethyl}-piperidine-4-carboxylic acid methyl ester, 1-{3-[4-(Benzooxazol-2-yloxy)-phenyl]-propyl}-4-phenyl-piperidin-4-ol, 2-[4-(3-Piperidin-1-yl-propyl)-phenoxy]-benzooxazole, {3-[4-(Benzooxazol-2-yloxy)-phenyl]-propyl}-dibutyl-amine, {3-[4-(Benzooxazol-2-yloxy)-phenyl]-propyl}-cyclopropylmethyl-propyl-amine, 1-[4-(Benzooxazol-2-yloxy)-phenoxy]-3-pyrrolidin-1-yl-propan-2-ol, 1-[2-(4-Benzooxazol-2-ylmethyl-phenoxy)-ethyl]-4-phenyl-piperidin-4-ol, 1-[2-(4-Benzooxazol-2-ylmethyl-phenoxy)-ethyl]-piperidine-4-carboxylic acid amide, 2-(4-Piperidin-1-ylmethyl-phenoxy)-benzooxazole, 2-[4-(2-Morpholin-4-yl-ethoxy)-phenoxy]-benzooxazole, and {2-[4-(Benzooxazol-2-yloxy)-phenoxy]-ethyl}-diethyl-amine and pharmaceutically acceptable salts, prodrugs, and solvates thereof of any of the foregoing compounds.

In some embodiments, the compound of formula (III) is selected from, {2-[4-(6-Chloro-benzothiazol-2-yloxy)-phenoxy]-ethyl}-diethyl-amine, 1-{2-[4-(Benzothiazol-2-yloxy)-phenoxy]-ethyl}-piperidin-4-ol, 1-{2-[4-(Benzothiazol-2-yloxy)-phenoxy]-ethyl}-piperidine-4-carboxylic acid ethyl ester, 1-{2-[4-(Benzothiazol-2-yloxy)-phenoxy]-ethyl}-piperidine-4-carboxylic acid, (1-{2-[4-(Benzothiazol-2-yloxy)-phenoxy]-ethyl}-piperidin-4-yl)-pyrrolidin-1-yl-methanone, 3-[(1-{2-[4-(Benzothiazol-2-yloxy)-phenoxy]-ethyl}-piperidine-4-carbonyl)-amino]-propionic acid ethyl ester, 1-{2-[4-(Benzothiazol-2-yloxy)-phenoxy]-ethyl}-piperidine-4-carboxylic acid amide, 1-(1-{2-[4-(Benzothiazol-2-yloxy)-phenoxy]-ethyl}-piperidin-4-yl)-pyrrolidin-2-one, 1'-{2-[4-(Benzothiazol-2-yloxy)-phenoxy]-ethyl}-[1,4']bipiperidinyl-2-one, 8-{2-[4-(Benzothiazol-2-yloxy)-phenoxy]-ethyl}-2,8-diaza-spiro[4.5]decan-1-one, 2-[4-(3-Pyrrolidin-1-yl-propoxy)-phenoxy]-benzothiazole, {2-[4-(Benzothiazol-2-yloxy)-phenyl]-ethyl}-cyclohexyl-ethyl-amine, 1-{2-[4-(Benzothiazol-2-yloxy)-phenyl]-ethyl}-piperidine-3-carboxylic acid amide, 1-(1-{2-[4-(Benzothiazol-2-yloxy)-phenyl]-ethyl}-piperidin-4-yl)-3-methyl-1,3-dihydro-benzoimidazol-2-one, 1-{2-[4-(Benzothiazol-2-yloxy)-phenyl]-ethyl}-piperidine-4-carboxylic acid methyl ester, (1-{2-[4-(Benzothiazol-2-yloxy)-phenyl]-ethyl}-piperidin-4-yl)-(4-methyl-piperazin-1-yl)-methanone, 1-[2-(4-Benzothiazol-2-ylmethyl-phenoxy)-ethyl]-piperidine-4-carboxylic acid methyl ester, 3-({2-[4-(Benzothiazol-2-yloxy)-phenoxy]-ethyl}-cyclopropyl-amino)-propionic acid, {2-[4-(Benzothiazol-2-yloxy)-phenoxy]-ethyl}-dimethyl-amine, 2-[4-(2-Pyrrolidin-1-yl-ethoxy)-phenoxy]-benzothiazole, {3-[4-(Benzothiazol-2-yloxy)-phenoxy]-propyl}-dimethyl-amine, 2-[4-(2-Azepan-1-yl-ethoxy)-phenoxy]-benzothiazole, 2-[4-(2-Azepan-1-yl-ethoxy)-phenoxy]-6-methoxy-benzothiazole, 1-{2-[4-(Benzothiazol-2-yloxy)-phenoxy]-ethyl}-4-phenyl-piperidin-4-ol, {2-[4-(Benzothiazol-2-yloxy)-phenoxy]-ethyl}-cyclohexyl-ethyl-amine, 1-{2-[4-(Benzothiazol-2-yloxy)-phenoxy]-ethyl}-4-(4-chloro-phenyl)-piperidin-4-ol, {2-[4-(Benzothiazol-2-yloxy)-phenoxy]-ethyl}-dibutyl-amine, 1-{2-[4-(Benzothiazol-2-yloxy)-phenoxy]-ethyl}-4-(4-bromo-phenyl)-piperidin-4-ol, 1-{2-[4-(Benzothiazol-2-yloxy)-phenoxy]-ethyl}-4-(4- chloro-3-trifluoromethyl-phenyl)-piperidin-4-ol, 1-{2-[4-(Benzothiazol-2-yloxy)-phenoxy]-ethyl}-4-benzyl-piperidin-4-ol, 1'-{2-[4-(Benzothiazol-2-yloxy)-phenoxy]-ethyl}-[1,4']bipiperidine, (1-{2-[4-(Benzothiazol-2-yloxy)-phenoxy]-ethyl}-piperidin-4-yl)-methanol, N-(1-{2-[4-(Benzothiazol-2-yloxy)-phenoxy]-ethyl}-piperidin-4-yl)-2-phenyl-acetamide, 1'-{2-[4-(Benzothiazol-2-yloxy)-phenoxy]-ethyl}-[1,4']bipiperidinyl-2-one, 2-(4-{2-[4-(2-Morpholin-4-yl-ethyl)-piperazin-1-yl]-ethoxy}-phenoxy)-benzothiazole, 2-(4-{2-[4-(2-Morpholin-4-yl-ethyl)-piperazin-1-yl]-ethyl}-phenoxy)-benzothiazole, 1-{3-[4-(Benzothiazol-2-yloxy)-phenoxy]-propyl}-4-phenyl-piperidin-4-ol, 1-{2-[4-(Benzothiazol-2-yloxy)-phenyl]-ethyl}-4-phenyl-piperidin-4-ol, 2-[4-(2-Pyrrolidin-1-yl-ethyl)-phenoxy]-benzothiazole, 2-[4-(2-Azepan-1-yl-ethyl)-phenoxy]-benzothiazole, {2-[4-(Benzothiazol-2-yloxy)-phenyl]-ethyl}-cyclopropylmethyl-propyl-amine, {2-[4-(Benzothiazol-2-yloxy)-phenyl]-ethyl}-dibutyl-amine, 2-[4-(2-Piperidin-1-yl-ethyl)-phenoxy]-benzothiazole, 1-{2-[4-(Benzothiazol-2-yloxy)-phenyl]-ethyl}-piperidin-4-ol, 1-{2-[4-(Benzothiazol-2-yloxy)-phenyl]-ethyl}-piperidine-4-carboxylic acid methyl ester, 1-{2-[4-(Benzothiazol-2-yloxy)-phenyl]-ethyl}-piperidine-4-carboxylic acid amide, 1-{2-[4-(Benzothiazol-2-yloxy)-phenyl]-ethyl}-piperidine-3-carboxylic acid ethyl ester, 1-{2-[4-(Benzothiazol-2-yloxy)-phenyl]-ethyl}-4-phenyl-piperidine-4-carboxylic acid ethyl ester, (1-{2-[4-(Benzothiazol-2-yloxy)-phenyl]-ethyl}-piperidin-4-yl)-acetic acid ethyl ester, 1-(1-{2-[4-(Benzothiazol-2-yloxy)-phenyl]-ethyl}-piperidin-4-yl)-1,3-dihydro-indol-2-one, 1-(1-{2-[4-(Benzothiazol-2-yloxy)-phenyl]-ethyl}-piperidin-4-yl)-pyrrolidin-2-one, N-(1-{2-[4-(Benzothiazol-2-yloxy)-phenyl]-ethyl}-piperidin-4-yl)-2-phenyl-acetamide, 8-{2-[4-(Benzothiazol-2-yloxy)-phenyl]-ethyl}-2,8-diaza-spiro[4.5]decan-1-one, 1-{2-[4-(Benzothiazol-2-yloxy)-phenyl]-ethyl}-piperidin-3-ol, 1-{2-[4-(Benzothiazol-2-yloxy)-phenyl]-ethyl}-piperidine-4-carboxylic acid ethyl ester, 1'-{2-[4-(Benzothiazol-2-yloxy)-phenyl]-ethyl}-[1,4']bipiperidine, 2-{4-[2-(4-Methyl-piperazin-1-yl)-ethyl]-phenoxy}-benzothiazole, 2-(4-{2-[4-(1-Benzyl-1H-tetrazol-5-yl)-piperidin-1-yl]-ethoxy}-phenoxy)-benzothiazole, 4-(1-{2-[4-(Benzothiazol-2-yloxy)-phenyl]-ethyl}-piperidine-4-carbonyl)-piperazine-1-carboxylic acid tert-butyl ester, 2-(4-{2-[4-(2-Morpholin-4-yl-ethyl)-piperazin-1-yl]-ethyl}-phenoxy)-benzothiazole, 1-[2-(4-Benzothiazol-2-ylmethyl-phenoxy)-ethyl]-piperidine-4-carboxylic acid amide, 1-{1-[2-(4-Benzothiazol-2-ylmethyl-phenoxy)-ethyl]-piperidin-4-yl}-pyrrolidin-2-one, 1-[4-(1-{2-[4-(Benzothiazol-2-yloxy)-phenyl]-ethyl}-piperidine-4-carbonyl)-piperazin-1-yl]-ethanone, 1-{2-[4-(Benzothiazol-2-yloxy)-phenyl]-ethyl}-piperidine-4-carboxylic acid, 1-(1-{2-[4-(Benzothiazol-2-yloxy)-phenoxy]-ethyl}-piperidin-4-yl)-pyrrolidine-2-thione, 2-(4-{2-[4-(Benzothiazol-2-yloxy)-phenoxy]-ethyl}-piperazin-1-yl)-ethanol, 2-(4-{2-[4-(Benzothiazol-2-yloxy)-phenoxy]-ethyl}-piperazin-1-yl)-1-pyrrolidin-1-yl-ethanone, 2-(4-{2-[4-(Benzothiazol-2-yloxy)-phenoxy]-ethyl}-piperazin-1-yl)-1-morpholin-4-yl-ethanone, 1-{2-[4-(Benzothiazol-2-yloxy)-phenyl]-ethyl}-piperidine-3-carboxylic acid, 1-{2-[4-(Benzothiazol-2-yloxy)-phenyl]-ethyl}-piperidine-2-carboxylic acid, (1-{2-[4-(Benzothiazol-2-yloxy)-phenyl]-ethyl}-piperidin-3-yl)-acetic acid, (1-{2-[4-(Benzothiazol-2-yloxy)-phenoxy]-ethyl}-piperidin-4-yl)-acetic acid ethyl ester, (1-{2-[4-(Benzothiazol-2-yloxy)-phenoxy]-ethyl}-piperidin-4-yl)-carbamic acid tert-butyl ester, (1-{2-[4-(Benzothiazol-2-yloxy)-phenoxy]-ethyl}-piperidin-4-yl)-acetic acid, (1-{2-[4-(Benzothiazol-2-yloxy)-phenyl]-ethyl}-piperidin-3-yl)-methanol, ({2-[4-(Benzothiazol-2-yloxy)-phenyl]-ethyl}-cyclohexyl-amino)-acetic acid methyl ester, (4-{2-[4-(Benzothiazol-2-yloxy)-phenoxy]-ethyl}-piperazin-1-yl)-acetic acid, 1-(1-{2-[4-(Benzothiazol-2-yloxy)-phenoxy]-ethyl}-piperidin-4-yl)-5-oxo-pyrrolidine-2-carboxylic acid ethyl ester, 1-(1-{2-[4-(Benzothiazol-2-yloxy)-phenoxy]-ethyl}-piperidin-4-yl)-5-oxo-pyrrolidine-2-carboxylic acid, 4-(4-{2-[4-(Benzothiazol-2-yloxy)-phenoxy]-ethyl}-piperazin-1-yl)-phenol, N-(1-{2-[4-(Benzothiazol-2-yloxy)-phenoxy]-ethyl}-piperidin-4-yl)-4-chloro-N-cyclopropyl-benzene sulfonamide, 3-({2-[4-(Benzothiazol-2-yloxy)-phenoxy]-ethyl}-cyclopropylmethyl-amino)-propionic acid, 3-({2-[4-(Benzothiazol-2-yloxy)-phenoxy]-ethyl}-isopropyl-amino)-propionic acid, 1-{2-[4-(Benzothiazol-2-yloxy)-phenoxy]-ethyl}-piperidin-4-ylamine, 3-[{2-[4-(Benzothiazol-2-yloxy)-phenoxy]-ethyl}-(1-methyl-piperidin-4-yl)-amino]-propionic acid, 3-({2-[4-(Benzothiazol-2-yloxy)-phenoxy]-ethyl}-benzyl-amino)-propionic acid, 3-((1-Acetyl-piperidin-4-yl)-{2-[4-(benzothiazol-2-yloxy)-phenoxy]-ethyl}-amino)-propionic acid, 4-(1-{2-[4-(Benzothiazol-2-yloxy)-phenoxy]-ethyl}-1H-tetrazol-5-yl)-piperidine-1-carboxylic acid tert-butyl ester, 3-({2-[4-(Benzothiazol-2-yloxy)-phenyl]-ethyl}-cyclopropyl-amino)-propionic acid, 3-((1-Acetyl-piperidin-4-yl)-{2-[4-(benzothiazol-2-yloxy)-phenyl]-ethyl}-amino)-propionic acid, 3-[{2-[4-(Benzothiazol-2-yloxy)-phenyl]-ethyl}-(1-methyl-piperidin-4-yl)-amino]-propionic acid, 3-({2-[4-(Benzothiazol-2-yloxy)-phenyl]-ethyl}-cyclopropylmethyl-amino)-propionic acid, 3-({2-[4-(Benzothiazol-2-yloxy)-phenyl]-ethyl}-isopropyl-amino)-propionic acid, 2-(4-{2-[4-(Benzothiazol-2-yloxy)-phenyl]-ethyl}-piperazin-1-yl)-1-pyrrolidin-1-yl-ethanone, (R)-1-{2-[4-(Benzothiazol-2-yloxy)-phenyl]-ethyl}-piperidine-3-carboxylic acid, 1-(1-{2-[4-(Benzothiazol-2-yloxy)-phenyl]-ethyl}-piperidin-4-yl)-1,3-dihydro-benzoimidazol-2-one, 2-(4-{2-[4-(6-Methyl-pyridin-2-yl)-piperazin-1-yl]-ethyl}-phenoxy)-benzothiazole, 2-{4-[2-(4-Ethanesulfonyl-piperazin-1-yl)-ethyl]-phenoxy}-benzothiazole, 2-(4-{2-[4-(Benzothiazol-2-yloxy)-phenyl]-ethyl}-piperazin-1-yl)-1-morpholin-4-yl-ethanone, 3-({2-[4-(Benzothiazol-2-yloxy)-phenyl]-ethyl}-methyl-amino)-propionic acid, 3-({2-[4-(Benzothiazol-2-yloxy)-phenyl]-ethyl}-cyclopentyl-amino)-propionic acid, 3-({2-[4-(Benzothiazol-2-yloxy)-phenyl]-ethyl}-cyclobutyl-amino)-propionic acid, 3-({2-[4-(Benzothiazol-2-yloxy)-phenyl]-ethyl}-benzyl-amino)-propionic acid, (1-{2-[4-(Benzothiazol-2-yloxy)-phenoxy]-ethyl}-piperidin-4-yl)-(4-hydroxymethyl-piperidin-1-yl)-methanone, {2-[4-(Benzothiazol-2-yloxy)-phenyl]-ethyl}-cyclopropyl-amine, (1-{2-[4-(Benzothiazol-2-yloxy)-phenoxy]-ethyl}-piperidin-4-yl)-[4-(2-hydroxy-ethyl)-piperazin-1-yl]-methanone, (1-{2-[4-(Benzothiazol-2-yloxy)-phenoxy]-ethyl}-piperidin-4-yl)-[4-(2-hydroxy-ethyl)-piperidin-1-yl]-methanone, 2-({2-[4-(Benzothiazol-2-yloxy)-phenyl]-ethyl}-cyclopropyl-amino)-ethanol, 3-({2-[4-(Benzothiazol-2-yloxy)-phenyl]-ethyl}-cyclopropyl-amino)-propan-1-ol, 4-({2-[4-(Benzothiazol-2-yloxy)-phenyl]-ethyl}-cyclopropyl-amino)-butyric acid, 3-[(1-{2-[4-(Benzothiazol-2-yloxy)-phenoxy]-ethyl}-piperidine-4-carbonyl)-amino]-propionic acid, 4-({2-[4-(Benzothiazol-2-yloxy)-phenyl]-ethyl}-cyclopropyl-amino)-butyronitrile, 3-(1-{2-[4-(Benzothiazol-2-yloxy)-phenyl]-ethyl}-piperidin-4-yl)-propionic acid, [(1-{2-[4-(Benzothiazol-2-yloxy)-phenoxy]-ethyl}-piperidine-4-carbonyl)-methyl-amino]-acetic acid, 3-(4-{2-[4-(Benzothiazol-2-yloxy)-phenyl]-ethyl}-piperazin-1-yl)-phenol, 2-(4-{2-[4-(4-Methoxy-phenyl)-piperazin-1-yl]-ethoxy}-phenoxy)-benzothiazole, 2-{4-[2-(5-Piperidin-4-yl-tetrazol-1-yl)-ethoxy]-phenoxy}-benzothiazole, (S)-1-(1-

{2-[4-(Benzothiazol-2-yloxy)-phenoxy]-ethyl}-piperidin-4-yl)-4-hydroxy-pyrrolidin-2-one, 2-[4-(Benzothiazol-2-yloxy)-phenyl]-ethyl}-cyclopropylmethyl-amine, 2-[({2-[4-(Benzothiazol-2-yloxy)-phenyl]-ethyl}-cyclopropyl-amino)-methyl]-cyclopropanecarboxylic acid ethyl ester, 4-(4-{2-[4-(Benzothiazol-2-yloxy)-phenoxy]-ethyl}-piperazine-1-carbonyl)-benzoic acid ethyl ester, 2-[({2-[4-(Benzothiazol-2-yloxy)-phenyl]-ethyl}-cyclopropyl-amino)-methyl]-cyclopropanecarboxylic acid, 1-({2-[4-(Benzothiazol-2-yloxy)-phenyl]-ethyl}-cyclopropyl-amino)-propan-2-ol, 3-({2-[4-(Benzothiazol-2-yloxy)-phenyl]-ethyl}-cyclopropyl-amino)-1,1,1-trifluoro-propan-2-ol, 3-({2-[4-(Benzothiazol-2-yloxy)-phenyl]-ethyl}-cyclopropyl-amino)-propionamide, 3-({2-[4-(Benzothiazol-2-yloxy)-phenyl]-ethyl}-cyclopropyl-amino)-propane-1,2-diol, 2-{4-[2-(5-Phenyl-tetrazol-2-yl)-ethoxy]-phenoxy}-benzothiazole, 2-{4-[2-(5-Phenyl-tetrazol-1-yl)-ethoxy]-phenoxy}-benzothiazole, N-{2-[4-(Benzothiazol-2-yloxy)-phenyl]-ethyl}-N-cyclopropyl-2-(2H-tetrazol-5-yl)-acetamide, (S)-3-({2-[4-(Benzothiazol-2-yloxy)-phenyl]-ethyl}-cyclopropyl-amino)-2-methyl-propan-1-ol, (R)-3-({2-[4-(Benzothiazol-2-yloxy)-phenyl]-ethyl}-cyclopropyl-amino)-2-methyl-propan-1-ol, 2-{4-[2-(5-Methylsulfanyl-tetrazol-2-yl)-ethoxy]-phenoxy}-benzothiazole, 2-{4-[2-(5-Methylsulfanyl-tetrazol-1-yl)-ethoxy]-phenoxy}-benzothiazole, 2-[4-(2-Tetrazol-2-yl-ethoxy)-phenoxy]-benzothiazole, 2-[4-(2-Tetrazol-1-yl-ethoxy)-phenoxy]-benzothiazole, (1R,2R)-2-{2-[4-(Benzothiazol-2-yloxy)-phenyl]-ethylamino}-cyclohexanecarboxylic acid, (1S,2R)-2-{2-[4-(Benzothiazol-2-yloxy)-phenyl]-ethylamino}-cyclohexanecarboxylic acid, (1R,2R)-2-{2-[4-(Benzothiazol-2-yloxy)-phenyl]-ethylamino}-cyclohexanol, (1S,2R)-2-{2-[4-(Benzothiazol-2-yloxy)-phenyl]-ethyl-amino}-cyclohexanol, 4-(1-{2-[4-(Benzothiazol-2-yloxy)-phenyl]-ethyl}-piperidin-4-yl)-butyric acid, 1-[4-(Benzothiazol-2-yloxy)-benzyl]-piperidine-4-carboxylic acid, 1-{1-[4-(Benzothiazol-2-yloxy)-benzyl]-piperidin-4-yl}-pyrrolidin-2-one, 2-(2-Fluoro-4-piperidin-1-ylmethyl-phenoxy)-benzothiazole, N-{1-[4-(Benzothiazol-2-yloxy)-benzyl]-piperidin-4-yl}-2-hydroxy-acetamide, 1-(2-{[4-(Benzothiazol-2-yloxy)-benzyl]-cyclopropyl-amino}-ethyl)-4-hydroxy-pyrrolidin-2-one, N-{1-[4-(Benzothiazol-2-yloxy)-benzyl]-piperidin-4-yl}-N-methyl-methanesulfonamide, 2-{4-[4-(1H-Tetrazol-5-yl)-piperidin-1-ylmethyl]-phenoxy}-benzothiazole, 1-{4-[4-(Benzothiazol-2-yloxy)-benzyl]-piperazin-1-yl}-2-hydroxy-ethanone, N-{1-[4-(Benzothiazol-2-yloxy)-benzyl]-piperidin-4-ylmethyl}-methanesulfonamide, 3-{1-[4-(Benzothiazol-2-yloxy)-benzyl]-piperidin-4-yl}-oxazolidin-2-one, 4-{1-[4-(Benzothiazol-2-yloxy)-benzyl]-piperidin-4-yl}-morpholin-3-one, (R) 1-(1-{2-[4-(Benzothiazol-2-yloxy)-phenoxy]-ethyl}-piperidin-4-yl)-4-hydroxy-pyrrolidin-2-one, 2-(4-{2-[4-(1H-Tetrazol-5-yl)-piperidin-1-yl]-ethyl}-phenoxy)-benzothiazole, (1-{2-[4-(Benzothiazol-2-yloxy)-phenoxy]-ethyl}-piperidin-2-yl)-methanol, (1-{2-[4-(Benzothiazol-2-yloxy)-phenoxy]-ethyl}-1H-tetrazol-5-yl)-acetic acid ethyl ester, (1-{2-[4-(Benzothiazol-2-yloxy)-phenoxy]-ethyl}-1H-tetrazol-5-yl)-acetic acid ethyl ester, 2-{4-[2-(5-Piperidin-4-yl-tetrazol-2-yl)-ethoxy]-phenoxy}-benzothiazole hydrochloride, 7-{2-[4-(Benzothiazol-2-yloxy)-phenoxy]-ethyl}-4-spiro-[3-phthalide]-piperidine, 1-{3-[4-(Benzothiazol-2-yloxy)-phenyl]-propyl}-piperidine-4-carboxylic acid ethyl ester, 2-[4-(Benzothiazol-2-yloxy)-phenyl]-ethylamine hydrochloride, 2-(4-{2-[4-(1H-Tetrazol-5-yl)-piperidin-1-yl]-ethoxy}-phenoxy)-benzothiazole, 2-Piperidin-1-ylmethyl-phenoxy)-benzooxazole, [4-(Benzothiazol-2-yloxy)-benzyl]-cyclohexyl-ethyl-amine, [4-(Benzothiazol-2-yloxy)-benzyl]-cyclopropylmethyl-propyl-amine, 1-[4-(Benzothiazol-2-yloxy)-benzyl]-piperidine-4-carboxylic acid amide, 1'-[4-(Benzothiazol-2-yloxy)-benzyl]-[1,4']bipiperidinyl-2-one, {4-[4-(Benzothiazol-2-yloxy)-benzyl]-piperazin-1-yl}-pyridin-3-yl-methanone, {1-[4-(Benzothiazol-2-yloxy)-benzyl]-piperidin-4-ylmethyl}-carbamic acid tert-butyl ester, {1-[4-(Benzothiazol-2-yloxy)-benzyl]-piperidin-4-ylmethyl}-carbamic acid methyl ester, N—{C-[[4-(benzothiazol-2-yloxy)-benzyl]-piperidin-4-yl]-methylamino sulfonyl}-carbamic acid tert-butyl ester, N-{1-[4-(Benzothiazol-2-yloxy)-benzyl]-piperidin-4-ylmethyl}-sulfamide hydrochloride, N-{1-[4-(Benzothiazol-2-yloxy)-benzyl]-piperidin-4-ylmethyl}-acetamide, {1-[4-(Benzothiazol-2-yloxy)-benzyl]-piperidin-4-yl}-acetic acid, Acetic acid ({1-[4-(benzothiazol-2-yloxy)-benzyl]-piperidin-4-ylmethyl}-carbamoyl)-methyl ester, [2-({1-[4-(Benzothiazol-2-yloxy)-benzyl]-piperidin-4-ylmethyl}-carbamoyl)-cyclobutyl]-carbamic acid tert-butyl ester, 2-Amino-cyclobutanecarboxylic acid {1-[4-(benzothiazol-2-yloxy)-benzyl]-piperidin-4-ylmethyl}-amide dihydrochloride, 2-(4-Pyrrolidin-1-ylmethyl-phenoxy)-benzothiazole, 2-{[4-(Benzothiazol-2-yloxy)-benzyl]-ethyl-amino}-ethanol, 2-{1-[4-(Benzothiazol-2-yloxy)-benzyl]-piperidin-2-yl}-ethanol, 1-{4-[4-(Benzothiazol-2-yloxy)-benzyl]-piperazin-1-yl}-ethanone, 8-[4-(Benzothiazol-2-yloxy)-benzyl]-2,8-diaza-spiro[4.5]decan-1-one, Spiro[isobenzofuran-1(3H), 4'-piperidin]-3-one, 1'-[4-(Benzothiazol-2-yloxy)-benzyl] (R)-1-[4-(Benzothiazol-2-yloxy)-benzyl]-pyrrolidin-3-ol, 2-[4-(2-Methyl-piperidin-1-ylmethyl)-phenoxy]-benzothiazole, [4-(Benzothiazol-2-yloxy)-benzyl]-diethyl-amine, [4-(Benzothiazol-2-yloxy)-benzyl]-butyl-methyl-amine, 2-{1-[4-(Benzothiazol-2-yloxy)-benzyl]-piperidin-4-yl}-ethanol, 1-[4-(Benzothiazol-2-yloxy)-benzyl]-piperidin-4-ol, {1-[4-(Benzothiazol-2-yloxy)-benzyl]-piperidin-2-yl}-methanol, (R)-{1-[4-(Benzothiazol-2-yloxy)-benzyl]-pyrrolidin-2-yl}-methanol, 2-(4-Azetidin-1-ylmethyl-phenoxy)-benzothiazole, 1-[4-(Benzothiazol-2-yloxy)-benzyl]-[1,4]diazepan-5-one, {1-[4-(Benzothiazol-2-yloxy)-benzyl]-piperidin-3-yl}-methanol, 1-[4-(Benzothiazol-2-yloxy)-benzyl]-piperidine-3-carboxylic acid amide, 9-[4-(Benzothiazol-2-yloxy)-benzyl]-3,9-diaza-spiro[5.5]undecane-3-carboxylic acid tert-butyl ester, 2-{1-[4-(Benzothiazol-2-yloxy)-benzyl]-piperidin-3-yl}-ethanol, cis-4-{2-[4-(Benzothiazol-2-yloxy)-phenyl]-ethylamino}-cyclohexanecarboxylic acid trifluoromethanesulfonate salt, (4-{2-[4-(Benzothiazol-2-yloxy)-phenyl]-ethyl}-piperazin-1-yl)-(tetrahydro-furan-2-yl)-methanone, propane-2-sulfonic acid (1-{2-[4-(benzothiazol-2-yloxy)-phenoxy]-ethyl}-piperidine-4-carbonyl)-amide, (4-{2-[4-(Benzothiazol-2-yloxy)-phenyl]-ethyl}-piperazin-1-yl)-oxo-acetic methyl ester, N-(1-{2-[4-(Benzothiazol-2-yloxy)-phenyl]-ethyl}-piperidine-4-carbonyl)-benzenesulfonamide trifluoromethanesulfonate salt, N-(1-{2-[4-(Benzothiazol-2-yloxy)-phenyl]-ethyl}-piperidine-4-carbonyl)-methanesulfonamide trifluoromethanesulfonate salt, (4-{2-[4-(Benzothiazol-2-yloxy)-phenyl]-ethyl}-piperazin-1-yl)-oxo-acetic acid trifluoromethanesulfonate salt, (4-{2-[4-(Benzothiazol-2-yloxy)-phenyl]-ethyl}-piperazin-1-yl)-morpholin-4-yl-methanone, 1-(4-{2-[4-(Benzothiazol-2-yloxy)-phenyl]-ethyl}-piperazin-1-yl)-2-thiophen-2-yl-ethanone, (4-{2-[4-(Benzothiazol-2-yloxy)-phenyl]-ethyl}-piperazin-1-yl)-pyridin-3-yl-methanone, (4-{2-[4-(Benzothiazol-2-yloxy)-phenyl]-ethyl}-piperazin-1-yl)-cyclopropyl-methanone, 1-(4-{2-[4-(Benzothiazol-2-yloxy)-phenyl]-ethyl}-piperazin-1-yl)-2-methoxy-ethanone, 1-(4-{2-[4-(Benzothiazol-2-yloxy)-phenyl]-ethyl}-piperazin-1-yl)-2,2,2-trifluoro-ethanone, 4-(4-{2-[4-(Benzothiazol-2-yloxy)-phenyl]-ethyl}-piperazine-1-carbonyl)-benzoic acid, (4-{2-[4-(Benzothiazol-2-yloxy)-phenyl]-ethyl}-piperazin-1-yl)-pyridin-4-yl-methanone, (4-{2-[4-(Benzothiazol-2-yloxy)-phenyl]-ethyl}-piperazin-1-yl)-(5-methyl-pyrazin-2-yl)-methanone, (R)-(4-{2-[4-(Benzothiazol-2-yloxy)-phenyl]-ethyl}-piperazin-1-yl)-(tetrahydro-furan-2-yl)-methanone, (S)-(4-{2-[4-(Benzothiazol-2-yloxy)-phenyl]-ethyl}-piperazin-1-yl)-(tetrahydro-furan-2-yl)-methanone, (4-{2-[4-(Benzothiazol-2-yloxy)-phenyl]-ethyl}-piperazin-1-yl)-(tetrahydro-furan-3-yl)-methanone, 1-(4-{2-[4-(Benzothiazol-2-yloxy)-phenyl]-ethyl}-piperazin-1-yl)-2-hydroxy-ethanone, 2-[2-(4-{2-[4-(Benzothiazol-2-yloxy)-phenyl]-ethyl}-piperazin-1-yl)-2-oxo-ethyl]-cyclopentanone, 3-(4-{2-[4-(Benzothiazol-2-yloxy)-phenyl]-ethyl}-piperazin-1-yl)-propionic acid trifluoromethanesufonate salt, 3-(1-{2-[4-(Benzothiazol-2-yloxy)-phenyl]-ethyl}-piperidin-4-yl)-oxazolidin-2-one, 4-(1-{2-[4-(Benzothiazol-2-yloxy)-phenyl]-ethyl}-piperidin-4-yl)-morpholin-3-one, 4-(1-{2-[4-(Benzothiazol-2-yloxy)-phenoxy]-ethyl}-piperidin-4-yl)-morpholin-3-one, 3-(1-{2-[4-(Benzothiazol-2-yloxy)-phenoxy]-ethyl}-piperidin-4-yl)-oxazolidin-2-one, 1-{2-[4-(Benzothiazol-2-yloxy)-phenyl]-ethyl}-piperidine-4-carboxylic acid benzyloxy-amide, (1-{2-[4-(Benzothiazol-2-yloxy)-phenyl]-ethyl}-piperidin-4-yl)-acetic acid, (R)-1-(1-{2-[4-(Benzothiazol-2-yloxy)-phenyl]-ethyl}-piperidin-4-yl)-4-hydroxy-pyrrolidin-2-one, 1-{2-[4-(Benzothiazol-2-yloxy)-phenyl]-ethyl}-piperidine-4-carboxylic acid hydroxyamide, (S)-1-(1-{2-[4-(Benzothiazol-2-yloxy)-phenyl]-ethyl}-piperidin-4-yl)-4-hydroxy-pyrrolidin-2-one, (1-{2-[4-(Benzothiazol-2-yloxy)-phenyl]-ethyl}-piperidin-4-yl)-carbamic acid tert-butyl ester, 2-{4-[2-(4-Fluoro-piperidin-1-yl)-ethyl]-phenoxy}-benzothiazole, 2-{4-[2-(4,4-Difluoro-piperidin-1-yl)-ethyl]-phenoxy}-benzothiazole, (R)-1-{2-[4-(Benzothiazol-2-yloxy)-phenyl]-ethyl}-pyrrolidin-3-ol, N-(1-{2-[4-(Benzothiazol-2-yloxy)-phenyl]-ethyl}-piperidin-4-yl)-Formamide, (1-{2-[4-(Benzothiazol-2-yloxy)-phenyl]-ethyl}-piperidin-4-yl)-urea, 1-(1-{2-[4-(Benzothiazol-2-yloxy)-phenyl]-ethyl}-piperidin-4-yl)-3-cyano-2-phenyl-isourea, 1-(1-{2-[4-(Benzothiazol-2-yloxy)-phenyl]-ethyl}-piperidin-4-yl)-3-cyano-2-methyl-isothiourea, N-(1-{2-[4-(Benzothiazol-2-yloxy)-phenyl]-ethyl}-piperidin-4-yl)-methanesulfonamide, 1-(1-{2-[4-(Benzothiazol-2-yloxy)-phenyl]-ethyl}-piperidin-4-yl)-3-cyano-2-methyl-guanidine, 8-{2-[4-(Benzothiazol-2-yloxy)-phenyl]-ethyl}-1-phenyl-1,3,8-triaza-spiro[4.5]decan-4-one, 8-{2-[4-(Benzothiazol-2-yloxy)-phenyl]-ethyl}-1,3,8-triaza-spiro[4.5]decane-2,4-dione, (1-{2-[4-(Benzothiazol-2-yloxy)-phenyl]-ethyl}-piperidin-4-yl)-methyl-carbamic acid tert-butyl ester, N-(1-{2-[4-(Benzothiazol-2-yloxy)-phenyl]-ethyl}-piperidin-4-yl)-N-methyl-acetamide, N-(1-{2-[4-(Benzothiazol-2-yloxy)-phenyl]-ethyl}-piperidin-4-yl)-N-methyl-methanesulfonamide, acetic acid [(1-{2-[4-(benzothiazol-2-yloxy)-phenyl]-ethyl}-piperidin-4-yl)-methyl-carbamoyl]-methyl ester, N-(1-{2-[4-(Benzothiazol-2-yloxy)-phenyl]-ethyl}-piperidin-4-yl)-N-acetamide, acetic acid (1-{2-[4-(benzothiazol-2-yloxy)-phenyl]-ethyl}-piperidin-4-ylcarbamoyl)-methyl ester, 2-({2-[4-(Benzothiazol-2-yloxy)-phenyl]-ethyl}-methyl-amino)-3-(1H-imidazol-2-yl)-propionic acid, 2-(4-{2-[4-(3-Nitro-pyridin-2-yl)-[1,4]diazepan-1-yl]-ethyl}-phenoxy)-benzothiazole, 2-(4-Piperidin-1-ylmethyl-phenoxy)-benzothiazole, 1-[4-(Benzothiazol-2-yloxy)-benzyl]-4-phenyl-piperidin-4-ol, 1-[4-(Benzothiazol-2-yloxy)-benzyl]-piperidin-4-ol, {1-[4-(Benzothiazol-2-yloxy)-benzyl]-piperidin-4-yl}-methanol, N-{1-[4-(Benzothiazol-2-yloxy)-benzyl]-piperidin-4-yl}-methanesulfonamide, N-{1-[4-(Benzothiazol-2-yloxy)-benzyl]-piperidin-4-ylmethyl}-2-hydroxy-acetamide, {1-[4-(Benzothiazol-2-yloxy)-benzyl]-piperidin-4-yl}-carbamic acid methyl ester, {1-[4-(Benzothiazol-2-yloxy)-benzyl]-piperidin-4-ylmethyl}-urea, N-{1-[4-(Benzothiazol-2-yloxy)-benzyl]-piperidin-4-ylmethyl}-2,2,2-trifluoro-acetamide, {4-[4-(Benzothiazol-2-yloxy)-benzyl]-piperazin-1-yl}-acetic acid, 2-[4-(4-Methanesulfonyl-piperazin-1-ylmethyl)-phenoxy]-benzothiazole, 1-{4-[4-(Benzothiazol-2-yloxy)-benzyl]-piperazin-1-yl}-2,2,2-trifluoro-ethanone, 2-(4-Morpholin-4-ylmethyl-phenoxy)-benzothiazole, {1-[4-(Benzothiazol-2-yloxy)-benzyl]-piperidin-4-yl}-carbamic acid phenyl ester, N-{1-[4-(Benzothiazol-2-yloxy)-benzyl]-piperidin-4-yl}-benzenesulfonamide, 3-[4-(Benzothiazol-2-yloxy)-benzylamino]-propionic acid ethyl ester, 3-[4-(Benzothiazol-2-yloxy)-benzylamino]-propionic acid, [(1-{2-[4-(Benzothiazol-2-yloxy)-phenoxy]-ethyl}-piperidine-4-carbonyl)-methyl-amino]-acetic acid ethyl ester, 1'-{2-[4-(Benzothiazol-2-yloxy)-phenoxy]-ethyl}-[1,4']bipiperidinyl-4-carboxylic acid ethyl ester, 1'-{2-[4-(Benzothiazol-2-yloxy)-phenoxy]-ethyl}-[1,4']bipiperidinyl-4-carboxylic acid, {2-[4-(Benzothiazol-2-yloxy)-phenyl]-ethyl}-cyclopropyl-ethyl-amine, 3-({2-[4-(Benzothiazol-2-yloxy)-phenyl]-ethyl}-cyclopropyl-amino)-2-methyl-propionic acid trifluoromethansulfonic acid salt, 2-({2-[4-(Benzothiazol-2-yloxy)-phenyl]-ethyl}-cyclopropylmethyl-amino)-ethanol, 2-[2-({2-[4-(Benzothiazol-2-yloxy)-phenyl]-ethyl}-cyclopropylmethyl-amino)-ethoxy]-ethanol, 3-({2-[4-(Benzothiazol-2-yloxy)-phenyl]-ethyl}-cyclopropylmethyl-amino)-propan-1-ol, {2-[4-(Benzothiazol-2-yloxy)-phenyl]-ethyl}-cyclopropylmethyl-(3-tetrazol-2-yl-propyl)-amine, {2-[4-(Benzothiazol-2-yloxy)-phenyl]-ethyl}-cyclopropyl-(3-pyrrol-1-yl-propyl)-amine, 4-({2-[4-(Benzothiazol-2-yloxy)-phenyl]-ethyl}-cyclopropylmethyl-amino)-butyronitrile, 1-{2-[4-(Benzothiazol-2-yloxy)-phenyl]-ethyl}-piperidine-4-carboxylic acid (2-cyano-ethyl)-amide, {2-[4-(Benzothiazol-2-yloxy)-phenyl]-ethyl}-cyclopropylmethyl-[3-(2H-tetrazol-5-yl)-propyl]-amine, 3-[5-(1-{2-[4-(Benzothiazol-2-yloxy)-phenyl]-ethyl}-piperidin-4-yl)-tetrazol-1-yl]-propionitrile, {2-[4-(Benzothiazol-2-yloxy)-phenyl]-ethyl}-cyclopropyl-[3-(2H-tetrazol-5-yl)-propyl]-amine, 1-{2-[4-(Benzothiazol-2-yloxy)-phenyl]-ethyl}-piperidine-4-carboxylic acid (2-hydroxy-1,1-dimethyl-ethyl)-amide, {2-[4-(Benzothiazol-2-yloxy)-phenyl]-ethyl}-cyclopropylmethyl-[3-(1H-[1,2,4]triazol-3-yl)-propyl]-amine, {2-[4-(Benzothiazol-2-yloxy)-phenyl]-ethyl}-cyclopropylmethyl-[3-(5-methyl-1H-[1,2,4]triazol-3-yl)-propyl]-amine, {2-[4-(Benzothiazol-2-yloxy)-phenyl]-ethyl}-cyclopropylmethyl-[3-(5-phenyl-1H-[1,2,4]triazol-3-yl)-propyl]-amine, 2-(4-{2-[4-(1-Methyl-1H-tetrazol-5-yl)-piperidin-1-yl]-ethyl}-phenoxy)-benzothiazole, 2-(4-{2-[4-(2-Methyl-2H-tetrazol-5-yl)-piperidin-1-yl]-ethyl}-phenoxy)-benzothiazole, 1-{2-[4-(Benzothiazol-2-yloxy)-phenyl]-ethyl}-piperidine-4-carbonitrile, 2-(4-{2-[4-(1H-[1,2,3]Triazol-4-yl)-piperidin-1-yl]-ethyl}-phenoxy)-benzothiazole, 4-{2-[4-(Benzothiazol-2-yloxy)-phenyl]-ethylamino}-butyric acid ethyl ester, 4-({2-[4-(Benzothiazol-2-yloxy)-phenyl]-ethyl}-cyclopropylmethyl-amino)-butyric acid ethyl ester, 2-[3-({2-[4-(Benzothiazol-2-yloxy)-phenyl]-ethyl}-cyclopropylmethyl-amino)-propyl]-isoindole-1,3-dione, 4-({2-[4-(Benzothiazol-2-yloxy)-phenyl]-ethyl}cyclopropylmethyl-amino)-butyric acid, 1-(3-{2-[4-(Benzothiazol-2-yloxy)-phenyl]-ethylamino}-propyl)-pyrrolidin-2-one, N-1-{2-[4-(Benzothiazol-2-yloxy)-phenyl]-ethyl}-N1-cyclopropylmethyl-propane-1,3-diamine, 5-({2-[4-(Benzothiazol-2-yloxy)-phenyl]- ethyl}-cyclopropyl-amino)-pentanoic acid methyl ester, N-[3-({2-[4-(Benzothiazol-2-yloxy)-phenyl]-ethyl}-cyclopropylmethyl-amino)-propyl]-acetamide, morpholine-4-carboxylic acid [3-({2-[4-(benzothiazol-2-yloxy)-phenyl]-ethyl}-cyclopropylmethyl-amino)-propyl]-amide, N-[3-({2-[4-(Benzothiazol-2-yloxy)-phenyl]-ethyl}-cyclopropylmethyl-amino)-propyl]-methanesulfonamide, 5-({2-[4-(Benzothiazol-2-yloxy)-phenyl]-ethyl}-cyclopropyl-amino)-pentanoic acid, 1-[3-({2-[4-(Benzothiazol-2-yloxy)-phenyl]-ethyl}-isopropyl-amino)-propyl]-pyrrolidin-2-one, 1-[3-({2-[4-(Benzothiazol-2-yloxy)-phenyl]-ethyl}-cyclopropylmethyl-amino)-propyl]-pyrrolidin-2-one, 1-[3-({2-[4-(Benzothiazol-2-yloxy)-phenyl]-ethyl}-cyclopropyl-amino)-propyl]-pyrrolidin-2-one, 1-[3-({2-[4-(Benzothiazol-2-yloxy)-phenyl]-ethyl}-propyl-amino)-propyl]-pyrrolidin-2-one, 4-((1-acetyl-piperidin-4-yl)-{2-[4-(benzothiazol-2-yloxy)-phenyl]-ethyl}-amino)-butyric acid ethyl ester, 4-((1-acetyl-piperidin-4-yl)-{2-[4-(benzothiazol-2-yloxy)-phenyl]-ethyl}-amino)-butyric acid ethyl ester, 4-({2-[4-(Benzothiazol-2-yloxy)-phenyl]-ethyl}-methanesulfonyl-amino)-butyric acid, ({2-[4-(Benzothiazol-2-yloxy)-phenyl]-ethyl}-cyclopropyl-amino)-acetic acid, 6-({2-[4-(Benzothiazol-2-yloxy)-phenyl]-ethyl}-cyclopropyl-amino)-hexanoic acid ethyl ester, 7-({2-[4-(Benzothiazol-2-yloxy)-phenyl]-ethyl}-cyclopropyl-amino)-heptanoic acid ethyl ester, 6-({2-[4-(Benzothiazol-2-yloxy)-phenyl]-ethyl}-cyclopropyl-amino)-hexanoic acid, 7-({2-[4-(Benzothiazol-2-yloxy)-phenyl]-ethyl}-cyclopropyl-amino)-heptanoic acid, N-1-{2-[4-(Benzothiazol-2-yloxy)-phenyl]-ethyl}-N1-cyclopropyl-propane-1,3-diamine, N-[3-({2-[4-(Benzothiazol-2-yloxy)-phenyl]-ethyl}-cyclopropyl-amino)-propyl]-acetamide, N-[3-({2-[4-(Benzothiazol-2-yloxy)-phenyl]-ethyl}-cyclopropyl-amino)-propyl]-isobutyramide, N-[3-({2-[4-(Benzothiazol-2-yloxy)-phenyl]-ethyl}l-cyclopropyl-amino)-propyl]-benzamide, N-[3-({2-[4-(Benzothiazol-2-yloxy)-phenyl]-ethyl}-cyclopropyl-amino)-propyl]-4-chloro-benzamide, N-[3-({2-[4-(Benzothiazol-2-yloxy)-phenyl]-ethyl}-cyclopropyl-amino)-propyl]-methanesulfonamide, propane-2-sulfonic acid [3-({2-[4-(benzothiazol-2-yloxy)-phenyl]-ethyl}-cyclopropyl-amino)-propyl]-amide trifluoromethanesulfonic acid salt, 8-({2-[4-(Benzothiazol-2-yloxy)-phenyl]-ethyl}-cyclopropyl-amino)-octanoic acid ethyl ester, 1-[3-({2-[4-(Benzothiazol-2-yloxy)-phenyl]-ethyl}-cyclopropyl-amino)-propyl]-3-phenyl-urea, 8-({2-[4-(Benzothiazol-2-yloxy)-phenyl]-ethyl}-cyclopropyl-amino)-octanoic acid, tetrahydro-furan-2-carboxylic acid [3-({2-[4-(benzothiazol-2-yloxy)-phenyl]-ethyl}-cyclopropyl-amino)-propyl]-amide, N-[3-({2-[4-(Benzothiazol-2-yloxy)-phenyl]-ethyl}-cyclopropyl-amino)-propyl]-2-hydroxy-acetamide, 4-({2-[4-(Benzothiazol-2-yloxy)-phenoxy]-ethyl}-cyclopropyl-amino)-butyric acid, 1-{3-[4-(Benzothiazol-2-yloxy)-benzylamino]-propyl}-pyrrolidin-2-one, 1-(3-{[4-(Benzothiazol-2-yloxy)-benzyl]-methyl-amino}-propyl)-pyrrolidin-2-one, 1-(3-{[4-(Benzothiazol-2-yloxy)-benzyl]-isopropyl-amino}-propyl)-pyrrolidin-2-one, 1-(3-{[4-(Benzothiazol-2-yloxy)-benzyl]-ethyl-amino}-propyl)-pyrrolidin-2-one, [4-(Benzothiazol-2-yloxy)-benzyl]-cyclopropyl-amine, N-1-[4-(Benzothiazol-2-yloxy)-benzyl]-N1-cyclopropyl-propane-1,3-diamine, N-(3-{[4-(Benzothiazol-2-yloxy)-benzyl]-cyclopropyl-amino}-propyl)-isobutyramide, 1-(3-{[4-(Benzothiazol-2-yloxy)-benzyl]-cyclopropyl-amino}-propyl)-3-isopropyl-urea, 1-{1-[4-(Benzothiazol-2-yloxy)-benzyl]-piperidin-4-yl}-3-isopropyl-urea, N-{1-[4-(Benzothiazol-2-yloxy)-benzyl]-piperidin-4-yl}-oxalamic acid methyl ester, N-{1-[4-(Benzothiazol-2-yloxy)-benzyl]-piperidin-4-yl}-isobutyramide, tetrahydro-furan-2-carboxylic acid {1-[4-(benzothiazol-2-yloxy)-benzyl]-piperidin-4-yl}-amide, 1-{1-[4-(Benzothiazol-2-yloxy)-benzyl]-piperidin-4-yl}-4-hydroxy-pyrrolidin-2-one, 1-{1-[4-(Benzothiazol-2-yloxy)-benzyl]-piperidin-4-yl}-4-hydroxy-pyrrolidin-2-one, {1-[4-(Benzothiazol-2-yloxy)-benzyl]-piperidin-4-yl}-urea, N-{1-[4-(Benzothiazol-2-yloxy)-benzyl]-piperidin-4-yl}-oxalamic acid, N-{1-[4-(Benzothiazol-2-yloxy)-benzyl]-piperidin-4-yl}-2-hydroxy-acetamide, N-{1-[4-(Benzothiazol-2-yloxy)-benzyl]piperidin-4-yl}-2,2,2-trifluoro-acetamide, 2-[4-(1,1-Dioxo-1|6-thiomorpholin-4-ylmethyl) phenoxy]-benzothiazole, N-{1-[4-(benzothiazol-2-yloxy)-benzyl]-piperidin-4-amino sulfonyl}-carbamic acid tert-butyl ester, N-{1-[4-(Benzothiazol-2-yloxy)-benzyl]-piperidin-4-yl}-acetamide, N-{1-[4-(Benzothiazol-2-yloxy)-benzyl]-piperidin-4-yl}-N,N-dimethylsulfamide, 1-{1-[4-(Benzothiazol-2-yloxy)-benzyl]-piperidin-4-yl}-3-ethyl-urea, 1-{1-[4-(Benzothiazol-2-yloxy)-benzyl]-piperidin-4-yl}-3-ethyl-thiourea, propane-1-sulfonic acid {1-[4-(benzothiazol-2-yloxy)-benzyl]-piperidin-4-yl}-amide, propane-2-sulfonic acid {1-[4-(benzothiazol-2-yloxy)-benzyl]-piperidin-4-yl}-amide, N-{1-[4-(Benzothiazol-2-yloxy)-benzyl]-piperidin-4-yl}-sulfamide, N-{1-[4-(Benzothiazol-2-yloxy)-benzyl]-piperidin-4-yl}-formamide, {1-[4-(Benzothiazol-2-yloxy)-benzyl]-piperidin-4-yl}-carbamic acid ethyl ester, N-{1-[4-(Benzothiazol-2-yloxy)-benzyl]-piperidin-4-yl}-propionamide, N-{1-[4-(Benzothiazol-2-yloxy)-benzyl]-piperidin-4-yl}-butyramide, 1-{1-[4-(Benzothiazol-2-yloxy)-benzyl]-piperidin-4-yl}-3-propyl-urea, {1-[4-(Benzothiazol-2-yloxy)-benzyl]-piperidin-4-yl}-carbamic acid propyl ester, 1-{1-[4-(Benzothiazol-2-yloxy)-benzyl]-piperidin-4-yl}-3-methyl-urea, 1-{-[4-(Benzothiazol-2-yloxy)-benzyl]-piperidin-4-yl}-1,3-dimethyl-urea, 1-{1-[4-(Benzothiazol-2-yloxy)-benzyl]-piperidin-4-yl}-1-methyl-urea, N-{1-[4-(Benzothiazol-2-yloxy)-benzyl]-piperidin-4-yl}-N-methyl-acetamide, {1-[4-(Benzothiazol-2-yloxy)-benzyl]-piperidin-4-yl}-methyl-carbamic acid methyl ester, N-{1-[4-(Benzothiazol-2-yloxy)-benzyl]-piperidin-4-yl}-N-methyl-oxalamic acid methyl ester, N-{1-[4-(Benzothiazol-2-yloxy)-benzyl]-piperidin-4-yl}-N-methyl-oxalamic acid, Guanidine, N-{1-[4-(Benzothiazol-2-yloxy)-benzyl]-piperidin-4-yl}-N'-hydroxy, {1-[4-(Benzothiazol-2-yloxy)-benzyl]-piperidin-4-yl}-carbamic acid isopropyl ester, 3-{1-[4-(Benzothiazol-2-yloxy)-benzyl]-piperidin-4-yl}-1,1-dimethyl-urea, acetic acid {1-[4-(Benzothiazol-2-yloxy)-benzyl]-piperidin-4-ylcarbamoyl}-methyl ester, {1-[4-(Benzothiazol-2-yloxy)-benzyl]-piperidin-4-yl}-thiourea, 2-[4-(2-Morpholin-4-yl-ethoxy)-phenoxy]-benzothiazole; and 2-[4-(2-Piperidin-1-yl-ethoxy)-phenoxy]-benzothiazole and pharmaceutically acceptable salts, prodrugs, and solvates thereof of any of the foregoing compounds.

In some embodiments, the compound of formula (III) is selected from, 1-{2-[4-(1H-Benzoimidazol-2-yloxy)-phenoxy]-ethyl}-4-phenyl-piperidin-4-ol, {2-[4-(1H-Benzoimidazol-2-yloxy)-phenyl]-ethyl}-cyclopropylmethyl-propyl-amine, cyclohexyl-ethyl-{2-[4-(1-methyl-1H-benzoimidazol-2-yloxy)-phenyl]-ethyl}-amine, 1-{2-[4-(1H-Benzoimidazol-2-yloxy)-phenoxy]-ethyl}-4-(4-bromo-phenyl)-piperidin-4-ol, 1-{2-[4-(1H-Benzoimidazol-2-yloxy)-phenoxy]-ethyl}-4-(4-chloro-phenyl)-piperidin-4-ol, 1-{2-[4-(1H-Benzoimidazol-2-yloxy)-phenoxy]-ethyl}-4-benzyl-piperidin-4-ol, {2-[4-(1H-Benzoimidazol-2-yloxy)-phenyl]-ethyl}-cyclohexyl-ethyl-amine, 2-[4-(2-Pyrrolidin-1-yl-ethyl)-phenoxy]-1H-benzoimidazole, 2-[4-(2-Azepan-1-yl-ethyl)-phenoxy]-1H-benzoimidazole, {2-[4-(1H-Benzoimidazol-2-yloxy)-phenyl]-ethyl}-dibutyl-amine, 1-{2-[4-(1H-Benzoimidazol-2-yloxy)-phenyl]-ethyl}-piperidin-4-ol, 1-{2-[4-(1H-Benzoimidazol-2-yloxy)-phenyl]-ethyl}-piperidine-4-carboxylic acid methyl ester, {2-[4-(1H-Benzoimidazol-2-yloxy)-phenoxy]-ethyl}-cyclohexyl-ethyl-amine, 2-{4-[2-(4-Methyl-piperidin-1-yl)-ethoxy]-phenoxy}-1H-benzoimidazole, 2-{4-[2-(2-Ethyl-piperidin-1-yl)-ethoxy]phenoxy}-1H-benzoimidazole, 2-[4-(2-Piperidin-1-yl-ethoxy)-phenoxy]-1H-benzoimidazole, (1-{2-[4-(1H-Benzoimidazol-2-yloxy)-phenoxy]-ethyl}-piperidin-4-yl)-methanol, 1-{2-[4-(1H-Benzoimidazol-2-yloxy)-phenoxy]-ethyl}-piperidin-4-ol, 2-[4-(2-Azepan-1-yl-ethoxy)-phenoxy]-1H-benzoimidazole amide, 3-[4-(1H-Benzoimidazol-2-yloxy)-phenoxy]-propyl}-dimethyl-amine, 2-[4-(2-Pyrrolidin-1-yl-ethoxy)-phenoxy]-1H-benzoimidazole, {2-[4-(1H-Benzoimidazol-2-yloxy)-phenoxy]-ethyl}-diethyl-amine, 2-[4-(2-Morpholin-4-yl-ethoxy)-phenoxy]-1H-benzoimidazole, 2-[4-(2-Piperidin-1-yl-ethyl)-phenoxy]-1H-benzoimidazole, 1-(1-{2-[4-(1H-Benzoimidazol-2-yloxy)-phenoxy]-ethyl}-piperidin-4-yl)-pyrrolidin-2-one, (1-{2-[4-(1H-Benzoimidazol-2-yloxy)-phenoxy]-ethyl}-piperidin-4-yl)-methanol; and 1-{2-[4-(1H-Benzoimidazol-2-yloxy)-phenoxy]-ethyl}-piperidine-4-carboxylic acid ethyl ester and pharmaceutically acceptable salts, prodrugs, and solvates thereof of any of the foregoing compounds.

In certain embodiments, the compound of formula (III) is the compound known as JNJ26993135, which has the following structure:

JNJ26993135

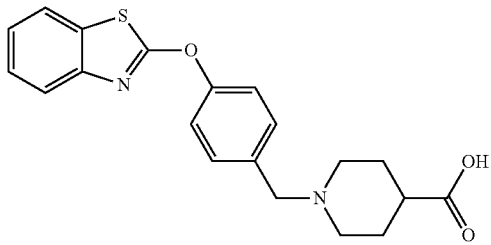

JNJ26993135 analogs and derivatives useful in the methods of the invention include the LTA4H inhibitor compounds described in US Patent Application Publication Nos. 20080194630A1; 20050043379A1 and 20050043378A1, each of which is incorporated herein by reference.

In certain cases, the LTA4H modulatory agent is a heterocyclic compound comprising a thiazolopyridine group. In certain embodiments the LTA4H modulatory agent is described by the formula (IV):

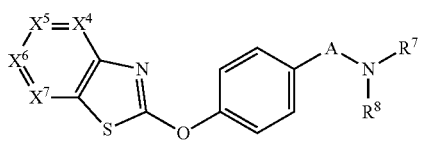

(IV)

where:
$X^4$, $X^5$, $X^6$, and $X^7$ are defined as one of the following a) and b):
a) one of $X^4$, $X^5$, $X^6$ and $X^7$ is N and the others are $CR^a$; where each $R^a$ is independently H, methyl, chloro, fluoro, or trifluoromethyl; and
b) each of $X^4$ and $X^7$ is N and each of $X^5$ and $X^6$ is CH;
each of $R^7$ and $R^8$ is independently H, —$(CH_2)_{2-3}OCH_3$, —$CH_2C(O)NH_2$, —$(CH_2)_3NH_2$, —$(CH_2)_{1-2}CO_2H$, —$CH_2CO_2CH_2CH_3$, benzyl, 3-(2-oxo-pyrrolidin-1-yl)-propyl, 1-acetyl-azetidin-3-ylmethyl, monocyclic cycloalkyl, 1-methyl-4-piperidinyl, or —$C_{1-4}$alkyl unsubstituted or substituted with phenyl, monocyclic cycloalkyl, OH, or $NR^bR^cC$; where $R^b$ and $R^c$ are each independently H, —$C(O)CH_3$, or $C_{1-4}$alkyl, or $R^b$ and $R^c$ taken together with the nitrogen to which they are attached form a saturated monocyclic heterocycloalkyl ring; or $R^7$ and $R^8$ taken together with the nitrogen to which they are attached form:

i) a saturated monocyclic heterocycloalkyl ring, optionally fused to a phenyl ring, and unsubstituted or substituted with one or two $R^d$ substituents; where each $R^d$ substituent is independently $C_{1-4}$alkyl unsubstituted or substituted with —OH; —OH; =O; —$(CH_2)O_{0-2}N(CH_3)_2$; —$CF_3$; halo; —$CO_2C_{1-4}$alkyl; —$(CH_2)O_2CO_2H$; —$C(O)NH_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —$C(O)NR^fC_{1-4}$alkyl; —$C(O)NHC(CH_3)_{0-2}CH_2OH$; —O-pyridinyl; —O-pyrimidinyl; —S-phenyl; (4-methylphenyl)sulfanyl; —S— pyridinyl; —$C(O)$—$C_{1-4}$alkyl; —$C(O)$-saturated monocyclic cycloalkyl; —$C(O)$—$(CH_2)_{0-1}$-2-thiophene-yl; —$C(O)$-2-furanyl; —$C(O)$-4-morpholinyl; —$C(O)$-pyridyl; —$C(O)$-1-pyrrolidinyl; —$C(O)$-phenyl optionally substituted with a chloro; —$C(O)$-1-piperazinyl optionally substituted with $C_{1-4}$alkyl; —$(CH_2)_{0-1}NHC(O)$—$C_{1-4}$alkyl; —NHC(O)-saturated monocyclic cycloalkyl; —$NHS(O)(O)CH_3$; —NHC(O)—$CH_2OCH_3$; —NHC(O)-pyridinyl; or —NHC(O)-2-thiophene-yl, where each phenyl in $R^d$ is unsubstituted or substituted with —$CF_3$, halo, or methoxy; or ii) one of the following moieties:

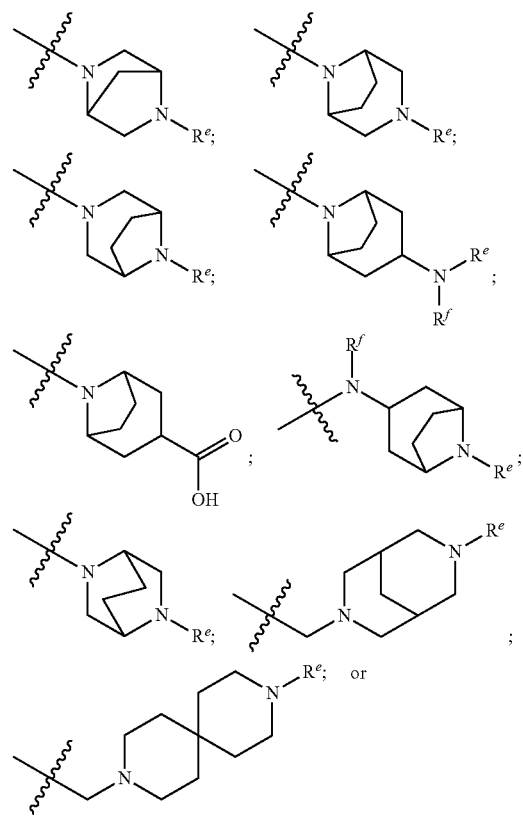

-continued

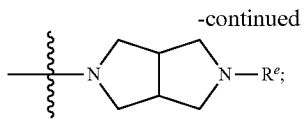

where $R^e$ is —$C_{1-4}$alkyl, C(O)$C_{1-4}$alkyl, —SO$_2$CH$_3$, —C(O)CH$_2$NH$_2$, or C(O)NH$_2$; $R^f$ is H or —CH$_3$; and A is —CH$_2$—, —CH$_2$CH$_2$—, or —OCH$_2$CH$_2$—.

In some embodiments, the compound of formula (IV) is selected from, 2-(4-{2-[4-(Pyrimidin-2-yloxy)piperidin-1-yl]ethoxy}phenoxy)[1,3]thiazolo[4,5-b]pyridine, 2-{4-[2-(1,3-Dihydro-2H-isoindol-2-yl)ethoxy]phenoxy}[1,3]thiazolo[4,5-b]pyridine, 2-(4-{2-[4-(Phenylsulfanyl)piperidin-1-yl]ethoxy}phenoxy)[1,3]thiazolo[4,5-b]pyridine, 2-(4-{2-[4-(Pyridin-3-yloxy)piperidin-1-yl]ethoxy}phenoxy)[1,3]thiazolo[4,5-b]pyridine, 4-Pyridin-2-yl-1-{2-[4-([1,3]thiazolo[4,5-b]pyridin-2-yloxy)phenoxy]ethyl}piperidin-4-ol, 2-{2-[4-([1,3]Thiazolo[4,5-b]pyridin-2-yloxy)phenoxy]ethyl}-1,2,3,4-tetrahydroisoquinoline, 1-{2-[4-([1,3]Thiazolo[4,5-b]pyridin-2-yloxy)phenoxy]ethyl}-1,2,3,4-tetrahydroquinoline, 2-{4-[2-(4-Phenoxypiperidin-1-yl)ethoxy]phenoxy}[1,3]thiazolo[4,5-b]pyridine, 2-[4-(2-Pyrrolidin-1-ylethoxy)phenoxy][1,3]thiazolo[4,5-b]pyridine, 2-[4-(2-Piperidin-1-ylethoxy)phenoxy][1,3]thiazolo[4,5-b]pyridine, 2-[4-(2-Morpholin-4-ylethoxy)phenoxy][1,3]thiazolo[4,5-b]pyridine, 2-(4-{2-[4-(Pyridin-2-yloxy)piperidin-1-yl]ethoxy}phenoxy)[1,3]thiazolo[4,5-b]pyridine, 2-(4-{2-[4-(Pyridin-4-yloxy)piperidin-1-yl]ethoxy}phenoxy)[1,3]thiazolo[4,5-b]pyridine, 2-(4-{2-[(1S,4S)-5-Acetyl-2,5-diazabicyclo[2.2.1]hept-2-yl]ethoxy}phenoxy)[1,3]thiazolo[4,5-b]pyridine, (1S,4S)-5-{2-[4-([1,3]Thiazolo[4,5-b]pyridin-2-yloxy)phenoxy]ethyl}-2,5-diazabicyclo[2.2.1]heptane-2-carboxamide, meso-N-[(3-endo)-8-{2-[4-([1,3]Thiazolo[4,5-b]pyridin-2-yloxy)phenoxy]ethyl}-8-azabicyclo[3.2.1]oct-3-yl]acetamide, meso-N-[(3-exo)-8-{2-[4-([1,3]Thiazolo[4,5-b]pyridin-2-yloxy)phenoxy]ethyl}-8-azabicyclo[3.2.1]oct-3-yl]acetamide, 2-{4-[2-(5-Acetylhexahydropyrrolo[3,4-c]pyrrol-2(1H)-yl)ethoxy]phenoxy}[1,3]thiazolo[4,5-b]pyridine, 5-{2-[4-([1,3]thiazolo[4,5-b]pyridin-2-yloxy)phenoxy]ethyl}hexahydropyrrolo[3,4-c]pyrrole-2(1H)-carboxamide, 4-Phenyl-1-{2-[4-([1,3]thiazolo[4,5-b]pyridin-2-yloxy)phenoxy]ethyl}piperidin-4-ol, 2-{4-[2-(4-Benzylpiperidin-1-yl)ethoxy]phenoxy}[1,3]thiazolo[4,5-b]pyridine, 2-{4-[2-(4-Pyridin-4-ylpiperidin-1-yl)ethoxy]phenoxy}[1,3]thiazolo[4,5-b]pyridine, 4-(4-Chlorophenyl)-1-{2-[4-([1,3]thiazolo[4,5-b]pyridin-2-yloxy)phenoxy]ethyl}piperidin-4-ol, 1-{2-[4-([1,3]Thiazolo[4,5-b]pyridin-2-yloxy)phenoxy]ethyl}piperidine-4-carboxamide, 1-(1-{2-[4-([1,3]Thiazolo[4,5-b]pyridin-2-yloxy)phenoxy]ethyl}piperidin-4-yl)pyrrolidin-2-one, 1-{2-[4-([1,3]Thiazolo[4,5-b]pyridin-2-yloxy)phenoxy]ethyl}-4-[3-(trifluoromethyl)phenyl]piperidin-4-ol, 2-{4-[2-(4-Pyridin-2-ylpiperidin-1-yl)ethoxy]phenoxy}[1,3]thiazolo[4,5-b]pyridine, N-Benzyl-N-methyl-2-[4-([1,3]thiazolo[4,5-b]pyridin-2-yloxy)phenoxy]ethanamine, (1S,4S)-5-{2-[4-([1,3]Thiazolo[4,5-b]pyridin-2-yloxy)phenyl]ethyl}-2,5-diazabicyclo[2.2.1]heptane-2-carboxamide, 1-(1-{2-[4-([1,3]Thiazolo[4,5-b]pyridin-2-yloxy)phenyl]ethyl}piperidin-4-yl)pyrrolidin-2-one, 4-(4-Chlorophenyl)-1-{2-[4-([1,3]thiazolo[4,5-b]pyridin-2-yloxy)phenyl]ethyl}piperidin-4-ol, 2-{4-[2-(4-Pyridin-2-ylpiperidin-1-yl)ethyl]phenoxy}[1,3]thiazolo[4,5-b]pyridine, meso-N-[(3-endo)-8-{2-[4-([1,3]Thiazolo[4,5-b]pyridin-2-yloxy)phenyl]ethyl}-8-azabicyclo[3.2.1]oct-3yl]acetamide, meso-1-[(3-exo)-8-{2-[4-([1,3]Thiazolo[4,5-b]pyridin-2-yloxy)phenyl]ethyl}-8-azabicyclo[3.2.1]oct-3-yl]urea, meso-8-{2-[4-([1,3]Thiazolo[4,5-b]pyridin-2-yloxy)phenyl]ethyl}-3,8-diazabicyclo[3.2.1]octane-3-carboxamide, meso-2-(4-{2-[3-Acetyl-3,8-diazabicyclo[3.2.1]oct-8-yl]ethyl}phenoxy)[1,3]thiazolo[4,5-b]pyridine, 2-(Ethyl{2-[4-([1,3]thiazolo[4,5-b]pyridin-2-yloxy)phenyl]ethyl}amino)ethanol, N-(Cyclopropylmethyl)-N-{2-[4-([1,3]thiazolo[4,5-b]pyridin-2-yloxy)phenyl]ethyl}propan-1-amine, (1R)—N-Methyl-1-phenyl-N-{2-[4-([1,3]thiazolo[4,5-b]pyridin-2-yloxy)phenyl]ethyl}ethanamine, 2-[4-(2-Morpholin-4-ylethyl)phenoxy][1,3]thiazolo[4,5-b]pyridine, 2-[4-(2-Piperidin-1-ylethyl)phenoxy][1,3]thiazolo[4,5-b]pyridine, 2-[4-(2-Pyrrolidin-1-ylethyl)phenoxy][1,3]thiazolo[4,5-b]pyridine, 4-Phenyl-1-{2-[4-([1,3]thiazolo[4,5-b]pyridin-2-yloxy)phenyl]ethyl}piperidin-4-ol, 2-{4-[2-(4-Benzylpiperidin-1-yl)ethyl]phenoxy}[1,3]thiazolo[4,5-b]pyridine, 1-{2-[4-([1,3]Thiazolo[4,5-b]pyridin-2-yloxy)phenyl]ethyl}-4-[3-(trifluoromethyl)phenyl]piperidin-4-ol, 2-{4-[2-(4-Pyridin-4-ylpiperidin-1-yl)ethyl]phenoxy}[1,3]thiazolo[4,5-b]pyridine, 1-{2-[4-([1,3]Thiazolo[4,5-b]pyridin-2-yloxy)phenyl]ethyl}piperidine-4-carboxamide, 2-{4-[2-(5-Acetylhexahydropyrrolo[3,4-c]pyrrol-2(1H)-yl)ethyl]phenoxy}[1,3]thiazolo[4,5-b]pyridine, 5-{2-[4-([1,3]Thiazolo[4,5-b]pyridin-2-yloxy)phenyl]ethyl}hexahydropyrrolo[3,4-c]pyrrole-2(1H)-carboxamide, 2-(4-{2-[(1S,4S)-5-Acetyl-2,5-diazabicyclo[2.2.1]hept-2-yl]ethyl}phenoxy)[1,3]thiazolo[4,5-b]pyridine, meso-N-[(3-endo)-8-{2-[4-([1,3]Thiazolo[4,5-b]pyridin-2-yloxy)phenyl]ethyl}-8-azabicyclo[3.2.1]oct-3-yl]acetamide, meso-1-[(3-endo)-8-{2-[4-([1,3]Thiazolo[4,5-b]pyridin-2-yloxy)phenyl]ethyl}-8-azabicyclo[3.2.1]oct-3-yl]urea, 2-(4-{2-[(1R,4R)-5-Acetyl-2,5-diazabicyclo[2.2.1]hept-2-yl]ethyl}phenoxy)[1,3]thiazolo[4,5-b]pyridine, (1R,4R)-5-{2-[4-([1,3]Thiazolo[4,5-b]pyridin-2-yloxy)phenyl]ethyl}-2,5-diazabicyclo[2.2.1]heptane-2-carboxamide, 1-{2-[4-([1,3]Thiazolo[4,5-b]pyridin-2-yloxy)phenyl]ethyl}piperidine-4-carboxylic acid, {-4-[([1,3]Thiazolo[4,5-b]pyridin-2-yloxy)benzyl]morpholin-2-yl}methanol, 1-{1-[4-([1,3]Thiazolo[4,5-b]pyridin-2-yloxy)benzyl]piperidin-4-yl}pyrrolidin-2-one, 2-[4-(Pyrrolidin-1-ylmethyl)phenoxy][1,3]thiazolo[4,5-b]pyridine, 2-[4-(Piperidin-1-ylmethyl)phenoxy][1,3]thiazolo[4,5-b]pyridine, 2-[4-(Morpholin-4-ylmethyl)phenoxy][1,3]thiazolo[4,5-b]pyridine, 2-(4-{[(3R)-3-Fluoropyrrolidin-1-yl]methyl}phenoxy)[1,3]thiazolo[4,5-b]pyridine, 2-(4-{[(3S)-3-Methylmorpholin-4-yl]methyl}phenoxy)[1,3]thiazolo[4,5-b]pyridine, 2-{1-[4-([1,3]Thiazolo[4,5-b]pyridin-2-yloxy)benzyl]piperidin-4-yl}propan-2-ol, 2-(4-{[(2S)-2-Methylpiperidin-1-yl]methyl}phenoxy)[1,3]thiazolo[4,5-b]pyridine, 2-Piperidin-1-yl-N-[4-([1,3]thiazolo[4,5-b]pyridin-2-yloxy)benzyl]ethanamine, 2-(4-{[4-(Trifluoromethyl)piperidin-1-yl]methyl}phenoxy)[1,3]thiazolo[4,5-b]pyridine, 2-{4-[(3,3-Difluoropyrrolidin-1-yl)methyl]phenoxy}[1,3]thiazolo[4,5-b]pyridine, (3R)-1-[4-([1,3]Thiazolo[4,5-b]pyridin-2-yloxy)benzyl]pyrrolidin-3-ol, {1-[4-([1,3]Thiazolo[4,5-b]pyridin-2-yloxy)benzyl]piperidin-4-yl}methanol, 2-{4-[(4-Fluoropiperidin-1-yl)methyl]phenoxy}[1,3]thiazolo[4,5-b]pyridine, 2-{4-[(4-Methylpiperidin-1-yl)methyl]phenoxy}[1,3]thiazolo[4,5-b]pyridine, 2-(4-{[4-(Pyridin-3-yloxy)piperidin-1-yl]methyl}phenoxy)[1,3]thiazolo[4,5-b]pyridine, 2-(4-{[4-(Pyrimidin-2-yloxy)piperidin-1-yl]methyl}phenoxy)[1,3]thiazolo[4,5-b]pyridine, 1-[4-([1,3]Thiazolo[4,5-b]pyridin-2-yloxy)benzyl]piperidine-4-carboxamide, 4-Pyridin-2-yl-1-[4-([1,3]thiazolo[4,5-b]pyridin-2-yloxy)benzyl]piperidin-4-ol, 2-{4-[(4-Benzylpiperidin-1-yl)methyl]phenoxy}[13]thiazolo[4,5-b]

pyridine, 1-[4-([1,3]Thiazolo[4,5-b]pyridin-2-yloxy)benzyl]-4-[3-(trifluoromethyl)phenyl]piperidin-4-ol, 4-(4-Chlorophenyl)-1-[4-([1,3]thiazolo[4,5-b]pyridin-2-yloxy)benzyl]piperidin-4-ol, 4-Phenyl-1-[4-([1,3]thiazolo[4,5-b]pyridin-2-yloxy)benzyl]piperidin-4-ol, (1S,4S)-5-[4-([1,3]Thiazolo[4,5-b]pyridin-2-yloxy)benzyl]-2,5-diazabicyclo[2.2.1]heptane-2-carboxamide, meso-2-(4-{[3-Acetyl-3,8-diazabicyclo[3.2.1]oct-8-yl]methyl}phenoxy)[1,3]thiazolo[4,5-b]pyridine, {(2S)-1-[4-([1,3]Thiazolo[4,5-b]pyridin-2-yloxy)benzyl]pyrrolidin-2-yl}methanol, meso-N-{(3-exo)-8-[4-([1,3]Thiazolo[4,5-b]pyridin-2-yloxy)benzyl]-8-azabicyclo[3.2.1]oct-3-yl}acetamide, meso-1-{(3-exo)-8-[4-([1,3]Thiazolo[4,5-b]pyridin-2-yloxy)benzyl]-8-azabicyclo[3.2.1]oct-3-yl}urea, N-Ethyl-N-[4-([1,3]thiazolo[4,5-b]pyridin-2-yloxy)benzyl]ethanamine, meso-N-{(3-endo)-8-[4-([1,3]Thiazolo[4,5-b]pyridin-2-yloxy)benzyl]-8-azabicyclo[3.2.1]oct-3-yl}acetamide, meso-8-[4-([1,3]Thiazolo[4,5-b]pyridin-2-yloxy)benzyl]-3,8-diazabicyclo[3.2.1]octane-3-carboxamide, 2-(4-{[(1S,4S)-5-Acetyl-2,5-diazabicyclo[2.2.1]hept-2-yl]methyl}phenoxy)-6-methyl[1,3]thiazolo[4,5-b]pyridine, 2-(4-{[(1S,4S)-5-Acetyl-2,5-diazabicyclo[2.2.1]hept-2-yl]methyl}phenoxy)-6-chloro[1,3]thiazolo[4,5-b]pyridine, 2-(4-{[(1S,4S)-5-Acetyl-2,5-diazabicyclo[2.2.1]hept-2-yl]methyl}phenoxy)-7-methyl[1,3]thiazolo[4,5-b]pyridine, 2-(4-{[(1S,4S)-5-Acetyl-2,5-diazabicyclo[2.2.1]hept-2-yl]methyl}phenoxy)-5-methyl[1,3]thiazolo[4,5-b]pyridine, 1-{(1S,4S)-5-[4-([1,3]Thiazolo[4,5-b]pyridin-2-yloxy)benzyl]-2,5-diazabicyclo[2.2.1]hept-2-yl}ethenone, 2-(4-{[(1S,4S)-5-Acetyl-2,5-diazabicyclo[2.2.1]hept-2-yl]methyl}phenoxy)-6-fluoro[1,3]thiazolo[4,5-b]pyridine, 6-Fluoro-2-[4-(piperidin-1-ylmethyl)phenoxy][1,3]thiazolo[4,5-b]pyridine, Ethyl 1-[4-([1,3]thiazolo[4,5-b]pyridin-2-yloxy)benzyl]piperidine-4-carboxylate, 1-[4-([1,3]Thiazolo[4,5-b]pyridin-2-yloxy)benzyl]piperidine-4-carboxylic acid, 2-(4-{2-[4-(2-Methoxyphenyl)piperazin-1-yl]ethoxy}phenoxy)[1,3]thiazolo[4,5-b]pyridine, 2-[4-(2-{4-[(4-Chlorophenyl)sulfanyl]piperidin-1-yl}ethoxy)phenoxy][1,3]thiazolo[4,5-b]pyridine, 1-[4-([1,3]Thiazolo[4,5-b]pyridin-2-yloxy)benzyl]piperidin-4-ol, 7-Methyl-2-[4-(piperidin-1-ylmethyl)phenoxy][1,3]thiazolo[4,5-b]pyridine, N-{2-[4-([1,3]Thiazolo[4,5-b]pyridin-2-yloxy)phenoxy]ethyl}cyclopropanamine, 2-Methyl-N-[1-(2-{4-[(6-methyl[1,3]thiazolo[4,5-b]pyridin-2-yl)oxy]phenoxy}ethyl)piperidin-4-yl]propenamide, meso-2-{4-[2-(3-Acetyl-3,8-diazabicyclo[3.2.1]oct-8-yl)ethoxy]phenoxy}[1,3]thiazolo[4,5-b]pyridine, meso-1-[(3-exo)-8-{2-[4-([1,3]Thiazolo[4,5-b]pyridin-2-yloxy)phenoxy]ethyl}-8-azabicyclo[3.2.1]oct-3-yl]urea, 7-Methyl-2-(4-{2-[4-(pyridin-4-ylcarbonyl)piperazin-1-yl]ethoxy}phenoxy)[1,3]thiazolo[4,5-b]pyridine, 6-Methyl-2-(4-{2-[4-(morpholin-4-ylcarbonyl)piperidin-1-yl]ethoxy}phenoxy)[1,3]thiazolo[4,5-b]pyridine, 2-(4-{2-[5-(Cyclobutylcarbonyl)hexahydropyrrolo[3,4-c]pyrrol-2(1H)-yl]ethoxy}phenoxy)-7-methyl[1,3]thiazolo[4,5-b]pyridine, 6-Chloro-2-(4-{2-[4-(furan-2-ylcarbonyl)piperazin-1-yl]ethoxy}phenoxy)[1,3]thiazolo[4,5-b]pyridine, meso-3-{2-[4-([1,3]Thiazolo[4,5-b]pyridin-2-yloxy)phenoxy]ethyl}-3,8-diazabicyclo[3.2.1]octane-8-carboxamide, N-[1-(2-{4-[(6-Methyl[1,3]thiazolo[4,5-b]pyridin-2-yl)oxy]phenoxy}ethyl)piperidin-4-yl]acetamide, 1-{3-[(2-{4-[(6-Chloro[1,3]thiazolo[4,5-b]pyridin-2-yl)oxy]phenoxy}ethyl)(methyl)amino]propyl}pyrrolidin-2-one, 1-(2-{4-[(7-Methyl[1,3]thiazolo[4,5-b]pyridin-2-yl)oxy]phenoxy}ethyl)-4-pyridin-2-ylpiperidin-4-ol, meso-(3-endo)-8-acetyl-N-{2-[4-([1,3]thiazolo[4,5-b]pyridin-2-yloxy)phenoxy]ethyl}-8-azabicyclo[3.2.1]octan-3-amine, N-Methyl-2-(methyloxy)-N-[2-({4-[(7-methyl[1,3]thiazolo[4,5-b]pyridin-2-yl)oxy]phenyl}oxy)ethyl]ethanamine, meso-2-{[4-({2-[8-Acetyl-3,8-diazabicyclo[3.2.1]oct-3-yl]ethyl}oxy)phenyl]oxy}[1,3]thiazolo[4,5-b]pyridine, N-1-(2-{[4-[1,3]Thiazolo[4,5-b]pyridin-2-yloxy)phenyl]oxy}ethyl)piperidin-4-yl]methanesulfonamide, N-Methyl-1-[2-({4-[(7-methyl[1,3]thiazolo[4,5-b]pyridin-2-yl)oxy]phenyl}oxy)ethyl]piperidine-4-carboxamide, meso-N-{(3-endo)-8-[2-({4-[(7-Methyl[1,3]thiazolo[4,5-b]pyridin-2-yl)oxy]phenyl}oxy)ethyl]-8-azabicyclo[3.2.1]oct-3-yl}glycinamide, meso-3-{[4-([1,3]Thiazolo[4,5-b]pyridin-2-yloxy)phenyl]methyl}-3,8-diazabicyclo[3.2.1]octane-8-carboxamide, N,N-Dimethyl-1-({4-[(6-methyl[1,3]thiazolo[4,5-b]pyridin-2-yl)oxy]phenyl}methyl)piperidine-4-carboxamide, N-Ethyl-N-(2-{4-[(6-methyl[1,3]thiazolo[4,5-b]pyridin-2-yl)oxy]phenyl}ethyl)butan-1-amine, meso-(3-exo)-8-Acetyl-N-({4-[(6-methyl[1,3]thiazolo[4,5-b]pyridin-2-yl)oxy]phenyl}methyl)-8-azabicyclo[3.2.1]octan-3-amine, meso-N-[(3-endo)-8-{[4-([1,3]Thiazolo[4,5-b]pyridin-2-yloxy)phenyl]methyl}-8-azabicyclo[3.2.1]oct-3-yl]methanesulfonamide, 2-({4-[(4-Cyclobutylpiperazin-1-yl)methyl]phenyl}oxy)-6-methyl[1,3]thiazolo[4,5-b]pyridine, meso-2-[(4-{[8-Acetyl-3,8-diazabicyclo[3.2.1]oct-3-yl]methyl}phenyl)oxy][1,3]thiazolo[4,5-b]pyridine, 6-Chloro-2-[(4-{[4-(2-thienylcarbonyl)piperazin-1-yl]methyl}phenyl)oxy][1,3]thiazolo[4,5-b]pyridine, 6-Chloro-2-[(4-{[5-(methylsulfonyl)hexahydropyrrolo[3,4-c]pyrrol-2(1H)-yl]methyl}phenyl)oxy][1,3]thiazolo[4,5-b]pyridine, 6-Chloro-2-{[4-(thiomorpholin-4-ylmethyl)phenyl]oxy}[1,3]thiazolo[4,5-b]pyridine, (1R,4R)-5-({4-[(6-Chloro[1,3]thiazolo[4,5-b]pyridin-2-yl)oxy]phenyl}methyl)-2,5-diazabicyclo[2.2.1]heptane-2-carboxamide, (1S,4S)-5-({4-[(6-Chloro[1,3]thiazolo[4,5-b]pyridin-2-yl)oxy]phenyl}methyl)-2,5-diazabicyclo[2.2.1]heptane-2-carboxamide, 6-Chloro-2-[(4-{2-[4-(cyclopropylcarbonyl)piperazin-1-yl]ethyl}phenyl)oxy][1,3]thiazolo[4,5-b]pyridine, 6-Methyl-2-[(4-{2-[4-(pyrrolidin-1-ylcarbonyl)piperidin-1-yl]ethyl}phenyl)oxy][1,3]thiazolo[4,5-b]pyridine, meso-3-{4-[(7-Methyl[1,3]thiazolo[4,5-b]pyridin-2-yl)oxy]benzyl}-3,8-diazabicyclo[3.2.1]octane-8-carboxamide, meso-7-Methyl-2-(4-{[3-(methylsulfonyl)-3,8-diazabicyclo[3.2.1]oct-8-yl]methyl}phenoxy)[1,3]thiazolo[4,5-b]pyridine, N-(1-{4-[(7-Methyl[1,3]thiazolo[4,5-b]pyridin-2-yl)oxy]benzyl}piperidin-4-yl)pyridine-4-carboxamide, meso-2-(4-{2-[8-Acetyl-3,8-diazabicyclo[3.2.1]oct-3-yl]ethyl}phenoxy)-7-methyl[1,3]thiazolo[4,5-b]pyridine, meso-3-{2-[4-([1,3]Thiazolo[4,5-b]pyridin-2-yloxy)phenyl]ethyl}-3,8-diazabicyclo[3.2.1]octane-8-carboxamide, meso-8-{2-[4-([1,3]Thiazolo[4,5-b]pyridin-2-yloxy)phenoxy]ethyl}-3,8-diazabicyclo[3.2.1]octane-3-carboxamide, meso-2-(4-{2-[8-Acetyl-3,8-diazabicyclo[3.2.1]oct-3-yl]ethyl}phenoxy)[1,3]thiazolo[4,5-b]pyridine, meso-2-(4-{2-[3-(Methylsulfonyl)-3,8-diazabicyclo[3.2.1]oct-8-yl]ethoxy}phenoxy)[1,3]thiazolo[4,5-b]pyridine, meso-(3-exo)-8-Acetyl-N-{2-[4-([1,3]thiazolo[4,5-b]pyridin-2-yloxy)phenyl]ethyl}-8-azabicyclo[3.2.1]octan-3-amine, meso-(3-exo)-8-Acetyl-N-{2-[4-([1,3]thiazolo[4,5-b]pyridin-2-yloxy)phenoxy]ethyl}-8-azabicyclo[3.2.1]octan-3-amine, 2-Methoxy-N-(1-{4-[(6-methyl[1,3]thiazolo[4,5-b]pyridin-2-yl)oxy]benzyl}piperidin-4-yl)acetamide, 2-{4-[(4-tert-Butylpiperidin-1-yl)methyl]phenoxy}-6-chloro[1,3]thiazolo[4,5-b]pyridine, N-(1-{4-[(6-Methyl[1,3]thiazolo[4,5-b]pyridin-2-yl)oxy]benzyl}piperidin-4-yl)thiophene-2-carboxamide, 1'-(2-{4-[(6-Chloro[1,3]thiazolo[4,5-b]pyridin-2-yl)oxy]phenyl}ethyl)-1,4'-bipiperidine, 3-(4-{2-[4-([1,3]Thiazolo[4,5-b]pyridin-2-yloxy)phenyl]ethyl}piperazin-1-yl)propanoic acid, 6-Methyl-2-(4-{[4-

(piperazin-1-ylcarbonyl)piperidin-1-yl]methyl}phenoxy)[1,3]thiazolo[4,5-b]pyridine, meso-3-(2-{4-[(6-Methyl[1,3]thiazolo[4,5-b]pyridin-2-yl)oxy]phenyl}ethyl)-3,8-diazabicyclo[3.2.1]octane-8-carboxamide, meso-(3-exo)-8-Acetyl-N-(2-{4-[(6-methyl[1,3]thiazolo[4,5-b]pyridin-2-yl)oxy]phenyl}ethyl)-8-azabicyclo[3.2.1]octan-3-amine, meso-(3-exo)-8-Acetyl-N-methyl-N-(2-{4-[(6-methyl[1,3]thiazolo[4,5-b]pyridin-2-yl)oxy]phenyl}ethyl)-8-azabicyclo[3.2.1]octan-3-amine, N2-(2-{4-[(6-Chloro[1,3]thiazolo[4,5-b]pyridin-2-yl)oxy]phenyl}ethyl)-N2-methylglycinamide, meso-8-[4-([1,3]Thiazolo[4,5-b]pyridin-2-yloxy)benzyl]-8-azabicyclo[3.2.1]octane-3-carboxylic acid, 6-Chloro-2-(4-{2-[5-(1-methylethyl)hexahydropyrrolo[3,4-c]pyrrol-2(1H)-yl]ethoxy}phenoxy)[1,3]thiazolo[4,5-b]pyridine, N-Methyl-N-(2-{4-[(6-methyl[1,3]thiazolo[4,5-b]pyridin-2-yl)oxy]phenoxy}ethyl)-beta-alanine, N-(2-{4-[(6-Chloro[1,3]thiazolo[4,5-b]pyridin-2-yl)oxy]phenyl}ethyl)-N,1-dimethylpiperidin-4-amine, 6-Methyl-2-{4-[2-(4-pyridin-2-ylpiperidin-1-yl)ethyl]phenoxy}[1,3]thiazolo[4,5-b]pyridine, 1-(1-Acetylazetidin-3-yl)-N-{4-[(6-chloro[1,3]thiazolo[4,5-b]pyridin-2-yl)oxy]benzyl}-N-methylmethanamine, meso-(3-exo)-3-{[4-([1,3]Thiazolo[4,5-b]pyridin-2-yloxy)benzyl]amino-8-azabicyclo[3.2.1]octane-8-carboxamide, 2-[4-(2-{4-[(4-Methylphenyl)sulfanyl]piperidin-1-yl}ethoxy)phenoxy][1,3]thiazolo[4,5-b]pyridine, 1'-[4-([1,3]Thiazolo[4,5-b]pyridin-2-yloxy)benzyl]-1,4'-bipiperidine, 2-{4-[(4-Morpholin-4-ylpiperidin-1-yl)methyl]phenoxy}[1,3]thiazolo[4,5-b]pyridine, N,N-Dimethyl-2-{1-[4-([1,3]thiazolo[4,5-b]pyridin-2-yloxy)benzyl]piperidin-2-yl}ethanamine, N,N-Dimethyl-1-[4-([1,3]thiazolo[4,5-b]pyridin-2-yloxy)benzyl]piperidin-4-amine, 2-{4-[(4-Phenoxypiperidin-1-yl)methyl]phenoxy}[1,3]thiazolo[4,5-b]pyridine, 2-(4-{[4-(Pyridin-2-yloxy)piperidin-1-yl]methyl}phenoxy)[1,3]thiazolo[4,5-b]pyridine, 2-(4-{[4-(Pyridin-4-yloxy)piperidin-1-yl]methyl}phenoxy)[1,3]thiazolo[4,5-b]pyridine, 2-(4-{[4-(Pyridin-2-ylsulfanyl)piperidin-1-yl]methyl}phenoxy)[1,3]thiazolo[4,5-b]pyridine, 2-(4-{[4-(Phenylsulfanyl)piperidin-1-yl]methyl}phenoxy)[1,3]thiazolo[4,5-b]pyridine, 2-(4-{[(1R,4R)-5-Acetyl-2,5-diazabicyclo[2.2.1]hept-2-yl]methyl}phenoxy)[1,3]thiazolo[4,5-b]pyridine, (1R,4R)-5-[4-([1,3]Thiazolo[4,5-b]pyridin-2-yloxy)benzyl]-2,5-diazabicyclo[2.2.1]heptane-2-carboxamide, 2-(4-{2-[(1R,4R)-5-Acetyl-2,5-diazabicyclo[2.2.1]hept-2-yl]ethoxy}phenoxy)[1,3]thiazolo[4,5-b]pyridine, (1R,4R)-5-{2-[4-([1,3]Thiazolo[4,5-b]pyridin-2-yloxy)phenoxy]ethyl}-2,5-diazabicyclo[2.2.1]heptane-2-carboxamide, (4R)-4-Hydroxy-1-{1-[4-([1,3]thiazolo[4,5-b]pyridin-2-yloxy)benzyl]piperidin-4-yl}pyrrolidin-2-one, (4R)-4-Hydroxy-1-{1-[4-([1,3]thiazolo[4,5-b]pyridin-2-yloxy)phenoxy]ethyl}piperidin-4-yl)pyrrolidin-2-one, N-Methyl-2-piperidin-1-yl-N-[4-([1,3]thiazolo[4,5-b]pyridin-2-yloxy)benzyl]ethanamine, N-(3-Methoxypropyl)-N-{2-[4-([1,3]thiazolo[4,5-b]pyridin-2yloxy)phenoxy]ethyl}cyclopropanamine, ethyl N-benzyl-N-[4-([1,3]thiazolo[4,5-b]pyridin-2-yloxy)benzyl]glycinate, N-Benzyl-N-[4-([1,3]thiazolo[4,5-b]pyridin-2-yloxy)benzyl]glycine, N-[4-([1,3]Thiazolo[4,5-b]pyridin-2-yloxy)benzyl]-beta-alanine, 2-{4-[(5-Acetylhexahydropyrrolo[3,4-c]pyrrol-2(1H)-yl)methyl]phenoxy}[1,3]thiazolo[4,5-b]pyridine, 5-[4-([1,3]Thiazolo[4,5-b]pyridin-2-yloxy)benzyl]hexahydropyrrolo[3,4-c]pyrrole-2(1H)-carboxamide, meso-1-{(3-endo)-8-[4-([1,3]Thiazolo[4,5-b]pyridin-2-yloxy)benzyl]-8-azabicyclo[3.2.1]oct-3-yl}urea, 6-Chloro-2-(4-piperidin-1-ylmethyl-phenyl) [1,3]thiazolo[4,5-b]pyridine, 1-{[(7-Methyl[1,3]thiazolo[4,5-b]pyridin-2-yl)oxy]benzyl}piperidine-4-carboxamide, 1-{4-[(6-Fluoro[1,3]thiazolo[4,5-b]pyridin-2-yl)oxy]benzyl}piperidine-4-carboxamide, 1-{4-[(6-Chloro[1,3]thiazolo[4,5-b]pyridin-2-yl)oxy]benzyl}piperidine-4-carboxamide, meso-endo-N-[8-{4-[(6-Chloro[1,3]thiazolo[4,5-b]pyridin-2-yl)oxy]benzyl}-8-azabicyclo[3.2.1]oct-3-yl]acetamide, meso-endo-N-[8-{4-[(6-Fluoro[1,3]thiazolo[4,5-b]pyridin-2-yl)oxy]benzyl}-8-azabicyclo[3.2.1]oct-3-yl]acetamide, meso-endo-N-[8-{4-[(7-Methyl[1,3]thiazolo[4,5-b]pyridin-2-yl)oxy]benzyl}-8-azabicyclo[3.2.1]oct-3-yl]acetamide, 2-(4-{[(1S,4S)-5-Acetyl-2,5-diazabicyclo[2.2.2]oct-2-yl]methyl}phenoxy)[1,3]thiazolo[4,5-b]pyridine, meso-N-{(3-endo)-8-[4-([1,3]Thiazolo[4,5-b]pyridin-2-ylmethyl)benzyl]-8-azabicyclo[3.2.1]oct-3-yl}acetamide, 2-(4-{[(1S,4S)-5-Acetyl-2,5-diazabicyclo[2.2.1]hept-2-yl]methyl}benzyl)[1,3]thiazolo[4,5-b]pyridine, meso-N-[(3-endo)-8-{2-[4-([,3]Thiazolo[4,5-b]pyridin-2-ylmethyl)phenoxy]ethyl}-8-azabicyclo[3.2.1]oct-3-yl]acetamide, 2-(4-{2-[(1S,4S)-5-Acetyl-2,5-diazabicyclo[2.2.1]hept-2-yl]ethoxy}benzyl)[1,3]thiazolo[4,5-b]pyridine, 2-[4-(Piperidin-1-ylmethyl)phenoxy][1,3]thiazolo[4,5-c]pyridine, meso-N-{(3-endo)-8-[4-([1,3]Thiazolo[4,5-c]pyridin-2-yloxy)benzyl]-8-azabicyclo[3.2.1]oct-3-yl}acetamide, N-(2-Hydroxy-1,1-dimethylethyl)-1-(2-{4-([1,3]thiazolo[4,5-c]pyridin-2-yloxy)phenyl]oxy}ethyl)piperidine-4-carboxamide, 2-{[4-({2-[4-(Trifluoromethyl)piperidin-1-yl]ethyl}oxy)phenyl]oxy}[1,3]thiazolo[4,5-c]pyridine, N-(Cyclopropylmethyl)-N-{[4-([1,3]thiazolo[4,5-c]pyridin-2-yloxy)phenyl]methyl}propan-1-amine, 2-({4-[(4-Pyridin-4-ylpiperidin-1-yl)methyl]phenyl}oxy)[1,3]thiazolo[4,5-c]pyridine, N-{1-[4-([1,3]Thiazolo[5,4-c]pyridin-2-yloxy)phenyl]ethyl}piperidin-4-yl)cyclopropanecarboxamide, (4-Chlorophenyl)(1-{2-[4-([1,3]thiazolo[4,5-c]pyridin-2-yloxy)phenyl]ethyl}piperidin-4-yl)methanone, N-Propyl-N-{2-[4-([1,3]thiazolo[4,5-c]pyridin-2-yloxy)phenyl]ethyl}propan-1-amine, meso-3-[4-([1,3]Thiazolo[4,5-c]pyridin-2-yloxy)benzyl]-3,8-diazabicyclo[3.2.1]octane-8-carboxamide, 2-[4-(2-Pyrrolidin-1-ylethyl)phenoxy][1,3]thiazolo[4,5-c]pyridine, 1-Methyl-4-[4-([1,3]thiazolo[4,5-c]pyridin-2-yloxy)benzyl]piperazin-2-one, meso-(3-exo)-8-Acetyl-N-[4-([1,3]thiazolo[4,5-c]pyridin-2-yloxy)benzyl]-8-azabicyclo[3.2.1]octan-3-amine, meso-8-{2-[4-([1,3]Thiazolo[4,5-c]pyridin-2-yloxy)phenoxy]ethyl}-3,8-diazabicyclo[3.2.1]octane-3-carboxamide, N-(Cyclopropylmethyl)-N-{2-[4-([1,3]thiazolo[4,5-c]pyridin-2-yloxy)phenoxy]ethyl}-beta-alanine, meso-2-(4-{2-[3-Acetyl-3,8-diazabicyclo[3.2.1]oct-8-yl]ethoxy}phenoxy)[1,3]thiazolo[4,5-c]pyridine, N-Ethyl-N-[4-([1,3]thiazolo[4,5-c]pyridin-2-yloxy)benzyl]cyclohexanamine, 2-[4-(Piperidin-1-ylmethyl)phenoxy][1,3]thiazolo[5,4-c]pyridine, meso-N-{(3-endo)-8-[4-([1,3]Thiazolo[5,4-c]pyridin-2-yloxy)benzyl]-8-azabicyclo[3.2.1]oct-3-yl}acetamide, 1-(1-{2-[4-([1,3]Thiazolo[5,4-c]pyridin-2-yloxy)phenoxy]ethyl}piperidin-4-yl)pyrrolidin-2-one, 2-(4-{2-[(1R,4R)-5-(Methylsulfonyl)-2,5-diazabicyclo[2.2.1]hept-2-yl]ethoxy}phenoxy)[1,3]thiazolo[5,4-c]pyridine, 3-[(Cyclopropylmethyl) {2-[4-([1,3]thiazolo[5,4-c]pyridin-2-yloxy)phenoxy]ethyl}amino]propan-1-ol, N-Methyl-N-[4-([1,3]thiazolo[5,4-c]pyridin-2-yloxy)benzyl]cyclohexanamine, 2-{4-[2-(4-Acetylpiperazin-1-yl)ethyl]phenoxy}[1,3]thiazolo[5,4-c]pyridine, meso-1-{(3-exo)-8-[4-([1,3]Thiazolo[5,4-c]pyridin-2-yloxy)benzyl]-8-azabicyclo[3.2.1]oct-3-yl}urea, N-(Cyclopropylmethyl)-N-[4-([1,3]thiazolo[5,4-c]pyridin-2-yloxy)benzyl]propane-1,3-diamine, 3-(Cyclopropyl{2-[4-([1,3]thiazolo[5,4-c]pyridin-2-yloxy)phenoxy]ethyl}amino)propan-1-ol, 2-(4-{[4-(Pyridin-2-ylcarbonyl)piperazin-1-yl]methyl}phenoxy)[1,3]thiazolo[5,4-c]pyridine, 2-{4-[(4-Acetyl-1,4-diazepan-1-yl)

methyl]phenoxy}[1,3]thiazolo[5,4-c]pyridine, 2-[4-({4-[(4-Methylpiperazin-1-yl)carbonyl]piperidin-1-yl}methyl)phenoxy][1,3]thiazolo[5,4-c]pyridine, 2-[4-(2-Azetidin-1-ylethoxy)phenoxy][1,3]thiazolo[5,4-c]pyridine, 5-{2-[4-([1,3]Thiazolo[5,4-c]pyridin-2-yloxy)phenyl] ethyl}hexahydropyrrolo[3,4-c]pyrrole-2(1H)-carboxamide, 2-(4-{[4-(Pyridin-3-yloxy)piperidin-1-yl]methyl}phenoxy) [1,3]thiazolo[5,4-c]pyridine, meso-N-{(3-exo)-8-[4-([1,3] Thiazolo[5,4-c]pyridin-2-yloxy)benzyl]-8-azabicyclo [3.2.1]oct-3-yl}methanesulfonamide, N-[(1-{2-[4-([1,3] Thiazolo[5,4-c]pyridin-2-yloxy)phenoxy]ethyl}piperidin-4-yl)methyl]acetamide, 2-(4-{2-[(1S,4S)-5-Acetyl-2,5-diazabicyclo[2.2.1]hept-2-yl]ethoxy}phenoxy) [1,3] thiazolo[5,4-b]pyridine, (1 S,4S)-5-{2-[4-([1,3]Thiazolo[5,4-b]pyridin-2-yloxy)phenoxy]ethyl}-2,5-diazabicyclo [2.2.1]heptane-2-carboxamide, 1-{2-[4-([1,3]Thiazoolo[5,4-b]pyridin-2-yloxy)phenoxy]ethyl}piperidine-4-carboxamide, 1-{2-[4-([1,3]Thiazolo[5,4-b]pyridin-2-yloxy)phenoxy]ethyl}-4-[3-(trifluoromethyl)phenyl]piperidin-4-ol, 2-{4-[2-(4-Pyridin-2-ylpiperidin-1-yl (ethoxy]phenoxy}[1,3]thiazolo[5,4-b]pyridine, 4-(4-Chlorophenyl)-1-{2-[4-([1,3]thiazolo[5,4-b]pyridin-2-yloxy)phenoxy]ethyl}piperidin-4-ol, 4-Phenyl-1-{2-[4-([1,3]Thiazolo[5,4-b]pyridin-2-yloxy)phenoxy]ethyl}piperidin-4-ol, 2-(4-{2-[4-(2-Methoxyphenyl)piperidin-1-yl] ethoxy}phenoxy)[1,3]thiazolo[5,4-b]pyridine, 2-{4-[2-(4-Pyridin-4-ylpiperidin-1-yl(ethoxy]phenoxy}[1,3]thiazolo[5,4-b]pyridine, 1-(1-{2-[4-([1,3]Thiazolo[5,4-b]pyridin-2-yloxy)phenoxy]ethyl}piperidin-4-yl)pyrrolidin-2-one, 1-{2-[4-([1,3]Thiazolo[5,4-b]pyridin-2-yloxy)phenoxy] ethyl}piperidine-4-carboxylic acid, 2-(4-{2-[(1S,4S)-5-Acetyl-2,5-diazabicyclo[2.2.1]hept-2-yl]ethyl}phenoxy)[1,3]thiazolo[5,4-b]pyridine, meso-N-[(3-endo)-8-{2-[4-([1,3]Thiazolo[5,4-b]pyridin-2-yloxy)phenyl]ethyl}-8-azabicyclo[3.2.1]oct-3-yl]acetamide, meso-2-(4-{2-[3-Acetyl-3,8-diazabicyclo[3.2.1]oct-8-yl]ethyl}phenoxy)[,3]thiazolo[5,4-b]pyridine, 1-{2-[4-([1,3]Thiazolo[5,4-b]pyridin-2-yloxy)phenyl]ethyl}piperidine-4-carboxamide, 1-(1-{2-[4-([1,3] Thiazolo[5,4-b]pyridin-2-yloxy)phenyl]ethyl}piperidin-4-yl)pyrrolidin-2-one, 2-{4-[2-(5-Acetylhexahydropyrrolo[3,4-c]pyrrol-2(1H)-yl)ethyl]phenoxy}[1,3]thiazolo[5,4-b]pyridine, 5-{2-[4-([1,3]Thiazolo[5,4-b]pyridin-2-yloxy)phenyl]ethyl}hexahydropyrrolo[3,4-c]pyrrole-2(1H)-carboxamide, meso-8-{2-[4-([1,3]Thiazolo[5,4-b]pyridin-2-yloxy)phenyl]ethyl}-3,8-diazabicyclo[3.2.1]octane-3-carboxamide, meso-1-[(3-endo)-8-{2-[4-([1,3]Thiazolo[5,4-b]pyridin-2-yloxy)phenyl]ethyl}-8-azabicyclo[3.2.1]oct-3-yl]urea, (1S,4S)-5-{2-[4-([1,3]Thiazolo[5,4-b]pyridin-2-yloxy)phenyl]ethyl}-2,5-diazabicyclo[2.2.1]heptane-2-carboxamide, 1-{1-[4-([1,3]Thiazolo[5,4-b]pyridin-2-yloxy)benzyl]piperidin-4-yl}pyrrolidin-2-one, 1-[4-([1,3]Thiazolo[5,4-b]pyridin-2-yloxy)benzyl]piperidine-4-carboxamide, 2-(4-{[(1S,4S)-5-Acetyl-2,5-diazabicyclo[2.2.1]hept-2-yl]methyl}phenoxy)-5-methyl[1,3]thiazolo[5,4-b]pyridine, meso-N-{(3-endo)-8-[4-([1,3]Thiazolo[5,4-b]pyridin-2-yloxy)benzyl]-8-azabicyclo[3.2.1]oct-3-yl}acetamide, 2-(4-{[(1S,4S)-5-Acetyl-2,5-diazabicyclo[2.2.1]hept-2-yl]methyl}phenoxy)-6-fluoro[1,3]thiazolo[5,4-b]pyridine, 2-(4-{[(1S,4S)-5-Acetyl-2,5-diazabicyclo[2.2.1]hept-2-yl]methyl}phenoxy)[1,3]thiazolo[5,4-b]pyridine, 1-[4-([1,3]Thiazolo[5,4-b]pyridin-2-yloxy)benzyl]piperidine-4-carboxylic acid, 2-{4-[2-(4-Methyl-1,4-diazepan-1-yl)ethoxy]phenoxy}[1,3]thiazolo[5,4-b]pyridine, meso-N-[(3-exo)-8-{2-[4-([1,3]Thiazolo[5,4-b]pyridin-2-yloxy)phenoxy]ethyl}-8-azabicyclo[3.2.1]oct-3-yl]acetamide, 2-[(Cyclopropylmethyl) {2-[4-([1,3]thiazolo [5,4-b]pyridin-2-yloxy)phenoxy]ethyl}amino]ethanol,
7-Methyl-2-({4-[(4-pyridin-4-ylpiperazin-1-yl)methyl]phenyl}oxy)[1,3]thiazolo[4,5-b]pyridine, meso-(3-endo)-8-Acetyl-N-{[4-([1,3]thiazolo[4,5-b]pyridin-2-yloxy)phenyl]methyl}-8-azabicyclo[3.2.1]octan-3-amine, meso-(3-exo)-8-Acetyl-N-{[4-([1,3]thiazolo[4,5-b]pyridin-2-yloxy) phenyl]methyl}-8-azabicyclo[3.2.1]octan-3-amine, N-Ethyl-N-{2-[4-([1,3]thiazolo[4,5-b]pyridin-2-yloxy)phenyl]ethyl}cyclopropanamine, meso-N-[(3-exo)-8-{2-[4-([1,3]Thiazolo[5,4-b]pyridin-2-yloxy)phenyl]ethyl}-8-azabicyclo[3.2.1]oct-3-yl]methanesulfonamide, meso-(3-exo)-3-{[4-([1,3]Thiazolo[5,4-b]pyridin-2-yloxy)benzyl]amino}-8-azabicyclo[3.2.1]octane-8-carboxamide, 4-Methyl-1-[4-([1,3]Thiazolo[5,4-b]pyridin-2-yloxy)benzyl]-1,4-diazepan-5-one, N-{1-[4-([1,3]Thiazolo[5,4-b]pyridin-2-yloxy)benzyl]piperidin-4-yl}propenamide, 2-(4-{2-[4-(Cyclopropylcarbonyl)-1,4-diazepan-1-yl]ethyl}phenoxy) [1,3]thiazolo[5,4-b]pyridine, meso-N-Methyl-N-{(3-exo)-8-[4-([1,3]thiazolo[5,4-b]pyridin-2-yloxy)benzyl]-8-azabicyclo[3.2.1]oct-3-yl}acetamide, 2-(Cyclopropyl{2-[4-([1,3]thiazolo[5,4-b]pyridin-2-yloxy)phenoxy]ethyl}amino) ethanol, 2-{4-[(4-Pyridin-2-ylpiperazin-1-yl)methyl]phenoxy}[1,3]thiazolo[5,4-b]pyridine, 2-(4-{2-[(1R,4R)-5-Acetyl-2,5-diazabicyclo[2.2.1]hept-2-yl]ethyl}phenoxy)[1,3]thiazolo[5,4-b]pyridine, 7-Methyl-2-[4-(piperidin-1-ylmethyl)phenoxy][1,3]thiazolo[5,4-b]pyridine, 2-(4-{[(1S,4S)-5-Acetyl-2,5-diazabicyclo[2.2.1]hept-2-yl] ethyl}phenoxy)-7-methyl[1,3]thiazolo[5,4-b]pyridine, 1-{4-[(7-Methyl[1,3]thiazolo[5,4-b]pyridin-2-yl)oxy] benzyl}piperidine-4-carboxamide, 4-Phenyl-1-{2-[4-([1,3]thiazolo[4,5-b]pyrazin-2-yloxy)phenoxy]ethyl}piperidin-4-ol, 2-{4-[2-(4-Benzylpiperidin-1-yl(ethoxy]phenoxy}[1,3]thiazolo[4,5-b]pyrazine, 1-{2-[4-([1,3]Thiazolo[4,5-b]pyrazin-2-yloxy)phenoxy]ethyl}-4-[3-(trifluoromethyl)phenyl]piperidin-4-ol, 4-(4-Chlorophenyl)-1-{2-[4-([1,3]thiazolo[4,5-b]pyrazin-2-yloxy)phenoxy]ethyl}piperidin-4-ol, 1-{2-[4-([1,3]Thiazolo[4,5-b]pyrazin-2-yloxy)phenoxy] ethyl}piperidine-4-carboxamide, 2-(4-{[(1S,4S)-5-Acetyl-2,5-diazabicyclo[2.2.1]hept-2-yl]methyl}phenoxy)[1,3]thiazolo[4,5-b]pyrazine, meso-N-[(3-endo)-8-{2-[4-([1,3]Thiazolo[4,5-b]pyrazin-2-yloxy)phenoxy]ethyl}-8-azabicyclo[3.2.1]oct-3-yl]acetamide, 2-[4-(2-Morpholin-4-ylethoxy)phenoxy][1,3]thiazolo[4,5-b]pyrazine, 2-({4-[(4-Pyrimidin-2-ylpiperazin-1-yl)methyl]phenyl}oxy)[1,3]thiazolo[4,5-b]pyrazine, 2-[(4-{[4-(2-Thienylacetyl) piperazin-1-yl]methyl}phenyl)oxy][1,3]thiazolo[4,5-b]pyrazine, 1-{2-[4-([1,3]Thiazolo[4,5-b]pyrazin-2-yloxy)phenyl]ethyl}-1,4-diazepan-5-one, 2-{[4-(2-Azepan-1-ylethyl)phenyl]oxy}[1,3]thiazolo[4,5-b]pyrazine, 2-({4-[2-(4-Fluoropiperidin-1-yl)ethyl]phenyl}oxy)[1,3]thiazolo[4,5-b]pyrazine, 2-[(4-{[4-(Pyrimidin-2-yloxy)piperidin-1-yl]methyl}phenyl)oxy][1,3]thiazolo[4,5-b]pyrazine, meso-1-{(3-exo)-8-[4-([1,3]Thiazolo[4,5-b]pyrazin-2-yloxy)benzyl]-8-azabicyclo[3.2.1]oct-3-yl}urea, 2-(4-{2-[4-(Pyridin-2-yloxy)piperidin-1-yl]ethyl}phenoxy)[1,3]thiazolo[4,5-b]pyrazine, 3-Acetyl-9-[4-([1,3]thiazolo[4,5-b]pyridin-2-yloxy)benzyl]-3,9-diazaspiro[5.5]undecane, and 1-[4-([1,3]Thiazolo[4,5-b]pyrazin-2-yloxy)benzyl]piperidine-4-carboxamide, and pharmaceutically acceptable salts, prodrugs, and solvates thereof of any of the foregoing compounds.

In certain embodiments, the compound of formula (IV) is the compound known as JNJ-40929837, which has the following structure:

JNJ-40929837

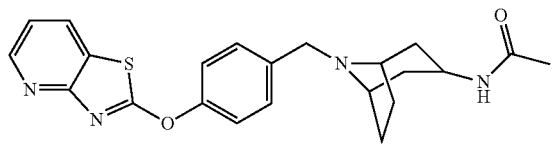

JNJ40929837 analogs and derivatives useful in the methods of the invention include the LTA4H inhibitor compounds described in U.S. Pat. Nos. 7,939,527; and 8,357,684, which are incorporated herein by reference.

In certain embodiments, the LTA4H modulatory agent is a diazabicyclo[2.2.1]heptane derivative. In some embodiments, the LTA4H modulatory agent is described by the formula (V):

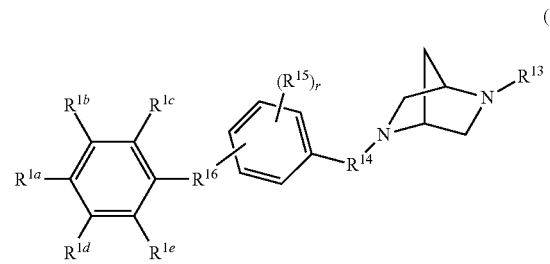

where:
r is 0 to 4;
$R^{1a}$, $R^{1b}$, $R^{1c}$, $R^{1d}$ and $R^{1e}$ are each independently selected from hydrogen, $-R^{13a}-OR^{10a}$, $-R^{13a}-C(=O)OR^{10a}$, $-R^{13a}-C(=O)R^{10a}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl;
$R^{16}$ is a direct bond, $-O-$, $-R^{12a}-O-$, $-O-R^{12a}-$, $-O-R^{12a}-O-$, an optionally substituted straight or branched alkylene chain, an optionally substituted straight or branched alkenylene chain, or an optionally substituted straight or branched alkynylene chain;
$R^{14}$ is a direct bond, $-O-R^{12b}-$, an optionally substituted straight or branched alkylene chain, an optionally substituted straight or branched alkenylene chain, or an optionally substituted straight or branched alkynylene chain;
$R^{13}$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13a}-OR^{10a}$, $-R^{13}-O-R^{14a}-C(=O)OR^{10a}$, $-R^{13a}-C(=O)R^{10a}$, $-R^{13a}-C(=O)OR^{10a}$, $-R^{13a}-C(=O)-R^{14a}-C(=O)OR^{10a}$, $-R^{13a}-C(=O)-R^{13a}-N(R^{10a})R^{11a}$, $-R^{13a}-C(=O)-R^{14a}-S(=O)_tN(R^{10a})R^{11a}$ (where t is 1 or 2), or $-R^{14a}-S(=O)_pR^{10a}$ (where p is 0, 1 or 2);
or $R^{13}$ is aralkyl optionally substituted with one or more substituents selected from the group consisting of halo, nitro, cyano, optionally substituted heteroaryl, hydroxyiminoalkyl, $-R^{13a}-OR^{10a}$, $-R^{13a}-C(=O)R^{10a}$, $-R^{13a}-C(=O)OR^{10a}$, $-R^{13a}-C(=O)-R^{13a}-N(R^{10a})R^{11a}$, $-R^{13a}-C(=O)N(R^{10a})-R^{14a}-N(R^{10a})R^{11a}$, $-R^{13a}-S(=O)_tN(R^{10a})R^{11a}$, $-R^{13a}-N(R^{10a})R^{11a}$, $-R^{13a}-N(R^{10a})C(=O)R^{10a}$, $-R^{13a}-N(R^{10a})C(=O)-R^{13a}-N(R^{10a})R^{11a}$, $-R^{13a}-N(R^{10a})-R^{13a}-C(=O)OR^{10a}$, $-R^{13a}-N(R^{10a})C(=O)-R^{14a}-S(=O)_tN(R^{10a})R^{11a}$, $-R^{13a}-N(R^{10a})C(=O)-R^{13a}-N(R^{10a})C(=O)R^{10a}$, $-R^{13a}-N(R^{10a})C(=O)-R^{13a}-N(R^{10a})-R^{14a}-N(R^{10a})R^{11a}$, $-R^{13a}-N(R^{10a})S(=O)_tN(R^{10a})R^{11a}$, and $-R^{13a}-O-R^{14a}-C(=O)OR^{10a}$, where t is 1 or 2;
each $R^{15}$ is independently selected from $-O-R^{10a}$, alkyl, hydroxyalkyl, halo, haloalkyl, aryl or aralkyl;
each $R^{10a}$ and $R^{11a}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl;
or $R^{10a}$ and $R^{11a}$, together with the nitrogen to which they are attached, form an optionally substituted N-heterocyclyl or an optionally substituted N-heteroaryl;
each $R^{12a}$ is an optionally substituted straight or branched alkylene chain, an optionally substituted straight or branched alkenylene chain, or an optionally substituted straight or branched alkynylene chain;
$R^{12b}$ is an optionally substituted straight or branched alkylene chain, an optionally substituted straight or branched alkenylene chain, or an optionally substituted straight or branched alkynylene chain;
each $R^{13a}$ is a direct bond, an optionally substituted straight or branched alkylene chain, an optionally substituted straight or branched alkenylene chain, or an optionally substituted straight or branched alkynylene chain;
and each $R^{14a}$ is an optionally substituted straight or branched alkylene chain, an optionally substituted straight or branched alkenylene chain, or an optionally substituted straight or branched alkynylene chain.

In certain embodiments of formula (V), the compound is selected from 4-[[(1S,4S)-5-[(4-phenoxyphenyl)methyl]-2,5-diazabicyclo[2.2.1]hept-2-yl]methyl]benzoic acid, 4-[[(1S,4S)-5-[[(4-fluorophenoxy)phenyl]methyl]-2,5-diazabicyclo[2.2.1]hept-2-yl]methyl]-benzoic acid, 4-[[(1S,4S)-5-[(4-(2-phenylethoxy)phenyl]methyl]-2,5-diazabicyclo[2.2.1]hept-2-yl]methyl]benzoic acid, 4-[[(1S,4S)-5-[3-(4-phenoxyphenyl)propyl]-2,5-diazabicyclo[2.2.1]hept-2-yl]methyl]benzoic acid, 4-[[(1S,4S)-5-[[4-(4-chlorophenoxy)phenyl]methyl]-2,5-diazabicyclo[2.2.1]hept-2-yl]methyl]benzoic acid, 4-[[(1S,4S)-5-[2-(4-phenoxyphenyl)ethyl]-2,5-diazabicyclo[2.2.1]hept-2-yl]methyl]benzoic acid, 4-[[(1S,4S)-5-[[4-(2-phenoxyethoxy)phenyl]methyl]-2,5-diazabicyclo[2.2.1]hept-2-yl]methyl]benzoic acid, 4-[[(1S,4S)-5-[[4-(4-bromophenoxy)phenyl]methyl]-2,5-diazabicyclo[2.2.1]hept-2-yl]methyl]benzoic acid, 4-[[(1S,4S)-5-[[4-[(2'-fluoro[1,1'-biphenyl]-4-yl)oxy]phenyl]methyl]-2,5-diazabicyclo[2.2.1]hept-2-yl]methyl]benzoic acid, 4-[[(1S,4S)-5-[[4-[4-(3-furanyl)phenoxy]phenyl]methyl]-2,5-diazabicyclo[2.2.1]hept-2-yl]methyl]benzoic acid, 4-[[(1S,4S)-5-[[4-[4-(trifluoromethyl)phenoxy]phenyl]methyl]-2,5-diazabicyclo[2.2.1]hept-2-yl]methyl]benzoic acid, 4-[[(1S,4S)-5-[[4-]4-acetylphenoxy]phenyl]methyl]-2,5-diazabicyclo[2.2.1]hept-2-yl]methyl]benzoic acid, 4-[[(1S,4S)-5-[[4-[4-(3-thienyl)phenoxy]phenyl]methyl]-2,5-diazabicyclo[2.2.1]hept-2-yl]methyl]benzoic acid, 4-[[(1S,4S)-5-[[4-[4-(3,5-dimethyl-4-isoxazolyl)phenoxy]phenyl]methyl]-2,5-diazabicyclo[2.2.1]hept-2-yl]methyl]benzoic acid, 4-[[(1S,4S)-5-[(3-fluoro-4-phenoxyphenyl)methyl]-2,5-diazabicyclo[2.2.1]hept-2-yl]methyl]benzoic acid, 4-[[(1S,4S)-5-[[3-(2-phenylethoxy)phenyl]methyl]-2,5-diazabicyclo[2.2.1]hept-2-yl]methyl]benzoic acid, 4-[[(1S,4S)-5-[[4-[4-(2-oxazolyl)phenoxy]phenyl]methyl]-2,5-diazabicyclo[2.2.1]hept-2-yl]methyl]benzoic acid, 4-[[(1 S,4S)-5-[(4-fluoro-2-phenoxyphenyl)methyl]-2,5-diazabicyclo[2.2.1]hept-2-yl]methyl]benzoic acid, 4-[[(1S,4S)-5-[(3-phenoxyphenyl)methyl]-2,5-diazabicyclo[2.2.1]hept-2-yl]methyl]benzoic acid, 4-[[(1S,4S)-5-[(2-fluoro-4-phenoxyphenyl)methyl]-2,5-diazabicyclo[2.2.1]hept-2-yl]methyl]benzoic acid, 4-[[(1S,4S)-5-[(2,4-diphenoxyphenyl)methyl]-2,5-diazabicyclo[2.2.1]hept-2-yl]methyl]benzoic acid, 4-[[(1S,4S)-5-([1,1'-biphenyl]-4-ylmethyl)-2,5-diazabicyclo[2.2.1]hept-2-yl]methyl]benzoic acid, 4-[[(1S,4S)-5-[(4-phenoxyphenyl)methyl]-2,5-diazabicyclo[2.2.1]hept-2-yl]methyl]benzeneacetic acid, 4-[[(1S,4S)-5-[[4-(2-phenoxyethoxy)phenyl]methyl]-2,5-diazabicyclo[2.2.1]hept-2-yl]methyl]benzeneacetic acid, 4-[[(1S,4S)-5-[[4-(2-phenylethoxy)phenyl]methyl]-2,5-diazabicyclo[2.2.1]hept-2-yl]methyl]benzeneacetic acid, methyl 4-[[(1 S,4S)-5-[[4-[4-(2-oxazolyl)phenoxy]phenyl]methyl]-2,5-diazabicyclo[2.2.1]hept-2-yl]methyl]benzoate, 4-[[(1 S,4S)-5-[[4-[4-(2-thiazolyl)phenoxy]phenyl]methyl]-2,5-diazabicyclo[2.2.1]hept-2-yl]methyl]benzoic acid, and methyl 4-[[(1S,4S)-5-[[4-[4-(2-thiazolyl)phenoxy]phenyl]methyl]-2,5-diazabicyclo[2.2.1]hept-2-yl]methyl]benzoate.

In some embodiments of formula (V), the compound is selected from 4-[[(1S,4S)-5-[[4-[4-(2-oxazolyl)phenoxy]phenyl]methyl]-2,5-diazabicyclo[2.2.1]hept-2-yl]methyl]benzoic acid, and methyl 4-[[(1 S,4S)-5-[[4-[4-(2-oxazolyl)phenoxy]phenyl]methyl]-2,5-diazabicyclo[2.2.1]hept-2-yl]methyl]benzoate.

In some embodiments of formula (V), the compound is selected from 4-[[(1S,4S)-5-[[4-[4-(2-thiazolyl)phenoxy]phenyl]methyl]-2,5-diazabicyclo[2.2.1]hept-2-yl]methyl]benzoic acid, and methyl 4-[[(1 S,4S)-5-[[4-[4-(2-thiazolyl)phenoxy]phenyl]methyl]-2,5-diazabicyclo[2.2.1]hept-2-yl]methyl]benzoate.

In certain embodiments, the compound of formula (V) is the compound known as Acebilustat (CTX-4430), which has the following structure:

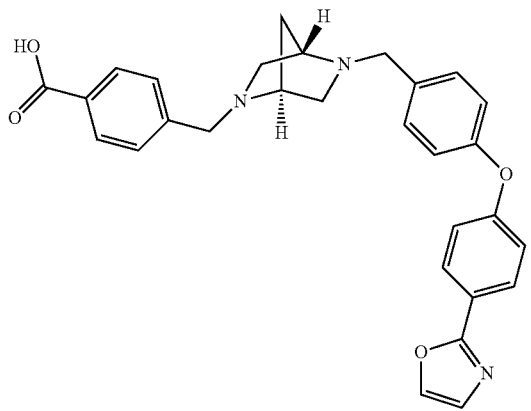

(CTX-4430)

Acebilustat

Acebilustat analogs and derivatives useful in the methods of the invention include the compounds described in U.S. Pat. No. 7,737,145; and U.S. Patent Application Publication No. 20100210630A1, the contents of each of which are incorporated by reference herein. LTA4H inhibitor compounds also include those described in U.S. Pat. Nos. 9,822,106; 9,856,249; and 9,777,006, the contents of each of which are incorporated by reference herein.

In some embodiments the LTA4H modulatory agent is a heterocyclic compound described by the formula (VI):

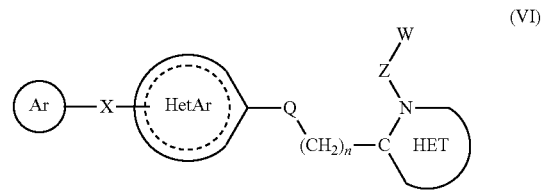

(VI)

where:
Ar is selected from aryl, heteroaryl, aryl substituted with from one to three substituents independently selected from the group consisting of halogen, loweralkyl, loweracyl, loweralkoxy, fluoroloweralkyl, fluoroloweralkoxy, hydroxy, hydroxy($C_1$-$C_4$) alkyl, formyl, formyl($C_1$-$C_4$)alkyl, cyano, cyano($C_1$-$C_4$)alkyl, benzyl, benzyloxy, phenyl, substituted phenyl, heteroaryl, heterocyclylalkyl, substituted heteroaryl, and nitro, and heteroaryl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, heteroaryl, heterocyclylalkyl and nitro;

X is selected from direct bond, O, SO, $S(O_2)$, $NR^{1f}$, $CH_2$, $CF_2$, $CH_2CH_2$, $CH_2NR^{1f}$, $NR^{1f}CH_2$, CH=CH, C=O, $CH_2$C=O, $CR^{1aa}R^{1bb}$, $OCR^{1aa}R^{1bb}$ $CR^{1aa}R^{1bb}$O; $SO_2NR^{1f}$, $NR^{1f}SO_2$, C(=O)$NR^{1f}$ and $NR^{1f}$C(=O);

$R^{1f}$ is selected separately in each occurrence from H and lower alkyl;

$R^{1aa}$ is selected from H, OH and lower alkyl;

$R^{1bb}$ is selected from H and lower alkyl, or $R^{1aa}$ and $R^{1bb}$ taken together may form a 3-6 membered ring, which may optionally contain a heteroatom chosen from O, S, and N;

HetAr is an aryl or heteroaryl ring attached via a ring carbon to Q, further characterized in that Q and X cannot be on adjacent positions in said aryl or heteroaryl ring;

Q is chosen from —O—, —$NR^{1f}$— and $S(O)_p$;

Q and X cannot be on adjacent positions in said benzene or pyridine ring;

p is zero, 1 or 2;

n is an integer selected from 1-5;

HET is selected from 4-7-membered saturated nitrogenous heterocycle, and 4-7-membered saturated nitrogenous heterocycle substituted with one or two substituents independently selected from halogen, hydroxyl, amino, carboxy, loweralkyl, loweracyl, loweralkoxy, N-oxide, fluoroloweralkyl, fluoroloweralkoxy, formyl, cyano, benzyl, benzyloxy, phenyl, heteroaryl and nitro; and taken together ZW is H or Z is $(CH_2)_{1-10}$, in which one or two ($CH_2$) may optionally be replaced by —O—, —$NR^{1f}$—, —SO—, —$S(O)_2$—, —C(=O)— or —CO(NH)—, provided that said —O—, —$NR^{1f}$—, —SO—, —$S(O)_2$—, —C(=O)— or —C=O(NH)— are not at the point of attachment to HET and are separated by at least one —($CH_2$)—;

W is selected from acyl, hydroxyl, carboxyl, amino, —C(O)$NHR^{4a}$, aminoacyl, —COOalkyl, —CHO, heterocyclyl, substituted aryl, substituted heterocyclyl, sulfonamide, —C(O)fluoroalkyl, —C(O)$CH_2$C(O)Oalkyl, —C(O)$CH_2$C(O)fluoroalkyl, —SH, —C(O)NH(OH), —C(O)N(OH)$R^{4a}$, —N(OH)C(O)OH, —N(OH)C(O)$R^{4a}$; and $R^{4a}$ is selected from H, ($C_1$-$C_4$) alkyl and phenyl($C_1$-$C_4$) alkyl.

In some embodiments of formula (VI), the compound is described by formula (VIa):

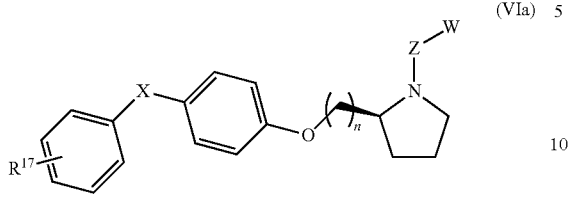
(VIa)

Where:
X is selected from the group consisting of direct bond, O, SO, S(O₂), NR¹, CH₂, CF₂, CH₂O, C=O and CH₂C=O;
R¹⁷ is chosen from halogen, CF₃, methyl, methoxy, CF₃O;
n is 1 or 2;
Z is (CH₂)₁₋₁₀, in which one or two (CH₂) may optionally be replaced by —O—, —NR¹ʹ—, —SO—, —S(O)₂—, —C(=O)— or —C=O(NH)—, provided that said —O—, —NR¹ʹ—, —SO—, —S(O)₂—, —C(=O)— or —C=O(NH)— are not at the point of attachment to HET and are separated by at least one —(CH₂)—;
W is selected from acyl, hydroxyl, carboxyl, amino, —C(O)NHR⁴ᵃ, aminoacyl, —COOalkyl, —CHO, heterocyclyl, substituted aryl, substituted heterocyclyl, sulfonamide, —C(O)fluoroalkyl, —C(O)CH₂C(O)Oalkyl, —C(O)CH₂C(O)Ofluoroalkyl, —SH, —C(O)NH(OH), —C(O)N(OH)R⁴ᵃ, —N(OH)C(O)OH, —N(OH)C(O)R⁴ᵃ; and
R⁴ᵃ is selected from H, (C₁-C₄) alkyl and phenyl(C₁-C₄) alkyl.

In certain embodiments of formula (VIa), X is O or CH₂, n is 1 or 2, Z is C₁₋₄ alkylene and W is COOH.

In certain embodiments, the compound of formula (VI) or (VIa) is the compound known as DG-051, which has the following structure:

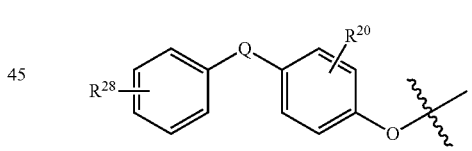
DG-051

DG051 analogs and derivatives useful in the methods of the invention include the LTA4H inhibitor compounds described in U.S. Pat. No. 7,402,684; and Sandanayaka et al. *J Med. Chem.* 2010 Jan. 28; 53(2):573-85; Bio-org Med Chem. Lett. 2009 Nov. 15; 19(22):6275-9, each of which is incorporated herein by reference.

In some embodiments the LTA4H modulatory agent is described by the formula (VII):

Ar¹-Q¹-AR²—Y¹—R¹⁸—Z¹    (VII)

where:
Ar¹ is an aryl moiety selected from phenyl, mono-, di-, or tri-substituted phenyl with the substituents selected from the Cl, Br, F, CF₃, lower alkyl, lower alkoxy, NH₂, NO₂ and OH;
Ar² is

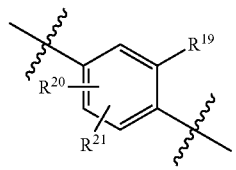

wherein R¹⁹ is selected from H, halogen, lower alkyl, lower alkoxy, nitro or hydroxy, R²⁰ and R²¹ are each independently selected from H, halogen, lower alkyl, lower alkoxy, amino, nitro or hydroxy;
Q¹ is —O—, or —CH₂—, —OCH₂—, —CH₂O—, —NH—, —NHCH₂—, —CH₂NH—, —CF₂—, —CH=CH—, —CH₂—CH₂—, and a carbon-carbon single bond;
Y¹ is selected from —O—, —S—, —NH—, —S(O)—, and —S(O₂)—;
R¹⁸ is selected from linear or branched C₂-C₆ alkylenyl, or C(R²²)(R²³)—(CH₂)m, wherein R²² and R²³ are each independently selected from H and lower alkyl, and m is 1, 2 or 2; and
Z is

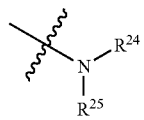

wherein at least one of R²⁴ and R²⁵ is —(CH₂)ₐCOR²⁶ and the other is selected from H, lower alkyl, allyl, benzyl, —(CH₂)ₐCOR²⁶, and —(CH₂)ₐ—OH;
R²⁶ is —OR²⁷, where R²⁷ is H, lower alkyl or benzyl; and a is an integer from 0 to 5, provided that when R²⁴ and R²⁵ are both —(CH₂)ₐCOR²⁶, then a is not 0.

In certain embodiments of formula (VII), Ar¹-Q¹-AR²—Y¹ is:

Where:
Q is —O— or —CH₂—;
R²⁰ and R²⁸ are each independently selected from H, lower alkyl, lower alkoxy, halogen, amino and nitro.

In certain embodiments of formula (VII), the compound is selected from 3-[[3-[4(phenylmethyl)phenoxy]propyl]amino]propanoic acid, 3-[methyl[3-[4(phenylmethyl)phenoxy]propyl]amino]propanoic acid, 3-[[4-[4(phenylmethyl)phenoxy]butyl]amino]propanoic acid, 3-[[3-(4-phenoxyphenoxy)propyl]amino]propanoic acid, 3-[methyl [3-(4-phenoxyphenoxy)propyl]amino]propanoic acid, 3-[[4-(4-phenoxyphenoxy)butyl]amino]propanoic acid; and 3-[[3-[4-[(4-fluorophenyl)methyl]phenoxy]propyl]methylamino] propanoic acid, monohydrochloride. In certain embodiments of formula (VII), the compound is selected from ethyl 3-[[3-[4-(phenylmethyl)phenoxy]propyl]amino]propanoate, phenylmethyl 3 [methyl[3-[4-(phenylmethyl)phenoxy]propyl]amino]propanoate, ethyl 3-[[3-(4-phenoxyphenoxy)propyl]-amino]propanoate, ethyl 3-[[methyl-[3-[4-(phenylmethyl)phenoxy]propyl]amino]propanoate, methyl 3-[methyl [3-[4-(phenylmethyl)phenoxy]propyl]amino]propanoate, hydrate, ethyl 3-[4-[4-(phenylmethyl)phenoxy]butyl]amino] propanoate, phenylmethyl 3-[4-[4-(phenylmethyl)phenoxy] butyl]amino]propanoate, phenylmethyl 3-[[3-(4-phenoxyphenoxy)propyl]amino]propanoate, phenylmethyl 3-[methyl[3-(4-phenoxyphenoxy)propyl]amino]propanoate, phenylmethyl 3-[[4-(4-phenoxyphenoxy)butyl]amino]propanoate, methyl 3-[3-[4-[(4-fluorophenyl)methyl]phenoxy] propyl]methylamino]propanoate, ethyl 3-[[4-[4-phenoxyphenoxy]butyl]amino]propanoate, and methyl 3-[[3-[4-(4-fluorophenoxy)phenoxy]propyl]methylamino]propanoate.

In certain embodiments, the compound of formula (VII) is the compound known as SC-57461A, which has the following structure:

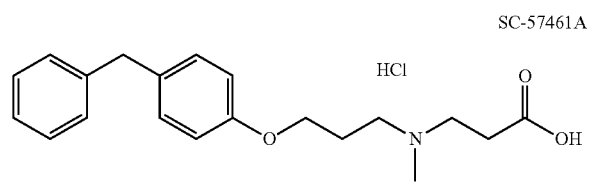 [SMILES: CN(CCCOc1ccc(Cc2ccccc2)cc1)CCC(=O)O ; Cl]

SC-57461A

SC-57461A analogs and derivatives useful in the methods of the invention include the LTA4H inhibitor compounds described in U.S. Pat. Nos. 5,723,492; 6,162,823; 5,585, 492; and 5,719,306, each of which is incorporated herein by reference.

In certain embodiments, the LTA4H modulatory agent is of the formula (VIII):

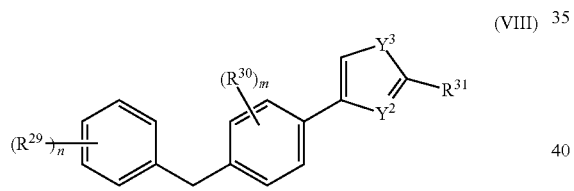

(VIII)

where:
$Y^2$ is selected from N, or $CR^{32}$, wherein $R^{32}$ is selected from hydrogen, alkyl or substituted alkyl;
$Y^3$ is selected from S, O, $NR^{33}$, wherein $R^{33}$ is selected from H, alkyl or substituted alkyl;
each $R^{29}$ and $R^{30}$ are independently selected from halogen, lower alkyl, lower alkoxy, amino, nitro, and hydroxy;
$R^{31}$ is selected from H, halogen, lower alkyl, lower alkoxy, amino, nitro, and hydroxy;
n is an integer from 0 to 5; and
m is an integer from 0 to 4.

In some embodiments the compound of formula (VIII) is 4-(4-benzylphenyl)thiazol-2-amine (ARM1), or an analog thereof. ARM1 has the following structure:

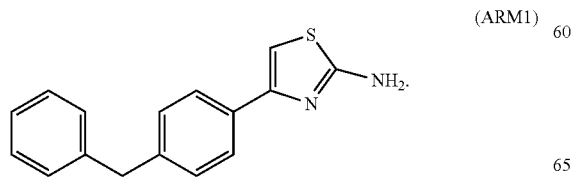

(ARM1)

In certain embodiments, ARM1 is in the form of a salt (e.g., a hydrogen bromide salt or a hydrogen chloride salt).

In some embodiments, the LTA4H modulatory agent is a proline derivative. In some embodiments, the LTA4H modulatory agent is described by the formula (IX):

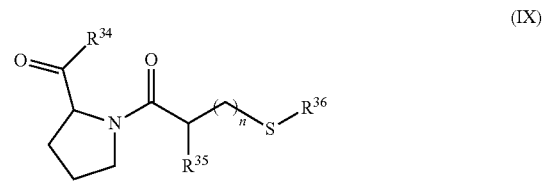

(IX)

where:
$R^{34}$ is hydroxy or lower alkoxy;
$R^{35}$ is hydrogen or lower alkyl;
$R^{36}$ is hydrogen or lower alkanoyl; and
n is 0, 1 or 2, or pharmaceutically acceptable salts thereof, wherein said lower alkoxy, lower alkyl and lower alkanoyl groups having up to 7 carbon atoms.

In certain embodiments of a compound of formula (IX), $R^{34}$ is hydroxy. In certain cases, $R^{34}$ is hydroxy, $R^{35}$ is methyl and $R^{36}$ is H. In certain cases, the compound of formula (IX) is a proline derivative in the L-form.

In some embodiments the compound of formula (IX) is captopril, or an analog thereof. The structure of captopril is as follows:

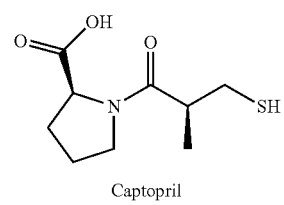

Captopril

Captopril analogs and derivatives useful in the methods of the invention include the compounds described in U.S. Pat. Nos. 4,046,889, and 4,105,776, each of which is incorporated herein by reference.

In some embodiments, the LTA4H modulatory agent is a resveratrol derivative. In some embodiments, the LTA4H modulatory agent is described by the formula (X):

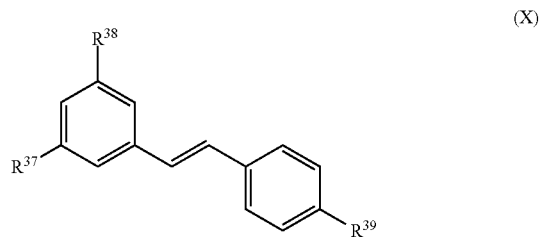

(X)

where:
$R^{37}$, $R^{38}$ and $R^{39}$ are each independently —$OR^{40}$, wherein each $R^{40}$ is independently selected from hydrogen, alkyl, substituted alkyl, alkoxy, substituted alkoxy.

In some embodiments compound of formula (X) is pinostilbene hydrate, or an analog thereof. The structure of pinostilbene hydrate is as follows:

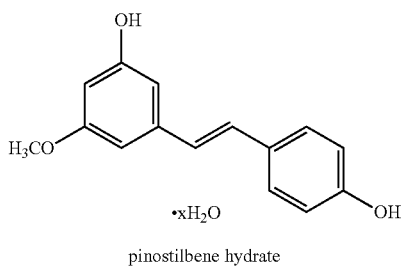 [SMILES: COc1cc(O)cc(/C=C/c2ccc(O)cc2)c1]

pinostilbene hydrate

Pinostilbene hydrate analogs useful in the methods of the invention include the LTA4H inhibitor compounds described in Low et al. *Scientific Reports*, (2017) 7:44449, which is incorporated herein by reference.

In some embodiments, the LTA4H modulatory agent is an arylpyrazole, or a pharmaceutically acceptable salt thereof. In certain embodiments, the LTA4H modulatory agent is of the formula (XI):

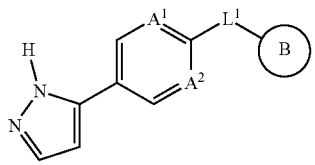
(XI)

or a pharmaceutically acceptable salt thereof, wherein:

$A^1$ and $A^2$ are each independently selected from the group consisting of CH and N;

$L^1$ is a linker selected from the group consisting of —O— and —CH$_2$—;

B is a 9- or 10-membered ring selected from:

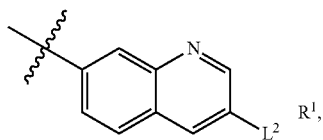
B-1

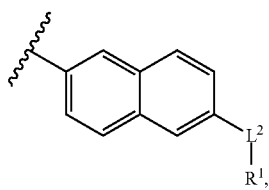
B-2

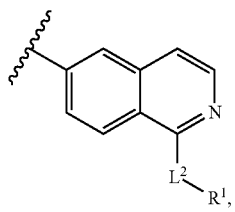
B-3

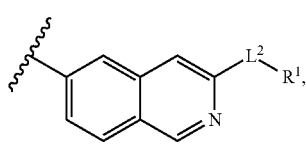
B-4

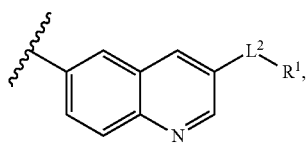
B-5

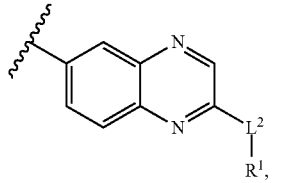
B-6

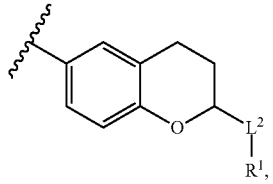
B-7

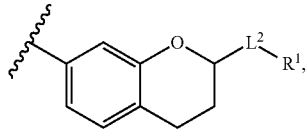
B-8

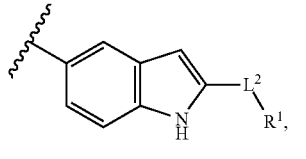
B-9

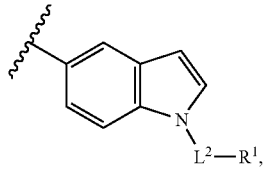
B-10

B-11

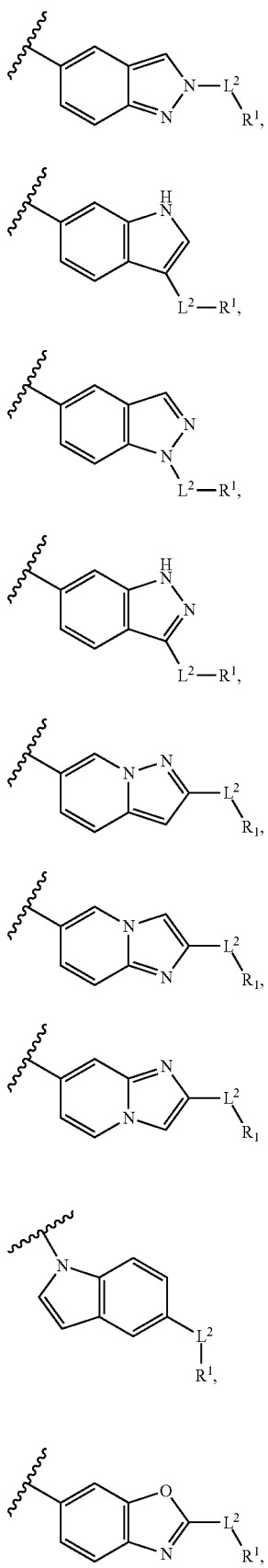

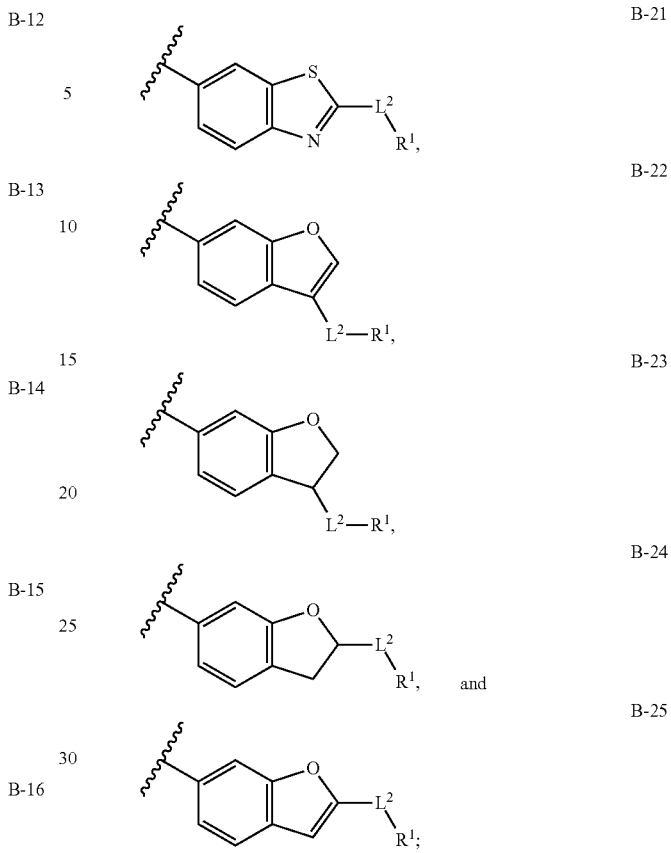

wherein each B ring may optionally be further substituted by —(C$_1$-C$_6$)alkyl;

L$^2$ is absent or a —(CH$_2$)$_n$— linker, wherein n is an integer selected from 1, 2 and 3, and wherein one —(CH$_2$)— moiety of said L$^2$ linker may optionally be replaced, where possible, by —O— and wherein each —(CH$_2$)— of said L$^2$ linker may be substituted with one to two groups selected from the group consisting of —OH, -halo, =O, —(C$_1$-C$_6$)alkyl, —(C$_3$-C$_6$)cycloalkyl, -(4-to 7-membered)heterocyclyl, and phenyl; wherein two —(C$_1$-C$_6$)alkyls groups, when attached to the same carbon atom of said L$^2$ linker moiety may join to form a —(C$_3$-C$_6$)cycloalkyl;

R$^1$ is selected from:

(a) a group of formula —N(R$^2$)(R$^3$), wherein R$^2$ and R$^3$ are each independently selected from the group consisting of —H, —(C$_1$-C$_6$)alkyl, —(C$_3$-C$_6$)cycloalkyl, and -(4-to 7-membered)heterocyclyl, wherein each of said —(C$_1$-C$_6$)alkyl, —(C$_3$-C$_6$)cycloalkyl, and -(4-to 7-membered)heterocyclyl of said R$^2$ and R$^3$ may optionally be independently substituted by 1 to 3 R$^4$ groups;

R$^4$ is selected from the group consisting of halo, —OH, =O, —(C$_1$-C$_6$)alkyl, —O(C$_1$-C$_6$)alkyl, N(R$^5$)$_2$, —C(O)—R$^5$, —N(R$^5$)—C(O)—R$^5$, —C(O)—N(R)$_2$, —(C$_3$-C$_6$)cycloalkyl optionally substituted by —C(O)—(C$_1$-C$_6$)alkyl, -(4-to 7-membered)heterocyclyl optionally substituted by —C(O)—(C$_1$-C$_6$)alkyl, and phenyl; and each R$^5$ is independently selected from the group consisting of —H, —(C$_1$-C$_6$)alkyl, —(C$_3$-C$_6$)cycloalkyl, and -(4-to 7-membered)heterocyclyl;

(b) a 4-to 9-membered N-heterocyclic ring, wherein said 4-to 9-membered N-heterocyclic ring is optionally independently substituted with one or more substituents selected from the group consisting of (i) 1 $G^1$ group or (ii) 1 to 3 $G^2$ groups; wherein $G^1$ is selected from the group consisting of -$L^4$-($C_1$-$C_6$)alkyl, -$L^4$-($C_3$-$C_6$)cycloalkyl, -$L^4$-($C_3$-$C_6$)heterocyclyl, and -$L^4$-phenyl; wherein each of said —($C_1$-$C_6$)alkyl, —($C_3$-$C_6$)cycloalkyl, -(4-to 7-membered)heterocyclyl, and phenyl substituents may optionally be individually substituted by 1 to 4 $R^6$ groups;

$L^4$ is absent or selected from the group consisting of —O—, —C(O)—, —N($R^7$)—, —C(O)—N($R^7$)—, —N($R^7$)—C(O)—, and —N($R^7$)—S(O)—;

—$R^6$ is selected from the group consisting of halo, —OH, =O, —CN, —($C_1$-$C_6$)alkyl, —O($C_1$-$C_6$)alkyl, —N($R^7$)$_2$, —C(O)—$R^7$, —C(O)—O—$R^7$, —N($R^7$)—C(O)—$R^7$, —C(O)—N($R^7$)$_2$, —S(O)$_j$—$R^7$, —($C_3$-$C_6$)cycloalkyl, -(4-to 7-membered)heterocyclyl, and phenyl optionally substituted with —C(O)—O—$R^7$;

each $R^7$ is independently selected from the group consisting of —H, —($C_1$-$C_6$)alkyl, —($C_3$-$C_6$)cycloalkyl, and -(4-to 7-membered)heterocyclyl; and $G^2$ is independently selected from the group consisting of -halo, —OH, =O, —CN, —O($C_1$-$C_6$)alkyl and —($C_1$-$C_6$)alkyl optionally substituted with —O($C_1$-$C_6$)alkyl; or (c) a group selected from the group consisting of a tetrahydro-2H-pyranyl, —C(O)—OH and OH, wherein j is an integer selected from 0, 1 and 2.

In some embodiments, the LTA4H modulatory agent is a compound selected from 2-Methoxy-1-(4-{6-[5-(2H-pyrazol-3-yl)-pyridin-2-yloxy]-naphthalen-2-ylmethyl}-piperazin-1-yl)-ethanone, 1-(4-{6-[5-(2H-Pyrazol-3-yl)-pyridin-2-yloxy]-naphthalen-2-ylmethyl}-piperazin-1-yl)-ethanone, 5-(2H-Pyrazol-3-yl)-2-(6-pyrrolidin-1-ylmethyl-naphthalen-2-yloxy)-pyridine, 1-{6-[5-(2H-Pyrazol-3-yl)-pyridin-2-yloxy]-naphthalen-2-ylmethyl}-piperidin-4-ol, 1-{6-[5-(2H-Pyrazol-3-yl)-pyridin-2-yloxy]-naphthalen-2-ylmethyl}-piperidine-4-carboxylic acid amide, N-(1-{6-[5-(2H-Pyrazol-3-yl)-pyridin-2-yloxy]-naphthalen-2-ylmethyl}-piperidin-4-yl)-acetamide, (S)-3-Hydroxy-1-(1-{6-[5-(2H-Pyrazol-3-yl)-pyridin-2-yloxy]-naphthalen-2-ylmethyl}-piperidin-4-yl)-pyrrolidin-2-one, Dimethyl-{6-[4-(2H-pyrazol-3-yl)-phenoxy]-chroman-2-ylmethyl}-amine, 1-{7-[5-(2H-Pyrazol-3-yl)-pyridin-2-yloxy]-chroman-2-ylmethyl}-piperidine-4-carboxylic acid amide, 2-Hydroxy-1-(4-{6-[4-(2H-pyrazol-3-yl)-phenoxy]-quinolin-2-ylmethyl}-piperazin-1-yl)-ethanone, 3-(1-{6-[5-(2H-Pyrazol-3-yl)-pyridin-2-yloxy]-quinolin-2-ylmethyl}-piperidin-4-yl)-oxazolidin-2-one, 1-(4-{6-[4-(2H-Pyrazol-3-yl)-phenoxy]-quinolin-2-ylmethyl}-piperazin-1-yl)-propan-1-one, (S)-2-Hydroxy-1-(4-{6-[4-(2H-pyrazol-3-yl)-phenoxy]-quinolin-2-ylmethyl}-piperazin-1-yl)-propan-1-one, 2-Morpholin-4-ylmethyl-6-[4-(2H-pyrazol-3-yl)-phenoxy]-pyrazolo[1,5-a]pyridine, (1-Hydroxy-cyclopropyl)-(4-{6-[4-(2H-pyrazol-3-yl)-phenoxy]-quinolin-2-ylmethyl}-piperazin-1-yl)-methanone, (S)-7-{6-[5-(2H-Pyrazol-3-yl)-pyridin-2-yloxy]-quinolin-2-ylmethyl}-hexahydro-oxazolo[3,4-a]pyrazin-3-one, 2-(2,2-Dioxo-2-λ-6-thia-5-aza-bicyclo[2.2.1]hept-5-ylmethyl)-6-[4-(2H-pyrazol-3-yl)-phenoxy]-quinoline, 2-{6-[5-(2H-Pyrazol-3-yl)-pyridin-2-yloxy]-quinolin-2-ylmethyl}-hexahydro-pyrrolo[1,2-a]pyrazin-6-one, 6-[5-(2H-Pyrazol-3-yl)-pyridin-2-yloxy]-2-pyrrolidin-1-ylmethyl-quinoline, 2-(2-Oxa-6-aza-spiro[3.4]oct-6-ylmethyl)-6-[5-(2H-pyrazol-3-yl)-pyridin-2-yloxy]-quinoline, 2-Azetidin-1-ylmethyl-6-[5-(2H-pyrazol-3-yl)-pyridin-2-yloxy]-quinoline, 2-Azepan-1-ylmethyl-6-[5-(2H-pyrazol-3-yl)-pyridin-2-yloxy]-quinoline, 2-Piperidin-1-ylmethyl-6-[5-(2H-pyrazol-3-yl)-pyridin-2-yloxy]-quinoline, 1-(8-{6-[5-(2H-Pyrazol-3-yl)-pyridin-2-yloxy]-quinolin-2-ylmethyl}-3,8-diaza-bicyclo[3.2.1]oct-3-yl)-ethanone, Methyl-{6-[5-(2H-pyrazol-3-yl)-pyridin-2-yloxy]-quinolin-2-ylmethyl}-amine, 2-Methyl-1-(4-{6-[5-(2H-pyrazol-3-yl)-pyridin-2-yloxy]-quinolin-2-ylmethyl}-piperazin-1-yl)-propan-1-one, 2-Hydroxy-1-(4-{6-[5-(2H-pyrazol-3-yl)-pyridin-2-yloxy]-quinolin-2-ylmethyl}-piperazin-1-yl)-ethanone, 2-Methoxy-1-(4-{6-[5-(2H-pyrazol-3-yl)-pyridin-2-yloxy]-quinolin-2-ylmethyl}-piperazin-1-yl)-ethanone, 1-(4-{6-[5-(2H-Pyrazol-3-yl)-pyridin-2-yloxy]-quinolin-2-ylmethyl}-piperazin-1-yl)-propan-1-one, 8-{6-[5-(2H-Pyrazol-3-yl)-pyridin-2-yloxy]-quinolin-2-ylmethyl}-1,8-diaza-spiro[4.5]decan-2-one, 3-Oxo-3-(4-{6-[5-(2H-pyrazol-3-yl)-pyridin-2-yloxy]-quinolin-2-ylmethyl}-piperazin-1-yl)-propionitrile, 1-(5-{6-[5-(2H-Pyrazol-3-yl)-pyridin-2-yloxy]-quinolin-2-ylmethyl}-hexahydro-pyrrolo[3,4-c]pyrrol-2-yl)-ethanone, 2-Hydroxy-N-methyl-N-(1-{6-[5-(2H-Pyrazol-3-yl)-pyridin-2-yloxy]-quinolin-2-ylmethyl}-piperidin-4-yl)-acetamide, (R)-2-({6-[5-(2H-Pyrazol-3-yl)-pyridin-2-yloxy]-quinolin-2-ylmethyl}-amino)-propionamide, (1a,5a,6a)-3-{6-[5-(2H-Pyrazol-3-yl)-pyridin-2-yloxy]-quinolin-2-ylmethyl}-3-aza-bicyclo[3.1.0]hexane-6-carboxylic acid amide, 1-{3-[(Methyl-{6-[5-(2H-pyrazol-3-yl)-pyridin-2-yloxy]-quinolin-2-ylmethyl}-amino)-methyl]-azetidin-1-yl}-ethanone, N-Methyl-N-(1-{6-[5-(2H-pyrazol-3-yl)-pyridin-2-yloxy]-quinolin-2-ylmethyl}-piperidin-4-yl)-acetamide, 2-Hydroxy-1-((R)-3-methyl-4-{6-[5-(2H-pyrazol-3-yl)-pyridin-2-yloxy]-quinolin-2-ylmethyl}-piperazin-1-yl)-ethanone, 2-Methanesulfonyl-1-(4-{6-[5-(2H-pyrazol-3-yl)-pyridin-2-yloxy]-quinolin-2-ylmethyl}-piperazin-1-yl)-ethanone, (1a,5a,6a)-3-{6-[5-(2H-Pyrazol-3-yl)-pyridin-2-yloxy]-quinolin-2-ylmethyl}-3-aza-bicyclo[3.1.0]hexane-6-carboxylic acid (2-hydroxy-2-methyl-propyl)-amide, N-((1a,5a,6a)-3-{6-[5-(2H-pyrazol-3-yl)-pyridin-2-yloxy]-quinolin-2-ylmethyl}-3-aza-bicyclo[3.1.0]hex-6-ylmethyl)-acetamide, 1-((S)-3-Hydroxymethyl-4-{6-[5-(2H-pyrazol-3-yl)-pyridin-2-yloxy]-quinolin-2-ylmethyl}-piperazin-1-yl)-ethanone, 4-{6-[5-(2H-Pyrazol-3-yl)-pyridin-2-yloxy]-quinolin-2-ylmethyl}-piperazine-1-carboxylic acid amide, 2-Hydroxy-1-(3-{6-[5-(2H-pyrazol-3-yl)-pyridin-2-yloxy]-quinolin-2-ylmethyl}-3,8-diaza-bicyclo[3.2.1]oct-8-yl)-ethanone, 2-({6-[5-(2H-Pyrazol-3-yl)-pyridin-2-yloxy]-quinolin-2-ylmethyl}-amino)-1-pyrrolidin-1-yl-ethanone, 2-Hydroxy-N-(4-methyl-1-{6-[5-(2H-pyrazol-3-yl)-pyridin-2-yloxy]-quinolin-2-ylmethyl}-piperidin-4-yl)-acetamide, 2-(Methyl-{6-[5-(2H-pyrazol-3-yl)-pyridin-2-yloxy]-quinolin-2-ylmethyl}-amino)-acetamide, 2-(2-Oxa-6-aza-spiro[3.5]non-6-ylmethyl)-6-[5-(2H-pyrazol-3-yl)-pyridin-2-yloxy]-quinoline, (S)-3-({6-[5-(2H-Pyrazol-3-yl)-pyridin-2-yloxy]-quinolin-2-ylmethyl}-amino)-pyrrolidin-2-one, 2-Hydroxy-1-(8-{6-[5-(2H-pyrazol-3-yl)-pyridin-2-yloxy]-quinolin-2-ylmethyl}-1,8-diaza-spiro[4.5]dec-1-yl)-ethanone, (S)-2-Phenyl-2-({6-[5-(2H-pyrazol-3-yl)-pyridin-2-yloxy]-quinolin-2-ylmethyl}-amino)-acetamide, 5-[4-(2H-Pyrazol-3-yl)-phenoxy]-2-pyrrolidin-1-ylmethyl-1H-benzoimidazole, 2-((2R,6S)-2,6-Dimethyl-morpholin-4-ylmethyl)-5-[4-(2H-pyrazol-3-yl)-phenoxy]-1H-benzoimidazole, 6-[4-(2H-Pyrazol-3-yl)-benzyl]-2-pyrrolidin-1-ylmethyl-1H-benzoimidazole, 2-((3S,5S)-3,5-Dimethyl-morpholin-4-ylmethyl)-5-[4-(2H-pyrazol-3-yl)-phenoxy]-1H-benzoimidazole, 2-((2S,6S)-2,6-Dimethyl-morpholin-4-ylmethyl)-6-[4-(2H-pyrazol-3-yl)-benzyl]-1H-benzoimidazole, 2,2,2-Trifluoro-1-(4-{5-[4-(2H-pyrazol-3-yl)-phenoxy]-1H-benzoimidazol-2-ylmethyl}-piperazin-1-yl)-ethanone, (1S,5S)-3-{5-[4-(2H-Pyrazol-3-yl)-phenoxy]-

1H-benzoimidazol-2-ylmethyl}-8-oxa-3-aza-bicyclo[3.2.1]octane, 2-(1-Morpholin-4-yl-cyclopropyl)-5-[4-(2H-pyrazol-3-yl)-phenoxy]-1H-benzoimidazole, 2-Morpholin-4-ylmethyl-6-[4-(2H-pyrazol-3-yl)-benzyl]-1H-benzoimidazole, 2-[4-(2-Methoxy-ethyl)-piperazin-1-ylmethyl]-5-[4-(2H-pyrazol-3-yl)-phenoxy]-1H-benzoimidazole, 2-((S)-3-Methyl-morpholin-4-ylmethyl)-5-[4-(2H-pyrazol-3-yl)-phenoxy]-1H-benzoimidazole, 5-[4-(2H-Pyrazol-3-yl)-phenoxy]-2-[4-(2,2,2-trifluoro-ethyl)-piperazin-1-ylmethyl]-1H-benzoimidazole, 2-(4-Isopropyl-piperazin-1-ylmethyl)-5-[4-(2H-pyrazol-3-yl)-phenoxy]-1H-benzoimidazole, 2-[4-(3-Methyl-[1,2,4]oxadiazol-5-yl)-piperidin-1-ylmethyl]-5-[4-(2H-pyrazol-3-yl)-phenoxy]-1H-benzoimidazole, (S)-1-{6-[4-(2H-Pyrazol-3-yl)-phenoxy]-1H-benzoimidazol-2-ylmethyl}-pyrrolidin-3-ol, 5-{6-[4-(2H-Pyrazol-3-yl)-phenoxy]-imidazo[1,2-a]pyridin-2-yl}-piperidin-2-one, (S)-5-{6-[4-(2H-Pyrazol-3-yl)-phenoxy]-quinolin-2-yloxy}-piperidin-2-one, 5-[4-(1H-Pyrazol-3-yl)-phenoxy]-1H-benzoimidazole-2-carboxylic acid, 2,2-Dimethyl-1-(4-{5-[4-(2H-pyrazol-3-yl)-phenoxy]-1H-benzoimidazol-2-ylmethyl}-piperazin-1-yl)-propan-1-one, 2,2,2-Trifluoro-1-(1-{5-[4-(2H-pyrazol-3-yl)-phenoxy]-1H-benzoimidazol-2-ylmethyl}-piperidin-4-yl)-ethanol, 2-(2-Oxa-6-aza-spiro[3.3]hept-6-ylmethyl)-5-[4-(2H-pyrazol-3-yl)-phenoxy]-1H-benzoimidazole, 5-[4-(2H-Pyrazol-3-yl)-phenoxy]-2-pyridin-3-ylmethyl-1H-benzoimidazole, ((S)-sec-Butyl)-methyl-{5-[4-(2H-pyrazol-3-yl)-phenoxy]-1H-benzoimidazol-2-ylmethyl}-amine, 5-[4-(2H-Pyrazol-3-yl)-phenoxy]-1-(2-pyrrolidin-1-yl-ethyl)-1H-indazole, Methyl-{5-[4-(2H-pyrazol-3-yl)-phenoxy]-1H-benzoimidazol-2-ylmethyl}-[(S)-1-(tetrahydro-furan-2-yl)methyl]-amine, Methyl-{5-[4-(2H-pyrazol-3-yl)-phenoxy]-1H-benzoimidazol-2-ylmethyl}-(S)-tetrahydro-furan-3-yl-amine, Methyl-{5-[4-(2H-pyrazol-3-yl)-phenoxy]-1H-benzoimidazol-2-ylmethyl}-(R)-tetrahydro-furan-3-yl-amine, 5-[4-(2H-Pyrazol-3-yl)-phenoxy]-1-(3-pyrrolidin-1-yl-propyl)-1H-indazole, ((R)-sec-Butyl)-methyl-{5-[4-(2H-pyrazol-3-yl)-phenoxy]-1H-benzoimidazol-2-ylmethyl}-amine, Methyl-{5-[4-(2H-pyrazol-3-yl)-phenoxy]-1H-benzoimidazol-2-ylmethyl}-[(R)-1-(tetrahydro-furan-2-yl)methyl]-amine, ((S)-2-Methoxy-1-methyl-ethyl)-methyl-{5-[4-(2H-pyrazol-3-yl)-phenoxy]-1H-benzoimidazol-2-ylmethyl}-amine, 5-[5-(2H-Pyrazol-3-yl)-pyridin-2-yloxy]-1-(2-pyrrolidin-1-yl-ethyl)-1H-indazole, 2-(3-Morpholin-4-yl-propyl)-5-[4-(2H-pyrazol-3-yl)-phenoxy]-2H-indazole, Methyl-{5-[4-(2H-pyrazol-3-yl)-phenoxy]-1H-benzoimidazol-2-ylmethyl}-(tetrahydro-furan-2-ylmethyl)-amine, Ethyl-((S)-2-methoxy-1-methyl-ethyl)-{5-[4-(2H-pyrazol-3-yl)-phenoxy]-1H-benzoimidazol-2-ylmethyl}-amine, [1,4]Dioxan-2-ylmethyl-methyl-{5-[4-(2H-pyrazol-3-yl)-phenoxy]-1H-benzoimidazol-2-ylmethyl}-amine, N-[1-(2-{5-[4-(2H-Pyrazol-3-yl)-phenoxy]-indazol-1-yl}-ethyl)-piperidin-4-yl]-acetamide, 2-((S)-1-Methyl-pyrrolidin-2-ylmethyl)-5-[4-(2H-pyrazol-3-yl)-phenoxy]-1H-benzoimidazole, 1-[4-(2-{5-[4-(2H-Pyrazol-3-yl)-phenoxy]-indazol-1-yl}-ethyl)-piperazin-1-yl]-ethanone, (2-Methoxy-ethyl)-{5-[4-(2H-pyrazol-3-yl)-phenoxy]-1H-benzoimidazol-2-ylmethyl}-amine, Methyl-{5-[4-(2H-pyrazol-3-yl)-phenoxy]-1H-benzoimidazol-2-ylmethyl}-(tetrahydro-pyran-3-ylmethyl)-amine, 1-[4-(2-{5-[4-(2H-Pyrazol-3-yl)-phenoxy]-indazol-2-yl}-ethyl)-piperazin-1-yl]-ethanone, 1-[4-(2-{5-[5-(2H-Pyrazol-3-yl)-pyridin-2-yloxy]-indazol-1-yl}-ethyl)-piperazin-1-yl]-ethanone, 1-[4-(3-{5-[4-(2H-Pyrazol-3-yl)-phenoxy]-indazol-2-yl}-propyl)-piperazin-1-yl]-ethanone, (1-{6-[5-(2H-Pyrazol-3-yl)-pyridin-2-yloxy]-quinolin-2-ylmethyl}-piperidin-4-yl)-acetonitrile, {5-[4-(2H-Pyrazol-3-yl)-phenoxy]-1H-benzoimidazol-2-ylmethyl}-(tetrahydro-furan-2-ylmethyl)-amine, 5-[4-(2H-Pyrazol-3-yl)-phenoxy]-2-thiomorpholin-4-ylmethyl-1H-benzoimidazole, 1-{6-[5-(2H-Pyrazol-3-yl)-pyridin-2-yloxy]-quinolin-2-ylmethyl}-piperidine-4-carbonitrile, {5-[4-(2H-Pyrazol-3-yl)-phenoxy]-1H-benzoimidazol-2-ylmethyl}-[(S)-1-(tetrahydro-furan-2-yl)methyl]-amine, {5-[4-(2H-Pyrazol-3-yl)-phenoxy]-1H-benzoimidazol-2-ylmethyl}-[(R)-1-(tetrahydro-furan-2-yl)methyl]-amine, 1-(2-Morpholin-4-yl-ethyl)-5-[4-(2H-pyrazol-3-yl)-phenoxy]-1H-indazole, N—((S)-sec-Butyl)-N-{5-[4-(2H-pyrazol-3-yl)-phenoxy]-1H-benzoimidazol-2-ylmethyl}-acetamide, Methyl-{5-[4-(2H-pyrazol-3-yl)-phenoxy]-1H-benzoimidazol-2-ylmethyl}-(tetrahydro-furan-3-ylmethyl)-amine, 5-[4-(2H-Pyrazol-3-yl)-phenoxy]-2-(3-pyrrolidin-1-yl-propyl)-2H-indazole, {5-[4-(2H-Pyrazol-3-yl)-phenoxy]-1H-benzoimidazol-2-ylmethyl}-(tetrahydro-pyran-4-ylmethyl)-amine, (R)-1-{6-[5-(2H-Pyrazol-3-yl)-pyridin-2-yloxy]-quinolin-2-ylmethyl}-pyrrolidine-3-carbonitrile, 1-[4-(2-{6-[5-(2H-Pyrazol-3-yl)-pyridin-2-yloxy]-quinolin-2-yl}-ethyl)-piperazin-1-yl]-ethanone, N-[1-(3-{5-[4-(2H-Pyrazol-3-yl)-phenoxy]-indazol-1-yl}-propyl)-piperidin-4-yl]-acetamide, 1-[4-(Methyl-{6-[5-(2H-Pyrazol-3-yl)-pyridin-2-yloxy]-quinolin-2-ylmethyl}-amino)-piperidin-1-yl]-ethanone, 1-(2-Morpholin-4-yl-ethyl)-5-[5-(2H-pyrazol-3-yl)-pyridin-2-yloxy]-1H-indazole, 2-Hydroxy-2-methyl-N-[1-(2-{5-[5-(2H-pyrazol-3-yl)-pyridin-2-yloxy]-indazol-2-yl}-ethyl)-piperidin-4-yl]-propionamide, 3-Morpholin-4-ylmethyl-6-[5-(2H-pyrazol-3-yl)-pyridin-2-yloxy]-1H-indazole, 2-Morpholin-4-ylmethyl-6-[4-(2H-pyrazol-3-yl)-phenoxy]-benzooxazole, 1-(4-{6-[5-(2H-Pyrazol-3-yl)-pyridin-2-yloxy]-quinolin-2-yl}-piperazin-1-yl)-ethanone, N-[1-(3-{5-[4-(2H-Pyrazol-3-yl)-phenoxy]-indazol-2-yl}-propyl)-piperidin-4-yl]-acetamide, (S)-5-{5-[5-(2H-Pyrazol-3-yl)-pyridin-2-yloxy]-indazol-1-ylmethyl}-pyrrolidin-2-one, 3-{5-[4-(2H-Pyrazol-3-yl)-phenoxy]-indazol-1-yl}-propan-1-ol, (S)-5-{6-[4-(2H-Pyrazol-3-yl)-phenoxy]-isoquinolin-1-yloxymethyl}-pyrrolidin-2-one, 2-(2-Morpholin-4-yl-ethoxy)-6-[5-(2H-pyrazol-3-yl)-pyridin-2-yloxy]-quinoline, N-[2-({6-[5-(2H-Pyrazol-3-yl)-pyridin-2-yloxy]-quinolin-2-ylmethyl}-amino)-ethyl]-acetamide, (2-Methoxy-ethyl)-methyl-{6-[5-(2H-pyrazol-3-yl)-pyridin-2-yloxy]-quinolin-2-ylmethyl}-amine, Dimethyl-{6-[4-(2H-Pyrazol-3-yl)-phenoxy]-quinolin-2-ylmethyl}-amine, 4-(1-{1-[4-(2H-Pyrazol-3-yl)-benzyl]-1H-indol-5-ylmethyl}-piperidin-4-yl)-benzoic acid, N-(1-{6-[5-(2H-Pyrazol-3-yl)-pyridin-2-yloxy]-2,3-dihydro-benzofuran-2-ylmethyl}-piperidin-4-yl)-acetamide, 5-(2H-Pyrazol-3-yl)-2-(2-pyrrolidin-1-ylmethyl-2,3-dihydro-benzofuran-6-yloxy)-pyridine, 5-(2H-Pyrazol-3-yl)-2-(2-pyrrolidin-1-ylmethyl-benzofuran-6-yloxy)-pyridine, N-(1-{6-[5-(2H-Pyrazol-3-yl)-pyridin-2-yloxy]-2,3-dihydro-benzofuran-2-ylmethyl}-piperidin-4-ylmethyl)-acetamide, 1-(1-{6-[5-(2H-Pyrazol-3-yl)-pyridin-2-yloxy]-2,3-dihydro-benzofuran-2-ylmethyl}-piperidin-4-yl)-pyrrolidin-2-one, 3-[1-(2-{6-[5-(2H-Pyrazol-3-yl)-pyridin-2-yloxy]-benzofuran-3-yl}-ethyl)-piperidin-4-yl]-oxazolidin-2-one, N-((endo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide, 2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone, N-[1-(2-{6-[5-(2H-Pyrazol-3-yl)-pyridin-2-yloxy]-benzofuran-3-yl}-ethyl)-piperidin-4-yl]-acetamide, 1-[4-(2-{6-[5-(2H-Pyrazol-3-yl)-pyridin-2-yloxy]-benzofuran-3-yl}-ethyl)-[1,4]diazepan-1-yl]-ethanone, 1-[4-(2-{6-[5-(2H-Pyrazol-3-yl)-pyridin-2-yloxy]-2,3-dihydro-benzofuran-3-yl}-ethyl)-[1,4]diazepan-1-yl]-ethanone, 1-[4-(2-

{6-[5-(2H-Pyrazol-3-yl)-pyridin-2-yloxy]-benzofuran-3-yl}-ethyl)-piperazin-1-yl]-ethanone, 1-{6-[4-(2H-Pyrazol-3-yl)-phenoxy]-2,3-dihydro-benzofuran-2-ylmethyl}-piperidine-4-carboxylic acid methylamide, 1-(2-{6-[5-(2H-Pyrazol-3-yl)-pyridin-2-yloxy]-benzofuran-3-yl}-ethyl)-piperidine-4-carboxylic acid methylamide, 2-Hydroxy-1-((1S,4S)-5-{6-[5-(2H-pyrazol-3-yl)-pyridin-2-yloxy]-quinolin-2-ylmethyl}-2,5-diaza-bicyclo[2.2.1]hept-2-yl)-ethanone, 2-Hydroxy-1-(4-{6-[5-(2H-pyrazol-3-yl)-pyridin-2-yloxy]-quinolin-2-ylmethyl}-[1,4]diazepan-1-yl)-ethanone, N-[1-(2-{6-[5-(2H-Pyrazol-3-yl)-pyridin-2-yloxy]-benzofuran-3-yl}-ethyl)-piperidin-4-yl]-methanesulfonamide, N-((exo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide, 1-[4-(2-{6-[5-(2H-Pyrazol-3-yl)-pyridin-2-yloxy]-2,3-dihydro-benzofuran-3-yl}-ethyl)-piperazin-1-yl]-ethanone, 1-{6-[4-(2H-Pyrazol-3-yl)-phenoxy]-2,3-dihydro-benzofuran-2-ylmethyl}-piperidine-4-carboxylic acid amide, 2-Hydroxy-1-((1R,4R)-5-{6-[5-(2H-pyrazol-3-yl)-pyridin-2-yloxy]-quinolin-2-ylmethyl}-2,5-diaza-bicyclo[2.2.1]hept-2-yl)-ethanone, 2-Hydroxy-1-(5-{6-[5-(2H-pyrazol-3-yl)-pyridin-2-yloxy]-quinolin-2-ylmethyl}-2,5-diaza-bicyclo[2.2.2]oct-2-yl)-ethanone, 1-((1R,4R)-5-{6-[5-(2H-Pyrazol-3-yl)-pyridin-2-yloxy]-quinolin-2-ylmethyl}-2,5-diaza-bicyclo[2.2.1]hept-2-yl)-ethanone, 1-(5-{6-[5-(2H-Pyrazol-3-yl)-pyridin-2-yloxy]-quinolin-2-ylmethyl}-2,5-diaza-bicyclo[2.2.2]oct-2-yl)-ethanone, 1-(4-{6-[5-(2H-Pyrazol-3-yl)-pyridin-2-yloxy]-benzofuran-3-ylmethyl}-piperazin-1-yl)-ethanone, 4-((1S,4S)-5-{5-[4-(2H-Pyrazol-3-yl)-phenoxy]-1H-benzoimidazol-2-ylmethyl}-2,5-diaza-bicyclo[2.2.1]hept-2-ylmethyl)-benzoic acid methyl ester, 4-(1-{5-[4-(2H-Pyrazol-3-yl)-phenoxy]-1H-benzoimidazol-2-ylmethyl}-piperidin-4-yl)-benzoic acid methyl ester, Diethyl-{5-[4-(2H-pyrazol-3-yl)-phenoxy]-1H-benzoimidazol-2-ylmethyl}-amine, 2-(4-Methyl-piperidin-1-ylmethyl)-5-[4-(2H-pyrazol-3-yl)-phenoxy]-1H-benzoimidazole, Ethyl-methyl-(2-{5-[4-(2H-pyrazol-3-yl)-phenoxy]-indazol-2-yl}-ethyl)-amine, Ethyl-(2-methoxy-ethyl)-{5-[4-(2H-pyrazol-3-yl)-phenoxy]-1H-benzoimidazol-2-ylmethyl}-amine, 2-(3-Methoxymethyl-piperidin-1-ylmethyl)-5-[4-(2H-pyrazol-3-yl)-phenoxy]-1H-benzoimidazole, 2-(3-Methoxy-pyrrolidin-1-ylmethyl)-5-[4-(2H-pyrazol-3-yl)-phenoxy]-1H-benzoimidazole, Dimethyl-(2-{5-[4-(2H-pyrazol-3-yl)-phenoxy]-indazol-2-yl}-ethyl)-amine, Methyl-{5-[4-(2H-pyrazol-3-yl)-phenoxy]-1H-benzoimidazol-2-ylmethyl}-(tetrahydro-pyran-4-ylmethyl)-amine, N—[(R)-1-(2-{5-[4-(2H-Pyrazol-3-yl)-phenoxy]-indazol-1-yl}-ethyl)-pyrrolidin-3-yl]-acetamide, ((S)-sec-Butyl)-{5-[4-(2H-pyrazol-3-yl)-phenoxy]-1H-benzoimidazol-2-ylmethyl}-amine, Dimethyl-(2-{5-[4-(2H-pyrazol-3-yl)-phenoxy]-indazol-1-yl}-ethyl)-amine, 2-Azepan-1-ylmethyl-5-[4-(2H-pyrazol-3-yl)-phenoxy]-1H-benzoimidazole, Cyclopentyl-methyl-{5-[4-(2H-pyrazol-3-yl)-phenoxy]-1H-benzoimidazol-2-ylmethyl}-amine, 2-((R)-2-Methyl-piperidin-1-ylmethyl)-5-[4-(2H-pyrazol-3-yl)-phenoxy]-1H-benzoimidazole, 2-(3-Methoxymethyl-pyrrolidin-1-ylmethyl)-5-[4-(2H-pyrazol-3-yl)-phenoxy]-1H-benzoimidazole, 2-((R)-2-Methoxymethyl-pyrrolidin-1-ylmethyl)-5-[4-(2H-pyrazol-3-yl)-phenoxy]-1H-benzoimidazole, 2-(2-Methoxymethyl-piperidin-1-ylmethyl)-5-[4-(2H-pyrazol-3-yl)-phenoxy]-1H-benzoimidazole, N,N-Dimethyl-2-(1-{6-[4-(2H-pyrazol-3-yl)-phenoxy]-2,3-dihydro-benzofuran-2-ylmethyl}-piperidin-4-yl)-acetamide, 2-Methoxy-N-(1-{6-[4-(2H-pyrazol-3-yl)-phenoxy]-2,3-dihydro-benzofuran-2-ylmethyl}-piperidin-4-yl)-acetamide, 2-((S)-2-Methyl-piperidin-1-ylmethyl)-5-[4-(2H-pyrazol-3-yl)-phenoxy]-1H-benzoimidazole, 2-(3-Methoxy-piperidin-1-ylmethyl)-5-[4-(2H-pyrazol-3-yl)-phenoxy]-1H-benzoimidazole, 2-((S)-2-Methoxymethyl-pyrrolidin-1-ylmethyl)-5-[4-(2H-pyrazol-3-yl)-phenoxy]-1H-benzoimidazole, 3-Methyl-1-{6-[5-(2H-pyrazol-3-yl)-pyridin-2-yloxy]-quinolin-2-ylmethyl}-azetidin-3-ol, 2-[1,4]Oxazepan-4-ylmethyl-5-[4-(2H-pyrazol-3-yl)-phenoxy]-1H-benzoimidazole, 2-[2-(1,1-Dioxo-1-λ-6-thiomorpholin-4-yl)-ethyl]-5-[4-(2H-pyrazol-3-yl)-phenoxy]-2H-indazole, 1-[1-(2-{5-[4-(2H-Pyrazol-3-yl)-phenoxy]-indazol-1-yl}-ethyl)-piperidin-4-yl]-pyrrolidin-2-one, 2-[((1S,4S)-1-(2-Oxa-5-aza-bicyclo[2.2.1]hept-5-yl)methyl]-6-[5-(2H-pyrazol-3-yl)-pyridin-2-yloxy]-quinoline, Cyclopropyl-methyl-{5-[4-(2H-pyrazol-3-yl)-phenoxy]-1H-benzoimidazol-2-ylmethyl}-amine, ((R)-sec-Butyl)-{5-[4-(2H-Pyrazol-3-yl)-phenoxy]-1H-benzoimidazol-2-ylmethyl}-amine, {5-[4-(2H-Pyrazol-3-yl)-phenoxy]-1H-benzoimidazol-2-ylmethyl}-(tetrahydro-pyran-3-yl)-amine, 2-(3,3-Dimethyl-morpholin-4-ylmethyl)-5-[4-(2H-pyrazol-3-yl)-phenoxy]-1H-benzoimidazole, Isopropyl-(2-methoxy-ethyl)-{5-[4-(2H-pyrazol-3-yl)-phenoxy]-1H-benzoimidazol-2-ylmethyl}-amine, (2-Methoxy-ethyl)-propyl-{5-[4-(2H-pyrazol-3-yl)-phenoxy]-1H-benzoimidazol-2-ylmethyl}-amine, {6-[4-(2H-Pyrazol-3-yl)-phenoxy]-2,3-dihydro-benzofuran-2-ylmethyl}-(tetrahydro-pyran-4-ylmethyl)-amine, Bis-(2-methoxy-ethyl)-{5-[4-(2H-pyrazol-3-yl)-phenoxy]-1H-benzoimidazol-2-ylmethyl}-amine, Morpholin-4-yl-(1-{6-[4-(2H-pyrazol-3-yl)-phenoxy]-2,3-dihydro-benzofuran-2-ylmethyl}-piperidin-4-yl)-methanone, Cyclopentyl-{5-[4-(2H-pyrazol-3-yl)-phenoxy]-1H-benzoimidazol-2-ylmethyl}-amine, ((S)-2-Methoxy-1-methyl-ethyl)-{5-[4-(2H-pyrazol-3-yl)-phenoxy]-1H-benzoimidazol-2-ylmethyl}-amine, 3-(1-{6-[5-(2H-Pyrazol-3-yl)-pyridin-2-yloxy]-quinolin-2-ylmethyl}-piperidin-4-yl)-[1,3]oxazinan-2-one, Ethyl-{5-[4-(2H-pyrazol-3-yl)-phenoxy]-1H-benzoimidazol-2-ylmethyl}-amine, 2-(Ethyl-{5-[4-(2H-pyrazol-3-yl)-phenoxy]-1H-benzoimidazol-2-ylmethyl}-amino)-ethanol, 2-(4-Ethoxymethyl-piperidin-1-ylmethyl)-5-[4-(2H-pyrazol-3-yl)-phenoxy]-1H-benzoimidazole, {5-[4-(2H-Pyrazol-3-yl)-phenoxy]-1H-benzoimidazol-2-ylmethyl}-(S)-tetrahydro-furan-3-yl-amine, (1-{5-[4-(2H-Pyrazol-3-yl)-phenoxy]-1H-benzoimidazol-2-ylmethyl}-piperidin-2-yl)-methanol, 5-[4-(2H-Pyrazol-3-yl)-phenoxy]-2-(3-trifluoromethyl-pyrrolidin-1-ylmethyl)-1H-benzoimidazole, 1-{6-[4-(2H-Pyrazol-3-yl)-phenoxy]-2,3-dihydro-benzofuran-2-ylmethyl}-piperidine-4-carboxylic acid dimethylamide, 1-(1-{6-[4-(2H-Pyrazol-3-yl)-phenoxy]-2,3-dihydro-benzofuran-2-ylmethyl}-piperidin-4-yl)-pyrrolidin-2-one, 2-(Propyl-{5-[4-(2H-pyrazol-3-yl)-phenoxy]-1H-benzoimidazol-2-ylmethyl}-amino)-ethanol, N—[(R)-1-(2-{5-[4-(2H-Pyrazol-3-yl)-phenoxy]-indazol-2-yl}-ethyl)-pyrrolidin-3-yl]-acetamide, 2-Methoxy-N-[1-(2-{5-[4-(2H-pyrazol-3-yl)-phenoxy]-indazol-1-yl}-ethyl)-piperidin-4-yl]-acetamide, 5-[4-(2H-Pyrazol-3-yl)-phenoxy]-2-(tetrahydro-pyran-4-ylmethyl)-1H-benzoimidazole, 3-(1-{6-[4-(2H-Pyrazol-3-yl)-phenoxy]-2,3-dihydro-benzofuran-2-ylmethyl}-piperidin-4-yl)-oxazolidin-2-one, 1-{6-[5-(2H-Pyrazol-3-yl)-pyridin-2-yloxy]-quinolin-2-ylmethyl}-piperidin-4-ol, 2-((R)-3-Methoxy-pyrrolidin-1-ylmethyl)-6-[5-(2H-pyrazol-3-yl)-pyridin-2-yloxy]-quinoline, (2-{5-[4-(2H-Pyrazol-3-yl)-phenoxy]-indazol-2-yl}-ethyl)-(tetrahydro-pyran-4-ylmethyl)-amine, 5-[4-(2H-Pyrazol-3-yl)-phenoxy]-2-(S)-1-pyrrolidin-2-ylmethyl-1H-benzoimidazole, 2-((S)-3-Methoxy-pyrrolidin-1-ylmethyl)-6-[5-(2H-pyrazol-3-yl)-pyridin-2-yloxy]-quinoline, 1'-{6-[5-(2H-Pyrazol-3-yl)-pyridin-2-yloxy]-quinolin-2-ylmethyl}-[1,4']bipiperidinyl-2-one, (S)-1-{6-[5-(2H-

Pyrazol-3-yl)-pyridin-2-yloxy]-quinolin-2-ylmethyl}-pyrrolidin-3-ol, 4-(1-{6-[5-(2H-Pyrazol-3-yl)-pyridin-2-yloxy]-quinolin-2-ylmethyl}-piperidin-4-yl)-morpholin-3-one, 2-(4-Methoxy-piperidin-1-ylmethyl)-6-[5-(2H-Pyrazol-3-yl)-pyridin-2-yloxy]-quinoline, (1R,5S)-3-{6-[5-(2H-Pyrazol-3-yl)-pyridin-2-yloxy]-quinolin-2-ylmethyl}-1,2,3,4,5,6-hexahydro-1,5-methano-pyrido[1,2-a][1,5]diazocin-8-one, {6-[5-(2H-Pyrazol-3-yl)-pyridin-2-yloxy]-quinolin-2-ylmethyl}-[2-(tetrahydro-pyran-4-yl)-ethyl]-amine, 6-[5-(2H-Pyrazol-3-yl)-pyridin-2-yloxy]-2-[4-(pyridin-2-yloxy)-piperidin-1-ylmethyl]-quinoline, 1-{1-[4-(2H-Pyrazol-3-yl)-benzyl]-1H-indol-5-ylmethyl}-azetidin-3-ol, 5-[4-(2H-Pyrazol-3-yl)-phenoxy]-2-(2-pyrrolidin-1-yl-ethyl)-2H-indazole, 5-[4-(2-Pyrrolidin-1-ylmethyl-2,3-dihydro-benzofuran-6-yloxy)-phenyl]-1H-pyrazole, N-(1-{6-[4-(2H-Pyrazol-3-yl)-phenoxy]-2,3-dihydro-benzofuran-2-ylmethyl}-piperidin-4-yl)-acetamide, 6-[5-(2H-Pyrazol-3-yl)-pyrimidin-2-yloxy]-2-pyrrolidin-1-ylmethyl-quinoline, 1-(4-{6-[5-(2H-Pyrazol-3-yl)-pyridin-2-yloxy]-1H-indol-2-ylmethyl}-piperazin-1-yl)-ethanone, 1-(4-{5-[5-(2H-Pyrazol-3-yl)-pyridin-2-yloxy]-1H-indol-2-ylmethyl}-piperazin-1-yl)-ethanone, 1-(4-{6-[5-(2H-Pyrazol-3-yl)-pyridin-2-yloxy]-isoquinolin-3-ylmethyl}-piperazin-1-yl)-ethanone, 1-[4-(2-{5-[5-(2H-Pyrazol-3-yl)-pyridin-2-yloxy]-indol-1-yl}-ethyl)-piperazin-1-yl]-ethanone, 2-(4-Morpholin-4-ylmethyl-piperidin-1-ylmethyl)-5-[4-(2H-pyrazol-3-yl)-phenoxy]-1H-benzoimidazole, 2-((S)-3-Methoxy-pyrrolidin-1-ylmethyl)-5-[4-(2H-pyrazol-3-yl)-phenoxy]-1H-benzoimidazole, 3-{5-[4-(2H-Pyrazol-3-yl)-phenoxy]-1H-benzoimidazol-2-ylmethyl}-8-oxa-3-aza-bicyclo[3.2.1]octane, 2-(4-Methoxy-piperidin-1-ylmethyl)-5-[4-(2H-pyrazol-3-yl)-phenoxy]-1H-benzoimidazole, (1S,2S)-2-(Methyl-{5-[4-(2H-pyrazol-3-yl)-phenoxy]-1H-benzoimidazol-2-ylmethyl}-amino)-cyclohexanol, Methyl-{5-[4-(2H-pyrazol-3-yl)-phenoxy]-1H-benzoimidazol-2-ylmethyl}-(tetrahydro-pyran-4-yl)-amine, 1-(4-{6-[5-(1H-Pyrazol-3-yl)-pyridin-2-yloxy]-quinolin-2-ylmethyl}-piperazin-1-yl)-ethanone, 2-(2-Morpholin-4-yl-ethoxy)-6-[4-(1H-pyrazol-3-yl)-phenoxy]-benzothiazole, Cyclopropanecarboxylic acid methyl-{5-[4-(2H-pyrazol-3-yl)-phenoxy]-1H-benzoimidazol-2-ylmethyl}-amide, 3,3-Dimethyl-1-{5-[4-(2H-pyrazol-3-yl)-phenoxy]-1H-benzoimidazol-2-ylmethyl}-pyrrolidin-2-one, Cyclopropanecarboxylic acid ethyl-{5-[4-(2H-pyrazol-3-yl)-phenoxy]-1H-benzoimidazol-2-ylmethyl}-amide, 2-Methoxy-N-(1-{6-[5-(1H-pyrazol-3-yl)-pyridin-2-yloxy]-quinolin-2-ylmethyl}-piperidin-4-yl)-acetamide, N-(1-{6-[5-(1H-Pyrazol-3-yl)-pyridin-2-yloxy]-quinolin-2-ylmethyl}-piperidin-4-yl)-acetamide, N-((endo)-8-{6-[5-(1H-Pyrazol-3-yl)-pyridin-2-yloxy]-quinolin-2-ylmethyl}-8-aza-bicyclo[3.2.1]oct-3-yl)-acetamide, N-((exo)-8-{6-[5-(1H-Pyrazol-3-yl)-pyridin-2-yloxy]-quinolin-2-ylmethyl}-8-aza-bicyclo[3.2.1]oct-3-yl)-acetamide, 1-((S)-5-{6-[5-(1H-Pyrazol-3-yl)-pyridin-2-yloxy]-quinolin-2-ylmethyl}-2,5-diaza-bicyclo[2.2.1]hept-2-yl)-ethanone, 1-(4-{6-[4-(2H-Pyrazol-3-yl)-phenoxy]-quinoxalin-2-ylmethyl}-piperazin-1-yl)-ethanone, 2-(1,1-Dioxo-1-λ-6-thiomorpholin-4-ylmethyl)-6-[5-(1H-pyrazol-3-yl)-pyridin-2-yloxy]-quinoline, 6-[4-(2H-Pyrazol-3-yl)-phenoxy]-2-pyrrolidin-1-ylmethyl-quinoline, 2-Azetidin-1-ylmethyl-6-[4-(2H-pyrazol-3-yl)-phenoxy]-quinoline, 1-(8-{6-[4-(2H-Pyrazol-3-yl)-phenoxy]-quinolin-2-ylmethyl}-3,8-diaza-bicyclo[3.2.1]oct-3-yl)-ethanone, 6-[4-(2H-Pyrazol-3-yl)-phenoxy]-2-pyrrolidin-1-ylmethyl-imidazo[1,2-a]pyridine, 1-(4-{6-[4-(2H-Pyrazol-3-yl)-phenoxy]-quinolin-2-ylmethyl}-piperazin-1-yl)-ethanone, N-((exo)-8-{6-[4-(2H-Pyrazol-3-yl)-phenoxy]-quinolin-2-ylmethyl}-8-aza-bicyclo[3.2.1]oct-3-yl)-acetamide, 3-Morpholin-4-ylmethyl-6-[4-(2H-pyrazol-3-yl)-phenoxy]-quinoline, 2-Morpholin-4-ylmethyl-6-[4-(2H-pyrazol-3-yl)-phenoxy]-imidazo[1,2-a]pyridine, (S)-5-{5-[4-(2H-Pyrazol-3-yl)-phenoxy]-indazol-2-ylmethyl}-pyrrolidin-2-one, 2-Morpholin-4-ylmethyl-6-[4-(2H-pyrazol-3-yl)-benzyl]-imidazo[1,2-a]pyridine, (S)-5-{5-[4-(2H-Pyrazol-3-yl)-phenoxy]-indazol-1-ylmethyl}-pyrrolidin-2-one, 2-Morpholin-4-ylmethyl-6-[4-(2H-pyrazol-3-yl)-phenoxy]-quinoline, 3-{6-[4-(2H-Pyrazol-3-yl)-phenoxy]-imidazo[1,2-a]pyridin-2-ylmethyl}-oxazolidin-2-one, 2-Methyl-6-[4-(2H-pyrazol-3-yl)-phenoxy]-3-pyrrolidin-1-ylmethyl-quinoline, 2-Morpholin-4-ylmethyl-7-[4-(2H-pyrazol-3-yl)-phenoxy]-imidazo[1,2-a]pyridine, Morpholin-4-yl-{7-[4-(2H-Pyrazol-3-yl)-phenoxy]-imidazo[1,2-a]pyridin-2-yl}-methanone, 1-{6-[4-(2H-Pyrazol-3-yl)-phenoxy]-imidazo[1,2-a]pyridin-2-ylmethyl}-piperidine-4-carboxylic acid, and (R)-5-{6-[4-(2H-Pyrazol-3-yl)-phenoxy]-imidazo[1,2-a]pyridin-2-ylmethoxy}-piperidin-2-one, and pharmaceutically acceptable salts thereof.

In some embodiments, the LTA4H modulatory agent is a compound selected from 2-Hydroxy-1-(4-{7-[5-(2H-pyrazol-3-yl)-pyridin-2-yloxy]-quinolin-3-ylmethyl}-piperazin-1-yl)-ethanone, 1-(4-{7-[5-(2H-Pyrazol-3-yl)-pyridin-2-yloxy]-quinolin-3-ylmethyl}-piperazin-1-yl)-ethanone, 1-{7-[5-(2H-Pyrazol-3-yl)-pyridin-2-yloxy]-quinolin-3-ylmethyl}-azetidin-3-ol, 2-Methoxy-1-(4-{7-[5-(2H-pyrazol-3-yl)-pyridin-2-yloxy]-quinolin-3-ylmethyl}-piperazin-1-yl)-ethanone, (S)-3-Hydroxy-1-(1-{7-[5-(2H-pyrazol-3-yl)-pyridin-2-yloxy]-quinolin-3-ylmethyl}-piperidin-4-yl)-pyrrolidin-2-one, 3-(1-{7-[5-(2H-Pyrazol-3-yl)-pyridin-2-yloxy]-quinolin-3-ylmethyl}-piperidin-4-yl)-oxazolidin-2-one, 1-{7-[5-(2H-Pyrazol-3-yl)-pyridin-2-yloxy]-quinolin-3-ylmethyl}-piperidin-4-ol, 3-Methyl-1-{7-[5-(2H-pyrazol-3-yl)-pyridin-2-yloxy]-quinolin-3-ylmethyl}-azetidin-3-ol, 2-Hydroxy-1-[(R)-3-(methyl-{7-[5-(2H-pyrazol-3-yl)-pyridin-2-yloxy]-quinolin-3-ylmethyl}-amino)-pyrrolidin-1-yl]-ethanone, 2-Hydroxy-1-[(S)-3-(methyl-{7-[5-(2H-pyrazol-3-yl)-pyridin-2-yloxy]-quinolin-3-ylmethyl}-amino)-pyrrolidin-1-yl]-ethanone, 2-Hydroxy-N-methyl-N—((S)-1-{7-[5-(2H-pyrazol-3-yl)-pyridin-2-yloxy]-quinolin-3-ylmethyl}-pyrrolidin-3-yl)-acetamide, 2-Hydroxy-N-methyl-N—((R)-1-{7-[5-(2H-pyrazol-3-yl)-pyridin-2-yloxy]-quinolin-3-ylmethyl}-pyrrolidin-3-yl)-acetamide, (S)-1-{7-[5-(2H-Pyrazol-3-yl)-pyridin-2-yloxy]-quinolin-3-ylmethyl}-pyrrolidin-3-ol, 1-(4-{7-[5-(2H-Pyrazol-3-yl)-pyridin-2-yloxy]-quinolin-3-ylmethyl}-piperazin-1-yl)-propan-1-one, 2-Hydroxy-N-methyl-N-(1-{7-[5-(2H-pyrazol-3-yl)-pyridin-2-yloxy]-quinolin-3-ylmethyl}-piperidin-4-yl)-acetamide, 1-{3-[(Methyl-{7-[5-(2H-pyrazol-3-yl)-pyridin-2-yloxy]-quinolin-3-ylmethyl}-amino)-methyl]-azetidin-1-yl}-ethanone, (R)-1-{7-[5-(2H-Pyrazol-3-yl)-pyridin-2-yloxy]-quinolin-3-ylmethyl}-pyrrolidin-3-ol, (S)-2-Hydroxy-1-(4-{7-[5-(2H-pyrazol-3-yl)-pyridin-2-yloxy]-quinolin-3-ylmethyl}-piperazin-1-yl)-propan-1-one, 1-{7-[5-(2H-Pyrazol-3-yl)-pyridin-2-yloxy]-quinolin-3-ylmethyl}-piperidine-4-carboxylic acid dimethylamide, 2-Hydroxy-2-methyl-1-(4-{7-[5-(2H-pyrazol-3-yl)-pyridin-2-yloxy]-quinolin-3-ylmethyl}-piperazin-1-yl)-propan-1-one, 2,2-Dimethyl-1-(4-{7-[5-(2H-pyrazol-3-yl)-pyridin-2-yloxy]-quinolin-3-ylmethyl}-piperazin-1-yl)-propan-1-one, Cyclopropyl-(4-{7-[5-(2H-pyrazol-3-yl)-pyridin-2-yloxy]-quinolin-3-ylmethyl}-piperazin-1-yl)-methanone, and 2-Methyl-1-(4-{7-[5-(2H-Pyrazol-3-yl)-pyridin-2-yloxy]-quinolin-3-ylmethyl}-piperazin-1-yl)-propan-1-one, and pharmaceutically acceptable salts thereof.

In certain embodiments, the LTA4H modulatory agent is of the formula (XII):

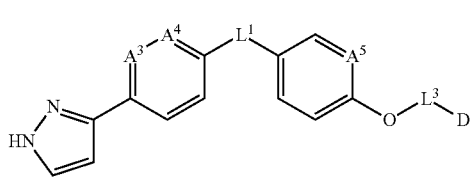

or a pharmaceutically acceptable salt thereof,
where:
$A^3$, $A^4$ and $A^5$ are each independently CH or N;
$L^1$ is a linker selected from —O— and —CH$_2$—;
$L^3$ is absent or a —(C$_1$-C$_6$)alkylene-linker; wherein said —(C$_1$-C$_6$)alkylene-linker is optionally substituted with one to three groups selected from —OH, halo, —(C$_1$-C$_6$)alkyl;
D is a ring selected from
(a) —(C$_3$-C$_7$)cycloalkyl, (C$_6$-C$_{10}$)aryl, and -(5-to 11-membered)heteroaryl;
(b) -(4-to 11-membered)heterocycloalkyl, comprising an O or S ring atom and optionally 1 to 3 additional ring heteroatoms selected from N, O, and S;
(c) 4-8 member monocyclic heterocyclic comprising a N ring atom and 1 to 3 additional ring heteroatoms selected from N, O, and S;
(d) a 6 to 11-membered fused bicyclic, bridged bicyclic or spirocyclic heterocyclic radical comprising a N ring atom and optionally 1 to 3 additional ring heteroatoms selected from N, O, and S; and
(e) a group selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl
wherein each of said D rings is optionally substituted with one to three $R^1$ groups; and wherein each of said D rings is further optionally substituted, where possible, by one or two groups independently selected from (═O) and (═S);
each $R^1$ is independently selected from halo, —OH, —CF$_3$, —CN, —(C$_1$-C$_6$)alkyl, —O(C$_1$-C$_6$)alkyl, —C(O)R$^2$, —C(O)OR$^2$, —C(O)N(R$^2$)$_2$, —N(R$^2$)$_2$, —N(R$^2$)C(O)R$^2$, —S(O)$_2$R$^2$, —N(R$^2$)—S(O)$_2$—R$^2$, —(C$_3$-C$_6$)cycloalkyl, -(5-to 11-membered)heterocycloalkyl, —(C$_6$-C$_{10}$)aryl, and -(5-to 11-membered)heteroaryl; wherein each of said, —(C$_1$-C$_6$)alkyl, —O(C$_1$-C$_6$)alkyl, —(C$_3$-C$_6$)cycloalkyl, -(5-to 11-membered)heterocycloalkyl, —(C$_6$-C$_{10}$)aryl, and -(5-to 11-membered)heteroaryl of said $R^1$ group is optionally substituted with one to three groups selected from halo, —OH, —CF$_3$, —(C$_1$-C$_6$)alkyl, —C(O)OH, —C(O)OC$_1$-C$_6$)alkyl, —C(O)(C$_1$-C$_6$)alkyl), —NH$_2$, —NH(C$_1$-C$_6$)alkyl, N((C$_1$-C$_6$)alkyl)$_2$ and —CN;
each $R^2$ is independently selected from the group consisting of —H, —(C$_1$-C$_6$)alkyl, —(C$_3$-C$_6$)cycloalkyl, -(5-to 11-membered)heterocycloalkyl, —(C$_6$-C$_{10}$)aryl, and -(5-to 11-membered)heteroaryl; wherein each of said, —(C$_1$-C$_6$)alkyl, —O(C$_1$-C$_6$)alkyl, —(C$_3$-C$_6$)cycloalkyl, -(5-to 11-membered)heterocycloalkyl, —(C$_6$-C$_{10}$)aryl, and -(5-to 11-membered)heteroaryl of said $R^2$ group is optionally independently substituted by one to three groups selected from halo, —OH, —CF$_3$, —(C$_1$-C$_6$)alkyl, —NH$_2$, —NH(C$_1$-C$_6$)alkyl, —N((C$_1$-C$_6$)alkyl)$_2$ and —CN.

In some embodiments of formula (XII), L3-D taken together are described by a group selected from (1-methyl-pyrrolidin-2-on-4-yl)methyl, (pyrrolidin-2-on-3yl)oxy, (pyrrolidin-2-on-5-yl)methyloxy, 2-(pyrrolidin-2-on-1-yl)ethyloxy, 3-(pyrrolidin-2-on-1-yl)propyloxy, (tetrahydrofuran-3-yl)oxy, (tetrahydrofuran-2-yl)methyloxy, (tetrahydrofuran-3-yl)methyloxy; (piperidin-2-on-5-yl)oxy, (1,3-oxazolidin-2-on-4-yl)methyloxy, (1,3-oxazolidin-2-on-5-yl)methyloxy, (morpholin-3-yl)methyloxy, (morpholin-4-yl)ethyloxy, 1H-pyrazol-5-yl, (1H-pyrazol-5-yl)methyloxy, (1H-pyrazol-3-yl)methyloxy, (1-methyl-1H-pyrazol-3-yl)methyloxy, (1-methyl-1H-pyrazol-5-yl)methyloxy, (1-methyl-2-(2-furyl)-pyrazol-5-yl)methyloxy, 3-(1H-pyrazol-1-yl)-ethyloxy, 2-(1H-pyrazol-4-yl)-ethyloxy, 3-(1H-pyrazol-1-yl)-3-methylpropyloxy, (furan-2-yl)methyloxy, (furan-3-yl)methyloxy, (dihydrofuran-2(3H)-on-3-yl)oxy, (dihydrofuran-2(3H)-on-5-yl)methyloxy, (pyridin-3-yl)methyloxy, (pyridin-4-yl)methyloxy, (2-(1H-pyrazol-1-yl)-pyridin-5-yl)methyloxy, 1-(pyridin2-yl)-ethyloxy, 2-(pyridin-2-yl)ethyloxy, 2-(pyridin-3-yl)ethyloxy, 2-(pyridin-4-yl)-ethyloxy, (pyrimidin-2-yl)methyloxy, (thien-3-yl)methyloxy, 2-(thien-2-yl)ethyloxy, (tetrahydro-2H-pyran-3-yl)oxy, (tetrahydro-2H-pyran-4-yl)oxy), (tetrahydro-2H-pyran-2-yl)methyloxy, (tetrahydro-2H-pyran-3-yl)methyloxy, (tetrahydro-2H-pyran-4-yl)methyloxy, 2-(tetrahydro-2H-pyran-2-yl)ethyloxy, 2-(tetrahydro-2H-pyran-4-yl)ethyloxy, (2-methyl-1H-imidazol-1-yl)ethyloxy, (pyrazin-2-yl)methyloxy, benzyloxy, (4-(methylsulfonyl)benzyl)oxy, (1,3-thiazol-2-yl)methyloxy, (1,3-thiazol-5-yl)methyloxy, 2-(1,3-thiazol-5-yl)ethyloxy, (4-methyl-1,2,3-thiadiazol-5-yl)methyloxy, (isoxazol-5-yl)methyloxy, 2-(isoxazol-4-yl)ethyloxy, (1-methyl-1,2,4-triazol-5-yl)methyloxy, (1,3-oxazol-4-yl)methyloxy, (1,3-oxazol-5-yl)methyloxy, (2-methyl-1,3-oxazol-4-yl)methyloxy, (4-methyl-1,3-oxazol-5-yl)methyloxy, (1H-benzimidazol-2-yl)methyloxy, (1H-benzimidazol-5-yl)methyloxy, (1H-benzimidazol-1-yl)ethyloxy, (1H-benzimidazol-2-yl)ethyloxy, 2-((1H-benzimidazol-2-yl)-amino)ethyloxy, (imidazo[2,1-b][1,3]thiazol-2-yl)methyloxy, (1H-pyrrolo[2,3-b]pyridin-5-yl)methyloxy, (6,7-dihydro-5H-cyclopenta[b]pyridin-7-yl)oxy, 2-(1H-pyrrolo[3,2-b]pyridin-6-yl)-ethyloxy, (imidazo[1,2-a]pyridin-2-yl)methyloxy, (1,3-benzothiazol-2-yl)methyloxy; and (imidazo[1,2-a]pyridin-6-yl)methyloxy.

In some embodiments the LTA4H modulatory agent includes an arylpyrazole small molecule described in any of U.S. Pat. Nos. 9,573,957; 9,403,830; 9,303,018; and 9,139,567, each of which is incorporated herein by reference.

In some embodiments, the LTA4H modulatory agent is a benzodioxane, or a pharmaceutically acceptable salt thereof. In certain embodiments, the LTA4H modulatory agent is of the formula (XIII):

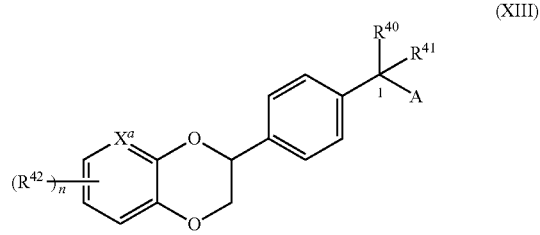

where:
$X^a$ is N or CH;
n is an integer from 0 to 3;
$R^{42}$ is selected from halo, —OH, —CN, —(C$_1$-C$_6$)alkyl, —O(C$_1$-C$_6$)alkyl, and —(C$_3$-C$_6$)cycloalkyl;
$R^{40}$ and $R^{41}$ are each independently selected from —H and —(C$_1$-C$_6$)alkyl; wherein $R^{40}$ and $R^{41}$ may join to form a 3-to 6-membered ring optionally comprising one to three heteroatoms, and further optionally substituted with one to three groups selected from halo, —OH, (=O), —(C$_1$-C$_6$) alkyl, —O(C$_1$-C$_6$)alkyl, —C(O)O—H, —C(O)(C$_1$-C$_6$)alkyl, and —C(O)NH$_2$;

A is a group of formula —NR$^{43}$R$^{44}$, wherein R$^{43}$ and R$^{44}$ are each independently selected from —H, —(C$_1$-C$_6$)alkyl, —(C$_3$-C$_6$)cycloalkyl, -(4-to 14-membered)heterocycloalkyl, —(C$_6$-C$_{10}$)aryl, and -(5-to 11-membered)heteroaryl; wherein each of the foregoing —(C$_1$-C$_6$)alkyl, —(C$_3$-C$_6$) cycloalkyl, -(4-to 14-membered)heterocycloalkyl, —(C$_6$-C$_{10}$)aryl, and -(5-to 11-membered)heteroaryl of said R$^4$ and R$^5$ groups is optionally independently substituted by one to three R$^6$ groups; wherein two R$^6$ groups when attached to the same carbon atom of said —(C$_1$-C$_6$)alkyl may join to form a 3-to 6-membered ring optionally comprising one to three heteroatoms, and further optionally substituted with one to three groups selected from halo, —OH, (=O), —(C$_1$-C$_6$) alkyl, —O(C$_1$-C$_6$)alkyl, —C(O)O—H, —C(O)(C$_1$-C$_6$)alkyl, and —C(O)NH$_2$;

A is a (4-to 14-membered)N-heterocyclic ring of formula B:

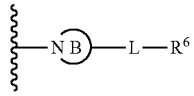

wherein said ring B is:
(a) a non-aromatic 4-8 membered monocyclic radical; or
(b) a bridged bicyclic radical, a spirocyclic radical, or a 6 to 11-membered fused bicyclic radical, wherein each of said bridged bicyclic radical, spirocyclic radical, and 6 to 11-membered fused bicyclic radical comprises at least a nonaromatic N-heterocyclic ring which is attached to the carbon atom 1 of the compound of formula (I); wherein each of said bridged bicyclic radical, spirocyclic radical, and 6 to 11-membered fused bicyclic radical may optionally comprise an aromatic ring;
wherein said ring B may additionally comprise one to three additional ring heteroatoms independently selected from N, O and S;
wherein said ring B may be further optionally substituted by one to three groups selected from halo, —OH, (=O), —C(O)O—H, —C(O)O—(C$_1$-C$_6$)alkyl, and —(C$_1$-C$_6$)alkyl; and
wherein L is absent or a linker selected from —(C$_1$-C$_6$) alkylene-;
each R$^6$ is independently selected from halo, —OR$^7$, —CF$_3$, —CN, —(C$_1$-C$_6$)alkyl, —O(C$_1$-C$_6$)alkyl, —C(O) R$^7$, —C(O)$_2$R$^7$, —C(O)N(R$^7$)$_2$, —N(R$^7$)$_2$, —NHC(O)R$^7$, —NHC(O)N(R$^7$)$_2$, —S(O)$_2$R$^7$, —NH—S(O)$_2$—R$^7$, —(C$_3$-C$_6$)cycloalkyl, -(4-to 14-membered)heterocycloalkyl, —(C$_6$-C$_{10}$)aryl, and -(5-to 11-membered)heteroaryl; wherein each of said, —(C$_1$-C$_6$)alkyl, —O(C$_1$-C$_6$)alkyl, —(C$_3$-C$_6$)cycloalkyl, -(4- to 14-membered)heterocycloalkyl, —(C$_6$-C$_{10}$)aryl, and -(5-to 11-membered)heteroaryl of said R$^6$ group is optionally substituted where possible with one to three groups selected from halo, —OH, —CF$_3$, —CN, (=O), —(C$_1$-C$_6$)alkyl, —C(O)O—H, —C(O)O— (C$_1$-C$_6$)alkyl, —NH$_2$, —NH(C$_1$-C$_6$)alkyl, —N((C$_1$-C$_6$)alkyl)$_2$, —S(O)$_2$(C$_1$-C$_6$)alkyl, —(C$_3$-C$_6$)cycloalkyl, -(4-to 14-membered)heterocycloalkyl, —(C$_6$-C$_{10}$)aryl, and -(5-to 11-membered)heteroaryl; and
each R$^7$ is independently selected from —H, —(C$_1$-C$_6$) alkyl, —(C$_1$-C$_6$)alkyl-OH, —(C$_1$-C$_6$)alkyl-O—(C$_1$-C$_6$)alkyl, —O(C$_1$-C$_6$)alkyl, —(C$_3$-C$_6$)cycloalkyl, —(C$_3$-C$_6$)cycloalkyl-OH, -(4-to 14-membered)heterocycloalkyl, —(C$_6$-C$_{10}$)aryl, and -(5-to 11-membered)heteroaryl; wherein each of said R$^7$ group is optionally substituted where possible with a group selected from —OH, —NH(C$_1$-C$_6$)alkyl, —NHC(O)(C$_1$-C$_6$)alkyl, —C(O)NH$_2$, —S(O)$_2$(C$_1$-C$_6$)alkyl, and -(4-to 14-membered)heterocycloalkyl; wherein said -(4-to 14-membered)heterocycloalkyl group is optionally substituted where possible with a (=O) group.

In some embodiments, the LTA4H modulatory agent is a compound selected from 3-[(4-{4-[(2S)-2,3-dihydro-1,4-benzodioxin-2-yl]benzyl}piperazin-1-yl)methyl]benzoic acid, 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid ethyl ester, 7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide, 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide, 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide, 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide, 6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide, 6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide, [(1a,5a,6a)-3-[(S)-4-(2,3-dihydro-[1,4]dioxino[2,3-b]pyridin-3-yl)-benzyl]-3-aza-bicyclo[3.1.0] hexane]-6-carboxylic acid ((S)-2-hydroxy-propyl)-amide, [(1α,5α,6α)-3-[(S)-4-(2,3-Dihydro-[1,4]dioxino[2,3-b] pyridin-3-yl)-benzyl]-3-aza-bicyclo[3.1.0]hexane]-6-carboxylic acid ((S)-2-hydroxy-1-methyl-ethyl)-amide, 7-[(S)-4-(2,3-Dihydro-[1,4]dioxino[2,3-b]pyridin-3-yl)-benzyl]-5,6,7,8-tetrahydro-imidazo[1,2-a]pyrazine-3-carbonitrile, N-{(1a,5a,6a)-3-[(S)-4-(2,3-Dihydro-[1,4]dioxino[2,3-b]pyridin-3-yl)-benzyl]-3-aza-bicyclo[3.1.0]hex-6-yl}-acetamide, [(1a,5a,6a)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide, N-{1-[(S)-4-(2, 3-Dihydro-[1,4]dioxino[2,3-b]pyridin-3-yl)-benzyl]-piperidin-4-yl}-2-methoxy-acetamide, 1-{4-[(S)-4-(2,3-Dihydro-[1,4]dioxino[2,3-b]pyridin-3-yl)-benzyl]-piperazin-1-yl}-2-hydroxy-ethanone, 4-{1-[(S)-4-(2,3-Dihydro-benzo[1,4] dioxin-2-yl)-benzyl]-azetidin-3-yl}-benzoic acid, 1-[(S)-4-(2,3-Dihydro-[1,4]dioxino[2,3-b]pyridin-3-yl)-benzyl]-piperidine-4-carboxylic acid (2-hydroxy-2-methyl-propyl)-amide, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone, 1-{4-[(S)-4-(2,3-Dihydro-[1,4]dioxino[2,3-b]pyridin-3-yl)-benzyl]-[1,4]diazepan-1-yl}-2-methoxy-ethanone, 5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine, {(endo)-8-[(S)-4-(2,3-Dihydro-[1,4]dioxino[2,3-b]pyridin-3-yl)-benzyl]-8-aza-bicyclo[3.2.1] oct-3-yl}-urea, 2-{1-[(S)-4-(2,3-Dihydro-[1,4]dioxino[2,3-b]pyridin-3-yl)-benzyl]-piperidin-4-yl}-N-methoxy-acetamide, (R)—N-{1-[(S)-4-(2,3-Dihydro-[1,4]dioxino[2, 3-b]pyridin-3-yl)-benzyl]-piperidin-4-yl}-2-methylamino-propionamide, N—{C1-[(S)-4-(2,3-Dihydro-[1,4]dioxino [2,3-b]pyridin-3-yl)-benzyl]-piperidin-4-ylmethyl}-2-hydroxy-2-methyl-propionamide, N-{(1a,5a,6a)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide, 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone, 4-{1-[(S)-4-(2,3-Dihydro-[1,4]dioxino[2,3-b]pyridin-3-yl)-benzyl]-piperidin-4-yl}-cyclohexanecarboxylic acid, 1-[(S)-4-(2,3-Dihydro-benzo[1,4]dioxin-2-yl)-benzyl]-azepane-4-carboxylic acid, [(1a,5a,6a)-3-[(S)-4-(2,3-Dihydro-benzo[1,4]dioxin-2-yl)-benzyl]-3-aza-bicyclo[3.1.0]hexane]-6-carboxylic acid, (1S,4S)-5-[(S)-4-(2,3-Dihydro-[1,4]dioxino[2,3-b]pyridin-3-yl)-benzyl]-2,5-diaza-bicyclo[2.2.1]heptane-2-carboxylic acid amide, 1-[(S)-4-(2,3-Dihydro-[1,4]dioxino[2,3-b]pyridin-3-yl)-benzyl]-4-phenyl-piperidin-4-ol, 1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone, 1-{8-[(S)-4-(2,3-Dihydro-[,4]dioxino[2,3-b]pyridin-3-yl)-benzyl]-3,8-diaza-bicyclo[3.2.1]oct-3-yl}-ethanone, 5-[(S)-4-(2,3-Dihydro-[1,4]dioxino[2,3-b]pyridin-3-yl)-benzyl]-hexahydro-pyrrolo[3,4-c]pyrrole-2-carboxylic acid amide, {(exo)-8-[(S)-4-(2,3-Dihydro-[1,4]dioxino[2,3-b]pyridin-3-yl)-benzyl]-8-aza-bicyclo[3.2.1]oct-3-yl}-urea, 2-{1-[(S)-4-(2,3-Dihydro-[1,4]dioxino[2,3-b]pyridin-3-yl)-benzyl]-piperidin-4-yloxy}-acetamide, (S)-3-[4-(1,1-Dioxo-1lambda6-[1,4]thiazepan-4-ylmethyl)-phenyl]-2,3-dihydro-[1,4]dioxino[2,3-b]pyridine, 1-[(S)-4-(2,3-Dihydro-[1,4]dioxino[2,3-b]pyridin-3-yl)-benzyl]-4-methyl-piperidin-4-ol, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone, N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide, N-{1-[(S)-4-(2,3-Dihydro-[1,4]dioxino[2,3-b]pyridin-3-yl)-benzyl]-piperidin-4-ylmethyl}-acetamide, [(S)-4-(2,3-Dihydro-[1,4]dioxino[2,3-b]pyridin-3-yl)-benzyl]-(1,1-dioxo-tetrahydro-1 lambda-6-thiophen-3-yl)-methyl-amine, 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone, {1-[(S)-4-(2,3-dihydro-[1,4]dioxino-[2,3-b]pyridin-3-yl)-benzyl]-spiro-[3H-indole-3,4'-piperidine]-1 (2H)-urea, {1-[(S)-4-(2,3-Dihydro-[1,4]dioxino[2,3-b]pyridin-3-yl)-benzyl]-piperidin-4-ylmethyl}-urea, {4-[(S)-4-(2,3-Dihydro-[1,4]dioxino[2,3-b]pyridin-3-yl)-benzyl]-piperazin-1-yl}-acetonitrile, (R)-7-[(S)-4-(2,3-Dihydro-[1,4]dioxino[2,3-b]pyridin-3-yl)-benzyl]-hexahydro-oxazolo[3,4-a]pyrazin-3-one, {1-[(S)-4-(2,3-Dihydro-[1,4]dioxino[2,3-b]pyridin-3-yl)-benzyl]-piperidin-4-yl}-(3-hydroxy-azetidin-1-yl)-methanone, 1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide, N-[3-[4-[[4-[(3S)-2,3-dihydro-[1,4]dioxino[2,3-b]pyridin-3-yl]phenyl]methyl]piperazin-1-yl]-3-oxo-propyl]acetamide, N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide, N-[1-[[4-[(3S)-2,3-dihydro-[1,4]dioxino[2,3-b]pyridin-3-yl]phenyl]methyl]-4-piperidyl]tetrahydropyran-4-carboxamide, 3-{1-[(S)-4-(2,3-Dihydro-[1,4]dioxino[2,3-b]pyridin-3-yl)-benzyl]-piperidin-4-yl}-[1,3]oxazinan-2-one, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone, (S)-3-{4-[4-(Pyridin-3-yloxy)-piperidin-1-ylmethyl]-phenyl}-2,3-dihydro-[1,4]dioxino[2,3-b]pyridine, 1-[(S)-4-(2,3-Dihydro-[1,4]dioxino[2,3-b]pyridin-3-yl)-benzyl]-4-phenyl-piperidine-4-carboxylic acid, (S)-3-[4-(1-Oxo-1 lambda4-thiomorpholin-4-ylmethyl)-phenyl]-2,3-dihydro-[1,4]dioxino[2,3-b]pyridine, and (S)-7-[(S)-4-(2,3-Dihydro-[1,4]dioxino[2,3-b]pyridin-3-yl)-benzyl]-hexahydro-oxazolo[3,4-a]pyrazin-3-one.

In some embodiments, the LTA4H modulatory agent is a compound selected from 1-[4-(2,3-dihydro-1,4-benzodioxin-2-yl)benzyl]pyrrolidine, 4-[4-(2,3-dihydro-1,4-benzodioxin-2-yl)benzyl]morpholine, 1-[4-(2,3-dihydro-1,4-benzodioxin-2-yl)benzyl]-4,4-dimethylpiperidine, 8-[4-(2,3-dihydro-1,4-benzodioxin-2-yl)benzyl]-2,8-diazaspiro[4,5]decan-1-one, 1-[4-(2,3-dihydro-1,4-benzodioxin-2-yl)benzyl]-4-fluoropiperidine, (1s,4s)-7-[4-(2,3-dihydro-1,4-benzodioxin-2-yl)benzyl]-7-azabicyclo[2.2.1]heptane, 4-[4-(2,3-dihydro-1,4-benzodioxin-2-yl)benzyl]thiomorpholine 1,1-dioxide, 1-{4-[(2S)-2,3-dihydro-1,4-benzodioxin-2-yl]benzyl}-N,N-dimethylpiperidine-4-carboxamide, (3S)-1-[4-(2,3-dihydro-1,4-benzodioxin-2-yl)benzyl]pyrrolidin-3-ol, 1-({1-[4-(2,3-dihydro-1,4-benzodioxin-2-yl)benzyl]piperidin-3-yl}methyl)pyrrolidin-2-one, 1-{4-[4-(2,3-dihydro-1,4-benzodioxin-2-yl)benzyl]piperazin-1-yl}ethenone, 2-{[4-(2,3-dihydro-1,4-benzodioxin-2-yl)benzyl]amino}-1-(pyrrolidin-1-yl)ethanone, N-{4-[(2S)-2,3-dihydro-1,4-benzodioxin-2-yl]benzyl}-N-methyl-1-(methylsulfonyl)piperidin-4-amine, 1-{4-[{4-[(2S)-2,3-dihydro-1,4-benzodioxin-2-yl]benzyl}(methyl)amino]piperidin-1-yl}ethenone, 3-[4-(pyrrolidin-1-ylmethyl)phenyl]-2,3-dihydro[1,4]dioxino[2,3-b]pyridine, 7-[4-(2,3-dihydro-1,4-benzodioxin-2-yl)benzyl]-5,6,7,8-tetrahydro[1,2,4]triazolo[4,3-a]pyrazine, 3-{4-[(1,1-dioxidothiomorpholin-4-yl)methyl]phenyl}-2,3-dihydro[1,4]dioxino[2,3-b]pyridine, 3-[4-(morpholin-4-ylmethyl)phenyl]-2,3-dihydro[1,4]dioxino[2,3-b]pyridine, (3R)-1-{4-[(2S)-2,3-dihydro-1,4-benzodioxin-2-yl]benzyl}piperidine-3-carboxylic acid, (3S)-1-{4-[(2S)-2,3-dihydro-1,4-benzodioxin-2-yl]benzyl}piperidine-3-carboxylic acid, 1-(1-{4-[(2S)-2,3-dihydro-1,4-benzodioxin-2-yl]benzyl}piperidin-4-yl)-2,2,2-trifluoroethanol, 2-(1-{4-[(2S)-2,3-dihydro-1,4-benzodioxin-2-yl]benzyl}piperidin-4-yl)-1,1,1,3,3,3-hexafluoropropan-2-ol, N-[4-(2,3-dihydro-1,4-benzodioxin-2-yl)benzyl]-2-methylpropan-2-amine, (2R)—N-[4-(2,3-dihydro-1,4-benzodioxin-2-yl)benzyl]butan-2-amine, 1-[4-(2,3-dihydro-1,4-benzodioxin-2-yl)benzyl]-N-methylpiperidine-4-carboxamide, 4-{1-[4-(2,3-dihydro-1,4-benzodioxin-2-yl)benzyl]piperidin-4-yl}butanoic acid, {1-[4-(2,3-dihydro-1,4-benzodioxin-2-yl)benzyl]piperidin-4-yl}methanol, 2-{1-[4-(2,3-dihydro-1,4-benzodioxin-2-yl)benzyl]piperidin-4-yl}propan-2-ol, 3-{1-[4-(2,3-dihydro-1,4-benzodioxin-2-yl)benzyl]piperidin-4-yl}propan-1-ol, 1-[4-(2,3-dihydro-1,4-benzodioxin-2-yl)benzyl]-4-methyl-1,4-diazepane, 1-{4-[4-(2,3-dihydro-1,4-benzodioxin-2-yl)benzyl]-1,4-diazepan-1-yl}ethenone, 4-[4-(2,3-dihydro-1,4-benzodioxin-2-yl)benzyl]-1,4-oxazepane, N-[4-(2,3-dihydro-1,4-benzodioxin-2-yl)benzyl]-2-methoxy-N-methylethanamine, (3R)-1-[4-(2,3-dihydro-1,4-benzodioxin-2-yl)benzyl]pyrrolidin-3-ol, 8-[4-(2,3-dihydro-1,4-benzodioxin-2-yl)benzyl]-1,3,8-triazaspiro[4.5]decane-2,4-dione, 1-[4-(2,3-dihydro-1,4-benzodioxin-2-yl)benzyl]-3-methoxyazetidine, {1-[4-(2,3-dihydro-1,4-benzodioxin-2-yl)benzyl]piperidin-4-yl}(morpholin-4-yl)methanone, 2-(1-[4-(2,3-dihydro-1,4-benzodioxin-2-yl)benzyl]piperidin-4-yl}-N,N-dimethylacetamide, 1-[4-(2,3-dihydro-1,4-benzodioxin-2-yl)benzyl]-4-(methylsulfonyl)piperidine, 1-[4-(2,3-dihydro-1,4-benzodioxin-2-yl)benzyl]azepane, N-[4-(2,3-dihydro-1,4-benzodioxin-2-yl)benzyl]cyclopentanamine, N-[4-(2,3-dihydro-1,4-benzodioxin-2-yl)benzyl]-N-methyl-2-(pyridin-2-yl)ethanamine, 1-cyclopropyl-N-[4-(2,3-dihydro-1,4-benzodioxin-2-yl)benzyl]methanamine, 1-[4-(2,3-dihydro-1,4-benzodioxin-2-yl)benzyl]-4-phenylpiperidin-4-ol, N-[4-(2,3-dihydro-1,4-benzodioxin-2-yl)benzyl]-N-ethylethanamine, 1-[4-(2,3-dihydro-1,4-benzodioxin-2-yl)benzyl]azetidine-3-carbonitrile, 1-[4-(2,3-dihydro-1,4-benzodioxin-2-yl)benzyl]-3-methoxypyrrolidine, N-{1-[4-(2,3-dihydro-1,4- benzodioxin-2-yl)benzyl]piperidin-4-yl}methanesulfonamide, N-[4-(2,3-dihydro-1,4-benzodioxin-2-yl)benzyl]-2-methyl-1-(pyrrolidin-1-yl)propan-2-amine, 1-({1-[4-(2,3-dihydro-1,4-benzodioxin-2-yl)benzyl]piperidin-4-yl}methyl)pyrrolidin-2-one, 1-[4-(2,3-dihydro-1,4-benzodioxin-2-yl)benzyl]-N,N-dimethylpiperidine-4-carboxamide, 1-[4-(2,3-dihydro-1,4-benzodioxin-2-yl)benzyl]-N-(2-hydroxyethyl)piperidine-4-carboxamide, 1-{1-[4-(2,3-dihydro-1,4-benzodioxin-2-yl)benzyl]piperidin-4-yl}urea, 1-[4-(2,3-dihydro-1,4-benzodioxin-2-yl)phenyl]-N-yridin-3-ylmethyl)methanamine, 1-[4-(2,3-dihydro-1,4-benzodioxin-2-yl)phenyl]-N-[(1-methyl-1H-imidazol-4-yl)methyl]methanamine, 2-{4-[(2S)-2,3-dihydro-1,4-benzodioxin-2-yl]benzyl}-1,2,3,4-tetrahydroisoquinoline-4-carboxylic acid, (1R,3S)-3-({4-[(2S)-2,3-dihydro-1,4-benzodioxin-2-yl]benzyl}amino)cyclopentanecarboxylic acid, 3-({4-[(2S)-2,3-dihydro-1,4-benzodioxin-2-yl]benzyl}amino)-4,4-dimethylpentanoic acid, 1-({4-[(2S)-2,3-dihydro-1,4-benzodioxin-2-yl]benzyl}amino)cyclopentanecarboxylic acid, N-{4-[(2S)-2,3-dihydro-1,4-benzodioxin-2-yl]benzyl}-N-methylglycine, 1-{4-[(2S)-2,3-dihydro-1,4-benzodioxin-2-yl]benzyl}pyrrolidine-3-carboxylic acid, trans-4-({4-[(2S)-2,3-dihydro-1,4-benzodioxin-2-yl]benzyl}amino)cyclohexanecarboxylic acid, cis-4-({4-[(2S)-2,3-dihydro-1,4-benzodioxin-2-yl]benzyl}amino)cyclohexanecarboxylic acid, 1-[(3R)-3-({4-[(2S)-2,3-dihydro-1,4-benzodioxin-2-yl]benzyl}amino)pyrrolidin-1-yl]ethenone, 1-[(3S)-3-({4-[(2S)-2,3-dihydro-1,4-benzodioxin-2-yl]benzyl}amino)pyrrolidin-1-yl]ethenone, trans-4-({4-[(2S)-2,3-dihydro-1,4-benzodioxin-2-yl]benzyl}amino)cyclohexanecarboxamide, N-{4-[(2S)-2,3-dihydro-1,4-benzodioxin-2-yl]benzyl}-N-methylcyclohexanamine, (1-{4-[(2S)-2,3-dihydro-1,4-benzodioxin-2-yl]benzyl}piperidin-3-yl)methanol, 2-(1-{4-[(2S)-2,3-dihydro-1,4-benzodioxin-2-yl]benzyl}piperidin-4-yl)ethanol, N-{4-[(2S)-2,3-dihydro-1,4-benzodioxin-2-yl]benzyl}propan-2-amine, N-{4-[(2S)-2,3-dihydro-1,4-benzodioxin-2-yl]benzyl}-1-methoxypropan-2-amine, N-{4-[(2S)-2,3-dihydro-1,4-benzodioxin-2-yl]benzyl}propan-1-amine, N-{4-[(2S)-2,3-dihydro-1,4-benzodioxin-2-yl]benzyl}-N-methylethanamine, 1-{4-[(2S)-2,3-dihydro-1,4-benzodioxin-2-yl]phenyl}-N,N-dimethylmethanamine, trans-4-({4-[(2S)-2,3-dihydro-1,4-benzodioxin-2-yl]benzyl}amino)cyclohexanol, 1-{4-[(2S)-2,3-dihydro-1,4-benzodioxin-2-yl]benzyl}piperidin-3-ol, N-{4-[(2S)-2,3-dihydro-1,4-benzodioxin-2-yl]benzyl}-N,N',N'-trimethylethane-1,2-diamine, 2-(cyclohexyl {4-[(2S)-2,3-dihydro-1,4-benzodioxin-2-yl]benzyl}amino)ethanol, (1R,2R,4S)—N-{4-[(2S)-2,3-dihydro-1,4-benzodioxin-2-yl]benzyl}bicyclo[2.2.1]heptan-2-amine, (4aR,8aS)-1-{4-[(2S)-2,3-dihydro-1,4-benzodioxin-2-yl]benzyl}decahydroquinoline, (1S,2R)-2-({4-[(2S)-2,3-dihydro-1,4-benzodioxin-2-yl]benzyl}amino)cyclohexanecarboxamide, [(1S,2R)-2-({4-[(2S)-2,3-dihydro-1,4-benzodioxin-2-yl]benzyl}amino)cyclohexyl]methanol, (3R)-1-{4-[(2S)-2,3-dihydro-1,4-benzodioxin-2-yl]benzyl}pyrrolidin-3-ol, [(1R,2R)-2-({4-[(2S)-2,3-dihydro-1,4-benzodioxin-2-yl]benzyl}amino)cyclohexyl]methanol, (1-{4-[(2S)-2,3-dihydro-1,4-benzodioxin-2-yl]benzyl}piperidin-4-yl)methanol, (3S)-1-{4-[(2S)-2,3-dihydro-1,4-benzodioxin-2-yl]benzyl}pyrrolidin-3-ol, 1-{4-[(2S)-2,3-dihydro-1,4-benzodioxin-2-yl]benzyl}imidazolidin-4-one, 1-{4-[(2S)-2,3-dihydro-1,4-benzodioxin-2-yl]benzyl}-N,N-dimethylpyrrolidin-3-amine, 1'-{4-[(2S)-2,3-dihydro-1,4-benzodioxin-2-yl]benzyl}-1,4'-bipiperidin-2-one, N-(cyclopropylmethyl)-N-{4-[(2S)-2,3-dihydro-1,4-benzodioxin-2-yl]benzyl}cyclohexanamine, (1R,2R)-2-({4-[(2S)-2,3-dihydro-1,4-benzodioxin-2-yl]benzyl}amino)cyclohexanol, 1-{4-[(2S)-2,3-dihydro-1,4-benzodioxin-2-yl]benzyl}-4-methoxypiperidine, 1-[(1-{4-[(2S)-2,3-dihydro-1,4-benzodioxin-2-yl]benzyl}piperidin-4-yl)methyl]pyrrolidin-2-one, trans-N-{4-[(2S)-2,3-dihydro-1,4-benzodioxin-2-yl]benzyl}-4-methylcyclohexanamine, (1S,2R)-2-({4-[(2S)-2,3-dihydro-1,4-benzodioxin-2-yl]benzyl}amino)cyclopentanol, (1S,2S)-2-({4-[(2S)-2,3-dihydro-1,4-benzodioxin-2-yl]benzyl}amino)cyclopentanol, N-{4-[(2S)-2,3-dihydro-1,4-benzodioxin-2-yl]benzyl}tetrahydro-2H-pyran-3-amine, (1S,2S)-2-[{4-[(2S)-2,3-dihydro-1,4-benzodioxin-2-yl]benzyl}(methyl)amino]cyclohexanol, (1R,2S)-2-[{4-[(2S)-2,3-dihydro-1,4-benzodioxin-2-yl]benzyl}(methyl)amino]cyclohexanol, 4-{4-[(2S)-2,3-dihydro-1,4-benzodioxin-2-yl]benzyl}-3-methylmorpholine, 5-({4-[(2S)-2,3-dihydro-1,4-benzodioxin-2-yl]benzyl}amino)-1-methylpiperidin-2-one, N-{4-[(2S)-2,3-dihydro-1,4-benzodioxin-2-yl]benzyl}-N,1-dimethylpiperidin-4-amine, 4-[({4-[(2S)-2,3-dihydro-1,4-benzodioxin-2-yl]benzyl}amino)methyl]phenol, 2-{4-[(2S)-2,3-dihydro-1,4-benzodioxin-2-yl]benzyl}-1,2,3,4-tetrahydroisoquinolin-6-ol, 1-[4-(2,3-dihydro-1,4-benzodioxin-2-yl)benzyl]piperidine-3-carboxylic acid, 1-[4-(2,3-dihydro-1,4-benzodioxin-2-yl)benzyl]piperidine-3-carboxamide, (3S)-1-[4-(2,3-dihydro-1,4-benzodioxin-2-yl)benzyl]-3-fluoropyrrolidine, 9-{4-[(2S)-2,3-dihydro-1,4-benzodioxin-2-yl]benzyl}-2,9-diazaspiro[5.5]undecan-1-one, 1-(7-{4-[(2S)-2,3-dihydro-1,4-benzodioxin-2-yl]benzyl}-1,7-diazaspiro[4.4]non-1-yl)ethenone, 9-{4-[(2S)-2,3-dihydro-1,4-benzodioxin-2-yl]benzyl}-2-methyl-2,9-diazaspiro[5.5]undecan-1-one, 8-{4-[(2S)-2,3-dihydro-1,4-benzodioxin-2-yl]benzyl}-2-methyl-2,8-diazaspiro[4.5]decan-1-one, 7-{4-[(2S)-2,3-dihydro-1,4-benzodioxin-2-yl]benzyl}-1-(methylsulfonyl)-1,7-diazaspiro[4.4]nonane, 2-(7-{4-[(2S)-2,3-dihydro-1,4-benzodioxin-2-yl]benzyl}-1,7-diazaspiro[4.4]non-1-yl)acetamide, (7-{4-[(2S)-2,3-dihydro-1,4-benzodioxin-2-yl]benzyl}-1,7-diazaspiro[4.4]non-1-yl)acetonitrile, 1-(7-{4-[(2S)-2,3-dihydro-1,4-benzodioxin-2-yl]benzyl}-1,7-diazaspiro[4.4]non-1-yl)-2-methoxyethanone, 9-[(S)-4-(2,3-Dihydro-benzo[1,4]dioxin-2-yl)-benzyl]-2-methyl-2,9-diaza-spiro[5.5]undecan-1-one, 1-{4-[(2S)-2,3-dihydro-1,4-benzodioxin-2-yl]benzyl}-1,4-diazepan-5-one, 1-{4-[(3S)-2,3-dihydro[1,4]dioxino[2,3-b]pyridin-3-yl]benzyl}-1,4-diazepan-5-one, N-[2-({4-[(3S)-2,3-dihydro[1,4]dioxino[2,3-b]pyridin-3-yl]benzyl}amino)ethyl]acetamide, 3-(1-{4-[(2S)-2,3-dihydro-1,4-benzodioxin-2-yl]benzyl}piperidin-4-yl)propanoic acid, N-{4-[(3S)-2,3-dihydro[1,4]dioxino[2,3-b]pyridin-3-yl]benzyl}cyclopentanamine, N-{4-[(3S)-2,3-dihydro[1,4]dioxino[2,3-b]pyridin-3-yl]benzyl}-N-methylethanamine, (3S)-3-{4-[(1s,4s)-7-azabicyclo[2.2.1]hept-7-ylmethyl]phenyl}-2,3-dihydro[1,4]dioxino[2,3-b]pyridine, (3S)-1-{4-[(3S)-2,3-dihydro[1,4]dioxino[2,3-b]pyridin-3-yl]benzyl}pyrrolidin-3-ol, 4-(1-{4-[(3S)-2,3-dihydro[1,4]dioxino[2,3-b]pyridin-3-yl]benzyl}piperidin-4-yl)butanoic acid, 1-[4-({4-[(3S)-2,3-dihydro[1,4]dioxino[2,3-b]pyridin-3-yl]benzyl}amino)piperidin-1-yl]ethenone, (3S)-3-{4-(5,6-dihydro[1,2,4]triazolo[4,3-a]pyrazin-7(8H)-ylmethyl)phenyl}-2,3-dihydro[1,4]dioxino[2,3-b]pyridine, (3S)-3-{4-[(1,1-dioxidothiomorpholin-4-yl)methyl]phenyl}-2,3-dihydro[1,4]dioxino[2,3-b]pyridine, 4-{4-[(3S)-2,3-dihydro[1,4]dioxino[2,3-b]pyridin-3-yl]benzyl}piperazine-1-carboxamide, (3S)-3-{4-[(3-methoxyazetidin-1-yl)methyl]phenyl}-2,3-dihydro[1,4]dioxino[2,3-b]pyridine, N-{4-[(3S)-2,3-dihydro[1,4]dioxino[2,3-b]pyridin-3-yl]benzyl}-N-methyl-1-(methylsulfonyl)piperidin-4-amine, (3S)-3-(4-{[4-(2-methoxyethoxy)piperidin-1-yl]methyl}phenyl)-2,3- dihydro[1,4]dioxino[2,3-b]pyridine, 2-(1-{4-[(3S)-2,3-dihydro[1,4]dioxino[2,3-b]pyridin-3-yl]benzyl}piperidin-4-yl)-N,N-dimethylacetamide, (3S)-3-(4-{[4-(methylsulfonyl)piperidin-1-yl]methyl}phenyl)-2,3-dihydro[1,4]dioxino[2,3-b]pyridine, N-{4-[(3S)-2,3-dihydro[1,4]dioxino[2,3-b]pyridin-3-yl]benzyl}cyclobutanamine, N-{4-[(2S)-2,3-dihydro-1,4-benzodioxin-2-yl]benzyl}-1-(methylsulfonyl)piperidin-4-amine, 1-{4-[(2S)-2,3-dihydro-1,4-benzodioxin-2-yl]benzyl}piperidine-4-carbonitrile, N-(1-{4-[(2S)-2,3-dihydro-1,4-benzodioxin-2-yl]benzyl}piperidin-4-yl)acetamide, [(3S)-1-{4-[(2S)-2,3-dihydro-1,4-benzodioxin-2-yl]benzyl}piperidin-3-yl]acetic acid, [(3R)-1-{4-[(2S)-2,3-dihydro-1,4-benzodioxin-2-yl]benzyl}pyrrolidin-3-yl]acetic acid, 1-(4-{4-[(3S)-2,3-dihydro[1,4]dioxino[2,3-b]pyridin-3-yl]benzyl}piperazin-1-yl)ethenone, 1-{4-[(3S)-2,3-dihydro[1,4]dioxino[2,3-b]pyridin-3-yl]benzyl}piperidin-4-ol, 1-(1-{4-[(3S)-2,3-dihydro[1,4]dioxino[2,3-b]pyridin-3-yl]benzyl}piperidin-4-yl)urea, (3S)-3-(4-{[4-(methylsulfonyl)piperazin-1-yl]methyl}phenyl)-2,3-dihydro[1,4]dioxino[2,3-b]pyridine, 1-{4-[(3S)-2,3-dihydro[1,4]dioxino[2,3-b]pyridin-3-yl]benzyl}piperidine-4-carboxylic acid, (1S,3R)-3-({4-[(2S)-2,3-dihydro-1,4-benzodioxin-2-yl]benzyl}amino)cyclopentanecarboxylic acid, 1-{4-[(2S)-2,3-dihydro-1,4-benzodioxin-2-yl]benzyl}piperidin-4-ol, 1-{4-[(2R)-2,3-dihydro-1,4-benzodioxin-2-yl]benzyl}piperidin-4-ol, 8-{4-[(2R)-2,3-dihydro-1,4-benzodioxin-2-yl]benzyl}-2,8-diazaspiro[4.5]decan-1-one, 1-{4-[(2S)-2,3-dihydro-1,4-benzodioxin-2-yl]benzyl}pyrrolidine, 1-{4-[(2R)-2,3-dihydro-1,4-benzodioxin-2-yl]benzyl}pyrrolidine, 4-{4-[(2S)-2,3-dihydro-1,4-benzodioxin-2-yl]benzyl}morpholine, 4-{4-[(2R)-2,3-dihydro-1,4-benzodioxin-2-yl]benzyl}morpholine, 1-{4-[(2R)-2,3-dihydro-1,4-benzodioxin-2-yl]benzyl}piperidine-4-carboxylic acid, 4-[4-(7-fluoro-2,3-dihydro-1,4-benzodioxin-2-yl)benzyl]morpholine, 1-[4-(7-fluoro-2,3-dihydro-1,4-benzodioxin-2-yl)benzyl]pyrrolidine, (3R)-3-[4-(morpholin-4-ylmethyl)phenyl]-2,3-dihydro[1,4]dioxino[2,3-b]pyridine, 1-{4-[(3R)-2,3-dihydro[1,4]dioxino[2,3-b]pyridin-3-yl]benzyl}piperidine-4-carboxamide, 1-[4-(2,3-dihydro[1,4]dioxino[2,3-b]pyridin-3-yl)benzyl]pyrrolidin-2-one, 3-[4-(2,3-dihydro[1,4]dioxino[2,3-b]pyridin-3-yl)benzyl]-1,3-oxazolidin-2-one, 1-[4-(2,3-dihydro[1,4]dioxino[2,3-b]pyridin-3-yl)phenyl]methanamine, 1-{4-[(2S)-2,3-dihydro-1,4-benzodioxin-2-yl]benzyl}-4-methylpiperidine-4-carboxylic acid, (3R,4R)-1-{4-[(2S)-2,3-dihydro-1,4-benzodioxin-2-yl]benzyl}-3-methylpiperidine-4-carboxylic acid, 1-{4-[(2S)-2,3-dihydro-1,4-benzodioxin-2-yl]benzyl}-4-fluoropiperidine-4-carboxylic acid, (3R)-1-{4-[(2S)-2,3-dihydro-1,4-benzodioxin-2-yl]benzyl}pyrrolidine-3-carboxylic acid, (3S)-1-{4-[(2S)-2,3-dihydro-1,4-benzodioxin-2-yl]benzyl}pyrrolidine-3-carboxylic acid, 1-{4-[(2S)-2,3-dihydro-1,4-benzodioxin-2-yl]benzyl}-4-(1H-tetrazol-5-yl)piperidine, 1-{4-[(2S)-2,3-dihydro-1,4-benzodioxin-2-yl]benzyl}piperidin-4-amine, N-(1-{4-[(2S)-2,3-dihydro-1,4-benzodioxin-2-yl]benzyl}piperidin-4-yl)-2-hydroxyacetamide, N-(1-{4-[(2S)-2,3-dihydro-1,4-benzodioxin-2-yl]benzyl}piperidin-4-yl)-2-methoxyacetamide, N-(1-{4-[(2S)-2,3-dihydro-1,4-benzodioxin-2-yl]benzyl}piperidin-4-yl)-2-hydroxy-2-methylpropanamide, 1-(1-{4-[(2S)-2,3-dihydro-1,4-benzodioxin-2-yl]phenyl}ethyl)pyrrolidine, 4-(1-{4-[(2S)-2,3-dihydro-1,4-benzodioxin-2-yl]phenyl}ethyl)morpholine, 1-(1-{4-[(2S)-2,3-dihydro-1,4-benzodioxin-2-yl]phenyl}ethyl)piperidine-4-carboxylic acid, 1-{4-[(3S)-2,3-dihydro[1,4]dioxino[2,3-b]pyridin-3-yl]benzyl}-4-methylpiperidine-4-carboxylic acid, 2-(1-{4-[(2S)-2,3-dihydro-1,4-benzodioxin-2-yl]benzyl}piperidin-4-yl)-2-methylpropanoic acid, 2-(1-{4-[(3S)-2,3-dihydro[1,4]dioxino[2,3-b]pyridin-3-yl]benzyl}piperidin-4-yl)-2-methylpropanoic acid, 2-{4-[(2S)-2,3-dihydro-1,4-benzodioxin-2-yl]benzyl}-1,2,3,4-tetrahydroisoquinoline-7-carboxylic acid, 4-{[{4-[(2S)-2,3-dihydro-1,4-benzodioxin-2-yl]benzyl}(ethyl)amino]methyl}benzoic acid, 4-[(butyl{4-[(2S)-2,3-dihydro-1,4-benzodioxin-2-yl]benzyl}amino)methyl]benzoic acid, 3-{[{4-[(2S)-2,3-dihydro-1,4-benzodioxin-2-yl]benzyl}(ethyl)amino]methyl}benzoic acid, and 3-[(4-{4-[(2S)-2,3-dihydro-1,4-benzodioxin-2-yl]benzyl}piperazin-1-yl)methyl]benzoic acid, or a pharmaceutically salt thereof of each of the foregoing.

In some embodiments, the LTA4H modulatory agent is a compound selected from 4-(1-{4-[(2S)-2,3-dihydro-1,4-benzodioxin-2-yl]benzyl}piperidin-4-yl)butanoic acid, 4-(1-{4-[(3S)-2,3-dihydro[1,4]dioxino[2,3-b]pyridin-3-yl]benzyl}piperidin-4-yl)benzoic acid, (3S)-3-{4-[(1s,4s)-7-azabicyclo[2.2.1]hept-7-ylmethyl]phenyl}-2,3-dihydro[1,4]dioxino[2,3-b]pyridine, N-(1-{4-[(3S)-2,3-dihydro[1,4]dioxino[2,3-b]pyridin-3-yl]benzyl}piperidin-4-yl)methanesulfonamide, (3S)-3-[4-(azepan-1-ylmethyl)phenyl]-2,3-dihydro[1,4]dioxino[2,3-b]pyridine, 1-{4-[(2S)-2,3-dihydro-1,4-benzodioxin-2-yl]benzyl}-2-methylpiperidine, 7-{4-[(2S)-2,3-dihydro-1,4-benzodioxin-2-yl]benzyl}-1,7-diazaspiro[4.4]nonane-1-carboxamide, 7-{4-[(3S)-2,3-dihydro[1,4]dioxino[2,3-b]pyridin-3-yl]benzyl}-1,7-diazaspiro[4.4]nonan-2-one, 1-{4-[(2S)-2,3-dihydro-1,4-benzodioxin-2-yl]benzyl}piperidine-4-carboxylic acid, (1-{4-[(2S)-2,3-dihydro-1,4-benzodioxin-2-yl]benzyl}piperidin-4-yl)(morpholin-4-yl)methanone, 8-{4-[(3S)-2,3-dihydro[1,4]dioxino[2,3-b]pyridin-3-yl]benzyl}-1,3,8-triazaspiro[4.5]decane-2,4-dione, (3S)-3-{4-[(3-methoxypiperidin-1-yl)methyl]phenyl}-2,3-dihydro[1,4]dioxino{2,3-b]pyridine, N-(1-{4-[(2S)-2,3-dihydro-1,4-benzodioxin-2-yl]benzyl}pyrrolidin-3-yl)-N-methylacetamide, 1-{4-[(2S)-2,3-dihydro-1,4-benzodioxin-2-yl]benzyl}-4-(1,1-dioxido-1,2-thiazolidin-2-yl)piperidine, (3R)-1-{4-[(3S)-2,3-dihydro[1,4]dioxino[2,3-b]pyridin-3-yl]benzyl}pyrrolidin-3-ol, N-(1-{4-[(3S)-2,3-dihydro[1,4]dioxino[2,3-b]pyridin-3-yl]benzyl}piperidin-4-yl)-2-hydroxyacetamide, 4-{(1-{4-[(3S)-2,3-dihydro[1,4]dioxino[2,3-b]pyridin-3-yl]benzyl}piperidin-4-yl)methyl}benzoic acid, (1-{4-[(3S)-2,3-dihydro[1,4]dioxino[2,3-b]pyridin-3-yl]benzyl}piperidin-4-yl)(morpholin-4-yl)methanone, (3S)-3-[4-(morpholin-4-ylmethyl)phenyl]-2,3-dihydro[1,4]dioxino[2,3-b]pyridine, 8-{4-[(2S)-2,3-dihydro-1,4-benzodioxin-2-yl]benzyl}-2,8-diazaspiro[4.5]decan-1-one, 1-{4-[(3S)-2,3-dihydro[1,4]dioxino[2,3-b]pyridin-3-yl]benzyl}piperidine-4-carbonitrile, 1-{4-[(2S)-2,3-dihydro-1,4-benzodioxin-2-yl]benzyl}-N-methylpiperidine-4-carboxamide, 8-{4-[(3S)-2,3-dihydro[1,4]dioxino[2,3-b]pyridin-3-yl]benzyl}-2,8-diazaspiro[4.5]decan-1-one, N-(1-{4-[(3S)-2,3-dihydro[1,4]dioxino[2,3-b]pyridin-3-yl]benzyl}piperidin-4-yl)-2-hydroxy-2-methylpropanamide, N-(1-{4-[(3S)-2,3-dihydro[1,4]dioxino[2,3-b]pyridin-3-yl]benzyl}piperidin-4-yl-1-hydroxycyclopropanecarboxamide, N-{4-[(2S)-2,3-dihydro-1,4-benzodioxin-2-yl]benzyl}-N-ethylcyclopentanamine, 1-{4-[(3S)-2,3-dihydro[1,4]dioxino[2,3-b]pyridin-3-yl]benzyl}-N-methylpiperidine-4-carboxamide, N-{4-[(3S)-2,3-dihydro[1,4]dioxino[2,3-b]pyridin-3-yl]benzyl}-N-methylcyclopentanamine, 1-{(1-{4-[(3S)-2,3-dihydro[1,4]dioxino[2,3-b]pyridin-3-yl]benzyl}piperidin-3-yl)methyl}pyrrolidin-2-one, 1-{4-[(2S)-2,3-dihydro-1,4-benzodioxin-2-yl]benzyl}-2-methylpyrrolidine, N-{4-[(3S)-2,3-dihydro[1,4]dioxino[2,3-b]pyridin-3-yl]benzyl}-2- methyl-1-(pyrrolidin-1-yl)propan-2-amine, N-cyclohexyl-N-{4-[(2S)-2,3-dihydro-1,4-benzodioxin-2-yl]benzyl}-N',N'-dimethylethane-1,2-diamine, N-(1-{4-[(3S)-2,3-dihydro[1,4]dioxino[2,3-b]pyridin-3-yl]benzyl}piperidin-4-yl)acetamide, N-{4-[(3S)-2,3-dihydro[1,4]dioxino[2,3-b]pyridin-3-yl]benzyl}-N-methyl-2-(pyridin-2-yl)ethanamine, (3S)-3-[4-(pyrrolidin-1-ylmethyl)phenyl]-2,3-dihydro[1,4]dioxino[2,3-b]pyridine, 1-{4-[(3S)-2,3-dihydro[1,4]dioxino[2,3-b]pyridin-3-yl]benzyl}piperidine-3-carboxamide, 1-{4-[(3S)-2,3-dihydro[1,4]dioxino[2,3-b]pyridin-3-yl]benzyl}piperidine-4-carboxamide, N-(1-{4-[(2S)-2,3-dihydro-1,4-benzodioxin-2-yl]benzyl}pyrrolidin-3-yl)acetamide, 1-{4-[(3S)-2,3-dihydro[1,4]dioxino[2,3-b]pyridin-3-yl]benzyl}-N-(2-hydroxyethyl)piperidine-4-carboxamide, (3S)-3-[4-(1,4-oxazepan-4-ylmethyl)phenyl]-2,3-dihydro[1,4]dioxino[2,3-b]pyridine, 1-{4-[(2S)-2,3-dihydro-1,4-benzodioxin-2-yl]benzyl}-N-(2-hydroxyethyl)piperidine-4-carboxamide, 4-(1-{4-[(2S)-2,3-dihydro-1,4-benzodioxin-2-yl]benzyl}piperidin-4-yl)benzoic acid, 1-(1-{4-[(2S)-2,3-dihydro-1,4-benzodioxin-2-yl]benzyl}piperidin-4-yl)urea, 7-{4-[(2S)-2,3-dihydro-1,4-benzodioxin-2-yl]benzyl}-1,7-diazaspiro[4.4]nonan-2-one, 8-{4-[(3S)-2,3-dihydro[1,4]dioxino[2,3-b]pyridin-3-yl]benzyl}-2-methyl-2,8-diazaspiro[4.5]decan-1-one, 1-{4-[(3S)-2,3-dihydro[1,4]dioxino[2,3-b]pyridin-3-yl]benzyl}piperidin-4-ol, N-(1-{4-[(2S)-2,3-dihydro-1,4-benzodioxin-2-yl]benzyl}piperidin-4-yl)methanesulfonamide, 3-(1-{4-[(3S)-2,3-dihydro[1,4]dioxino[2,3-b]pyridin-3-yl]benzyl}piperidin-4-yl)propan-1-ol, (3S)-3-{4-[(4-methylpiperidin-1-yl)methyl]phenyl}-2,3-dihydro[1,4]dioxino{2,3-b}pyridine, N-{4-[(3S)-2,3-dihydro[1,4]dioxino[2,3-b]pyridin-3-yl]benzyl}-N-ethylethanamine, N-{4-[(3S)-2,3-dihydro[1,4]dioxino[2,3-b]pyridin-3-yl]benzyl}-1-(methylsulfonyl)piperidin-4-amine, (3S)-3-{4-[(4-fluoropiperidin-1-yl-methyl]phenyl}-2,3-dihydro[1,4]dioxino{2,3-b}pyridine, 1-(4-{4-[(3S)-2,3-dihydro[1,4]dioxino[2,3-b]pyridin-3-yl]benzyl}-1,4-diazepan-1-yl)ethanone, [(3R)-1-{4-[(2S)-2,3-dihydro-1,4-benzodioxin-2-yl]benzyl}piperidin-3-yl]acetic acid, (1-{4-[(3S)-2,3-dihydro[1,4]dioxino[2,3-b]pyridin-3-yl]benzyl}piperidin-4-yl-methanol, 4-[(1-{4-[(2S)-2,3-dihydro-1,4-benzodioxin-2-yl]benzyl}piperidin-4-yl-methyl]benzoic acid, (3S)-3-{4-[(4-methyl-1,4-diazepan-1-yl)methyl]phenyl}-2,3-dihydro[1,4]dioxino {2,3-b}pyridine, (3S)-3-{4-[(3-methoxypyrrolidin-1-yl)methyl]phenyl}-2,3-dihydro[1,4]dioxino {2,3-b}pyridine, and N-{4-[(2S)-2,3-dihydro-1,4-benzodioxin-2-yl]benzyl}-N,2-dimethylpropan-2-amine, or a pharmaceutically salt thereof of each of the foregoing.

In some embodiments, the LTA4H modulatory agent is 4-{4-[(3S)-2,3-Dihydro[1,4]dioxino[2,3-b]pyridin-3-yl]benzyl}piperazine-1-carboxamide, or a pharmaceutically acceptable salt thereof. In some embodiments, the LTA4H modulatory agent is 4-{4-[(3S)-2,3-Dihydro[1,4]dioxino[2,3-b]pyridin-3-yl]benzy}piperazine-1-carboxamide. In some cases, the LTA4H modulatory agent is 1-{4-[(2S)-2,3-Dihydro-1,4-benzodioxin-2-yl]benzyl}piperidine-4-carboxylic acid, or a pharmaceutically acceptable salt thereof. In some cases, the LTA4H modulatory agent is 1-{4-[(2S)-2,3-Dihydro-1,4-benzodioxin-2-yl]benzyl}piperidine-4-carboxylic acid. In some cases, the LTA4H modulatory agent is [(3R)-1-{4-[(2S)-2,3-Dihydro-1,4-benzodioxin-2-yl]benzyl}piperidin-3-yl]acetic acid, or a pharmaceutically acceptable salt thereof. In some cases, the LTA4H modulatory agent is [(3R)-1-{4-[(2S)-2,3-Dihydro-1,4-benzodioxin-2-yl]benzyl}piperidin-3-yl]acetic acid.

In some embodiments the LTA4H modulatory agent includes an benzodioxane small molecule described in any of U.S. Pat. Nos. 9,133,146; 8,551,982; 8,946,203; 9,133,146 and 9,662,339; each of which is incorporated herein by reference.

In some embodiments, the LTA4H modulatory agent is a biarylamide, or a pharmaceutically acceptable salt thereof. In certain embodiments, the LTA4H modulatory agent is of the formula (XIX):

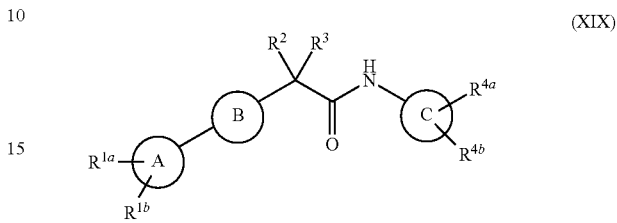

(XIX)

or a pharmaceutically acceptable salt thereof, wherein:

A is selected from pyrazolyl, imidazolyl, pyrrolyl, thienyl, thiazolyl, triazolyl, pyridinyl, pyrimidinyl, pyrazinyl, pyridazinyl, indolyl, pyrrolopyridinyl, dihydropyrrolopyridinyl, imidazopyridinyl, pyrazolopyridinyl and quinolinyl;

B is selected from phenyl, pyridinyl, pyrimidinyl, pyrazinyl and pyridazinyl;

C is pyridinyl;

$R^{1a}$ and $R^{1b}$ are each independently selected from —H, C1-6 alkyl, $C_{1-3}$alkoxyl, —$C_{1-3}$ alkyl-OH, hydroxy, —C(O)—$C_{1-3}$ alkyl and —$NR^5R^6$;

$R^2$ and $R^3$ together with the carbon atom to which they are attached form a cyclopropyl, cyclobutyl, cyclopentyl, cyclohexyl, tetrahydrofuranyl or a tetrahydropyranyl ring;

$R^{4a}$ and $R^{4b}$ are each independently selected from —H, $C_{1-3}$ alkyl, $C_{1-3}$alkoxyl, —$C_{1-3}$ alkyl-OH, phenyl, —O-phenyl, thiazolyl, oxazolyl, isoxazolyl, furanyl, thienyl, pyrrolyl, thiadiazolyl, tetrazolyl, pyridinyl, pyrimidinyl, pyridazinyl, pyrazinyl, cyclopropyl, cyclopbutyl, cyclopenyl, cyclohexyl, pyrrolidinyl, tetrahydrothienyl, piperidinyl, piperazinyl, morpholinyl, —$C_{1-3}$alkyl-phenyl, —$C_{1-3}$ alkyl-pyridinyl, —$C_{1-3}$ alkyl-pyrimidinyl, —$C_{1-3}$ alkyl-pyridazinyl, —$C_{1-3}$ alkyl-pyrazinyl, —$C_{1-3}$ alkyl-heterocyclyl, —O—$C_{1-3}$ alkyl-phenyl, —O—$C_{1-3}$ alkyl-pyridinyl, —$OC_{1-3}$ alkyl, $CF_3$, O—$CF_3$, —$COOR^5$, —C(O) $C_{1-3}$ alkyl-S(O)$_2$—$NR^5R^6$, —S(O)$_2CF_3$, —S(O)$_2C_{1-3}$ alkyl, —C(O)$NR^7R^8$, hydroxy, halogen, and cyano, wherein each group is optionally independently substituted with 1-3 substituents chosen from $C_{1-6}$ alkyl, $C_{1-6}$ alkoxyl, hydroxy and halogen;

$R^5$ and $R^6$ are each independently chosen from H, $C_{1-5}$ alkyl, —$C_{1-3}$alkylhydroxy and $C_{1-3}$ alkyl-O—$C_{1-3}$ alkyl;

or, $R^5$ and $R^6$ together with the nitrogen atom to which they are attached form a piperidinyl, morpholinyl or thiomorpholinyl ring;

$R^7$ and $R^8$ are each independently chosen from H, $C_{1-6}$ alkyl, —S(O)$_2C_{1-3}$ alkyl, and —C(NH)—$NH_2$.

In some embodiments the LTA4H modulatory agent includes a biarylamide small molecule described in U.S. Pat. No. 9,073,895, which is incorporated herein by reference.

In some instances, the LTA4H modulatory agent is not a compound disclosed in U.S. Pat. Nos. 8,569,303; 9,822,106; 9,856,249; 9,777,006; and 9,856,249; or United States Published Patent Application Publication Nos. 20180118735; 20180162854 and 20180162854.

In some cases, the modulating agent exhibits an affinity (Kd) for LTA4H that is sufficient to provide for the desired modulation of LTA4H. The affinity of the agent can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of the agent for unrelated transporter. In some cases, the affinity of an agent to LTA4H can be, for example, from about 100 nanomolar (nM) to about 1 nM, from about 100 nanomolar (nM) to about 0.1 nM, from about 100 nM to about 1 picomolar (pM), or from about 100 nM to about 1 femtomolar (fM), or from about 10 nanomolar (nM) to about 0.1 nM. In some embodiments, the affinity between the agent and LTA4H is characterized by a Kd (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. Modulating agents include antibodies that specifically bind to LTA4H. In some cases, the antibody specifically binds an epitope of LTA4H that provides for inhibition of the function of LTA4H. Antibodies that can be used as modulating agents in connection with the present disclosure can encompass, but are not limited to, monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules can be fully human antibodies, humanized antibodies, or chimeric antibodies. The antibodies that can be used in connection with the present disclosure can include any antibody variable region, mature or unprocessed, linked to any immunoglobulin constant region. Minor variations in the amino acid sequences of antibodies or immunoglobulin molecules are encompassed by the present disclosure, providing that the variations in the amino acid sequence maintain 75% or more, e.g., 80% or more, 90% or more, 95% or more, or 99% or more of the sequence. In particular, conservative amino acid replacements are contemplated.

Conservative replacements are those that take place within a family of amino acids that are related in their side chains. Whether an amino acid change results in a functional peptide can be determined by assaying the specific activity of the polypeptide derivative. "Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen-combining sites and is still capable of cross-linking antigen. Antibodies that can be used in connection with the present disclosure thus can encompass monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules can be fully human antibodies, humanized antibodies, or chimeric antibodies. In some embodiments, the antibody molecules are monoclonal, fully human antibodies. The antibodies that can be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4. As such, additional LTA4H modulatory agents include antibodies, including monoclonal antibodies, which selectively bind to the LTA4H enzyme to modulate its activity. Such antibodies may reduce one or more of the LTA4H enzyme's activities including, for example, its epoxide hydrolase and/or aminopeptidase activities.

In some instances, the agent modulates the activity of a LTA4H following expression, such that the agent is one that changes the activity of the protein encoded by the target gene following expression of the protein from the target gene. In other embodiments, the modulating agent modulates expression of the RNA and/or protein from the gene encoding the LTA4H, such that it changes the expression of the RNA or protein from the target gene in some manner. In these instances, the agent may change expression of the RNA or protein in a number of different ways. As would be readily understood by one of ordinary skill in the art, one can reduce expression (protein production) of an endogenous gene at the DNA, RNA, or protein level. For example, expression can be reduced by reducing the total amount of wild type protein made by the endogenous locus, and this can be accomplished either by changing the nature of the protein produced (e.g., via gene mutation to generate a loss of function allele such as a null allele or an allele that encodes a protein reduced function) or by reducing the overall levels of protein produced without changing the nature of the protein itself. In certain embodiments, the agent is one that reduces, including inhibits, expression of functional LTA4H. Inhibition of protein expression may be accomplished using any convenient means, and one of ordinary skill in the art will be aware of multiple suitable methods. For example, in order to reduce/inhibit expression, one can reduce protein levels post-translationally; one can block production of protein by blocking/reducing translation of mRNA (e.g., using an RNAi agent such as an shRNA or siRNA that targets the mRNA of an endogenous gene); one can reduce mRNA levels post-transcriptionally (e.g., using an RNAi agent such as an shRNA or siRNA that targets the mRNA of an endogenous gene); one can reduce mRNA levels by blocking transcription (e.g., using gene editing tools to either alter a promoter and/or enhancer sequence or to modulate transcription, or by using modified gene editing tools, e.g., CRISPRi, that can modify transcription without cutting the target DNA). Additionally, one can alter the nature of the protein made from an endogenous locus by inducing (e.g., using gene editing technology) a loss of function mutation, which can range from an allele with reduced wild type activity to a dead protein or no protein (e.g., catalytically inactive mutant, a frameshift allele, a gene knockout, etc.). Moreover, one can reduce mRNA levels via gene editing methods that result in low net transcript levels (e.g., frameshift mutations can trigger nonsense mediated mRNA decay). Any convenient inhibitor of expression can be utilized as an antagonist in the subject methods. Such antagonists can act to inhibit expression at a transcriptional, translational, or post-translational level. In some embodiments, the inhibitors are nucleic-acid based, including, without limitation, DNA, RNA, chimeric RNA/DNA, protein nucleic acid, and other nucleic acid derivatives. In some embodiments, the expression inhibitors encompass RNA molecules capable of inhibiting receptor production when introduced into a receptor-expressing cell (termed RNAi), including short hairpin double-stranded RNA (shRNA). In some instances, the expression inhibitors are small interfering RNA (siRNA). In some instances, the expression inhibitors are small interfering microRNA. It will be understood that any sequence capable of reducing the cell surface expression of a receptor, or reducing the expression of a receptor ligand, can be used in practicing the methods of the present disclosure. Examples of agents that inhibit expression of an endogenous gene (.g., as described herein) include but are not limited to: (a) an RNAi agent such as an shRNA or siRNA that specifically targets mRNA encoded by the endogenous gene; (b) a genome editing agent (e.g., a Zinc finger nuclease, a TALEN, a CRISPR/Cas genome editing agent such as Cas9, Cpf1, CasX, CasY, and the like) that cleaves the target cell's genomic DNA at a locus encoding the endogenous gene (e.g., SLC19A1)—thus inducing a genome editing event (e.g., null allele, partial loss of function allele) at the locus of the endogenous gene; (c) a modified genome editing agent such as a nuclease dead zinc finger, TALE, or CRISPR/Cas nuclease fused to a transcriptional repressor protein that modulates (e.g. reduces) transcription at the locus encoding the endogenous gene (e.g., SLC19A1) (see, e.g., Qi et al., Cell. 2013 Feb. 28; 152(5): 1173-83'; Gilbert et al, Cell. 2014 Oct. 23; 159(3):647-61; Larson et al., Nat Protoc. 2013 November; 8(11):2180-96). Examples of agents that increase or activate expression of an endogenous gene (e.g., as described herein) include, but are not limited to, CRISPR activation (CRISPRa) agents. When the agent is a CRISPR/Cas editing agent, the agent can include both the protein and guide RNA component. The guide nucleic acid (e.g., guide RNA) can be introduced into the cell as an RNA or as a DNA encoding the RNA (e.g., encoded by a DNA vector—on a plasmid, virus, and the like). The CRISPR/Cas protein can be introduced into the cell as a protein or as a nucleic acid (mRNA or DNA) encoding the protein. Programmable gene editing agents and their guide nucleic acids include, but are not limited to, CRISPR/Cas RNa-guided proteins such as Cas9, CasX, CasY, and Cpf1, Zinc finger proteins such as Zinc finger nucleases, TALE proteins such as TALENs, CRISPR/Cas guide RNAs, and the like. Antisense molecules can be used to down-regulate expression of a target gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences. Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), Nucl. Acids Res. 23:4434-42). In addition, the transcription level of a protein can be regulated by gene silencing using RNAi agents, e.g., double-strand RNA (Sharp (1999) Genes and Development 13: 139-141). RNAi, such as double-stranded RNA interference (dsRNAi) or small interfering RNA (siRNA), has been extensively documented in the nematode *C. elegans* (Fire, A., et al, Nature, 391, 806-811, 1998) and routinely used to "knock down" genes in various systems. RNAi agents may be dsRNA or a transcriptional template of the interfering ribonucleic acid that can be used to produce dsRNA in a cell. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct. As such, other embodiments of the LTA4H modulatory agents include siRNA or other agents which reduce the translation of LTA4H mRNA into active protein enzyme form. Additional embodiments of the invention include small molecule antagonists, antibodies, and mRNA reducing agents (e.g. siRNA) against the $LTB_4$ receptor(s).

The LTA4H enzyme protein level may be reduced using any convenient protocol. In some instances, the LTA4H level is reduced by removing systemic LTA4H from a subject, e.g., by removing LTA4H from the circulatory system of the subject. In some instances, any convenient protocol for removing circulatory LTA4H may be employed. For example, blood may be obtained from the subject and extra-corporeally processed to remove LTA4H from the blood to produce LTA4H-depleted blood. The resultant LTA4H-depleted blood may then be returned to the subject. Such protocols may employ a variety of different techniques in order to remove LTA4H from the obtained blood. For example, the obtained blood may be contacted with a filtering component, e.g., a membrane, etc., which allows passage of LTA4H but inhibits passage of other blood components, e.g. cells, etc. In some instances, the obtained blood may be contacted with a LTA4H absorptive component, e.g., porous bead or particulate composition, which absorbs LTA4H from the blood. In yet other instances, the obtained blood may be contacted with a LTA4H binding member stably associated with a solid support, such that LTA4H binds to the binding member and is thereby immobilized on the solid support, thereby providing for separation of LTA4H from other blood constituents. The protocol employed may or may not be configured to selectively remove LTA4H from the obtained blood, as desired. A number of different technologies are known for removing specific proteins from blood, and may be employed in embodiments of the invention, where such technologies include those described in U.S. Pat. Nos. 5,240,614; 6,416, 487; 6,419,830; 6,423,024; 6,855,121; 7,066,900; 8,211, 310; 8,349,550; as well as published PCT Application Publication No.: WO/2003/020403; the disclosures of which applications are herein incorporated by reference.

D. Administration

Aspects of the methods of the inventions described herein include treatment of a subject with an LTA4H modulatory agent, e.g., as described above. One of skill in the art would recognize that methods of treatment of subjects with an LTA4H modulatory agent are recognized in the art.

An embodiment of the invention includes treating a subject diagnosed with a cognitive or motor impairment, or neuroinflammation by administering to the subject an effective amount of an LTA4H modulatory agent. Another embodiment of the invention includes administering the effective amount of an LTA4H modulatory agent and subsequently monitoring the subject for improved cognitive or motor function, or a reduction in neuroinflammation or increase in neurogenesis.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse the progression of the cognitive impairment, age-associated dementia, motor disfunction, or neuroinflammation.

E. Indications

The subject methods and LTA4H modulatory agent(s) find use in treating, including preventing, aging-associated conditions, such as impairments in the cognitive ability of individuals, e.g., cognitive disorders, including (but not limited to) age-associated dementia, immunological conditions, cancer, and physical and functional decline. Individuals suffering from or at risk of developing an aging-associated cognitive impairment that will benefit from treatment with the subject LTA4H modulatory agent(s), e.g., by the methods disclosed herein, include individuals that are about 50 years old or older, e.g., 60 years old or older, 70 years old or older, 80 years old or older, 90 years old or older, and 100 years old or older, i.e., between the age of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

1. Mild Cognitive Impairment (M.C.I.)

Mild cognitive impairment is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function. Individuals suffering from or at risk of developing an aging-associated cognitive impairment that will benefit from treatment with the subject LTA4H modulatory agents, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

2. Alzheimer's Disease

Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus coeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

3. Parkinson's Disease

Parkinson's Disease (PD) is an idiopathic, slowly progressive, degenerative CNS disorder characterized by slow and decreased movement (bradykinesia), muscular rigidity, resting tremor (dystonia), muscle freezing, and postural instability. Originally considered primarily a motor disorder, PD is now recognized to also cause depression and emotional changes. PD also can affect cognition, behavior, sleep, autonomic function, and sensory function. The most common cognitive impairments include an impairment in attention and concentration, working memory, executive function, producing language, and visuospatial function. A characteristic of PD is symptoms related to reduced motor function usually precede those related to cognitive impairment, which aids in diagnosis of the disease.

In primary Parkinson's disease, the pigmented neurons of the substantia nigra, locus coeruleus, and other brain stem dopaminergic cell groups degenerate. The cause is not known. The loss of substantia nigra neurons, which project to the caudate nucleus and putamen, results in depletion of the neurotransmitter dopamine in these areas. Onset is generally after age 40, with increasing incidence in older age groups.

Parkinson's disease is newly diagnosed in about 60,000 Americans each year and currently affects approximately one million Americans. Even though PD is not fatal in itself, its complications are the fourteenth leading cause of death in the United States. At present, PD cannot be cured, and treatment is generally prescribed to control symptoms, with surgery prescribed in later, severe cases.

Treatment options for PD include administration of pharmaceuticals to help manage motor deficits. These options increase or substitute for the neurotransmitter, dopamine, of which PD patients have low brain concentrations. Such medications include: carbidopa/levodopa (which create more dopamine in the brain); apomorphine, pramipexolole, ropinirole, and rotingotine (dopamine agonists); selegiline and rasagiline (MAO-B inhibitors which prevent breakdown of dopamine); entacapone and tolcapone (Catechol-O-methyltransferase [COMT] inhibitors which make more levodopa available in the brain); benztropine and trihexyphenidyl (anticholinergics); and amantadine (controls tremor and stiffness). Exercise/physical therapy is also commonly prescribed to help maintain physical and mental function.

Current treatment options, however treat the symptoms of PD, are not curative, and fail to prevent disease progression. Additionally, current medications tend to lose efficacy in late stage PD. The most prescribed drug, levodopa, commonly results in adverse effects within 5 to 10 years after commencing the medication. These adverse effects can be severe and can result in motor fluctuations and unpredictable swings in motor control between doses as well as jerking/twitching (dyskinesia) which are difficult to manage and are even as disabling as PD's own symptoms. Thus, there remains a need for new therapies with new mechanisms of action which can either be administered along or in combination with current PD medications.

4. Parkinsonism

Secondary parkinsonism (also referred to as atypical Parkinson's disease or Parkinson's plus) results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including nigrostriatal degeneration. Certain disorders like Progressive Supranuclear Palsy (PSP), Multiple System Atrophy (MSA), Corticobasal degeneration (CBD) and Dementia with Lewy Bodies (DLB) can exhibit Parkinsonism symptoms before the cardinal symptoms necessary to the specific diagnosis can be made, and thus may be labeled as "Parkinsonism."

5. Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected:

Behavioral variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies." Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses, and patients often die within two to ten years.

6. Huntington's Disease

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

7. Amyotrophic Lateral Sclerosis

Amyotrophic lateral sclerosis (ALS) is a rapidly progressive, invariably fatal, neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years.

Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

8. Multiple Sclerosis

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

9. Glaucoma

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

10. Myotonic Dystrophy

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

11. Dementia

Dementia describes a class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short-term memory will rise and fall.

Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (POD) would be the diagnosis when dementia onset is more than a year after the onset of Parkinson's. DLB is diagnosed when cognitive symptoms begin at the same time or within a year of Parkinson symptoms.

12. Progressive Supranuclear Palsy

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

13. Ataxia

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

14. Multiple-System Atrophy

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation.

The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

15. Frailty

Frailty Syndrome ("Frailty") is a geriatric syndrome characterized by functional and physical decline including decreased mobility, muscle weakness, physical slowness, poor endurance, low physical activity, malnourishment, and involuntary weight loss. Such decline is often accompanied and a consequence of diseases such as cognitive dysfunction and cancer. However, Frailty can occur even without disease. Individuals suffering from Frailty have an increased risk of negative prognosis from fractures, accidental falls, disability, comorbidity, and premature mortality. (C. Buigues, et al. Effect of a Prebiotic Formulation on Frailty Syndrome: A Randomized, Double-Blind Clinical Trial, Int. J. Mol. Sci. 2016, 17, 932). Additionally, individuals suffering from Frailty have an increased incidence of higher health care expenditure. (Id.)

Common symptoms of Frailty can be determined by certain types of tests. For example, unintentional weight loss involves a loss of at least 10 lbs. or greater than 5% of body weight in the preceding year; muscle weakness can be determined by reduced grip strength in the lowest 20% at baseline (adjusted for gender and BMI); physical slowness can be based on the time needed to walk a distance of 15 feet; poor endurance can be determined by the individual's self-reporting of exhaustion; and low physical activity can be measured using a standardized questionnaire. (Z. Palace et al., The Frailty Syndrome, Today's Geriatric Medicine 7(1), at 18 (2014)).

In some embodiments, the subject methods and compositions find use in slowing the progression of aging-associated cognitive, motor, neuroinflammatory, neurodegenerative, or other age-related impairment or condition. In other words, cognitive, motor, neuroinflammatory, neurodegenerative, or other abilities or conditions in the individual will decline more slowly following treatment by the disclosed methods than prior to or in the absence of treatment by the disclosed methods. In some such instances, the subject methods of treatment include measuring the progression of cognitive, motor, neuroinflammation, or other age-related ability or symptom decline after treatment, and determining that the progression of decline is reduced. In some such instances, the determination is made by comparing to a reference, e.g., the rate of decline in the individual prior to treatment, e.g., as determined by measuring cognitive, motor, neuroinflammatory, or other age-related abilities or conditions prior at two or more time points prior to administration of the subject blood product.

The subject methods and compositions also find use in stabilizing the cognitive, motor, neuroinflammatory, or other abilities or conditions of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive, motor, neuroinflammatory, or other age-related impairment in an individual suffering from an aging-associated impairment. In other words, the affected ability is improved in the individual following treatment by the subject methods. For example, the cognitive or motor ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-old or more, following treatment by the subject methods relative to the cognitive or motor ability that is observed in the individual prior to treatment by the subject methods.

In some instances, treatment by the subject methods and compositions restores the cognitive, motor, or other ability in the individual suffering from aging-associated cognitive or motor decline, e.g., to their level when the individual was about 40 years old or less. In other words, cognitive or motor impairment is abrogated.

16. Neuromyelitis Optica Spectrum Disorder

Neuromyelitis Optica Spectrum Disorder (NMOSD), also known as Devic disease, is a rare, inflammatory disease of the central nervous system. It is characterized by optic neuritis (optic nerve inflammation) and myelitis (spinal cord inflammation). Typically, patients experience reoccurring bouts of inflammation separated by periods of remission. The disease is thought to be caused by auto-antibodies that often target myelin oligodendrocyte glycoprotein (MOG-IgG) or aquaporin 4 (AQP4-IgG), which leads to demyelination and axonal damage in the optic nerve and spinal cord.

17. Post-Operative Cognitive Dysfunction

Post-operative cognitive decline occurs following anesthesia and a surgical procedure. It is common in patients older than 60 and is diagnosed by pre- and post-surgery cognitive testing. Patients typically present with memory impairment, delirium, and impairment in performance on intellectual tasks.

18. Chronic Traumatic Encephalopathy

Chronic traumatic encephalopathy (CTE) is a neurodegenerative brain disorder most commonly found in athletes, veterans, or others with a history of repeated head trauma. It is one of many tauopathies that is characterized by the overabundance of Tau protein in the brain of patients that leads to neuron loss. Symptoms include memory loss, changes in mood or personality, confusion, impaired judgement, impulse control, aggression, and depression.

19. Traumatic Brain Injury

Traumatic brain injury (TBI) is caused by a violent hit to the head or body. It can also be caused by an object penetrating brain tissue during an injury. It results in bleeding, torn tissue, and physical damage to brain cells and cell death. The physical symptoms are varied, but include loss of consciousness, headaches, nausea, extreme fatigue, impaired speech, trouble sleeping, dizziness, blurred vision, sensitivity to light or sound, memory loss, and concentration problems.

F. Methods of Diagnosing and Monitoring for Improvement

In some instances, among the variety of methods to diagnose and monitor disease progression and improvement in cognitive disease, motor impairment, neuroinflammatory, or neurodegenerative disease the following types of assessments are used alone or in combination with subjects suffering from neurodegenerative disease, as desired. The following types of methods are presented as examples and are not limited to the recited methods. Any convenient methods to monitor disease may be used in practicing the invention, as desired. Those methods are also contemplated by the methods of the invention.

1. General Cognition

Embodiments of the methods of the invention further comprise methods of monitoring the effect of a medication or treatment on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy. In one embodiment, monitoring the effect on cognitive impairment and/or age-related dementia includes a 1, 2, 3, 4, 5, 6, 7, 8, 9, 10, 11, or 12-point improvement using the Alzheimer's Disease Assessment Scale-Cognitive Subscale (ADAS-COG).

In one embodiment, examinations of the peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

2. Parkinson's Disease

Embodiments of the methods of the invention further comprise methods of monitoring the effect of a medication or treatment on a subject for treating motor impairment, the method comprising comparing motor function before and after treatment. Those having ordinary skill in the art recognize that there are well-known methods of evaluating motor function. For example, and not by way of limitation, the method may comprise evaluation of motor function based on medical history, family history, physical and neurological examinations by clinicians who specialize neurodegeneration and motor impairment, laboratory tests, and neurodegenerative assessment. Additional embodiments which are contemplated by the invention include employment of the rating scales discussed below.

Several rating scales have been utilized for evaluating the progression of PD. The most widely-used scales include the Unified Parkinson's Disease Rating Scale (UPDRS, which was introduced in 1987) (J. Rehabil Res. Dev., 2012 49(8): 1269-76), and the Hoehn and Yahr scale (Neurology, 1967 17(5): 427-42). Additional scales include the Movement Disorder Society (MDS)'s updated UPDRS scale (MDS-UPDRS) as well as the Schwab and England Activities of Daily Living (ADL) Scale.

The UPDRS scale evaluates 31 items that contributed to three subscales: (1) mentation, behavior, and mood; (2) activities of daily living; and (3) motor examination. The Hoehn and Yahr scale classifies PD into five stages with discreet substages: 0—no signs of disease; 1—symptoms on one side only; 1.5—symptoms on one side but also involving neck and spine; 2—symptoms on both sides with no balance impairment; 2.5—mild symptoms on both sides, with recovery when the 'pull' test is given; 3—balance impairment with mild to moderate disease; 4—severe disability, but ability to walk or stand unassisted; and 5—need a wheelchair or bedridden without assistance. The Schwab and England scale classifies PD into several percentages (from 100%—complete independent to 10%—total dependent).

General motor function can be evaluated using widely-used scales including the General Motor Function Scale (GMF). This tests three components: dependence, pain, and insecurity. (Aberg A. C., et al. (2003) Disabil. Rehabil. 2003 May 6; 25(9):462-72.). Motor function can also be assessed using home-monitoring or wearable sensors. For example: gait (speed of locomotion, variability, leg rigidity) can be sensed with an accelerometer; posture (trunk inclination) by a gyroscope; leg movement by an accelerometer; hand movement by an accelerometer and gyroscope; tremor (amplitude, frequency, duration, asymmetry) by an accelerometer; falling by an accelerometer; gait freezing by an accelerometer; dyskinesia by an accelerometer, gyroscope, and inertial sensors; bradykinesia (duration and frequency) by an accelerometer plus gyroscope, and aphasia (pitch) using a microphone. (Pastorino M, et al., Journal of Physics: Conference Series 450 (2013) 012055).

3. Multiple Sclerosis

In addition to monitoring improvement for symptoms associated with cognition, the progression or improvement of neurodegeneration associated with multiple sclerosis (MS) can be monitored using techniques well-known to those having ordinary skill in the art. By way of example, and not limitation, monitoring can be performed through techniques such as: cerebrospinal fluid (CSF) monitoring; magnetic resonance imaging (MRI) to detect lesions and development of demyelinating plaques; evoked potential studies; and gait monitoring.

CSF analysis may be performed, for example, through lumbar puncture to obtain pressure, appearance, and CSF content. Normal values typically range as follows: pressure (70-180 mm H20); appearance is clear and colorless; total protein (15-60 mg/100 mL); IgG is 3-12% of the total protein; glucose is 50-80 mg/100 mL; cell count is 0-5 white blood cells and no red blood cells; chloride (110-125 mEq/L). Abnormal results may indicate the presence or progression of MS.

MRI is another technique that may be performed to monitor disease progression and improvement. Typical criteria for monitoring MS with MRI include the appearance of patchy areas of abnormal white matter in cerebral hemisphere and in paraventricular areas, lesions present in the cerebellum and/or brain stem as well as in the cervical or thoracic regions of the spinal cord.

Evoked potentials may be used to monitor the progression and improvement of MS in subjects. Evoked potentials measure slowing of electrical impulses such as in Visual Evoked Response (VER), Brain Stem Auditory Evoked Responses (BAER), and Somatosensory Evoked Responses (SSER). Abnormal responses help to indicate that there is a decrease in the speed of conduction in central sensory pathways.

Gait monitoring can also be used to monitor disease progression and improvement in MS subjects. MS is often accompanied by an impairment in mobility and an abnormal gait due in part to fatigue. Monitoring may be performed, for example, with the use of mobile monitoring devices worn by subjects. (Moon, Y., et al., Monitoring gait in multiple sclerosis with novel wearable motion sensors, PLOS One, 12(2):e0171346 (2017)).

4. Huntington's Disease

In addition to monitoring improvement for symptoms associated with cognition, the progression or improvement of neurodegeneration associated with Huntington's Disease (HD) can be monitored using techniques well-known to those having ordinary skill in the art. By way of example, and not limitation, monitoring can be performed through techniques such as: motor function; behavior; functional assessment; and imaging.

Examples of motor function that may be monitored as an indication of disease progression or improvement include chorea and dystonia, rigidity, bradykinesia, oculomotor dysfunction, and gait/balance changes. Techniques for performing the monitoring of these metrics are well-known to those having ordinary skill in the art. (See Tang C, et al., Monitoring Huntington's disease progression through preclinical and early stages, Neurodegener Dis Manag 2(4):421-35 (2012)).

The psychiatric effects of HD present opportunities to monitor disease progression and improvement. For example, psychiatric diagnoses may be performed in order to determine whether the subject suffers from depression, irritability, agitation, anxiety, apathy and psychosis with paranoia. (Id.)

Functional assessment may also be employed to monitor disease progression or improvement. Total functional score techniques have been reported (Id.), and often declines by one point per year in some HD groups.

MRI or PET may be employed also to monitor disease progression or improvement. For example, there is a loss of striatal projection neurons in HD and change in number of these neurons may be monitored in subjects. Techniques to determine neuronal change in HD subjects include imaging Dopamine D2 receptor binding. (Id.)

5. ALS

In addition to monitoring improvement for symptoms associated with cognition, the progression or improvement of neurodegeneration associated with Amyotrophic Lateral Sclerosis (ALS) can be monitored using techniques well-known to those having ordinary skill in the art. By way of example, and not limitation, monitoring can be performed through techniques such as: functional assessment; determining muscle strength; measuring respiratory function; measuring lower motor neuron (LMN) loss; and measuring upper motor neuron (UMN) dysfunction.

Functional assessment can be performed using a functional scale well-known to those having ordinary skill in the art, such as the ALS Functional Rating Scale (ALSFRS-R), which evaluates symptoms related to bulbar, limb, and respiratory function. The rate of change is useful in predicting survival as well as disease progression or improvement. Another measure includes the Combined Assessment of Function and Survival (CAFS), ranking subjects' clinical outcomes by combining survival time with change in ALSFRS-R. (Simon N G, et al., Quantifying Disease Progression in Amyotrophic Lateral Sclerosis, Ann Neurol 76:643-57 (2014)).

Muscle strength may be tested and quantified through use of composite Manual Muscle Testing (MMT) scoring. This entails averaging measures acquired from several muscle groups using the Medical Research Council (MRC) muscle strength grading scale. (Id.) Hand-held dynamometry (HHD) may also be used, among other techniques. (Id.)

Respiratory function can be performed using portable spirometry units, used to obtain Forced Vital Capacity (FVC) at baseline to predict the progression or improvement of the disease. Additionally, maximal inspiratory pressure, sniff nasal inspiratory pressure (SNIP), and supping FVC may be determined and used to monitor disease progression/improvement. (Id.)

Loss in lower motor neurons is another metric which can be utilized to monitor disease progression or improvement in ALS. The Neurophysiological Index may be determined by measuring compound muscle action potentials (CMAPs) on motor nerve conduction studies, of which parameters include CMAP amplitude and F-wave frequency. (Id. and de Carvalho M, et al., Nerve conduction studies in amyotrophic lateral sclerosis. Muscle Nerve 23:344-352, (2000)). Lower motor neuron unit numbers (MUNE) may be estimated as well. In MUNE, the number of residual motor axons supplying a muscle through estimation of the contribution of individual motor units to the maximal CMAP response is estimated and used to determine disease progression or improvement. (Simon N G, et al., supra). Additional techniques for determining loss of LMN include testing nerve excitability, electrical impedance myography, and using muscle ultrasound to detect changes in thickness in muscles. (Id.)

Dysfunction of upper motor neurons is another metric which can be utilized to monitor disease progression or improvement in ALS. Techniques for determining dysfunction include performing MRI or PET scans on the brain and spinal cord, transcranial magnetic stimulation; and determining levels of biomarkers in the cerebrospinal fluid (CSF).

6. Glaucoma

In addition to monitoring improvement for symptoms associated with cognition, the progression or improvement of neurodegeneration associated with glaucoma can be monitored using techniques well-known to those having ordinary skill in the art. By way of example, and not limitation, monitoring can be performed through techniques such as: determining intraocular pressure; assessment of the optic disc or optic nerve head for damage; visual field testing for peripheral vision loss; and imaging of the optic disc and retina for topographic analysis.

7. Progressive Supranuclear Palsy (PSP)

In addition to monitoring improvement for symptoms associated with cognition, the progression or improvement of neurodegeneration associated with Progressive Supranuclear Palsy (PSP) can be monitored using techniques well-known to those having ordinary skill in the art. By way of example, and not limitation, monitoring can be performed through techniques such as: functional assessment (activities of daily living, or ADL); motor assessment; determination of psychiatric symptoms; and volumetric and functional magnetic resonance imaging (MRI).

The level of function of a subject in terms of independence, partial dependence upon others, or complete dependence can be useful for determining the progression or improvement in the disease. (See Duff, K, et al., Functional impairment in progressive supranuclear palsy, Neurology 80:380-84, (2013)). The Progressive Supranuclear Palsy Rating Scale (PSPRS) is a rating scale that comprises twenty-eight metrics in six categories: daily activities (by history); behavior; bulbar, ocular motor, limb motor and gait/midline. The result is a score ranging from 0-100. Six items are graded 0-2 and twenty-two items graded 0-4 for a possible total of 100. The PSPRS scores are practical measures, and robust predictors of patient survival. They are also sensitive to disease progression and useful in monitoring disease progression or improvement. (Golbe L I, et al., A clinical rating scale for progressive supranuclear palsy, Brain 130:1552-65, (2007)).

The ADL section from the UPDRS (Unified Parkinson's Disease Rating Scale) can also be used to quantify functional activity in subjects with PSP. (Duff K, et al., supra). Similarly, the Schwab & England Activities Daily Living Score (SE-ADL) can be used for evaluating independence. (Id.) Additionally, the motor function sections of the UPDRS are useful as a reliable measure for assessing disease progression in PSP patients. The motor section may contain, for example, 27 different measures for quantifying motor function in PSP patients. Examples of these include resting tremor, rigidity, finger tapping, posture, and gait). A subject's disease progression or improvement may also be assessed by performing a baseline neuropsychological evaluation completed by trained medical personnel, the assessment using the Neuropsychiatric Inventory (NPI) to determine the frequency and severity of behavior abnormalities (e.g. delusions, hallucinations, agitation, depression, anxiety, euphoria, apathy, disinhibition, irritability, and aberrant motor behavior). (Id.)

Functional MRI (fMRI) can be employed to monitor disease progression and improvement as well. fMRI is a technique using MRI to measure changes in brain activity in certain regions of the brain, usually based on blood flow to those regions. Blood flow is considered to correlate with brain region activation. Patients with neurodegenerative disorders like PSP can be subjected to physical or mental tests before or during being scanned in an MRI scanner. By way of example, and not limitation, tests can be a well-established force control paradigm where patients as asked to produce force with the hand most affected by PSP and maximum voluntary contraction (MVC) is measured by fMRI immediately after the test takes place. Burciu, R G, et al., Distinct patterns of brain activity in progressive supranuclear palsy and Parkinson's disease, Mov. Disord. 30(9): 1248-58 (2015)).

Volumetric MRI is a technique where MRI scanners determine volume differences in regional brain volume. This may be done, for example, by contrasting different disorders, or by determining differences in volume of a brain region in a patient over time. Volumetric MRI may be employed to determine disease progression or improvement in neurodegenerative disorders like PSP. The technique is well-known to those having ordinary skill in the art. (Messina D, et al., Patterns of brain atrophy in Parkinson's disease, progressive supranuclear palsy and multiple system atrophy, Parkinsonism and Related Disorders, 17(3):172-76 (2011)). Examples of cerebral regions which may be measured include, but are not limited to, intracranial volume, cerebral cortex, cerebellar cortex, thalamus, caudate, putamen, pallidum, hippocampus, amygdala, lateral ventricles, third ventricle, fourth ventricle, and brain stem.

8. Neurogenesis

The invention also contemplates treating or improving neurogenesis in a subject with declining or impaired neurogenesis, which may manifest itself, for example, through reduced cognitive or motor function, or through association with neuroinflammation. An embodiment of the invention includes administering, by way of example and not limitation, an LTA4H modulatory agent to the subject with reduced or impaired neurogenesis using a Pulsed Dosing treatment regimen.

An embodiment of the invention also contemplates determining the level of neurogenesis before, during, and/or after administration of the LTA4H modulatory agent. Noninvasive techniques for evaluating neurogenesis have been reported. (Tamura Y. et al., J. Neurosci. (2016) 36(31):8123-31). Positron emission tomography (PET) used with the tracer, [18F]FLT, in combinations with the BBB transporter inhibitor probenecid, allows for accumulation of the tracer in neurogenic regions of the brain. Such imaging allows for an evaluation of neurogenesis in patients being treated for neurodegenerative disease.

9. Neuromyelitis Optica Spectrum Disorder

Neuromyelitis Optica Spectrum Disorder (NMOSD) can be diagnosed with a blood test to detect AQP4-IgG or MOG-IgG antibodies. Disease monitoring uses blood tests, cerebrospinal fluid tests, spinal taps, and magnetic resonance imaging (MRI) or computed tomography (CT) scans.

G. Reagents, Devices, and Kits

Also provided are reagents, devices, and kits thereof for practicing one or more of the above-described methods. The subject reagents, devices, and kits thereof may vary greatly. Reagents and devices of interest include those mentioned above with respect to the methods of administering the compositions described herein (e.g., LTA4H modulatory agents) to the subject.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g. diskette, CD, portable flash drive, etc., on which the information has been recorded. Yet another means that may be present is a website address which may be used via the internet to access the information at a remote site. Any convenient means may be present in the kits.

H. Exercise

Exercise can be characterized by aerobic or anaerobic activity and can involve high calorie-burning activity and moderate calorie-burning activity. Exercise may involve strength training (e.g. weight training or isometric exercise). Exercise may also involve, for example, running, bicycling, walking, dancing, marching, swimming, yoga, Tai Chi, balance exercises, leg bends, jumping rope, surfing, rowing, rotating or flexing the arms or legs, gardening, cleaning, active games such as bowling, aerobics, Pilates, and martial arts.

An exercise regimen may include performing a single exercise at a certain frequency, or a combination of exercises at a certain frequency. The frequency may be one, two, three, four, five, six, or seven times per week. The frequency may vary from week-to-week. The exercise regimen may be at the same level of intensity and/or frequency as the subject practiced before administration of the compositions of the invention. The exercise regimen may also be at a higher level of intensity and/or frequency compared to the levels the subject practiced before administration of the compositions of the invention. The exercise regimen may have been suggested or prescribed by a health or fitness professional, or the exercise regimen may have been initiated by the subject himself or herself.

VII. EXPERIMENTAL EXAMPLES

The following examples are provided by way of illustration and not by way of limitation.

A. Experimental Procedures

1. Open Field/Novel Object Recognition

The open field test was used to evaluate general locomotor activity and exploratory behavior in a novel environment. It consisted of a square arena (50 cm×50 cm). Mice were brought to the experimental room for at least 30 min of acclimation to the experimental room conditions (dim lighting) prior to testing. Mice were placed in the center of the arena and tracked using automated software (CleverSys or San Diego Instruments) for 15 min. Total distance traveled, average velocity, and time spent in the peripheral and center zones were analyzed.

2. Y-Maze

A large Y-maze test assessed short-term memory of the familiarity of a specific context. Mice were brought to the experimental room for at least 30 min of acclimation to the experimental room conditions (dim lighting) prior to testing. For the initial training trial, the mouse was placed at the end of one arm of a large Y-maze designated "start arm" (arm length: 15 inches). The third arm of the maze was blocked off, allowing the mouse to explore two of the three arms freely ("start arm" and "familiar arm") for 5 min. Each arm contained spatial cues. Three hours later, the mouse was placed back into the maze in the "start arm," and allowed to explore all three arms with the third arm unblocked ("novel arm"). Movements in and out of each arm were tracked using automated tracking software (CleverSys or San Diego Instruments). Testing was performed under dim lighting, and the apparatus was cleaned with 70% ethanol between trials. The time spent and number of entireties into the "novel arm" and "familiar arm" were analyzed, as well as total distance travelled and velocity as measures of general locomotor activity.

3. Radial Arm Water Maze (RAWM)

The water maze (see, e.g. Alamed J, et al., *Two-day radial-arm water maze learning and memory tasks; robust resolution of amyloid-related memory deficits in transgenic mice.*, Nat. Protoc., 1(4):1671-79 (2006)), was filled with water at least 24 hours prior to the test to equilibrate to 25° C. The water was dyed with white latex paint to make the animals visible for tracking and to allow for the use of a hidden platform. Eight distinct visual cues were placed at the end of each of eight arms of the RAWM inserts. On day 1 animals were subjected to 5 trials each with a visible platform and a 30-minute inter-trial interval. Animals had 60 seconds to reach the platform. If they did not reach the platform in that time they were guided to it and allowed to remain for 15 seconds before being removed from the tank. The goal arm remained constant and a different start arm was randomly assigned for each of the 5 trials so that mouse started in every arm once except for the two arms directly across from the platform. The goal arm was switched after every two mice and balanced between all treatment groups. After each trial the mice were placed in an empty cage with blue pads and allowed to dry off under a heat lamp before being placed back into their home cage. Testing day was 48 hours after training, when animals were subjected to the same test of 5 trials each and a 30-minute inter-trial interval, but with a hidden platform. Animals were scored for the number of errors (entry into a non-goal arm) and for latency to reach the platform. All trials were recorded using TopScan software (CleverSys, Inc., Reston, Va.).

4. Contextual Fear Conditioning (CFC)

Mice were brought into the testing room immediately before their trial to avoid exposure to sounds and scents from testing. Day 1: For training, mice were placed in the chambers, bright house light and fan on, for 2 minutes. Then an auditory cue (2000 Hz, 70 dB, conditioned stimulus (CS)) was presented for 30 seconds. A 2 second foot shock (0.6 mA; unconditioned stimulus (US)) was administered for the final 2 seconds of the CS. This procedure was repeated once, each after a 2 minute interval, and the mouse was removed from the chamber 30 seconds after the second shock. The pans, chamber walls and grid floors were cleaned with 70% ethanol between trials. Day 2: Seventy-two hours after the training, the mouse was returned to the same chamber in which the training occurred (memory for context), and freezing behavior was recorded for 3 min. The mouse was returned to its home cage. The pans, chamber walls, and grid floors were cleaned with 70% ethanol between trials. Day 3: 24 hours after context testing, the mouse was returned to the same chamber and freezing was recorded in a novel environment (altered context) and in response to the cue (memory for cue). The novel environment included different odors (Peppermint water), sounds, a chamber divider, and different floor material. The mouse was placed in the novel environment and freezing was recorded for 2 minutes. The auditory cue (2000 Hz, 70 dB, CS) was then presented for 30 seconds, and freezing was again recorded for 2 minutes. Mice were returned to their home cages, and the pans, chamber walls, and floors were cleaned with Ethanol and with Peppermint water between trials.

5. Tissue Collection and Histology/Biochemistry

On the final day of dosing, mice were deeply anesthetized with Avertin (250 mg/kg IP). The mice are subjected to cardiac puncture and blood samples were collected using syringes pre-filled with EDTA or heparin. Blood was either subjected to calcimycin stimulation assay or separated into plasma by centrifugation. Plasma from each mouse was aliquoted and stored at −80° C.

Brains were collected following saline perfusion and separated by mid-sagittal slice with one-half drop fixed in freshly prepared 4% PFA. PFA was changed to 30% sucrose 24-48 hours later. A second change to 30% sucrose occurred 24 hours later. The second half was dissected into hippocampus and cortex and then snap frozen on dry ice.

Brain tissue was sectioned or lysed and analyzed for markers of neurogenesis and aging by standard histological and biochemical methods, including qRT-PCR, Western blot, ELISA, and immunohistochemistry.

6. Experimental Reagents and Study Blinding

Recombinant human LTA4H (Bio-techne, 4008—SN) was buffer-exchanged into sterile PBS and dosed at 4.6 ug/150 uL by tail vein i.v. injection. SC-57461A (Cayman Chemical, 423169-68) stock solution was prepared at 10 mg/mL in DMSO. Stock solution was diluted into sterile PBS immediately prior to p.o. dosing to a final concentration of 10% DMSO and 1 mg/mL SC-57461A. Mice were p.o. dosed at 5 mg/kg. CP-105,696 (Sigma, PZ0363), Pinostilbene hydrate (Sigma, SML0098), and Montelukast (Cayman Chemical, 10008318) stock solutions were prepared at 30 mg/mL in EtOH/Solutol. Stock solutions were diluted into sterile PBS immediately prior to p.o. dosing to a final concentration of 10% EtOH and 3.3 mg/mL inhibitor. Administration to mice was performed p.o. at a dose of 10 mg/kg. Vehicle was 10% EtOH/Solutol and was dosed p.o. at a volume of 150 uL.

SC-57461A ("SC") is an LTA4H dual inhibitors, inhibiting both the hydrolase and peptidase activity of the enzyme. Pinostilbene hydrate ("PH") is an inhibitor of the hydrolase activity of the enzyme. CP-105,696 ("CP") is an LTB4 receptor antagonist, and Montelukast ("M") is a cysteinyl receptor antagonist.

B. Example 1

The concentration of LTA4H protein or LTB4 lipid in young and old human plasma was measured using a commercially-available LTA4H enzyme-linked immunosorbent assay (ELISA) (Quantikine ELISA, R&D Systems) or LTB4 Parameter Kit (Enzo). Plasma samples were collected by plasmapheresis at Grifols and frozen within 30 min of collection. Per age group five individual plasma samples were combined per pool and 7-9 pools were measured for the young and old plasma group representing 35-45 individual donors.

Figure 1A:
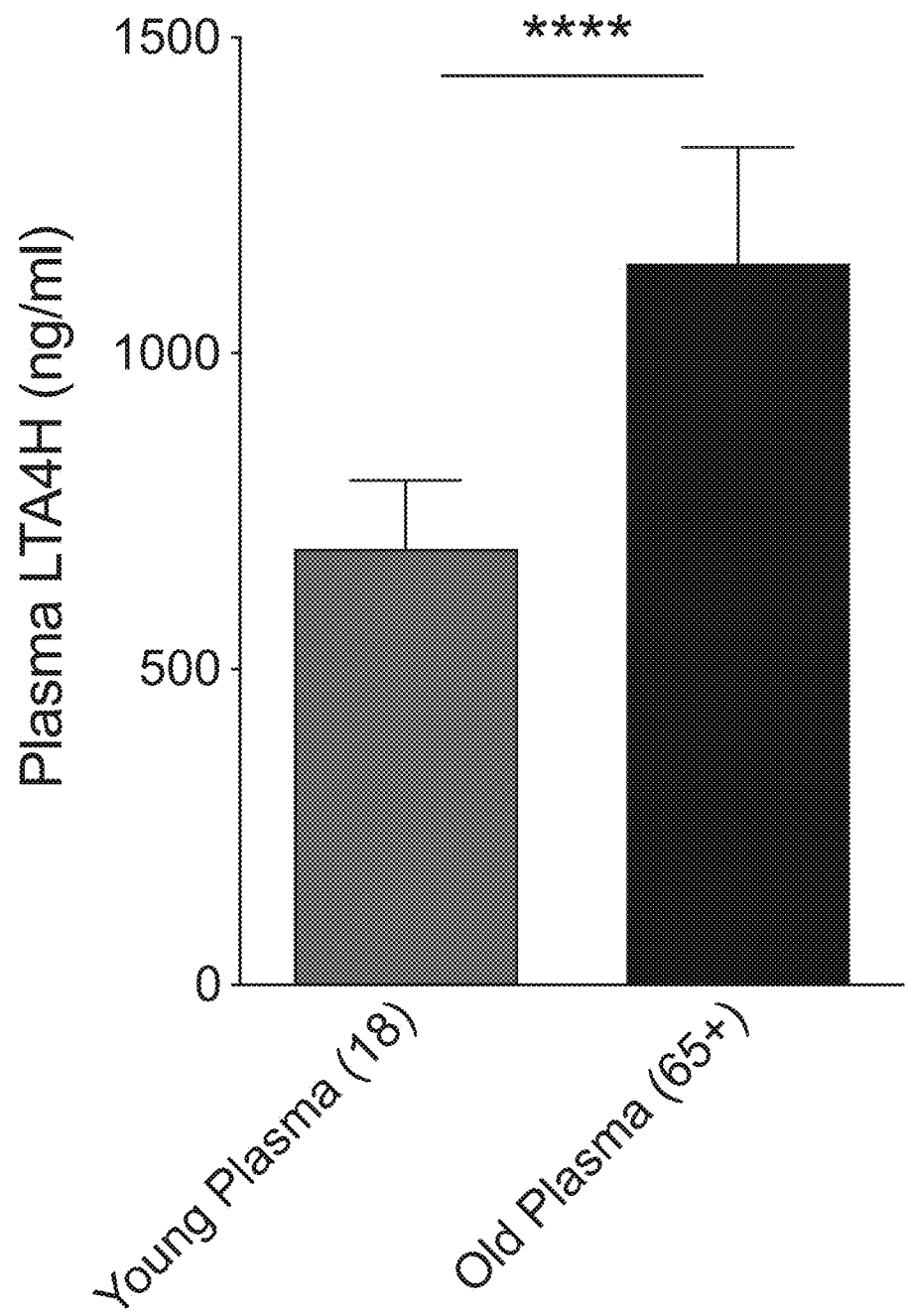
FIG. 1A depicts the concentration of LTA4H in young (18-year-old) and old (65-year-old) human plasma.

FIG. 1A reports that quantification by ELISA shows a significant increase in LTA4H with age between young and old human plasma samples. Young plasma from 20-year-old donors had an average concentration of 690 ng/mL LTA4H while old plasma from 65-year-old donors had an average concentration of 1140 ng/mL LTA4H. All data shown are mean±s.e.m; ****$p<0.0001$, Unpaired t test. n=8-9

Figure 1B:
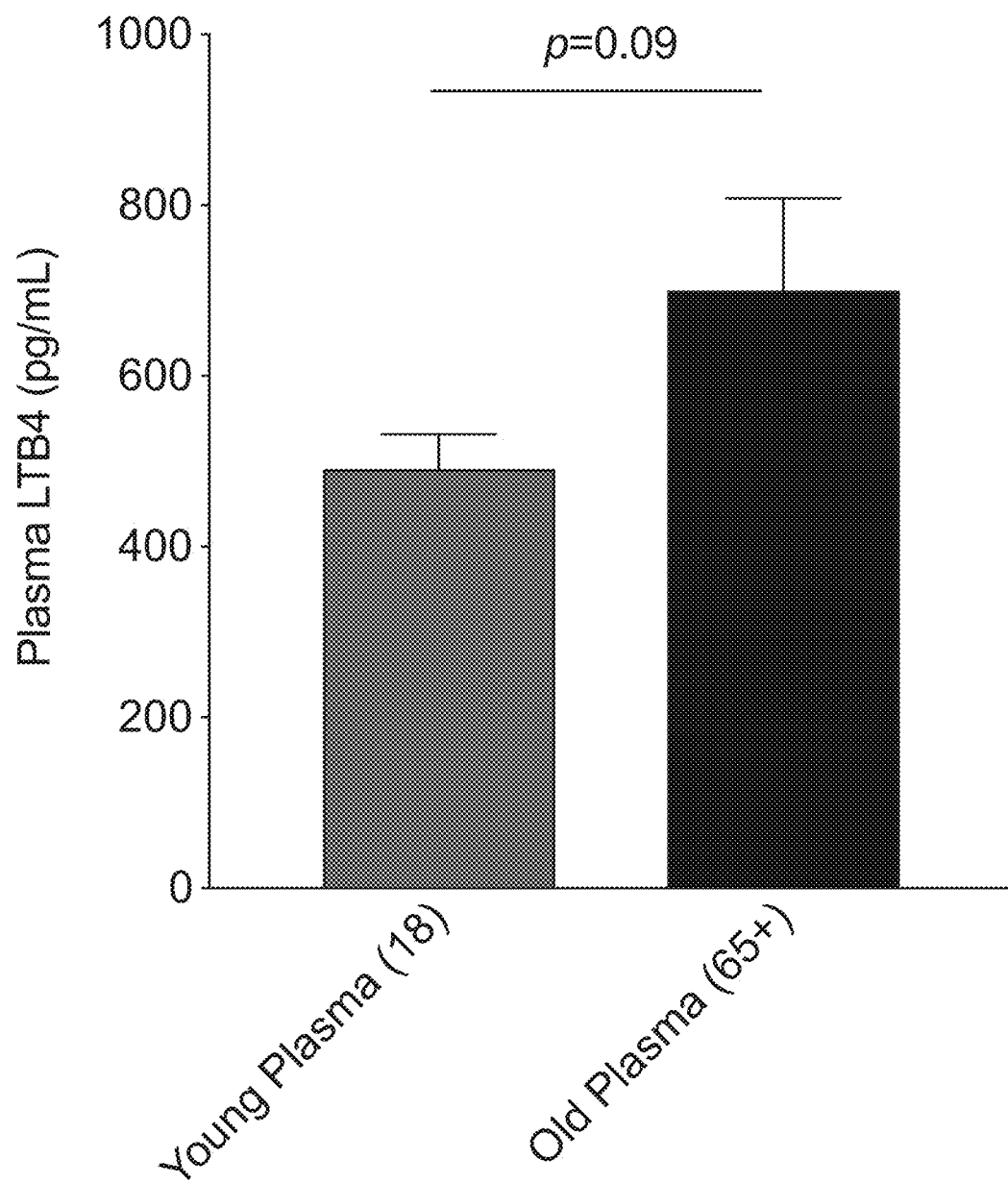
FIG. 1B depicts the concentration of LTB4 in young (18-year-old) and old (65-year-old) human plasma.

FIG. 1B reports that quantification by ELISA shows an increase in LTB4 levels with age between young and old human plasma samples. Young plasma from 20-year-old donors had an average concentration of 491 pg/mL LTB4 while old plasma from 65-year-old donors had an average concentration of 700 pg/mL LTB4. All data shown are mean±s.e.m; Unpaired t test. n=7.

C. Example 2

The concentration of mouse LTB4, the product of LTA4H enzyme hydrolysis activity, was measured using commercially-available LTB4 parameter assay kits (R&D Systems and Enzo). Blood samples were collected by cardiac puncture into pre-filled syringes with EDTA and injected into a microcentrifuge tube. The plasma was separated by centrifugation at 1000 g for 15 minutes at 4 C. Alternatively, blood was subjected to a calcimycin stimulation assay to increase the production of LTB4 prior to plasma collection. All plasma was stored at −80 C until measurement of LTB4 levels. LTB4 levels were measured from the plasma from 4-15 individual young (3 month, 3M) or aged (22.5 month, 22.5M) wild-type mice (WT; C57BL/6).

Figure 2A:
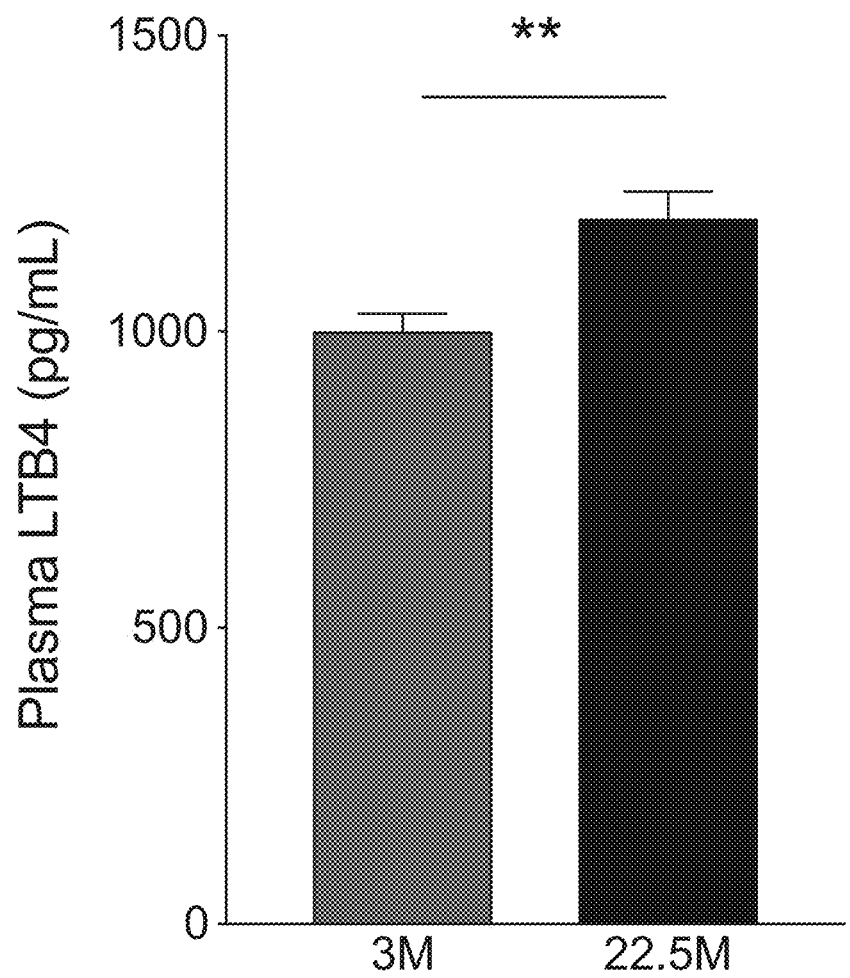
FIG. 2A depicts the concentration of LTB4 in young (3 month, 3M) and old (22.5 month, 22.5M) mouse plasma.

FIG. 2A reports that quantification by ELISA shows a significant increase in LTB4 levels with age between young and old mouse plasma samples. Young plasma from 3-month-old mice had an average concentration of 1000 pg/mL LTB4 while old plasma from 22.5-month-old mice had an average concentration of 1191 pg/mL LTB4. All data shown are mean±s.e.m; **$p<0.01$, Unpaired t test. n=11-15.

Figure 2B:
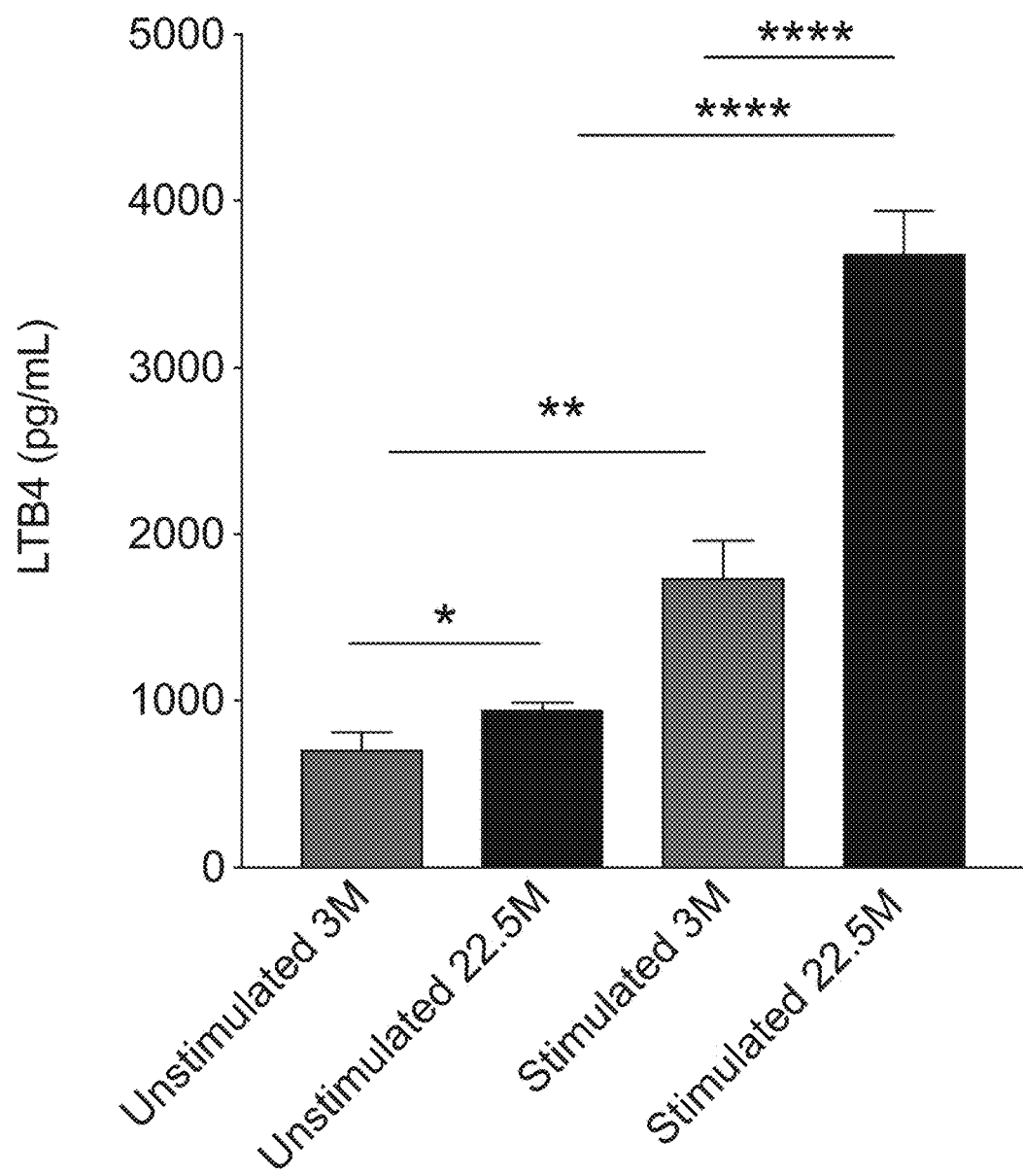
FIG. 2B depicts the concentration of LTB4 in young (3 month, 3M) and old (22.5 month, 22.5M) mouse plasma either unstimulated or stimulated with calcimycin to increase LTB4 production.

FIG. 2B reports that quantification by ELISA shows a significant increase in LTB4 levels with age between young and old mouse plasma samples from both unstimulated and calcimycin stimulated blood. Young plasma from 3-month-old mice had an average concentration of 708 pg/mL LTB4 while old plasma from 22.5-month-old mice had an average concentration of 946 pg/mL LTB4. Stimulated young plasma from 3-month-old mice had an average concentration of 1739 pg/mL LTB4 while stimulated old plasma from 22.5-month-old mice had an average concentration of 3686 pg/mL LTB4. All data shown are mean±s.e.m; *$p<0.05$, $p<0.01$, **$p<0.0001$. Unpaired t test. n=4-8.

D. Example 3

Figure 3:
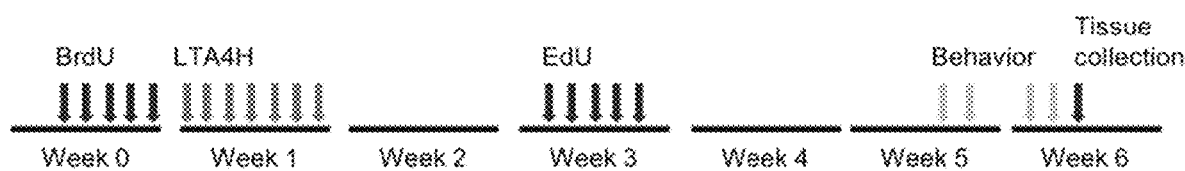
FIG. 3 depicts treatment paradigm 1 of LTA4H recombinant protein or phosphate buffered saline (PBS) administration in 8-week old (young) wild-type (C57BL/6) mice.

Young, 8-week old wild-type (WT; C57BL/6) mice were homogenized between groups by body weight. Following group determination, mice were injected intraperitoneally (IP) with BrdU (5-bromo-2'-deoxyuridine) formulated in PBS (phosphate buffered saline) at a final concentration of 10 mg/mL dosed at 150 mg/kg for 5 days. Immediately following the BrdU dosing, group 1 was injected intravenously (IV) with PBS control and group 2 with recombinant human LTA4H protein daily for 7 consecutive days. One week after the completion of LTA4H administration, in week 3, mice in both treatment groups were injected IP with EdU (5-ethynyl-2'-deoxyuridine) formulated in PBS at a final concentration of 10 mg/mL and dosed at 50 mg/kg for 5 days. Behavioral assays were executed in week 5 and 6, and animals were sacrificed, and tissues collected immediately after completion of behavior testing in week 6. FIG. 3 depicts the treatment paradigm and injection timing for the study.

Behavior:

FIG. 4 reports the results of the open field testing in mice treated with either PBS control or human recombinant LTA4H protein. FIGS. 4A and 4B report no change in total distance travelled or average velocity between treatment groups. FIG. 4C reports the percent time spent in the periphery or center of the open field in both treatment groups. All mice spend significantly more time in the periphery than in the center of the open field. Taken together the data indicates that general locomotion as measured by total distance travelled and average velocity, and anxiety as measured by percent time spent in periphery or center of the open field are not affected by treatment with LTA4H. All data shown are mean±s.e.m; ****$p<0.0001$, Paired t test, n=14.

FIG. 5 depicts the results of fear conditioning testing in mice treated with either PBS control or human recombinant LTA4H protein. In the training paradigm, mice were placed in the fear conditioning chamber and allowed to explore for 2 min. Then an auditory cue (2000 Hz, 70 dB, conditioned stimulus) was presented for 30 sec, terminating in a 2 sec foot shock (0.6 mA, unconditioned stimulus). This procedure was repeated once after a 2 min interval and the mouse was removed from the chamber 30 sec after the second shock. 72 hours after training the mouse was returned to the same chamber in which the training occurred (memory for context) and freezing was recorded for 3 min (Context). 24 hours after context testing the mouse was returned to the same chamber with a novel environment (novel context) and freezing was recorded for 2 min (Pre-cue). The auditory cue (2000 Hz, 70 dB, CS) was then presented for 30 sec, and freezing was again recorded for 2 min (Post-cue). FIGS. 5A and 5B show the percent time freezing during the contextual testing, with LTA4H treated mice showing significantly decreased freezing compared to PBS treated control mice. FIG. 5C shows the percent time freezing during the cued testing, with both treatment groups showing significantly increased freezing after the cue tone, but no significant difference between treatment groups. The contextual testing measures hippocampal dependent spatial memory and shows that LTA4H treatment significantly impairs the recall of the negative context. Cued testing is administered to determine whether there is a lack of ability to perform the fear conditioning task. Animals in both treatment groups show significantly increased freezing after the cue tone, showing that they are able to complete the task and show normal fear behavior. All data shown are mean±s.e.m; *$p<0.05$, ***$p<0.001$, 5B Unpaired t test, 5C paired t test, n=14.

Histology:

FIG. 6 reports the number of EdU-labeled cells within the granule cell layer of the dentate gyrus in mice treated with either PBS control or human recombinant LTA4H protein. There is a significant decrease in the number of EdU-labeled cells in the LTA4H treated animals. This data indicates that there is a decrease in the number of proliferating cells that incorporate the EdU label in week 3 of the treatment paradigm. All data shown are mean±s.e.m; *$p<0.05$, unpaired t test, n=14.

FIG. 7 depicts representative images of cell nuclei labeled with Hoechst 33342 (Trihydrochloride trihydrate) and Ki67 antibody labeled proliferating cells in the hippocampus of PBS or recombinant LTA4H treated mice. There are fewer Ki67 labeled cells in the hippocampus of LTA4H treated mice than in the PBS treated mice.

FIG. 8 reports the number of Ki67-labeled cells within the granule cell layer of the dentate gyrus in mice treated with either PBS control or human recombinant LTA4H protein. There is a significant decrease in the number of Ki67-labeled cells in the LTA4H treated animals. This data indicates that there is a decrease in the number of proliferating cells that express Ki67 in study week 6. All data shown are mean±s.e.m; *$p<0.05$, unpaired t test, n=14.

FIG. 9 reports the results of quantitative polymerase chain reaction (qPCR) quantifying mRNA levels of vesicular glutamate receptor (vglut1), synapsin 1 (syn1), synaptophysin (syp), early growth response 1 (egr1), doublecortin (dcx), beta III tubulin (tuj1), glial acidic fibrillary protein (gfap), SRY-Box 2 (sox2), oligodendrocyte transcription factor 2 in 3 months old (young) wild-type (C57BL/6) mice treated with recombinant human LTA4H protein or phosphate buffered saline (PBS) control. There is a significant decrease in egr1 and tuj1 expression. Egr1 is an immediate early gene and a reduction in expression is indicative of a depression of neuronal activity. Tuj1 is a neuronal marker and the reduction in expression points to detrimental effects on neurons. Furthermore, there is a trend towards a decrease in olig 2, a marker of oligodendrocytes suggesting detrimental effects on this cell type as well. Overall the decreases in neuronal markers and trends towards decreases in oligodendrocyte markers indicate a detrimental effect on neuronal activity and integrity in LTA4H treated animals. All data shown are mean±s.e.m; **$p<0.01$, unpaired t test, n=14.

These results show that there is significant detrimental effect of peripherally administered human recombinant LTA4H protein on hippocampus-dependent cognition in the contextual fear conditioning test as well as significant detrimental effects on proliferation of neural stem and progenitor cells in the dentate gyrus of the hippocampus of 3 months old wild-type (C57BL/6) mice. Furthermore, there is also a detrimental effect on the expression of the neuronal activity marker egr1 and the mature neuron marker tuj1 indicated additional negative effects of peripherally administered LTA4H protein.

The initial study in young, 8-week old wild-type (WT; C57BL/6) mice was repeated in a second cohort of mice with additional timepoints and readouts. Mice were homogenized between 3 treatment groups by body weight. Group 1 (Vehicle) was injected intravenously (IV) with PBS control 3 times per week for 6 weeks, group 2 (LTA4H Pulse) with recombinant human LTA4H protein daily for 7 consecutive days, and group 3 (LTA4H Continuous) with recombinant human LTA4H protein 3 times per week for 6 weeks. In week 4 after the initiation of dosing, mice in all treatment groups were injected IP with BrdU (5-bromo-2'-deoxyuridine) formulated in PBS (phosphate buffered saline) at a final concentration of 10 mg/mL dosed at 150 mg/kg for 5 days. Behavioral assays were executed in week 5 and 6, and animals were sacrificed, and tissues collected immediately after completion of behavior testing in week 6. FIG. 10 depicts the treatment paradigm and injection timing for the study.

Behavior:

FIG. 11 reports the results of the open field testing in mice treated with PBS control, human recombinant LTA4H protein pulse dosing, or human recombinant LTA4H protein continuous dosing. FIGS. 11A and 11B report a significant reduction in distance traveled and average velocity with LTA4H continuous dosing. FIG. 11C reports the percent time spent in the periphery or center of the open field in both treatment groups. All mice spend significantly more time in the periphery than in the center of the open field. The data indicates that general locomotion as measured by total distance travelled and average velocity is impaired with continuous dosing of LTA4H, but not with pulse dosing of LTA4H. Additionally, the data indicate that anxiety as measured by percent time spent in periphery or center of the open field are not affected by treatment with LTA4H with either dosing paradigm. All data shown are mean±s.e.m; Distance and Velocity: One-way ANOVA with multiple comparisons p<0.01. Percent time in center vs. periphery, Two-way ANOVA with paired t tests **p<0.0001. n=14.

FIG. 12 reports the results of the Y-maze behavioral task in mice treated with PBS control, human recombinant LTA4H protein pulse dosing, or human recombinant LTA4H protein continuous dosing. The Y-maze task tests hippocampus-dependent spatial memory and is designed to have unique cues in the form of black shapes adhered to walls at the ends of two of the arms, while the third is un-cued and designated as the starting point for the mice. First, mice were individually placed in the starting arm and allowed to explore only one of the other two arms for 5 minutes of training. FIG. 12A reports that there were no differences in number of entries into the familiar arm between treatment groups during training. During testing, a significant increase in entries into the novel over the familiar arm signifies contextual memory of the familiar arm. FIG. 12B reports that PBS vehicle treated mice had intact memory of the familiar arm, while mice treated with LTA4H by pulse or continuous dosing had impaired memory. All data shown are mean±s.e.m; Two-way ANOVA with paired t tests *p<0.05. n=14.

Histology:

FIG. 13 reports the number of BrdU and DCX co-labeled cells within the granule cell layer of the dentate gyrus in mice treated with PBS control or human recombinant LTA4H protein either by pulse or continuous dosing. There is a significant decrease in the number of BrdU/DCX-labeled cells in the continuously dosed LTA4H treated animals and a statistical trend towards a decrease in BrdU/DCX-labeled in mice pulse dosed with LTA4H. This data indicates that there is a decrease in the number of proliferating neuronal cells that incorporate the BrdU label in week 4 of the treatment paradigm. All data shown are mean±s.e.m; *p<0.05, unpaired t test, n=14.

FIG. 14 reports the average number of Iba1-labeled cells in the hippocampus of mice treated with PBS control or human recombinant LTA4H protein either by pulse or continuous dosing. There is a significant increase in the number of Iba1-labled cells in mice that are pulsed dosed with LTA4H relative to mice dosed with vehicle PBS control. This data indicates that there is an increase in the number of microglia cells, marking an increase in inflammation, upon LTA4H pulse treatment. All data shown are mean±s.e.m; One-way ANOVA with multiple comparisons *p<0.05, n=14.

To test if dosing with recombinant human LTA4H had short-term effects on histological markers of inflammation, a third cohort of 8-week old wild-type (WT; C57BL/6) mice was tested 10 days following pulse dosing. Mice were homogenized between 2 treatment groups by body weight. Group 1 (Vehicle) was injected intravenously (IV) with PBS control for 7 consecutive days and group 2 (LTA4H) with recombinant human LTA4H protein daily for 7 consecutive days. BrdU (5-bromo-2'-deoxyuridine) formulated in PBS (phosphate buffered saline) at a final concentration of 10 mg/mL dosed at 150 mg/kg for 5 days immediately following PBS or LTA4H dosing in week 2. Animals were sacrificed and tissues collected 10 days following PBS or LTA4H dosing in week 4. FIG. 15 depicts the treatment paradigm and injection timing for the study.

Histology:

FIG. 16 reports the average number of CD68-labeled cells in the hippocampus of mice treated with PBS control or human recombinant LTA4H protein. There is a significant increase in the number of CD68-labled cells in mice that are pulsed dosed with LTA4H relative to mice dosed with vehicle PBS control 10 days following dosing. This data indicates that there is an increase in the number of activated microglia cells, marking an increase in inflammation, upon LTA4H pulse. All data shown are mean±s.e.m; Unpaired t test *p<0.05, n=14.

E. Example 4

FIG. 17A depicts the signaling pathway of LTA4H enzyme and FIG. 17B depicts the key to the diagram in panel A.

Nineteen-month-old (19 mo) wild type (WT; C57BL/6) mice were homogenized into five (5) groups by body weight, total distance travelled in the open field test, and average velocity in the open field test. Group 1 was administered 10% EtOH control PO daily for 4 weeks, Group 2 was administered 5 mg/kg of SC-57461A LTA4H dual inhibitor PO daily for 4 weeks; Group 3 was administered 10 mg/kg of CP-105,696 LTB4 receptor (BLTR) antagonist PO daily for 4 weeks, Group 4 was administered 10 mg/kg of Montelukast cysteinyl receptor (CysLTR) antagonist daily for 4 weeks, and Group 5 was administered 10 mg/kg of pinostilbene hydrate daily for 4 weeks. During Week 4 of treatment all groups were tested using open field, radial arm water maze, and Y-maze. During Week 5 animals were sacrificed, and tissues collected for histological and biochemical analysis.

Behavior:

FIG. 18 reports the results of the open field testing. FIGS. 18A and 18B report no change in total distance travelled or average velocity between treatment groups. FIG. 18C reports the percent time spent in the periphery or center of the open field in all treatment groups. All mice spend significantly more time in the periphery than in the center of the open field. Taken together the data indicates that general locomotion as measured by total distance travelled and average velocity, and anxiety as measured by percent time spent in periphery or center of the open field are not affected by treatment with inhibitors to LTA4H or LTA4H downstream effectors. All data shown are mean±s.e.m; ****p<0.0001, Paired t test, n=13-15.

FIG. 19A reports the mean latency for the mice to locate the target platform in the radial arm water maze over the course of training and testing. FIG. 19B reports the mean number of errors made by the mice in locating the target platform in the radial arm water maze over the course of training and testing. FIG. 19C reports the mean latency for the mice to locate the target platform for last two training trials depicted in FIG. 19A. FIG. 19D reports the mean latency for the mice to locate the target platform for last two testing trials depicted in FIG. 19A. FIG. 19E reports the mean number of errors made by the mice in locating the target platform for last two training trials depicted in FIG. 19B. FIG. 19F reports the mean number of errors for the mice to locate the target platform for last two testing trials depicted in FIG. 19B. All data shown are mean±s.e.m; *p<0.05, **p<0.01 Unpaired t test, n=13-15. Taken together, FIG. 19 reports that there are no differences in learning between treatment groups and that mice treated with the LTA4H inhibitor SC 57461A or the cysteinyl leukotriene receptor inhibitor Montelukast have an improvement in hippocampus-dependent spatial memory.

FIG. 20A reports the percentage of entries into the novel and familiar arms of the Y-maze. The Y-maze task tests hippocampus-dependent memory and is designed to have unique cues in the form of black shapes adhered to walls at the ends of two of the arms, while the third is un-cued and designated as the starting point for the mice. First, mice were individually placed in the starting arm and allowed to explore only one of the other two arms for 5 minutes of training. Then mice are tested with the novel arm open for exploration. During testing, a significant increase in entries into the novel over the familiar arm signifies contextual memory of the familiar arm. Aged mice treated with vehicle control are impaired in the Y-maze and do not have any preference for the novel versus the familiar arms. Mice treated with the LTA4H inhibitor SC 57461A have a trend towards preference for the novel arm and mice treated with the LTB4 receptor BLTR inhibitor CP 105,696 have a statistically significant preference for the novel arm in this task. FIG. 20B reports the total distance traveled in the Y-maze and there are no differences between treatment groups. Taken together FIG. 20 shows that inhibition of LTA4H or the LTB4 receptor leads to an improvement in the hippocampus spatial-dependent memory Y-maze task. All data shown are mean±s.e.m; *p<0.05, Paired t test, n=13-15.

Histology:

FIG. 21A reports the integrated optical density of aquaporin 4 (AQP4) in the hippocampus. There is a significant decrease in integrated optical density of AQP4 in mice that were treated with the inhibitors Montelukast and a trend towards a decrease with mice treated with the inhibitor pinostilbene hydrate. This data indicates that there is a reduction of aquaporin 4, marking astrocyte end feet, upon LTA4H or downstream effector inhibition. All data shown are mean±s.e.m; Unpaired t test *p<0.05, n=13-15. FIG. 21B reports the fluorescence intensity of aquaporin 4 (AQP4) in the hippocampus in the perivascular space. There are no changes with any treatment groups. All data shown are mean±s.e.m; n=13-15. FIG. 21C reports the fluorescence intensity of aquaporin 4 (AQP4) in the hippocampus in the space immediately surrounding blood vessels (vascular). There is a trend towards a decrease in the fluorescence intensity AQP4 in mice that were treated with the inhibitors Montelukast and pinostilbene hydrate. All data shown are mean±s.e.m; Unpaired t tests, n=13-15. Together these data indicate that there is a reduction of aquaporin 4 surrounding blood vessels in the hippocampus upon LTA4H or downstream effector inhibition.

ELISA:

FIG. 22 reports plasma concentration of LTB4 in pg/mL measured by ELISA. Inhibition of LTA4H with SC 57461A reduces the plasma levels of LTB4. All data shown are mean±s.e.m; *p<0.05, **p<0.01 Unpaired t test, n=13-15.

Gene Expression:

FIG. 23 reports the results of quantitative polymerase chain reaction (qPCR) quantifying the hippocampal mRNA levels of ionized calcium-binding adapter molecule 1 (Iba-1), interleukin 6 (IL-6), interleukin 1-beta (IL-1β), Eotaxin, nuclear factor kappa-light-chain-enhancer of activated B cells (NF-κB), and tumor necrosis factor alpha (TNFα) in aged wild-type (C57BL/6) mice treated with inhibitors to LTA4H or downstream effectors. FIG. 23B reports a significant decrease in IL-6 expression in mice treated with the LTA4H inhibitor SC-5761A. FIG. 23C reports a significant decrease in IL-1β expression in mice treated with the LTA4H inhibitor SC-5761A and the inhibitor Montelukast. FIG. 23F reports a significant decrease in TNFα expression in mice treated with the LTA4H inhibitors SC-5761A and pinostilbene hydrate and the inhibitor Montelukast. All data shown are mean±s.e.m; *p<0.05, **p<0.01, Unpaired t test, n=13-15.

FIG. 24A reports the results of quantitative polymerase chain reaction (qPCR) quantifying the hippocampal mRNA levels of the neuronal genes beta III tubulin (tuj1), synapsin 1 (syn1), post-synaptic density protein 95 (dlg4), and brain derived neurotrophic factor (bdnf) in aged wild-type (C57BL/6) mice treated with vehicle or the LTA4H inhibitor SC 57461A. All data shown are mean±s.e.m; Unpaired t test, n=13-15.

FIG. 24B reports the results of quantitative polymerase chain reaction (qPCR) quantifying the hippocampal mRNA levels of the microglia genes (total, M1-type, M2-type) cluster of differentiation molecule 11b (CD11b), interleukin 18 (IL-18), cluster of differentiation (CD68), interleukin 1α (IL-1α), interleukin 4 (IL-4), insulin-like growth factor 1 (IGF-1), and transforming growth factor β (TGFβ) in aged wild-type (C57BL/6) mice treated with vehicle or the LTA4H inhibitor SC 57461A. All data shown are mean±s.e.m; Unpaired t test, n=13-15.

FIG. 24C reports the results of quantitative polymerase chain reaction (qPCR) quantifying the hippocampal mRNA levels of the astrocytic genes (total, A1-type, A2-type) aquaporin 4 (aqp4), glial acidic fibrillary protein (gfap), six transmembrane epithelial antigen of prostate 4 (steap4), sphingosine-1-phosphate receptor 1 (slpr3), tissue inhibitor of metalloproteinases (timp1), H2 class I histocompatibility antigen (h2d1), guanylate-binding protein 2 (gbp2), N-acetyllactosaminide alpha-1 3-galactosyltransferase (ggta1), H2T23 protein (h2t23), and cardiotrophin-like cytokine factor 1 (clcf1) in aged wild-type (C57BL/6) mice treated with vehicle or the LTA4H inhibitor SC 57461A. FIG. 24C reports a significant decrease in aqp4 and h2d1 expression in mice treated with the LTA4H inhibitor SC-5761A and a trend towards a decrease in expression of timp1. All data shown are mean±s.e.m; *p<0.05, Unpaired t test, n=13-15.

FIG. 24D reports the results of quantitative polymerase chain reaction (qPCR) quantifying the hippocampal mRNA levels of the immediate early genes FBJ osteosarcoma oncogene (cfos), early growth response 1 (egr1), and CAMP responsive element binding protein 1 (creb1) in aged wild-type (C57BL/6) mice treated with vehicle or the inhibitors to LTA4H and downstream effectors. There is a significant increase in cfos expression with mice treated with the inhibitor to cysteinyl leukotriene receptors Montelukast. Cfos is an immediate early gene and increased gene expression is indicative of increased neuronal activity. All data shown are mean±s.e.m; **p<0.01, Unpaired t test, n=13-15.

In summary, this example investigated the hypothesis that inhibition of the specific detrimental factor LTA4H upregulated in age can improve cognitive deficits in old animals.

Specifically, we tested the LTA4H pathway with the following inhibitors: SC-57461A (LTA4H dual inhibitor), pinostilbene hydrate (LTA4H hydrolase inhibitor), CP-105, 696 (LTB4 Receptor1 inhibitor), and Montelukast (cysteinyl leukotriene receptor inhibitor). Montelukast was used as a positive control because it has previously been reported to improve cognition and reduce inflammation in aged mice. (Marschallinger J, supra). The results from this study suggest that there are beneficial effects of LTA4H inhibition on cognitive performance in aged mice, possibly due to a reduction in proinflammatory cytokines in the hippocampus.

Treatment with the LTA4H dual inhibitor SC-57461A resulted in improvements in the Radial Arm Water Maze test. Treated mice had significantly shorter latency and made fewer errors when compared to vehicle mice during the hidden platform testing phase (FIG. 19D). Our positive control Montelukast also showed improvements in this behavior, replicating what has been reported in the literature (Marschallinger, et al. *Nature Communications* 9 Dec. 2014). To determine the potential mechanisms for improvements in cognition, we analyzed numerous histological and biochemical markers in the hippocampus of these mice. There was a significant reduction in the mRNA levels of a number of proinflammatory cytokines and astrocyte markers, including IL6 IL1b, tnfa, aqp4, and h2d1 (FIG. 21, FIG. 23 and FIG. 24). The gene expression data suggests that there may be more subtle changes occurring with microglia or astrocytes, which secrete the proinflammatory cytokines. Our positive control Montelukast, showed reductions in many of the same inflammatory readouts as SC-57461A, as well as, an increase in the mRNA immediate early gene cfos (FIG. 23 and FIG. 24). Taken together, these data suggest that Montelukast may be acting via slightly different mechanisms to improve cognition.

Figure 23A:
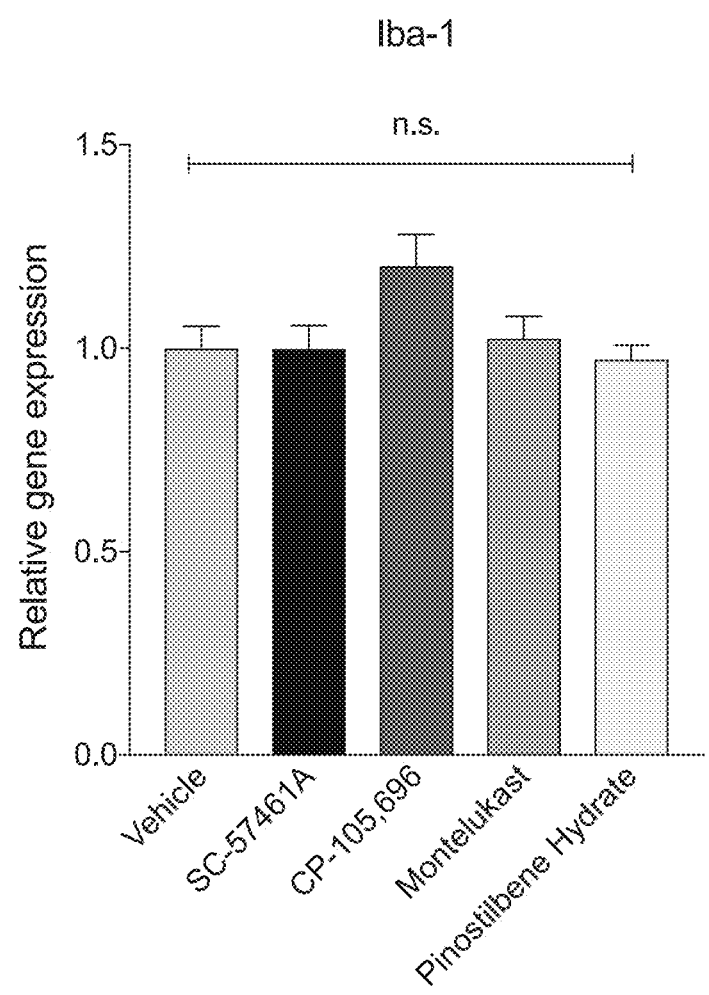
Figure 23B:
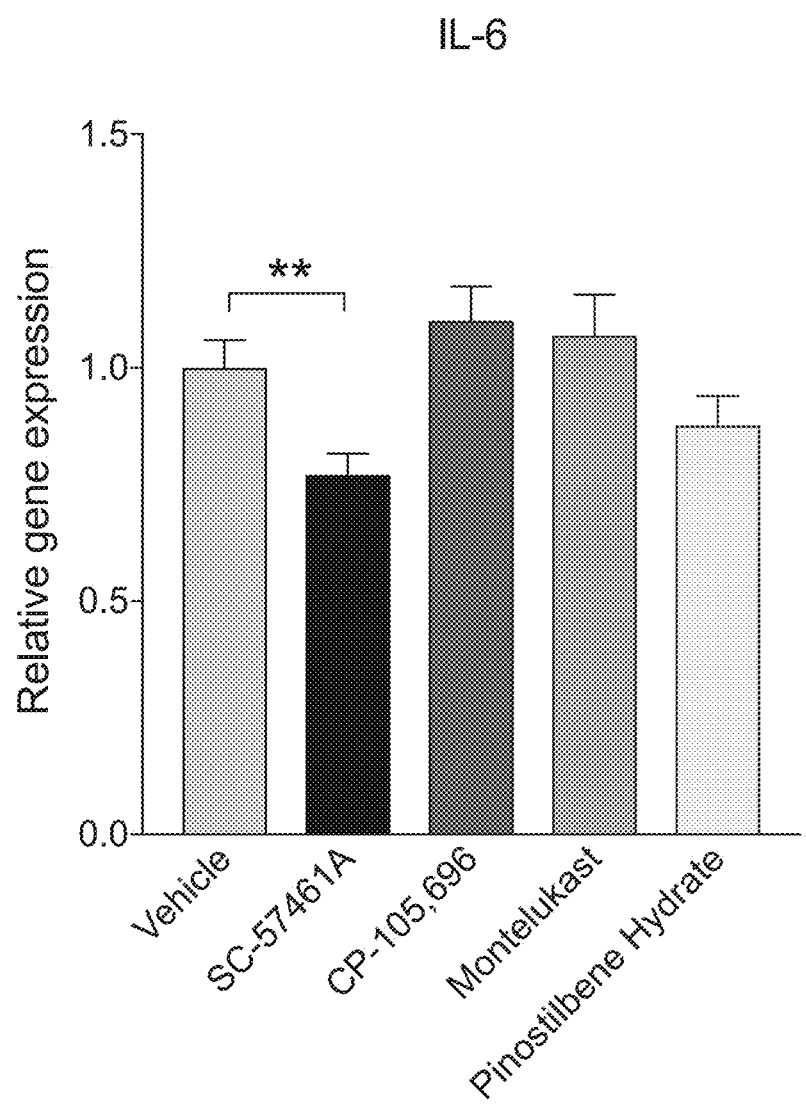
Figure 23C:
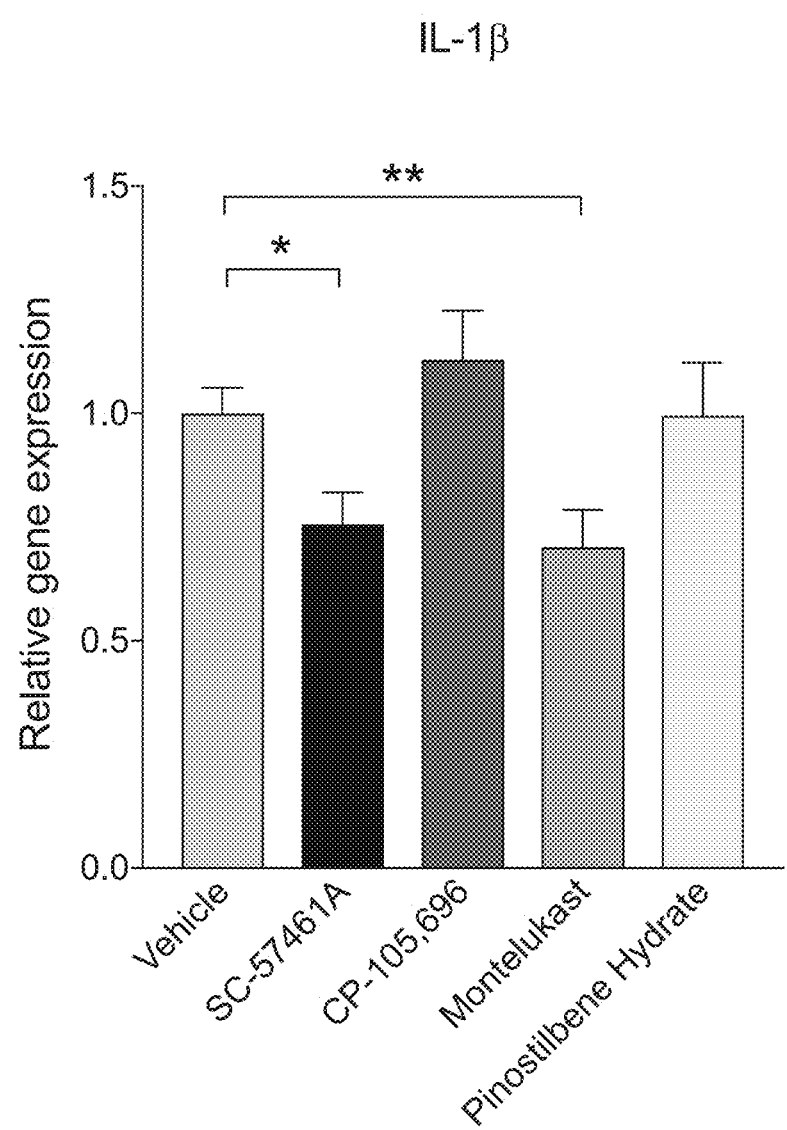
Figure 23D:
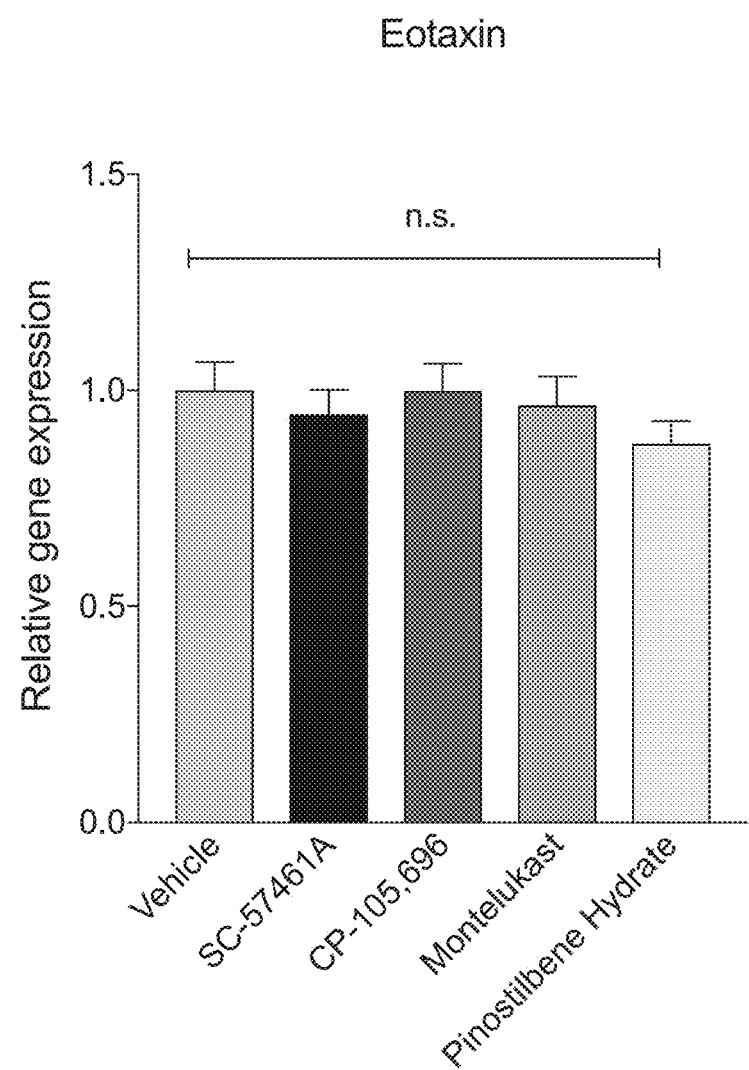
Figure 23E:
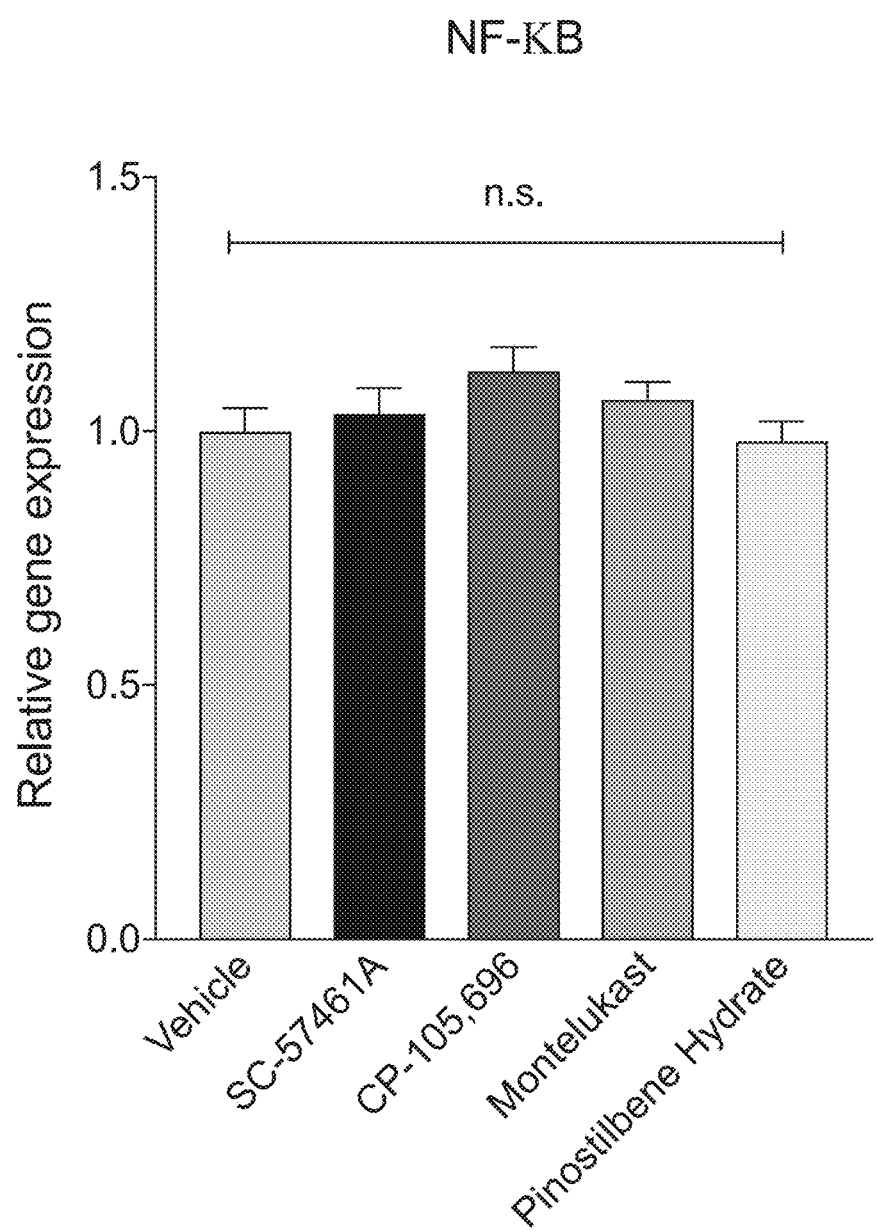
Figure 23F:
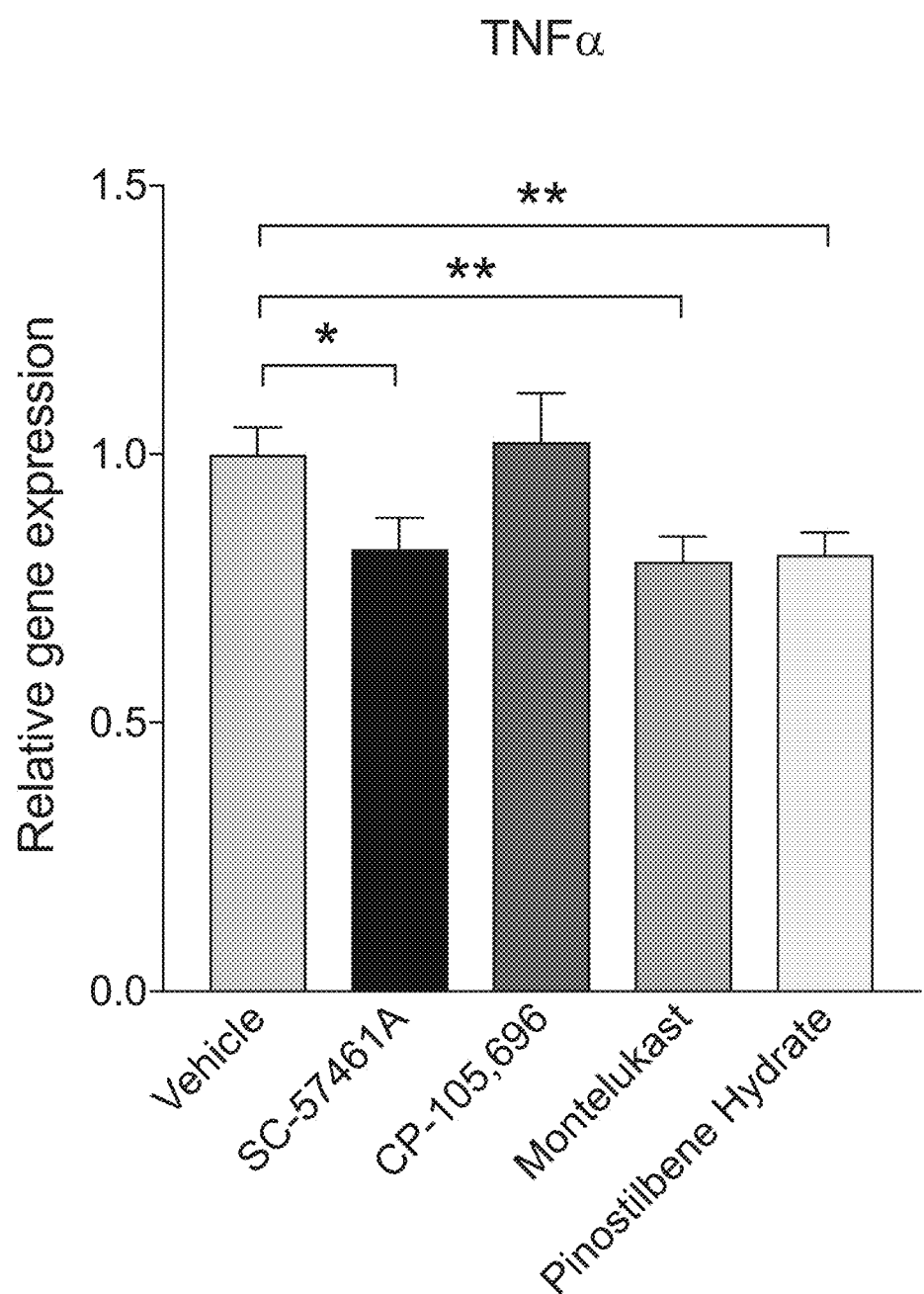

A secondary question we wanted to answer with this study was regarding the importance of inhibiting the dual enzymatic activities of LTA4H in aged mice. LTA4H has a hydrolase activity that metabolizes LTA4 to LTB4 and it also has a peptidase activity where it digests PGP. (Snelgrove R J (2010), supra). Previous publications have shown that the hydrolase activity of LTA4H produces as a proinflammatory signal, while the peptidase activity of LTA4H produces an anti-inflammatory signal. (Y. Michael Shim M P, supra; and Snelgrove, R. J. *Leukotriene A4 hydrolase: an anti-inflammatory role for a proinflammatory enzyme.* Thorax, 66(6): p. 550-51 (2011)). In order to test if the inhibition of the hydrolase activity alone was sufficient to see improvements in cognition in aged mice, we included a treatment group with pinostilbene hydrate, which has been reported to only inhibit the hydrolase activity and not the peptidase activity of LTA4H in vitro. (Low C. M., et al., *The development of novel LTA4H modulators to selectively target LTB4 generation.* Sci Rep, 7: p. 44449 (2017)). However, in contrast to the dual inhibitor SC-57461A, we did not detect a reduction in LTB4 levels in the terminal plasma from mice treated with pinostilbene hydrate relative to vehicle treated mice (FIG. 22), suggesting that our dosing concentration, frequency, or route of administration was insufficient to inhibit LTA4H in vivo. Therefore, those studies were inconclusive, and it is still unclear the importance of the dual enzyme activities of LTA4H. Despite not observing a reduction in terminal plasma LTB4, we found that pinostilbene hydrate did cause a significant reduction in AQP4 levels measured by immunofluorescence (FIG. 21) and in mRNA levels of tnfa measured by qPCR (FIG. 23F). Therefore, it is possible the pinostilbene hydrate does have some effect on neuroinflammation.

Taken together these data show that inhibition of LTA4H, which is upregulated in human aging, can significantly improve cognitive deficits and neuroinflammation in aged mice and strongly support the hypothesis that inhibiting LTA4H in age-related cognitive disease would be beneficial and effective at improving cognitive function and neuroinflammation.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed:

1. A method of improving cognitive function in a subject diagnosed with an age-related cognitive impairment caused by neuroinflammation, the method comprising administering, as a sole active agent, a therapeutically effective amount of a small organic molecule that inhibits LTA4H aminopeptidase and epoxide hydrolase activity.

2. The method of claim 1 wherein the cognitive impairment is caused by a neuroinflammatory disease selected from the group consisting of Alzheimer's Disease, mild cognitive impairment, Parkinson's Disease, Parkinsonism, Frontotemporal dementia, Huntington's Disease, amyotrophic lateral sclerosis, multiple sclerosis, dementia, dementia with Lewy bodies, and progressive supranuclear palsy.

3. The method of claim 1 wherein the subject is a mammal.

4. The method of claim 3 wherein the mammal is a human.

5. The method of claim 1 wherein the small organic molecule that inhibits LTA4H activity has the following formula:

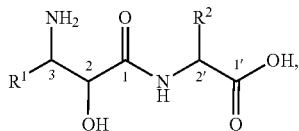

or a pharmaceutically acceptable salt, or solvate thereof where:
$R^1$ is selected from alkyl, substituted alkyl, cycloalkanoalkyl, phenyl, substituted phenyl, benzyl, substituted benzyl; and
$R^2$ is selected from hydrogen, alkyl, substituted alkyl, hydroxylalkyl, mercaptoalkyl, carboxyamidoalkyl, alkoxyalkyl, alkylmercaptoalkyl, carboxylalkyl, aryl, substituted aryl, aralkyl, substituted aralkyl, amidinealkyl, substituted amidinealkyl.

6. The method of claim 1 wherein the small organic molecule that inhibits LTA4H is ubenimex or a pharmaceutically acceptable salt, or solvate thereof.

7. The method of claim 1 wherein the small organic molecule that inhibits LTA4H activity has the following formula:

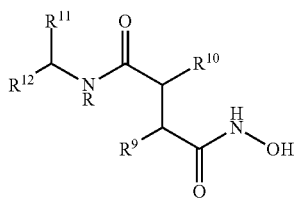

(II)

or a pharmaceutically acceptable salt, hydrate or solvate thereof,
where:
$R^9$ is selected from hydrogen, hydroxy, amino, methyl, and thrifluoromethyl;
$R^{10}$ is $R_{10a}$—$(X)_n$-(ALK)-, wherein $R^{10a}$ is selected from hydrogen, a $C_1$-$C_6$ alkyl, $C_2$-$C_6$ alkenyl, $C_2$-$C_6$ alkynyl, cycloalkyl, aryl, or heterocycle group, any of which may be unsubstituted or substituted by ($C_1$-$C_6$)alkyl, ($C_1$-$C_6$)alkoxy, hydroxy, mercapto, ($C_1$-$C_6$)alkylthio, amino, trifluoromethyl, cyano, nitro, —COOH, —CONH$_2$, —COOR$^A$, —NHCOR$^A$, —CONHR$^A$, —NHR$^A$, —NR$^A$R$^B$, or CONR$^A$R$^B$ wherein R$^A$ and R$^B$ are independently a ($C_1$-$C_6$)alkyl group;
ALK represents a straight or branched divalent $C_1$-$C_6$ alkylene, $C_2$-$C_6$ alkenylene, $C_2$-$C_6$ alkynylene radical, and may be interrupted by one or more non-adjacent —NH—, —O— or —S— linkages;
X represents —NH—, —O— or —S—, and n is 0 or 1;
R is selected from hydrogen or $C_1$-$C_6$ alkyl;
$R^{11}$ is a characterizing group of a natural or non-natural amino acid in which any functional groups may be protected; and
$R_4$ represents an ester or thioester group.

8. The method of claim 1 wherein the small organic molecule that inhibits LTA4H activity is tosedostat or a pharmaceutically acceptable salt, or solvate thereof.

9. The method of claim 1 wherein the small organic molecule that inhibits LTA4H activity has the following formula:

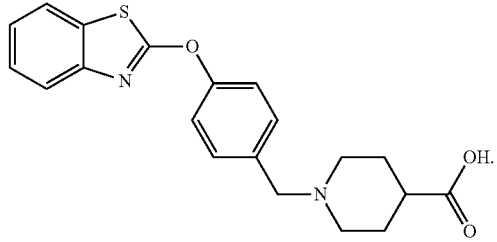 [SMILES: O=C(O)C1CCN(Cc2ccc(Oc3nc4ccccc4s3)cc2)CC1]

10. The method of claim 1 wherein the small organic molecule that inhibits LTA4H activity has the following formula:

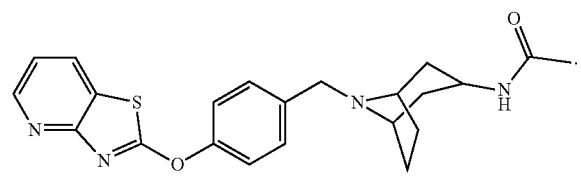 [SMILES: CC(=O)NC1CC2CCC(C1)N2Cc1ccc(Oc2nc3ncccc3s2)cc1]

11. The method of claim 1 wherein the small organic molecule that inhibits LTA4H activity has the following formula:

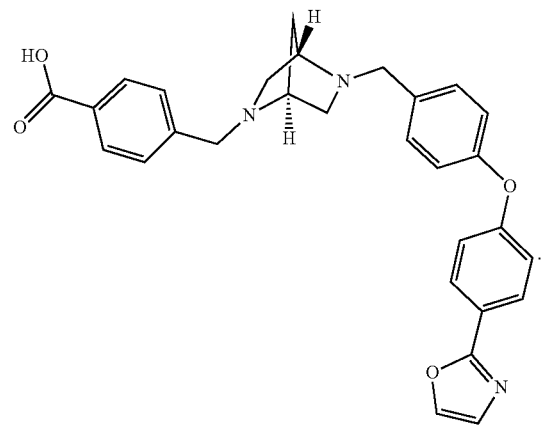 [SMILES: O=C(O)c1ccc(CN2C[C@@H]3C[C@H]2CN3Cc2ccc(Oc3ccc(-c4ncco4)cc3)cc2)cc1]

12. The method of claim 1 wherein the small organic molecule that inhibits LTA4H activity has the following formula:

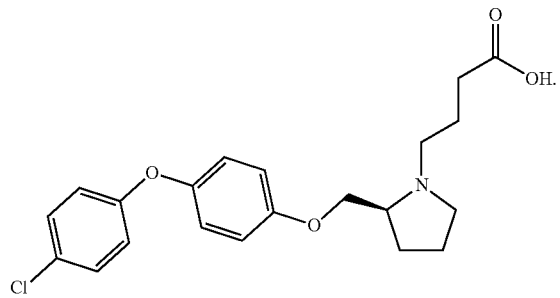 [SMILES: O=C(O)CCCN1CCC[C@H]1COc1ccc(Oc2ccc(Cl)cc2)cc1]

13. The method of claim 1 wherein the small organic molecule that inhibits LTA4H activity has the following formula:

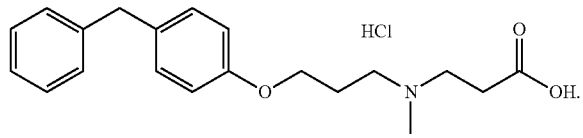 [SMILES: CN(CCCOc1ccc(Cc2ccccc2)cc1)CCC(=O)O ; Cl]

14. The method of claim 1 wherein the small organic molecule that inhibits LTA4H activity has the following formula:

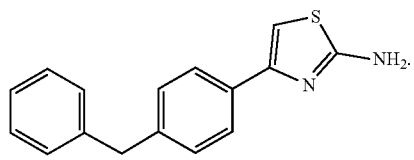 [SMILES: Nc1nc(-c2ccc(Cc3ccccc3)cc2)cs1]

15. The method of claim 1 wherein the small organic molecule that inhibits LTA4H activity has the following formula:

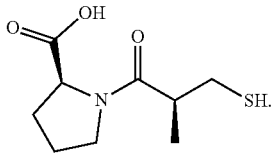

16. The method of claim 1 wherein the small organic molecule that inhibits LTA4H activity has the following formula:

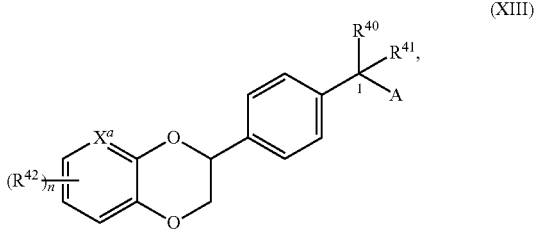

or a pharmaceutically acceptable salt, hydrate or solvate thereof,
where:
$X^a$ is N or CH;
n is an integer from 0 to 3;
$R^{42}$ is selected from halo, —OH, —CN, —($C_1$-$C_6$)alkyl, —($C_1$-$C_6$)alkyl, and —($C_3$-$C_6$)cycloalkyl;
$R^{40}$ and $R^{41}$ are each independently selected from —H and —($C_1$-$C_6$)alkyl; wherein $R^{40}$ and $R^{41}$ may join to form a 3- to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)—H, —C(O)($C_1$-$C_6$)alkyl, and —C(O)$NH_2$;
A is a group of formula —$NR^{43}R^{44}$, wherein $R^{43}$ and $R^{44}$ are each independently selected from —H, —($C_1$-$C_6$) alkyl, —($C_3$-$C_6$)cycloalkyl, -(4-to 14-membered)heterocycloalkyl, —($C_6$-$C_{10}$)aryl, and -(5-to 11-membered)heteroaryl; wherein each of the foregoing —($C_1$-$C_6$)alkyl, —($C_3$-$C_6$)cycloalkyl, -(4-to 14-membered) heterocycloalkyl, —($C_6$-$C_{10}$)aryl, and -(5-to 11-membered)heteroaryl of said $R^4$ and $R^5$ groups is optionally independently substituted by one to three $R^6$ groups; wherein two $R^6$ groups when attached to the same carbon atom of said —($C_1$-$C_6$)alkyl may join to form a 3-to 6-membered ring optionally comprising one to three heteroatoms, and further optionally substituted with one to three groups selected from halo, —OH, (=O), —($C_1$-$C_6$)alkyl, —O($C_1$-$C_6$)alkyl, —C(O)O—H, —C(O)($C_1$-$C_6$)alkyl, and —C(O)$NH_2$;
A is a (4-to 14-membered)N-heterocyclic ring of formula B:

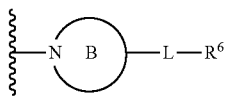

wherein said ring B is:
(a) a non-aromatic 4-8 membered monocyclic radical; or
(b) a bridged bicyclic radical, a spirocyclic radical, or a 6 to 11-membered fused bicyclic radical, wherein each of said bridged bicyclic radical, spirocyclic radical, and 6 to 11-membered fused bicyclic radical comprises at least a nonaromatic N-heterocyclic ring which is attached to the carbon atom 1 of the compound of formula (I); wherein each of said bridged bicyclic radical, spirocyclic radical, and 6 to 11-membered fused bicyclic radical may optionally comprise an aromatic ring;
wherein said ring B may additionally comprise one to three additional ring heteroatoms independently selected from N, O and S;
wherein said ring B may be further optionally substituted by one to three groups selected from halo, —OH, (=O), —C(O)O—H, —C(O)O—($C_1$-$C_6$)alkyl, and —($C_1$-$C_6$)alkyl; and
wherein L is absent or a linker selected from —($C_1$-$C_6$) alkylene-;
each $R^6$ is independently selected from halo, —$OR^7$, —$CF_3$, —CN, —($C_1$-$C_6$)alkyl, —O($C_1$-$C_6$)alkyl, —C(O)$R^7$, —C(O)$_2R^7$, —C(O)N($R^7$)$_2$, —N($R^7$)$_2$, —NHC(O)$R^7$, —NHC(O)N($R^7$)$_2$, —S(O)$_2R^7$, —NH—S(O)$_2$—$R^7$, —($C_3$-$C_6$)cycloalkyl, -(4-to 14-membered)heterocycloalkyl, —($C_6$-$C_{10}$)aryl, and -(5-to 11-membered)heteroaryl; wherein each of said, —($C_1$-$C_6$)alkyl, —O($C_1$-$C_6$)alkyl, —($C_3$-$C_6$)cycloalkyl, -(4-to 14-membered)heterocycloalkyl, —($C_6$-$C_{10}$) aryl, and -(5-to 11-membered)heteroaryl of said $R^6$ group is optionally substituted where possible with one to three groups selected from halo, —OH, —$CF_3$, —CN, (=O), —($C_1$-$C_6$)alkyl, —C(O)O—H, —C(O) O—($C_1$-$C_6$)alkyl, —$NH_2$, —NH($C_1$-$C_6$)alkyl, —N(($C_1$-$C_6$)alkyl)$_2$, —S(O)$_2$($C_1$-$C_6$)alkyl, —($C_3$-$C_6$) cycloalkyl, -(4-to 14-membered)heterocycloalkyl, —($C_6$-$C_{10}$)aryl, and -(5-to 11-membered)heteroaryl; and
each $R^7$ is independently selected from —H, —($C_1$-$C_6$) alkyl, —($C_1$-$C_6$)alkyl-OH, —($C_1$-$C_6$)alkyl-O—($C_1$-$C_6$)alkyl, —O($C_1$-$C_6$)alkyl, —($C_3$-$C_6$)cycloalkyl, —($C_3$-$C_6$)cycloalkyl-OH, -(4-to 14-membered)heterocycloalkyl, —($C_6$-$C_{10}$)aryl, and -(5-to 11-membered)

heteroaryl; wherein each of said R⁷ group is optionally substituted where possible with a group selected from —OH, —NH($C_1$-$C_6$)alkyl, —NHC(O)($C_1$-$C_6$)alkyl, —C(O)NH$_2$, —S(O)$_2$($C_1$-$C_6$)alkyl, and -(4-to 14-membered)heterocycloalkyl; wherein said -(4-to 14-membered)heterocycloalkyl group is optionally substituted where possible with a (=O) group.

17. The method of claim 1 wherein the small organic molecule that inhibits LTA4H activity is selected from:

1-[4-(2,3-dihydro-1,4-benzodioxin-2-yl)benzyl]pyrrolidine,
4-[4-(2,3-dihydro-1,4-benzodioxin-2-yl)benzyl]morpholine,
1-[4-(2,3-dihydro-1,4-benzodioxin-2-yl)benzyl]-4,4-dimethylpiperidine,
8-[4-(2,3-dihydro-1,4-benzodioxin-2-yl)benzyl]-2,8-diazaspiro[4,5]decan-1-one,
1-[4-(2,3-dihydro-1,4-benzodioxin-2-yl)benzyl]-4-fluoropiperidine,
(1 s,4s)-7-[4-(2,3-dihydro-1,4-benzodioxin-2-yl)benzyl]-7-azabicyclo[2.2.1]heptane,
4-[4-(2,3-dihydro-1,4-benzodioxin-2-yl)benzyl]thiomorpholine 1,1-dioxide,
1-{4-[(2S)-2,3-dihydro-1,4-benzodioxin-2-yl]benzyl}-N,N-dimethylpiperidine-4-carboxamide, (3S)-1-[4-(2,3-dihydro-1,4-benzodioxin-2- yl)benzyl]pyrrolidin-3-ol,
1-({1-[4-(2,3-dihydro-1,4-benzodioxin-2-yl)benzyl]piperidin-3-yl}methyl)pyrrolidin-2-one,
1-{4-[4-(2,3-dihydro-1,4-benzodioxin-2-yl)benzyl]piperazin- 1-yl}ethenone,
2-{[4-(2,3-dihydro-1,4-benzodioxin-2-yl)benzyl]amino}-1-(pyrrolidin-1-yl)ethenone,
N-{4-[(2S)-2,3-dihydro-1,4-benzodioxin-2-yl]benzyl}-N-methyl-1-(methylsulfonyl)piperidin-4-amine,
1-{4-[{4-[(2S)-2,3-dihydro-1,4-benzodioxin-2-yl]benzyl}(methyl)amino]piperidin-1-yl}ethenone,
3-[4-(pyrrolidin-1-ylmethyl)phenyl]-2,3-dihydro[1,4]dioxino[2,3-b]pyridine,
7-[4-(2,3-dihydro-1,4-benzodioxin-2-yl)benzyl]-5,6,7,8-tetrahydro[1,2,4]triazolo[4,3-a]pyrazine,
3-{4-[(1,1-dioxidothiomorpholin-4-yl)methyl]phenyl}-2,3-dihydro [1,4]dioxino [2,3-b]pyridine,
3-[4-(morpholin-4-ylmethyl)phenyl]-2,3-dihydro[1,4]dioxino[2,3-b]pyridine,
(3R)-1-{4-[(2S)-2,3-dihydro-1,4-benzodioxin-2-yl]benzyl}piperidine-3-carboxylic acid,
(3S)-1-{4-[(2S)-2,3-dihydro-1,4-benzodioxin-2-yl]benzyl}piperidine-3-carboxylic acid,
1-(1-{4-[(2S)-2,3-dihydro-1,4-benzodioxin-2-yl]benzyl}piperidin-4-yl)-2,2,2-trifluoroethanol,
2-(1-{4-[(2S)-2,3-dihydro-1,4-benzodioxin-2-yl]benzyl}piperidin-4-yl)-1,1,1,3,3,3-hexafluoropropan-2-ol,
N-[4-(2,3-dihydro-1,4-benzodioxin-2-yl) benzyl]-2-methylpropan-2-amine,
(2R)-N-[4-(2,3-dihydro-1,4-benzodioxin-2-yl)benzyl]butan-2-amine,
1-[4-(2,3-dihydro-1,4-benzodioxin-2-yl)benzyl]-N-methylpiperidine-4-carboxamide,
4-{1-[4-(2,3-dihydro-1,4-benzodioxin-2-yl)benzyl]piperidin-4-yl}butanoic acid,
{1-[4-(2,3-dihydro-1,4-benzodioxin-2-yl)benzyl]piperidin-4-yl}methanol,
2-{1-[4-(2,3-dihydro-1,4-benzodioxin-2-yl)benzyl]piperidin-4-yl}propan-2-ol,
3-{1-[4-(2,3-dihydro-1,4-benzodioxin-2-yl)benzyl]piperidin-4-yl}propan-1-ol,
1-[4-(2,3-dihydro-1,4-benzodioxin-2-yl)benzyl]-4-methyl-1,4-diazepane,
1-{4-[4-(2,3-dihydro-1,4-benzodioxin-2-yl)benzyl]-1,4-diazepan-1-yl}ethenone,
4-[4-(2,3-dihydro-1,4-benzodioxin-2-yl)benzyl]-1,4-oxazepane,
N-[4-(2,3-dihydro-1,4-benzodioxin-2-yl)benzyl]-2-methoxy-N-methylethanamine,
(3R)-1-[4-(2,3-dihydro-1,4-benzodioxin-2-yl)benzyl]pyrrolidin-3-ol,
8-[4-(2,3-dihydro-1,4-benzodioxin-2-yl)benzyl]-1,3,8-triazaspiro[4.5]decane-2,4-dione,
1-[4-(2,3-dihydro-1,4-benzodioxin-2-yl)benzyl]-3-methoxyazetidine,
{1-[4-(2,3-dihydro-1,4-benzodioxin-2-yl)benzyl]piperidin-4-yl}(morpholin-4-yl)methanone,
2-{1-[4-(2,3-dihydro-1,4-benzodioxin-2-yl)benzyl]piperidin-4-yl}-N,N-dimethylacetamide,
1-[4-(2,3-dihydro-1,4-benzodioxin-2-yl)benzyl]-4-(methylsulfonyl)piperidine,
1-[4-(2,3-dihydro-1,4-benzodioxin-2-yl)benzyl]azepane,
N-[4-(2,3-dihydro-1,4-benzodioxin-2-yl)benzyl]cyclopentanamine,
N-[4-(2,3-dihydro-1,4-benzodioxin-2-yl)benzyl]-N-methyl-2-(pyridin-2-yl)ethanamine,
1-cyclopropyl-N-[4-(2,3-dihydro-1,4-benzodioxin-2-yl)benzyl]methanamine,
1-[4-(2,3-dihydro-1,4-benzodioxin-2-yl)benzyl]-4-phenylpiperidin-4-ol,
N-[4-(2,3-dihydro-1,4-benzodioxin-2-yl)benzyl]-N-ethylethanamine,
1-[4-(2,3-dihydro-1,4-benzodioxin-2-yl)benzyl]azetidine-3-carbonitrile,
1-[4-(2,3-dihydro-1,4-benzodioxin-2-yl)benzyl]-3-methoxypyrrolidine,
N-{1-[4-(2,3-dihydro- 1,4-benzodioxin-2-yl)benzyl]piperidin-4-yl}methanesulfonamide,
N-[4-(2,3-dihydro-1,4-benzodioxin-2-yl)benzyl]-2-methyl-1-(pyrrolidin-1-yl)propan-2-amine,
1-({1-[4-(2,3-dihydro-1,4-benzodioxin-2-yl)benzyl]piperidin-4-yl}methyl)pyrrolidin-2-one,
1-[4-(2,3-dihydro-1,4-benzodioxin-2-yl)benzyl]-N,N-dimethylpiperidine-4-carboxamide,
1-[4-(2,3-dihydro-1,4-benzodioxin-2-yl)benzyl]-N-(2-hydroxyethyl)piperidine-4-carboxamide,
1-{1-[4-(2,3-dihydro-1,4-benzodioxin-2-yl)benzyl]piperidin-4-yl}urea,
1-[4-(2,3-dihydro-1,4-benzodioxin-2-yl)phenyl]-N-yridin-3-ylmethyl)methanamine,
1-[4-(2,3-dihydro-1,4-benzodioxin-2-yl)phenyl]-N-[(1-methyl-1H-imidazol-4-yl)methyl]methanamine,
2-{4-[(2S)-2,3-dihydro-1,4-benzodioxin-2-yl]benzyl}-1,2,3,4-tetrahydroisoquinoline-4-carboxylic acid,
(1R,3S)-3-({4- [(2S)-2,3-dihydro-1,4-benzodioxin-2-yl]benzyl }amino)cyclopentanecarboxylic acid,
3({4-[(2S)-2,3-dihydro-1,4-benzodioxin-2-yl]benzyl}amino)-4,4-dimethylpentanoic acid,
1-({4-[(2S)-2,3-dihydro-1,4-benzodioxin-2-yl]benzyl}amino)cyclopentanecarboxylic acid,
N-{4-[(2S)-2,3-dihydro-1,4-benzodioxin-2-yl]benzyl}-N-methylglycine,
1-{4-[(2S)-2,3-dihydro-1,4-benzodioxin-2-yl]benzyl}pyrrolidine-3carboxylic acid,
trans-4- [(2S)-2,3-dihydro-1,4-benzodioxin-2-yl]benzyl}amino)cyclohexanecarboxylic acid, cis-4-({4-[(2S)-2,3-dihydro-1,4-benzodioxin-2-yl]benzyl}amino)cyclohexanecarboxylic acid,
1-[(3R)-3-({4-[(2S)-2,3-dihydro-1,4-benzodioxin-2-yl]benzyl}amino)pyrrolidin-1-yl]ethenone,
1-[(3S)-3-({4-[(2S)-2,3-dihydro-1,4-benzodioxin-2-yl]benzyl}amino)pyrrolidin-1-yl]ethenone,
trans-4-({4[(2S)-2,3-dihydro-1,4-benzodioxin-2-yl]benzyl}amino)cyclohexanecarboxamide,
N-{4[(2S)-2,3-dihydro-1,4-benzodioxin-2-yl]benzyl}-N-methylcyclohexanamine,
(1-{4-[(2S)-2,3-dihydro-1,4-benzodioxin-2-yl]benzyl}piperidin-3-yl)methanol,
2-(1-{4-[(2S)-2,3-dihydro-1,4-benzodioxin-2-yl]benzyl}piperidin-4-yl)ethanol,
N-{4-[(2S)-2,3-dihydro-1,4-benzodioxin-2-yl]benzyl}propan-2-amine,
N-{4-[(2S)-2,3-dihydro-1,4-benzodioxin-2-yl]benzyl}-1-methoxypropan-2-amine,
N-{4-[(2S)-2,3-dihydro-1,4-benzodioxin-2-yl]benzyl}propan-1-amine,
N-{4-[(2S)-2,3-dihydro-1,4-benzodioxin-2-yl]benzyl}-N-methylethanamine,
1-{4-[(2S)-2,3-dihydro-1,4-benzodioxin-2-yl]phenyl}-N,N-dimethylmethanamine,
trans-4-({4-[(2S)-2,3-dihydro-1,4-benzodioxin-2-yl]benzyl}amino)cyclohexanol,
1-{4-[(2S)-2,3-dihydro-1,4-benzodioxin-2-yl]benzyl}piperidin-3-ol,
N-{4-[(2S)-2,3-dihydro-1,4-benzodioxin-2-yl]benzyl}-N,N',N'-trimethylethane-1,2-diamine,
2-(cyclohexyl {4-[(2S)-2,3-dihydro-1,4-benzodioxin-2-yl]benzyl}amino)ethanol,
(1R,2R,4S)—N-{4-[(2S)-2,3-dihydro-1,4-benzodioxin-2-yl]benzyl}bicyclo[2.2.1]heptan-2-amine,
(4aR,8aS)-1-{4-[(2S)-2,3-dihydro-1,4-benzodioxin-2-yl]benzyl},
(1S,2R)-2-({4-[(2S)-2,3-dihydro-1,4-benzodioxin-2-yl]benzyl}amino)cyclohexanecarboxamide,
[(1S,2R)-2-({4-[(2S)-2,3-dihydro-1,4-benzodioxin-2-yl]benzyl}amino)cyclohexyl]methanol,
(3R)-1-{4-[(2S)-2,3-dihydro-1,4-benzodioxin-2-yl]benzyl}pyrrolidin-3-ol,
[(1R,2R)-2-({4-[(2S)-2,3-dihydro-1,4-benzodioxin-2-yl]benzyl}amino)cyclohexyl]methanol,
(1-{4-[(2S)-2,3-dihydro-1,4-benzodioxin-2-yl]benzyl}piperidin-4-yl)methanol,
(3S)-1-{4-[(2S)-2,3-dihydro-1,4-benzodioxin-2-yl]benzyl}pyrrolidin-3-ol,
1-{4-[(2S)-2,3-dihydro-1,4-benzodioxin-2-yl]benzyl}imidazolidin-4-one,
1-{4-[(2S)-2,3-dihydro-1,4-benzodioxin-2-yl]benzyl}-N,N-dimethylpyrrolidin-3-amine,
1'-{4-[(2S)-2,3-dihydro-1,4-benzodioxin-2-yl]benzyl}-1,4'-bipiperidin-2-one,
N-(cyclopropylmethyl)-N-{4-[(2S)-2,3-dihydro-1,4-benzodioxin-2-yl]benzyl}cyclohexanamine,
(1R,2R)-2-({4-[(2S)-2,3-dihydro-1,4-benzodioxin-2-yl]benzyl}amino)cyclohexanol,
1-{4-[(2S)-2,3-dihydro-1,4-benzodioxin-2-yl]benzyl}-4-methoxypiperidine,
1-[(1-{4-[(2S)-2,3-dihydro-1,4-benzodioxin-2-yl]benzyl}piperidin-4-yl)methyl]pyrrolidin-2-one,
trans-N-{4-[(2S)-2,3-dihydro-1,4-benzodioxin-2-yl]benzyl}-4-methylcyclohexanamine,
(1S,2R)-2-({4-[(2S)-2,3-dihydro-1,4-benzodioxin-2-yl]benzyl}amino)cyclopentanol,
(1S,2S)-2-({4-[(2S)-2,3-dihydro-1,4-benzodioxin-2-yl]benzyl}amino)cyclopentanol,
N-{4-[(2S)-2,3-dihydro-1,4-benzodioxin-2-yl]benzyl}tetrahydro-2H-pyran-3-amine,
(1S,2S)-2-[{4-[(2S)-2,3-dihydro-1,4-benzodioxin-2-yl]benzyl}(methyl)amino]cyclohexanol,
(1R,2S)-2-[{4-[(2S)-2,3-dihydro-1,4-benzodioxin-2-yl]benzyl}(methyl)amino]cyclohexanol,
4-{4-[(2S)-2,3-dihydro-1,4-benzodioxin-2-yl]benzyl}-3-methylmorpholine,
5-({4-[(2S)-2,3-dihydro-1,4-benzodioxin-2-yl]benzyl}amino)-1-methylpiperidin-2-one,
N-{4-[(2S)-2,3-dihydro-1,4-benzodioxin-2-yl]benzyl}-N,1-dimethylpiperidin-4-amine,
4-[({4-[(2S)-2,3-dihydro-1,4-benzodioxin-2-yl]benzyl}amino)methyl]phenol,
2-{4-[(2S)-2,3-dihydro-1,4-benzodioxin-2-yl]benzyl}-1,2,3,4-tetrahydroisoquinolin-6-ol,
1-[4-(2,3-dihydro-1,4-benzodioxin-2-yl)benzyl]piperidine-3-carboxylic acid,
1-[4-(2,3-dihydro-1,4-benzodioxin-2-yl)benzyl]piperidine-3-carboxamide,
(3S)-1-[4-(2,3-dihydro-1,4-benzodioxin-2-yl)benzyl]-3-fluoropyrrolidine,
9-{4[(2S)-2,3-dihydro-1,4-benzodioxin-2-yl]benzyl}-2,9-diazaspiro[5.5]undecan-1-one,
1-(7-{4-[(2S)-2,3-dihydro-1,4-benzodioxin-2-yl]benzyl}-1,7-diazaspiro[4.4]non-1-yl)ethenone,
9-{4-[(2S)-2,3-dihydro-1,4-benzodioxin-2-yl]benzyl}-2-methyl-2,9-diazaspiro[5.5]undecan-1-one,
8-{4-[(2S)-2,3-dihydro-1,4-benzodioxin-2-yl]benzyl}-2-methyl-2,8-diazaspiro[4.5]decan-1-one,
7-{4-[(2S)-2,3-dihydro-1,4-benzodioxin-2-yl]benzyl}-1-(methylsulfonyl)-1,7-diazaspiro[4.4]nonane,
2-(7-{4-[(2S)-2,3-dihydro-1,4-benzodioxin-2-yl]benzyl}-1,7-diazaspiro[4.4]non-1-yl)acetamide,
(7-{4-[(2S)-2,3-dihydro-1,4-benzodioxin-2-yl]benzyl}-1,7-diazaspiro[4.4]non-1-yl)acetonitrile,
1-(7-{4-[(2S)-2,3-dihydro-1,4-benzodioxin-2-yl]benzyl}-1,7-diazaspiro[4.4]non-1-yl)-2-methoxyethanone,
9-[(S)-4-(2,3-Dihydro-benzo[1,4]dioxin-2-yl)-benzyl]-2-methyl-2,9-diaza-spiro[5.5]undecan-1-one,
1-{4-[(2S)-2,3-dihydro-1,4-benzodioxin-2-yl]benzyl}-1,4-diazepan-5-one,
1-{4-[(3S)-2,3-dihydro[1,4]dioxino[2,3]pyridin-3-yl]benzyl}-1,4-diazepan-5-one,
N-[2-({4-[(3S)-2,3-dihydro[1,4]dioxino[2,3-b]pyridin-3-yl]benzyl}amino)ethyl]acetamide,
3-(1-{4-[(2S)-2,3-dihydro-1,4-benzodioxin-2-yl]benzyl}piperidin-4-yl)propanoic acid,
N-{4-[(3S)-2,3-dihydro[1,4]dioxino[2,3-b]pyridin-3-yl]benzyl}cyclopentanamine,
N-{4-[(3S)-2,3-dihydro[1,4]dioxino[2,3-b]pyridin-3-yl]benzyl}-N-methylethanamine,
(3S)-3-{4-[(1s,4s)-7-azabicyclo[2.2.1]hept-7-ylmethyl]phenyl}-2,3-dihydro[1,4]dioxino[2,3-b]pyridine,
(3S)-1-{4-[(3S)-2,3-dihydro[1,4]dioxino[2,3-b]pyridin-3-yl]benzyl}pyrrolidin-3-ol,
4(1-{4-[(3S)-2,3-dihydro[1,4]dioxino[2,3-b]pyridin-3-yl]benzyl}piperidin-4-yl)butanoic acid,
1-[4-({4-[(3S)-2,3-dihydro[1,4]dioxino[2,3-b]pyridin-3-yl]benzyl}amino)piperidin-1-yl]ethenone,
(3S)-3-{4-(5,6-dihydro[1,2,4]triazolo[4,3-a]pyrazin-7(8H)-ylmethyl)phenyl}-2,3-dihydro[1,4]dioxino[2,3-b]pyridine,
(3S)-3-{4-[(1,1-dioxidothiomorpholin-4-yl)methyl]phenyl}-2,3-dihydro[1,4]dioxino[2,3-b]pyridine, 4-{4-[(3S)-2,3-dihydro[1,4]dioxino[2,3-b]pyridin-3-yl]
   benzyl}piperazine-1-carboxamide,
(3S)-3-{4-[(3-methoxyazetidin-1-yl)methyl]phenyl}-2,3-
   dihydro[1,4]dioxino[2,3-b]pyridine,
N-{4-[(3S)-2,3-dihydro[1,4]dioxino[2,3-b]pyridin-3-yl]
   benzyl}-N-methyl-1-(methylsulfonyl)piperidin-4-
   amine,
(3S)-3-(4-{[4-(2-methoxyethoxyl)piperidin-1-yl]
   methyl}phenyl)-2,3-dihydro[1,4]dioxino[2,3-b]pyri-
   dine,
2-(1-{4-[(3S)-2,3-dihydro[1,4]dioxino[2,3-b]pyridin-3-
   yl]benzyl}piperidin-4-yl)-N,N-dimethylacetamide,
(3S)3-(4-{[4-(methylsulfonyl)piperidin-1-yl]
   methyl}phenyl)-2,3-dihydro[1,4]dioxino[2,3-b]pyri-
   dine,
N-{4-[(3S)-2,3-dihydro[1,4]dioxino[2,3-b]pyridin-3-yl]
   benzyl }cyclobutanamine,
N-{4-[(2S)-2,3-dihydro-1,4-benzodioxin-2-yl]benzyl}-1-
   (methylsulfonyl)piperidin-4- amine,
1-{4-[(2S)-2,3-dihydro-1,4-benzodioxin-2-yl]
   benzyl}piperidine-4-carbonitrile,
N-(1-{4-[(2S)-2,3-dihydro-1,4-benzodioxin-2-yl]
   benzyl}piperidin-4-yl)acetamide,
[(3S)-1-{4-[(2S)-2,3-dihydro-1,4-benzodioxin-2-yl]
   benzyl}piperidin-3-yl]acetic acid,
[(3R)-1-{4-[(2S)-2,3-dihydro-1,4-benzodioxin-2-yl]
   benzyl}pyrrolidin-3-yl]acetic acid,
1(4-{4-[(3S)-2,3-dihydro[1,4]dioxino   [2,3-b]pyridin-3-
   yl]benzyl}piperazin-1-yl)ethenone,
1-{4(3S)-2,3-dihydro[1,4]dioxino[2,3-b]pyridin-3-yl]
   benzyl}piperidin-4-ol,
1-(1-[(3S)-2,3-dihydro[1,4]dioxino[2,3-b]pyridin-3-yl]
   benzyl}piperidin-4-yl)urea,
(3S)-3-(4-{[4-(methylsulfonyl)piperazin-1-yl]
   methyl}phenyl)-2,3-dihydro[1,4]dioxino[2,3-b]pyri-
   dine,
1-{4-[(3S)-2,3-dihydro[1,4]dioxino[2,3-b]pyridin-3-yl]
   benzyl }piperidine-4-carboxylic acid,
(1S ,3R)-3-({4-[(2S)-2,3-dihydro-1,4-benzodioxin-2-yl]
   benzyl}amino)cyclopentanecarboxylic acid,
1-{4-[(2S)-2,3-dihydro-1,4-benzodioxin-2-yl]
   benzyl}piperidin-4-ol,
1-{4-[(2R)-2,3-dihydro-1,4-benzodioxin-2-yl]
   benzyl}piperidin-4-ol,
8-{4-[(2R)-2,3-dihydro-1,4-benzodioxin-2-yl]benzyl}-2,
   8-diazaspiro[4.5]decan-1-one,
1-{4-[(2S)-2,3-dihydro-1,4-benzodioxin-2-yl]
   benzyl}pyrrolidine,
1-{4-[(2R)-2,3-dihydro-1,4-benzodioxin-2-yl]
   benzyl}pyrrolidine,
4-{4-[(2S)-2,3-dihydro-1,4-benzodioxin-2-yl]
   benzyl}morpholine,
4-{4-[(2R)-2,3-dihydro-1,4-benzodioxin-2-yl]
   benzyl}morpholine,
1-{4-[(2R)-2,3-dihydro-1,4-benzodioxin-2-yl]
   benzyl}piperidine-4-carboxylic acid,
4-[4-(7-fluoro-2,3-dihydro-1,4-benzodioxin-2-yl)benzyl]
   morpholine,
1-[4-(7-fluoro-2,3-dihydro-1,4-benzodioxin-2-yl)benzyl]
   pyrrolidine,
(3R)-3-[4-(morpholin-4-ylmethyl)phenyl]-2,3-dihydro[1,
   4]dioxino[2,3-b]pyridine,
1-{4-[(3R)-2,3-dihydro-1,4-benzodioxin-2-yl]
   benzyl}piperidine-4-carboxamide,
1-[4-(2,3-dihydro[1,4]dioxino[2,3-b]pyridin-3-yl)benzyl]
   pyrrolidin-2-one,
3-[4-(2,3-dihydro[1,4]dioxino[2,3-b]pyridin-3-yl)ben-
   zyl]-1,3 -oxazolidin-2-one,
1-[4-(2,3-dihydro[1,4]dioxino[2,3-b]pyridin-3-yl)phenyl]
   methanamine,
1-{4-[(2S)-2,3-dihydro-1,4-benzodioxin-2-yl]benzyl}-4-
   methylpiperidine-4-carboxylic acid,
(3R,4R)-1-{4-[(2S)-2,3-dihydro-1,4-benzodioxin-2-yl]
   benzyl}-3-methylpiperidine-4-carboxylic acid,
1-{4-[(2S)-2,3-dihydro-1,4-benzodioxin-2-yl]benzyl}-4-
   fluoropiperidine-4-carboxylic acid,
(3R)-1-{4-[(2S)-2,3-dihydro-1,4-benzodioxin-2-yl]
   benzyl}pyrrolidine-3-carboxylic acid,
(3S)-1-{4-[(2S)-2,3-dihydro-1,4-benzodioxin-2-yl]
   benzyl}pyrrolidine-3-carboxylic acid,
1-{4-[(2S)-2,3-dihydro-1,4-benzodioxin-2-yl]benzyl}-4-
   (1H-tetrazol-5-yl)piperidine,
1-{4-[(2S)-2,3-dihydro-1,4-benzodioxin-2-yl]
   benzyl}piperidin-4-amine,
N-(1-{4-[(2S)-2,3-dihydro-1,4-benzodioxin-2-yl]
   benzyl}piperidin-4-yl)-2-hydroxyacetamide,
N-(1-{4-[(2S)-2,3-dihydro-1,4-benzodioxin-2-yl]
   benzyl}piperidin-4-yl)-2-methoxyacetamide,
N-(1-{4-[(2S)-2,3-dihydro-1,4-benzodioxin-2-yl]
   benzyl}piperidin-4-yl)-2-hydroxy-2-methylpropana-
   mide,
1-(1-{4-[(2S)-2,3-dihydro-1,4-benzodioxin-2-yl]
   phenyl}ethyl)pyrrolidine,
4-(1-{4-[(2S)-2,3-dihydro-1,4-benzodioxin-2-yl]
   phenyl}ethyl)morpholine,
1-(1-{4-[(2S)-2,3-dihydro-1,4-benzodioxin-2-yl]
   phenyl}ethyl)piperidine-4-carboxylic acid,
1-{4-[(3S)-2,3-dihydro[1,4]dioxino   [2,3-b]pyridin-3-yl]
   benzyl}-4-methylpiperidine-4-carboxylic acid,
2-(1-{4-[(2S)-2,3-dihydro-1,4-benzodioxin-2-yl]
   benzyl}piperidin-4-yl)-2-methylpropanoic acid,
2-(1-{4-[(3S)-2,3-dihydro[1,4]dioxino[2,3-b]pyridin-3-
   yl]benzyl}piperidin-4-yl)-2-methylpropanoic acid,
2-{4-[(2S)-2,3-dihydro-1,4-benzodioxin-2-yl]benzyl}-1,
   2,3,4-tetrahydroisoquinoline-7-carboxylic acid,
4-{[{4-[(2S)-2,3-dihydro-1,4-benzodioxin-2-yl]benzyl}
   (ethyl)amino]methyl}benzoic acid,
4-[(butyl{4-[(2S)-2,3-dihydro-1,4-benzodioxin-2-yl]
   benzyl}amino)methyl]benzoic acid,
3-{[{4-[(2S)-2,3-dihydro-1,4-benzodioxin-2-yl]benzyl}
   (ethyl)amino]methyl}benzoic acid,
3-[(4-{4-[(2S)-2,3-dihydro-1,4-benzodioxin-2-yl]
   benzyl}piperazin-1-yl)methyl]benzoic acid,
4-(1-[4-[(2S)-2,3-dihydro-1,4-benzodioxin-2-yl]
   benzyl}piperidin-4-yl)butanoic acid,
4(1-{4-[(3S)-2,3-dihydro[1,4]dioxino[2,3-b]pyridin-3-yl]
   benzyl}piperidin-4-yl)benzoic acid,
(3S)-3-{4-[(1s,4s)-7-azabicyclo[2.2.1]hept-7-ylmethyl]
   phenyl}-2,3-dihydro[1,4]dioxino[2,3-b]pyridine,
N-(1-{4-[(3S)-2,3-dihydro[1,4]dioxino[2,3-b]pyridin-3-
   yl]benzyl}piperidin-4-yl)methanesulfonamide,
(3S)-3-[4-(azepan-1-ylmethyl)phenyl]-2,3-dihydro[1,4]
   dioxino[2,3-b]pyridine,
1-{4-[(2S)-2,3-dihydro-1,4-benzodioxin-2-yl]benzyl}-2-
   methylpiperidine,
7-{4-[(2S)-2,3-dihydro-1,4-benzodioxin-2-yl]benzyl}-1,
   7-diazaspiro[4.4]nonane-1-carboxamide,
7-{4-[(3S)-2,3-dihydro[1,4]dioxino[2,3-b]pyridin-3-yl]
   benzyl}-1,7-diazaspiro[4.4]nonan-2-one,
1-{4-[(2S)-2,3-dihydro-1,4-benzodioxin-2-yl]
   benzyl}piperidine-4-carboxylic acid,
(1-{4-[(2S)-2,3-dihydro-1,4-benzodioxin-2-yl]benzyl
   }piperidin-4-yl)(morpholin-4-yl)methanone, 8-{4-[(3S)-2,3-dihydro[1,4]dioxino[2,3-b]pyridin-3-yl]benzyl}-1,3,8-triazaspiro[4.5]decane-2,4-dione,
(3S)-3-{4-[(3-methoxypiperidin-1-yl)methyl]phenyl}-2,3-dihydro[1,4]dioxino{2,3-b}pyridine,
N-(1-{4-[(2S)-2,3-dihydro-1,4-benzodioxin-2-yl]benzyl}pyrrolidin-3-yl)-N-methylacetamide,
1-{4-[(2S)-2,3-dihydro-1,4-benzodioxin-2-yl]benzyl}-4-(1,1-dioxido-1,2-thiazolidin-2-yl)piperidine,
(3R)-1-{4-[(3S)-2,3-dihydro[1,4]dioxino[2,3-b]pyridin-3-yl]benzyl}pyrrolidin-3-ol,
N-(1-{4-[(3S)-2,3-dihydro[1,4]dioxino[2,3-b]pyridin-3-yl]benzyl}piperidin-4-yl)-2-hydroxyacetamide,
4-{(1-{4-[(3S)-2,3-dihydro[1,4]dioxino[2,3-b]pyridin-3-yl]benzyl}piperidin-4-yl)methyl}benzoic acid,
(1-{4-[(3S)-2,3-dihydro[1,4]dioxino[2,3-b]pyridin-3-yl]benzyl}piperidin-4-yl)(morpholin-4-yl)methanone,
(3S)-3-[4-(morpholin-4-ylmethyl)phenyl]-2,3-dihydro[1,4]dioxino[2,3-b]pyridine,
8-{4-[(2S)-2,3-dihydro-1,4-benzodioxin-2-yl]benzyl}-2,8-diazaspiro[4.5]decan-1-one,
1-{4-[(3S)-2,3-dihydro[1,4]dioxino[2,3-b]pyridin-3-yl]benzyl}piperidine-4-carbonitrile,
1-{4-[(2S)-2,3-dihydro-1,4-benzodioxin-2-yl]benzyl}-N-methylpiperidine-4-carboxamide,
8-{4[(3S)-2,3-dihydro[1,4]dioxino[2,3-b]pyridin-3-yl]benzyl}-2,8-diazaspiro[4.5]decan-1-one,
N-(1-{4-[(3S)-2,3-dihydro[1,4]dioxino[2,3-b]pyridin-3-yl]benzyl}piperidin-4-yl)-2-hydroxy-2-methylpropanamide,
N-(1-{4-[(3S)-2,3-dihydro[1,4]dioxino[2,3-b]pyridin-3-yl]benzyl}piperidin-4-yl-1-hydroxycyclopropanecarboxamide,
N-{4-[(2S)-2,3-dihydro-1,4-benzodioxin-2-yl]benzyl}-N-ethylcyclopentanamine,
1-{4-[(3S)-2,3-dihydro[1,4]dioxino[2,3-b]pyridin-3-yl]benzyl}-N-methylpiperidine-4-carboxamide,
N-{4-[(3S)-2,3-dihydro[1,4]dioxino[2,3-b]pyridin-3-yl]benzyl}-N-methylcyclopentanamine,
1-{(1-{4-[(3S)-2,3-dihydro[1,4]dioxino[2,3-b]pyridin-3-yl]benzyl}piperidin-3-yl)methyl}pyrrolidin-2-one,
1-{4-[(2S)-2,3-dihydro-1,4-benzodioxin-2-yl]benzyl}-2-methylpyrrolidine,
N-{4-[(3S)-2,3-dihydro[1,4]dioxino[2,3-b]pyridin-3-yl]benzyl}-2-methyl-1-(pyrrolidin-1-yl)propan-2-amine,
N-cyclohexyl-N-{4-[(2S)-2,3-dihydro-1,4-benzodioxin-2-yl]benzyl}-N',N'-dimethylethane-1,2-diamine,
N-(1-1{4-[(3S)-2,3-dihydro[1,4]dioxino[2,3-b]pyridin-3-yl]benzyl}piperidin-4-yl)acetamide,
N-{4-[(3S)-2,3-dihydro[1,4]dioxino[2,3-b]pyridin-3-yl]benzyl}-N-methyl-2-(pyridin-2-yl)ethanamine,
(3S)-3-[4-(pyrrolidin-1-ylmethyl)phenyl]-2,3-dihydro[1,4]dioxino[2,3-b]pyridine,
1-{4-[(3S)-2,3-dihydro[1,4]dioxino[2,3-b]pyridin-3-yl]benzyl}piperidine-3-carboxamide,
1-{4-[(3S)-2,3-dihydro[1,4]dioxino[2,3-b]pyridin-3-yl]benzyl}piperidine-4-carboxamide,
N-(1-{4-[(2S)-2,3-dihydro-1,4-benzodioxin-2-yl]benzyl}pyrrolidin-3-yl)acetamide,
1-{4-[(3S)-2,3-dihydro[1,4]dioxino[2,3-b]pyridin-3-yl]benzyl}-N-(2-hydroxyethyl)piperidine-4-carboxamide,
(3S)-3-[4-(1,4-oxazepan-4-ylmethyl)phenyl]-2,3-dihydro[1,4]dioxino[2,3-b]pyridine,
1-{4-[(2S)-2,3-dihydro-1,4-benzodioxin-2-yl]benzyl}-N-(2-hydroxyethyl)piperidine-4-carboxamide,
4-(1-{4-[(2S)-2,3-dihydro-1,4-benzodioxin-2-yl]benzyl}piperidin-4-yl)benzoic acid,
1-(1-{4-[(2S)-2,3-dihydro-1,4-benzodioxin-2-yl]benzyl}piperidin-4-yl)urea,
7-{4-[(2S)-2,3-dihydro-1,4-benzodioxin-2-yl]benzyl}-1,7-diazaspiro[4.4]nonan-2-one,
8-{4-[(3S)-2,3-dihydro[1,4]dioxino[2,3-b]pyridin-3-yl]benzyl}-2-methyl-2,8-diazaspiro[4.5]decan-1-one,
1-{4-[(3S)-2,3-dihydro[1,4]dioxino[2,3-b]pyridin-3-yl]benzyl}piperidin-4-ol,
N-(1-{4-[(2S)-2,3-dihydro-1,4-benzodioxin-2-yl]benzyl}piperidin-4-yl)methanesulfonamide,
3(1-{4-[(3S)-2,3-dihydro[1,4]dioxino[2,3-b]pyridin-3-yl]benzyl}piperidin-4-yl)propan-1-ol,
(3S)-3-{4-[(4-methylpiperidin-1-yl)methyl]phenyl}-2,3-dihydro[1,4]dioxino{2,3-b}pyridine,
N-{4-[(3S)-2,3-dihydro[1,4]dioxino[2,3-b]pyridin-3-yl]benzyl}-N-ethylethanamine,
N-{4-[(3S)-2,3-dihydro[1,4]dioxino[2,3-b]pyridin-3-yl]benzyl}-1-(methylsulfonyl)piperidin-4-amine,
(3S)-3-{4-[(4-fluoropiperidin-1-yl-methyl]phenyl}-2,3-dihydro[1,4]dioxino{2,3-b}pyridine,
1(4-{4-[(3S)-2,3-dihydro[1,4]dioxino[2,3-b]pyridin-3-yl]benzyl}-1,4-diazepan-1-yl)ethenone,
[(3R)-1-{4-[(2S)-2,3-dihydro-1,4-benzodioxin-2-yl]benzyl}piperidin-3-yl]acetic acid,
(1-{4-[(3S)-2,3-dihydro[1,4]dioxino[2,3-b]pyridin-3-yl]benzyl}piperidin-4-yl-methanol,
4-[(1-{4-[(2S)-2,3-dihydro-1,4-benzodioxin-2-yl]benzyl}piperidin-4-yl-methyl]benzoic acid,
(3S)-3-{4-[(4-methyl-1,4-diazepan-1-yl)methyl]phenyl}-2,3-dihydro[1,4]dioxino{2,3-b}pyridine,
(3S)-3-{4-[(3-methoxypyrrolidin-1-yl)methyl]phenyl}-2,3-dihydro[1,4]dioxino{2,3-b}pyridine, and
N-{4-[(2S)-2,3-dihydro-1,4-benzodioxin-2-yl]benzyl}-N,2-dimethylpropan-2-amine.

\* \* \* \* \*

UNITED STATES PATENT AND TRADEMARK OFFICE
CERTIFICATE OF CORRECTION

PATENT NO. : 11,426,399 B2
APPLICATION NO. : 16/412275
DATED : August 30, 2022
INVENTOR(S) : Meghan Kerrisk Campbell et al.

It is certified that error appears in the above-identified patent and that said Letters Patent is hereby corrected as shown below:

In the Specification

Please replace "1-{-[4-(Benzothiazol-2-yloxy)-benzyl]-piperidin-4-yl}-1" with -- 1-{1-[4-(Benzothiazol-2-yloxy)-benzyl]-piperidin-4-yl}-1 -- (Column 30, Line 32);

Please replace "meso-N-[(3-endo)-8-{2-[4-([,3]Thiazolo[4,5-b]pyridin-2-ylmethyl)phenoxy]ethyl}-8-azabicyclo[3.2.1]oct-3-yl]acetamide" with -- meso-N-[(3-endo)-8-{2-[4-([1,3]Thiazolo[4,5-b]pyridin-2-ylmethyl)phenoxy]ethyl}-8-azabicyclo[3.2.1]oct-3-yl]acetamide -- (Column 38, Line 16);

Please replace "Thiazoolo" with -- Thiazolo -- (Column 39, Line 16);

Please replace "meso-2-(4-{2-[3-Acetyl-3,8-diazabicyclo[3.2.1]oct-8-yl]ethyl}phenoxy)[,3]thiazolo[5,4-b]pyridine" with -- meso-2-(4-{2-[3-Acetyl-3,8-diazabicyclo[3.2.1]oct-8-yl]ethyl}phenoxy)[1,3]thiazolo[5,4-b]pyridine -- (Column 39, Line 36);

Please replace "$R^{13}$" with -- $R^{13a}$ -- (Column 41, Line 56);

Please replace "$N(R)_2$" with -- $N(R^5)_2$ -- (Column 52, Line 59);

Please replace "(1a,5a,6a)" with -- (1α,5α,6α) -- (Column 54, Line 22);

Please replace "(1a,5a,6a)" with -- (1α,5α,6α) -- (Column 54, Lines 32-33);

Please replace "(1a,5a,6a)" with -- (1α,5α,6α) -- (Column 54, Line 35);

Please replace "(1a,5a,6a)" with -- (1α,5α,6α) -- (Column 64, Line 30);

Please replace "(1a,5a,6a)" with -- (1α,5α,6α) -- (Column 64, Line 38);

Signed and Sealed this
Twenty-seventh Day of December, 2022

Katherine Kelly Vidal
*Director of the United States Patent and Trademark Office*

CERTIFICATE OF CORRECTION (continued)
U.S. Pat. No. 11,426,399 B2

Please replace "(1a,5a,6a)" with -- (1α,5α,6α) -- (Column 64, Line 40);

Please replace "N-{C1-[(S)-4-(2,3-Dihydro-[1,4]dioxino[2,3-b]pyridin-3-yl)-benzyl]-piperidin-4-ylmethyl}" with -- N-{1-[(S)-4-(2,3-Dihydro-[1,4]dioxino[2,3-b]pyridin-3-yl)-benzyl]-piperidin-4-ylmethyl} -- (Column 64, Lines 62-63);

Please replace "(1a,5a,6a)" with -- (1α,5α,6α) -- (Column 64, Line 64);

Please replace "(1a,5a,6a)" with -- (1α,5α,6α) -- (Column 65, Line 5); and

Please replace "16. Neuromvelitis Optica Spectrum Disorder" with -- 16. Neuromyelitis Optica Spectrum Disorder -- (Column 85, Line 7).

In the Claims

In Claim 16:

Please replace "$R^{42}$ is selected from halo, —OH, —CN, —($C_1$-$C_6$)alkyl, —($C_1$-$C_6$)alkyl, and —($C_3$-$C_6$)cycloalkyl;" with -- $R^{42}$ is selected from halo, —OH, —CN, —(C1-C6)alkyl, —O(C1-C6)alkyl, and —(C3-C6)cycloalkyl; -- (Column 105, Lines 57-58);

Please replace "$R^4$" with -- R40 -- (Column 105, Line 59); and

Please replace "—C(O)—H" with -- —C(O)O—H -- (Column 105, Line 64).

In Claim 17:

Please replace "1-{4-[(3S)-2,3-dihydro[1,4]dioxino[2,3]pyridin-3-yl]benzyl}-1" with -- 1-{4-[(3S)-2,3-dihydro[1,4]dioxino[2,3-b]pyridin-3-yl]benzyl}-1 -- (Column 110, Lines 45-46).